US011384148B2

(12) United States Patent
Finney et al.

(10) Patent No.: US 11,384,148 B2
(45) Date of Patent: Jul. 12, 2022

(54) ANTI-FCRN ANTIBODIES

(71) Applicant: UCB Biopharma SPRL, Brussels (BE)

(72) Inventors: Helene Margaret Finney, Slough (GB); Alastair David Griffiths Lawson, Slough (GB); Stevan Graham Shaw, Slough (GB); Bryan John Smith, Slough (GB); Kerry Louise Tyson, Slough (GB); Lara Kevorkian, Slough (GB); Christoph Meier, Slough (GB); Kaushik Sarkar, Slough (GB); Paul Alan Atherfold, Slough (GB)

(73) Assignee: UCB Biopharma SRL ( * ) Notice: Subject to any disclaimer, the term of this patent is extended or adjusted under 35 U.S.C. 154(b) by 346 days.

(21) Appl. No.: 16/271,086

(22) Filed: Feb. 8, 2019

(65) Prior Publication Data
US 2019/0248890 A1 Aug. 15, 2019

Related U.S. Application Data

(62) Division of application No. 14/400,812, filed as application No. PCT/EP2013/059802 on May 13, 2013, now Pat. No. 10,233,243.

(30) Foreign Application Priority Data

May 14, 2012 (GB) ..................................... 1208370

(51) Int. Cl.
A61K 39/395 (2006.01)
A61K 39/40 (2006.01)
C07K 16/28 (2006.01)
G01N 33/50 (2006.01)
G01N 33/564 (2006.01)
G01N 33/68 (2006.01)
A61K 47/60 (2017.01)
A61K 47/64 (2017.01)
C07K 16/00 (2006.01)
A61K 39/00 (2006.01)

(52) U.S. Cl.
CPC ........ C07K 16/283 (2013.01); A61K 39/3955 (2013.01); A61K 47/60 (2017.08); A61K 47/643 (2017.08); G01N 33/5047 (2013.01); G01N 33/564 (2013.01); G01N 33/6854 (2013.01); G01N 33/6857 (2013.01); G01N 33/6893 (2013.01); A61K 2039/505 (2013.01); C07K 2317/21 (2013.01); C07K 2317/24 (2013.01); C07K 2317/33 (2013.01); C07K 2317/55 (2013.01); C07K 2317/565 (2013.01); C07K 2317/76 (2013.01); C07K 2317/92 (2013.01); G01N 2333/70535 (2013.01); G01N 2500/02 (2013.01); G01N 2500/10 (2013.01); G01N 2800/104 (2013.01); G01N 2800/24 (2013.01); G01N 2800/28 (2013.01)

(58) Field of Classification Search
None
See application file for complete search history.

(56) References Cited

U.S. PATENT DOCUMENTS

| 4,741,900 | A | 5/1988 | Alvarez |
| 5,219,996 | A | 6/1993 | Bodmer |
| 5,585,089 | A | 12/1996 | Queen |
| 5,667,425 | A | 9/1997 | Pineau |
| 7,662,928 | B2 | 2/2010 | Balthasar |
| 8,017,739 | B2 | 9/2011 | Eichner |
| 8,163,881 | B2 | 4/2012 | Ober |
| 8,834,871 | B2 | 9/2014 | Ober |
| 10,233,243 | B2 | 3/2019 | Finney |
| 10,273,302 | B2 | 4/2019 | Atherfold |
| 2002/0138863 | A1 | 9/2002 | Roopenian |
| 2007/0092507 | A1 | 4/2007 | Balthasar |
| 2010/0266530 | A1 | 10/2010 | Roopenian |
| 2014/0248287 | A1 | 9/2014 | Tenhoor |
| 2015/0118240 | A1 | 4/2015 | Finney |
| 2016/0264668 | A1 | 9/2016 | Atherfold |

FOREIGN PATENT DOCUMENTS

| EP | 0392745 | 10/1990 |
| EP | 0948544 | 10/1999 |
| EP | 1090037 | 4/2001 |
| GB | 1320066 | 6/1973 |
| GB | 12083705 | 6/2013 |
| GB | 13200662 | 5/2015 |
| KR | 20130071961 A | 7/2013 |
| WO | 8601533 | 3/1986 |
| WO | 1986001533 | 3/1986 |
| WO | 8900195 | 1/1989 |
| WO | 1989000195 | 1/1989 |
| WO | 8901476 | 2/1989 |
| WO | 1989001476 | 2/1989 |

(Continued)

OTHER PUBLICATIONS

Zanella et al. Haematologica 2014, 99(10):1547-1554. (Year: 2014).*
Aalberse et al., "IgG4 breaking the rules," (2002), Immunology 105, pp. 9-19.
Adair, J.R., et al., "Therapeutic antibodies," Drug Design Reviews—Online, 2005, vol. 2, No. 3, pp. 209-217.
Akilesh S et al., "Neonatal FcR Expression in Bone Marrow-Derived Cells Functions to Protect Serum IgG from Catabolism," (2007), J Immunol; vol. 179, pp. 4580-4588.

(Continued)

Primary Examiner — Chun W Dahle
(74) Attorney, Agent, or Firm — Saul Ewing Arnstein & Lehr LLP; Doreen Y. Trujillo

(57) ABSTRACT

The disclosure relates to antibodies specific to FcRn, formulations comprising the same, use of each in therapy, processes for expressing and optionally formulating said antibody, DNA encoding the antibodies and hosts comprising said DNA.

16 Claims, 60 Drawing Sheets
Specification includes a Sequence Listing.

(56) References Cited

FOREIGN PATENT DOCUMENTS

| WO | 9109967 | 7/1991 |
|---|---|---|
| WO | 1991009967 | 7/1991 |
| WO | 9202551 | 2/1992 |
| WO | 1992002551 | 2/1992 |
| WO | 9222583 | 12/1992 |
| WO | 1992022583 | 12/1992 |
| WO | 9306231 | 4/1993 |
| WO | 1993006231 | 4/1993 |
| WO | 9820734 | 5/1998 |
| WO | 9825971 | 6/1998 |
| WO | 1998025971 | 6/1998 |
| WO | 02060919 | 8/2002 |
| WO | 03031581 | 4/2003 |
| WO | 2003031581 | 4/2003 |
| WO | 03048208 | 6/2003 |
| WO | 2003048208 | 6/2003 |
| WO | 2004051268 | 6/2004 |
| WO | 2004106377 | 12/2004 |
| WO | 2005003169 | 1/2005 |
| WO | 2005003170 | 1/2005 |
| WO | 2005003171 | 1/2005 |
| WO | 2005013912 | 2/2005 |
| WO | 05113605 | 12/2005 |
| WO | 05117984 | 12/2005 |
| WO | 2005113605 | 12/2005 |
| WO | 2005117984 | 12/2005 |
| WO | 2006106323 | 10/2006 |
| WO | 2006118772 | 11/2006 |
| WO | 2007024715 | 3/2007 |
| WO | 2007087289 | 8/2007 |
| WO | 2007098420 A2 | 8/2007 |
| WO | 2008038024 | 4/2008 |
| WO | 2008043822 A2 | 4/2008 |
| WO | 2009020867 A2 | 2/2009 |
| WO | 2009040562 | 4/2009 |
| WO | 2009080764 | 7/2009 |
| WO | 2009131702 | 10/2009 |
| WO | 2010014909 A1 | 2/2010 |
| WO | 2010035012 | 4/2010 |
| WO | 2011030107 | 3/2011 |
| WO | 2011061492 | 5/2011 |
| WO | 2011086091 | 7/2011 |
| WO | 2012167039 A1 | 12/2012 |
| WO | 2013068571 | 5/2013 |
| WO | 2014019727 | 2/2014 |
| WO | 2014204280 | 12/2014 |
| WO | 2014204280 A1 | 12/2014 |
| WO | 2015071330 | 5/2015 |

OTHER PUBLICATIONS

Akilesh S et al., "The MHC class I-like Fc receptor promotes humorally mediated autoimmune disease," (2004), J Clin Invest; vol. 113, No. 9, pp. 1328-1333.
Alina Sesarman et al., "The neonatal Fc receptor as therapeutic target in IgG-mediated autoimmune diseases," CMLS Cellular and Molecular Life Sciences, vol. 67, No. 15, Mar. 9, 2010, pp. 2533-2550.
Altschul, S.F. et al., "Basic local alignment search tool," J. Mol. Biol., vol. 215, No. 3, pp. 403-410, 1990.
Altschul, S.F. et al., "Gapped BLAST and PSI-BLAST: a new generation of protein database search programs," Nucleic Acids Res., vol. 25, No. 17, pp. 3389-3402, 1997.
Altshuler, E.P. et al., "Generation of Recombinant Antibodies and Means for Increasing Their Affinity," Biochemistry, Dec. 1, 2010, vol. 75, No. 13, pp. 1584-1605.
Andersen JT et al., "Cross-species Binding Analyses of Mouse and Human Neonatal Fc Receptor Show Dramatic Differences in Immunoglobulin G and Albumin Binding," (2010), J Biol Chem; vol. 285, No. 7, pp. 4826-4836.
Anderson CL et al., "Perspective—FcRn transports albumin: relevance to immunology and medicine," (2006), Trends Immunol; vol. 27, No. 7, pp. 343-348.

Angal, S., et al. "A single amino acid substitution abolishes the heterogeneity of chimeric mouse/human (IgG4) antibody", Molecular Immunology, vol. 30, No. 1, pp. 105-108, 1993.
Babcook, J. S. et al., "A novel strategy for generating monoclonal antibodies from single, isolated lymphocytes producing antibodies of defined specificities (PCR/antibody-forming cells/VH and VL genes/immunoglobulin/plaque assays)", Proceedings of the National Academy of Science, Jul. 1996, pp. 7843-7848, vol. 93, Immunology, USA.
Berger, Melvin, "Subcutaneous IgG in neurologic diseases," (2014), Immunotherapy vol. 6, No. 1, pp. 71-83.
Besada, Emilio, "Low immunoglobulin levels increase the risk of severe hypogammaglobulinemia in granulomatosis with polyangiitis patients receiving rituximab," (2016), BMC Musculoskelet Disord; vol. 17:6, pp. 1-7.
Borvak, J. et al., "Functional expression of the MHC class I-related receptor, FcRn, in endothelial cells of mice," 1998, Int. Immunol., vol. 10, No. 9, pp. 1289-1298.
Burmesiter, et al., "Crystal structure of the complex of rat neonatal Dc receptor with Fc," Nature, vol. 372, Nov. 24, 1994 ,pp. 379-383.
Cain K et al., "A CHO Cell Line Engineered to Express XBP1 and ERO1-Lx Has Increased Levels of Transient Protein Expression," (2013), Biotechnol Prog; vol. 29, No. 3, pp. 697-706.
Casset et al., "A peptide mimetic of an anti-CD4 monoclonal antibody by rational design," Biochemical and Biophysical Research Communication, vol. 307 (2003), pp. 198-205.
Cauza, K. et al., "Expression of FcRn, the MHC Class I-Related Receptor for IgG, in Human Keratinocytes," Jan. 2005, J. Invest. Dermatol., vol. 124, No. 1, pp. 132-139.
Chapman, A., 'PEGylated antibodies and antibody fragments for improved therapy: a review', Advanced Drug Delivery Reviews, vol. 54, No. 4, pp. 531-545, 2002.
Chothia, C. and Lesk, A.M., "Canonical Structures for the Hypervariable Regions of Immunoglobulins," J. Mol. Biol., vol. 196, pp. 901-917, 1987.
Chowdhury, P.S. et al., "Improving Antibody Infinite by Mimicking Somatic Hypermutation in Vitro," Nature Biotechnology, vol. 17, Nature Publishing Group, New York, NY, Jun. 1, 1999, pp. 568-572.
Christianson, Gregory J. et al., "Monoclonal antibodies directed against human FcRn and their applications," mAbs, vol. 4, No. 2, Mar. 2012, pp. 208-216.
Claypool et al., "Bidirectional Transepithelial IgG Transport by a Strongly Polarized Basolateral Membrane Fcγ-Receptor," Apr. 2004, Mol. Biol. Cell, vol. 15, No. 4, pp. 1746-1759.
Claypool et al., "Functional Reconstitution of Human FcRn in Madin-Darby Canine Kidney Cells Requires Co-expressed Human Beta2-Microglobulin," 2002, Journal of Biological Chemistry, vol. 277, No. 31, pp. 28038-28050.
Cole, S.P.C., et al., "The EBV-hybridoma technique and its application to human lung cancer," Monoclonal Antibodies and Cancer Therapy, vol. 27, (UCLA Symposia on Molecular and Cellular Biology, New Series, R.A. Reisfeld and S. Sell (eds.)), pp. 77-96, Alan R. Liss, Inc., N.Y., 1985.
Crameri, A., et al., "DNA shuffling of a family of genes from diverse species accelerates directed evolution," Nature, Jan. 15, 1998, vol. 391, pp. 288-291.
Dall'Acqua, WF et al., "Increasing the Affinity of a Human IgG1 for the Neonatal Fc Receptor: Biological Consequences," (2002), J Immunol; vol. 169, pp. 5171-5180.
Dall'Acqua, WF et al., "Properties of Human IgG1s Engineered for Enhanced Binding to the Neonatal Fc Receptor (FcRn)," (2006), J Biol Chem; vol. 281, No. 33, pp. 23514-2324.
Datta-Mannan, A et al., "Monoclonal Antibody Clearance Impact of Modulating the Interaction of IgG with the Neonatal Fc Receptor," (2007), J Biol Chem; vol. 282, No. 3, pp. 1709-1717.
Dubowchik, G.M., et al., "Receptor-mediated and enzyme-dependent targeting of cytotoxic anticancer drugs," Pharmacology and Therapeutics, vol. 83, No. 2, pp. 67-123, 1999.
Fagerberg, L et al., "Analysis of the Human Tissue-specific Expression by Genome-wide Integration of Transcriptomics and Antibody-based Proteomics," (2014), Mol Cell Proteomics; 13, pp. 397-406.

(56) References Cited

OTHER PUBLICATIONS

Feng Y. et al., "Design, expression and characterization of a soluble single-chain functional human neonatal Fc receptor," Protein expression and purification, Sep. 2011, vol. 79, No. 1, pp. 66-71.
Firan et al., "The MHC class I-related receptor, FcRn, plays an essential role in the maternofetal transfer of y-globulin in humans," 2001, International Immunology, vol. 13, No. 8, pp. 993-1002.
Getman, Kate, E. et al., "Pharmacokinetic effects of 4C9, an anti-FcRn antibody, in rates: implications for the use of FcRn inhibitors for the treatment of humoral autoimmune conditions," Journal of Pharmaceutical Sciences, vol. 94, No. 4, Apr. 1, 2005, pp. 718-729.
Gish, W., and States, D.M., "Identification of protein coding regions by data base similarity search," Nature Genet., vol. 3, No. 3, pp. 266-272, 1993.
Gonzalez-Noriega, A et al., "Chloroquine inhibits lysosomal enzyme pinocytosis and enhances lysosomal enzyme secretion by impairing receptor recycling," (1980), J Cell Biol; vol. 85, pp. 839-852.
Harris, J.M., and Zalipsky, S., eds., "Poly(ethyleneglycol) Chemistry and Biological Applications", American Chemical Society, Washington DC, 1997.
Harris, R.J., "Processing of C-terminal lysine and arginine residues of proteins isolated from mammalian cell culture," Journal of Chromatography, vol. 705, No. 1, pp. 129-134, 1995.
Hellstrom, K.E. et al., 'Antibodies for drug delivery,' Controlled Drub Delivery, Robinson, et al., eds, Marcel Dekker, Inc., Ed. 2, Chapter 15, pp. 623-653 (1987).
Hieter, P.A., et al., 'Evolution of human immunoglobulin kappa J region genes', J. Biol. Chem., vol. 257, No. 3, pp. 1516-1522, 1982.
Holliger and Hudson, "Engineered antibody fragments and the rise of single domains," Nature Biotechnology, vol. 23, No. 9, pp. 1126-1136, Sep. 2005.
Humphreys, F et al., "The characteristics of urticaria in 390 patients," (1998), Br J Dermatol; vol. 138, pp. 635-638.
International Search Report, International Application PCT/EP2013/ 059802, dated Jan. 2, 2014.
Janeway et al., Immunology Third Edition, Garland Publishing Inc. 1997, Chapter 3, Structure of the Antibody Molecule and Immunoglobulin Genes, pp. 3:1-3:11.
Junghans, RP et al., "The ptoection receiption for IgG catabolism is the Beta 2-microglobulin-containing neonatal intestinal transport receptor," (1996), Proc Natl Acad Sci U S A; vol. 93, pp. 5512-5516.
Kabat, et al., 'Sequences of Proteins of Immunological Interest', 4th ed., US Department of Health and Human Services, Public Health Service, National Institutes of Health, 1983, pp. xv-xviii.
Kashmiri, S.V.S., et al., 'SDR grafting—a new approach to antibody humanization', Methods, vol. 36, pp. 25-34, 2005.
Kiessling, P et al., "The FcRn inhibitor rozanolixizumab reduces human serum IgG concentration: A randomized phase 1 study," (2017), Sci Transl Med; col. 9, pp. 1-12.
Kim, J et al., "Kinetics of FcRn-mediated recycling of IgG and albumin in human: pathophysiology and therapeutic implications using a simplified mechanism-based model," (2007), Clin. Immunol. vol. 122, pp. 146-155.
Kohler & Milstein, "Continuous cultures of fused cells secreting antibody of predefined specificity," Nature, Aug. 7, 1975, pp. 495-497, vol. 256, nature Publishing Group.
Kozbor, D., et al., "The production of monoclonal antibodies from human lymphocytes," Immunology Today, vol. 4, No. 3, pp. 72-79, 1983.
Krishna, M et al., "Immunogenicity to Biotherapeutics—The Role of Anti-drug Immune Complexes," (2016) Front Immunol; vol. 7, Article 21, pp. 1-13.
Li, N et al., "Complete FcRn dependence for intravenous Ig therapy in autoimmune skin blistering diseases," (2005), J Clin Invest; vol. 115, No. 12, pp. 3440-3450.
Lightwood, D et al., "The Discovery, Engineering and Characterisation of a Highly Potent Anti-Human IL-13 Fab Fragment Designed for Administration by Inalation," (2013), J Mol Biol; vol. 425, pp. 577-593.

Liu L. et al., "Amelioration of experimental autoimmune myasthenia gravis in rats by neonatal FcR blockade," J Immunol, Apr. 15, 2007, vol. 178, No. 8, pp. 5390-5398.
Liu, Z et al., "Beta 2-microglobulin-deficient Mice Are Resistant to Bullous Pemphigoid," (1997), J Exp Med; vol. 186, No. 5, pp. 777-783.
Low, N. M., et al., 'Mimicking Somatic Hypermutation Affinity Maturation of Antibodies Displayed on Bacteriophage Using a Bacterial Mutator Strain', J. Mol. Biol., vol. 260, No. 3, pp. 359-368, 1996.
Madden, T.L., et al., 'Applications of Network Blast Server', Meth. Enzymol., vol. 266, pp. 131-141, 1996.
Marks, J.D., et al., "By-passing Immunization Human: Building High Affinity Human Antibodies by Chain Shuffling," Bio/ Technology, vol. 10, pp. 779-783, 1992.
Martins, JP et al., "A comprehensive review of the neonatal Fc receptor and its application in drug delivery," (2016), Pharmacol Ther; vol. 161, pp. 22-39.
Matucci, A et al., "Mechanisms of action of Ig preparations: immunolodulatory and anti-inflammatory effects," (2014), Front Immunol; vol. 5, Article 690, pp. 1-5.
Mezo, AR et al., "Reduction of IgG in nonhuman primates by a peptide antagonist of the neonatal Fc receptor FcRn," (2008), Proc Natl Acad Sci U S A; vol. 105, No. 7, pp. 2337-2342.
Neuber, T et al., "Characterization and screening of IgG binding to the neonatal Fc receptor," (2014), MAbs, vol. 6, Issue 4, pp. 928-942.
Nixon, AE et al., "Fully human monoclonal antibody inhibitors of the neonatal Fc receptor reduce circulating IgG in non-human primates," (2015), Front Immunol; vol. 6, Article 176, pp. 1-13.
Ober et al., "Differences in promiscuity for antibody-FcRn interactions across species: implications for therapeutic antibodies," 2001, Int. Immunol. vol. 13, No. 12, pp. 1551-1559.
Ober, RJ, et al., "Visualizing the Site and Dynamics of IgG Salvage by the MHC Class I-Related Receptor, FcRn," 2004, The Journal of Immunology, 172, pp. 2021-2029.
Oganesyan, V et al., "Structural Insights into Neonatal Fc Receptor-based Recycling Mechanisms," (2014), Journal of Biological Chemistry; vol. 289, No. 11, pp. 7812-7824.
Ohkubo, A et al., "Removal Characteristics of Immunoglobulin G Subclasses by Conventional Plasma Exchange and Selective Plasma Exchange," (2015), Ther Apher Dial; vol. 19, No. 4, pp. 361-366.
Patel, DA et al., "FcRn blockade by Fc engineering ameliorates arthritis in a murine model," (2011), J Immunol; vol. 187, No. 2, pp. 1015-1022.
Patten, P., et al., "Applications of DNA shuffling to pharmaceuticals and vaccines," Curr. Opin. Biotechnol., vol. 8, No. 6, pp. 724-733, 1997.
Paul et al, Fundamental Immunology, 3rd ed. 1993, p. 242.
Petkova, SB et al., "Enhanced half-life of genetically engineered human IgG1 antibodies in a humanized FcRn mouse model: potential application in humorally mediated autoimmune disease," (2006), Int Immunol; vol. 18, No. 12, pp. 1759-1769.
Portolano et al., "Lack of Promiscuity in Autoantigen-Specific H and L Chain Combinations as Revealed by Human H and L Chain Roulette," Journal of Immunology, 1993, vol. 150, pp. 880-887.
Pyzik, M et al., "FcRn: The architect behind the immune and non-immune functions of IgG and albumin," (2015), J Immunol; vol. 194, No. 10, pp. 4595-4603.
Raghavan, M et al., "Investigation of the Interaction between the Class I MHC-Related Fc Receptor and its Immunoglobulin G Ligand," (1994), Immunity; vol. 1, pp. 303-315.
Raghavan, M. et al., "Analysis of pH Dependence of the Neonatal Fc Receptor/ Immunoglobulin G Interaction Using Antibody and Receptor Variants," Biochemistry, vol. 34, No. 45, 1995, pp. 14649-14657.
Ravetch, J.V., et al., 'Structure of the human immunoglobulin mu locus: characterization of embryonic and rearranged J and D genes', Cell, vol. 27, No. 3, Pt 2, pp. 583-591, 1981.
Riechmann, et al., 'Reshaping human antibodies for therapy', Nature, vol. 332, pp. 323-327, 1988.
Roopenian and Akilesh, "FcRn: the neonatal Fc receptor comes of age," Nature Reviews Immunology, Sep. 2007, vol. 7, pp. 715-725.

(56) References Cited

OTHER PUBLICATIONS

Roopenian, DC et al., "The MHC Class I_Like IgG Receptor Controls Perinatal IgG Transport, IgG Homeostasis, and Fate of IgG-Fc-Coupled Drugs," (2003), J Immunol; vol. 170, pp. 3528-3533.
Rudikoff et al., "Single amino acid substitution altering antigen-binding specificity," PNAS, 1982, vol. 79, pp. 1979-1983.
Sand, KMK et al., "Unraveling the interaction between FcRn and albumin: opportunities for design of albumin-based therapeutics," (2014), Front. Immunol; vol. 5, Article 682, pp. 1-21.
Scatchard et al., "The attractions of proteins for small molecules and ions," Annals New York Academy of Science, vol. 51, pp. 660-672 (1949).
Schmidt, MM et al., "Crystal Structure of an HSA/FcRn Complex Reveals Recycling by Competitive Mimicry of HSA Ligands ata pH-Dependent Hydrophobic Interface," (2013); vol. 21, pp. 1966-1978.
Schwartz, J et al., "Guidelines on the Use of Therapeutic Apheresis in Clinical Practice—Evidence-Based Approach from the Writing Committee of the American Society for Apheresis: The Sixth Special Issue," (2013), J Clin Apher 2013; vol. 28, pp. 145-284.
Sewell, WA et al., "European consensus proposal for immunoglobulin therapies," (2014), Eur. J. Immunol; vol. 44, pp. 2207-2214.
Thompson, J., et al., "Affinity maturation of a high-affinity human monoclonal antibody against the third hypervariable loop of human immunodeficiency virus: use of phage display to improve affinity and broaden strain reactivity," J. Mol. Biol., vol. 256, No. 1, pp. 77-88, 1996.
Thorpe, P.E., et al., 'The preparation and cytotoxic properties of antibody-toxin conjugates', Immunol. Rev., vol. 62, pp. 119-158, 1982.
Uno, Y et al., "Polymorphisms of Neonatal Fc Receptor in Cynomolgus and Rhesus Macaques," (2014), Drug Metab Pharmacokinet; vol. 29, No. 5, pp. 427-430.
Vaccaro C. et al., "Engineering the Fc region of immunoglobulin G to modulate in vivo antibody levels," Nature Biotechnology, Oct. 2005, vol. 23, No. 10, pp. 1283-1288.
Vaughan, et al., 'Human antibodies by design,' Nature Biotechnology, vol. 16, No. 6, pp. 535-539, 1998.
Verma, R., et al., "Antibody engineering: comparison of bacterial, yeast, insect and mammalian expression systems," Journal of Immunological Methods, vol. 216, Nos. 1-2, pp. 165-181, 1998.
Waldmann, TA et al., "Familial Hypercatabolic Hypoproteinemia," (1990), J Clin Invest; vol. 86, pp. 2093-2098.
Wang, J et al., "Intravenous immunoglobulin in critically ill adults: When and what is the evidence?" (2015), J Crit Care; vol. 30, pp. 652.e9-652e.16.
Wani, MA et al., "Familial hypercatabolic hypoproteinemia caused by deficiency of the neonatal Fc receptor, FcRn, due to a mutant beta2-microglobulin gene," (2006), Proc Natl Acad Sci U S A; vol. 103, No. 13, pp. 5084-2089.
Ward, ES et al., "Targeting FcRn for therapy: from live cell imaging to in vivo studies in mice," (2014), Immunol Lett; vol. 160, No. 2, pp. 158-162.
Wark, K. L. et al., "Latest Technologies for the enhancement of antibody affinity," Advanced Drug Delivery Reviews, Aug. 7, 2006, vol. 58, No. 5-6, Elsevier BV, Amsterdam, NL, pp. 657-670.
Warncke, M et al., "Different Adaptations of IgG Effector Function in Human and Nonhuman Primates and Implications for Therapeutic Antibody Treatment," (2012), J Immunol; vol. 188, pp. 4405-4411.
West, AP et al., "Crystal Structure and Immoglobulin G Binding Properties of the Human Major Histocompatibility Complex-Related Fc Receptor," (2000), Biochemistry; vol. 39, pp. 9698-96708.
Wolff et al., "Monoclonal Antibody Homodimers: Enhanced Antitumor Activity in Nude Mice," Cancer Research, vol. 53, pp. 2560-2565 (1993).
Written Opinion of the International Searching Authority for International Application No. PCT/EP2013/059802 dated Jan. 2, 2014.
Yang, W.P. et al., "CDR Walking Mutagenesis for the Affinity Maturation of a Potent Human Anti-HIV-1 Antibody into the Picomolar Range," J. Mol. Biol., vol. 254, No. 3, pp. 392-403, 1995.
Zhang, J. & Madden, T.L., "PowerBlast: a new network Blast application for interactive or automated sequence analysis and annotation", Genome Res., vol. 7, No. 6, pp. 649-656, 1997.
Zhou, J et al., "Conferring the Binding Properties of the Mouse MHC Class I-related Receptor, FcRn, onto the Human Ortholog by Sequential Rounds of Site-directed Mutagenesis," (2005), J Mol Biol; vol. 345, pp. 1071-1081.
Zhou, J et al., "High Affinity Nucleocapsid Protein Binding to the Mu Psi RNA Packaging Signal of Rous Sarcoma Virus," (2005), J Mol Biol; vol. 349, pp. 976-988.
Zubler, R. H. et al., "Mutant EL-4 thymoma cells polyclonally activate murine and human B cells via direct cell interaction," J. Immunol., vol. 134, pp. 3662-3668 (1985).
International Search Report of International Application No. PCT/EP2016/060305 dated Jun. 14, 2016.
International Search Report dated Feb. 17, 2015 for International Application No. PCT/EP2014/074409.
Written Opinion of the International Searching Authority dated Feb. 17, 2015 for International Application No. PCT/EP2014/074409.
Co-pending U.S. Appl. No. 15/036,209, filed May 12, 2016—now U.S. Pat. No. 10,273,302.
Co-pending U.S. Appl. No. 15/573,185, filed Nov. 10, 2017.
William E. Paul, M.D. ed., Fundamental Immunology 3rd ed. 1993, p. 242 (Year: 1993).
Casset et al. (BBRC(2003) 307, 198-205. (Year: 2003).
Written Opinion of the International Searching Authority for International Application No. PCT/EP2016/060305 dated Jun. 14, 2016.
Lu, D. et al., "Fab-scFv fusion protein: an efficient approach to production of bispecific antibody fragments," Journal of Immunological Methods, vol. 267, No. 2, Sep. 15, 2002, pp. 213-226.
Luo, D. et al., "VI-Linker-Vh Orientation-Dependent Expression of Single Chain Fv Containing an Engineered Disulfide-Stabilized Bond in the Framework Region," J. Biochem., vol. 118, No. 4, pp. 825-831 (1995).
Young et al, "Thermal stabilization of a single-chain Fv antibody fragment by introduction of a disulphide bond," FEBS Letters vol. 377, Issue 2, pp. 135-139 (1995).
Glockshuber et al, "A comparison of strategies to stabilize immunoglobulin Fv-fragments," Biochemistry vol. 29, No. 6, pp. 1362-1367 (1990).
Zhu et al, "Remodeling domain interfaces to enhance heterodimer formation," Protein Science vol. 6, pp. 781-788 (1997).
Brinkmann et al., "A recombinant immunotoxin containing a disulfide-stabilized Fv fragment," Proc. Natl. Acad. Sci. USA, vol. 90, Issue 16, pp. 7538-7542 , (1993).
Rajagopal et al., "A form of anti-Tac(Fv) which is both single-chain and disulfide stabilized: comparison with its single-chain and disulfide-stabilized homologs," Protein Engineering, vol. 10 No. 12 pp. 1453-1459 (1997).
Reiter, et al., "Improved Binding and Antitumor Activity of a Recombinant Anti-erbB2 Immunotoxin by Disulfide Stabilization of the Fv Fragment," Journal of Biological Chemistry vol. 269 No. 28 pp. 18327-18331 (1994).
Co-pending U.S. Appl. No. 14/400,812, filed Nov. 13, 2014—now U.S. Pat. No. 10,233,243.
Co-pending U.S. Appl. No. 16/271,086, filed Feb. 8, 2019.
Co-pending U.S. Appl. No. 16/299,407, filed Mar. 12, 2019.
Co-pending U.S. Appl. No. 17/286,247, filed Apr. 16, 2021.
Co-pending U.S. Appl. No. 16/615,419, filed Nov. 21, 2019.
Office Action, Japanese Patent Application No. JP2020-093532, dated Jul. 20, 2021.
English translation of Office Action, Japanese Patent Application No. JP2020-093532, dated Jul. 20, 2021.

* cited by examiner

FIG. 1

CA170_1519 Ab sequences
CDRH1
GFTFSNYGMV          SEQ ID NO: 1

CDRH2
YIDSDGDNTYYRDSVKG   SEQ ID NO: 2

CDRH3
GIVRPFLY            SEQ ID NO: 3

CDRL1
KSSQSLVGASGKTYLY    SEQ ID NO: 4

CDRL2
LVSTLDS             SEQ ID NO: 5

CDRL3
LQGTHFPHT           SEQ ID NO: 6

Rat Ab 1519 VL region    SEQ ID NO: 7
DVVMTQTPLS LSVALGQPAS ISCKSSQSLV GASGKTYLYW LFQRSGQSPK
RLIYLVSTLD SGIPDRFSGS GAETDFTLKI RRVEADDLGV YYCLQGTHFP
HTFGAGTKLE LK Rat Ab 1519 VL region    SEQ ID NO: 8

```
gatgttgtga tgacccagac tccactgtct tgtcggttg ccccttggaca
accagcctcc atctcttgca agtcaagtca gagcctcgta ggtgctagtg
gaaagacata tttgtattgg ttatttcaga ggtccggcca gtctccaaag
cgactaatct atctggtgtc cacactggac tctggaattc ctgataggtt
cagtggcagt ggagcagaga cagattttac tcttaaaatc cgcagagtgg
aagccgatga tttgggagtt tattactgct tgcaaggtac acatttcct
cacacgtttg gagctgggac caagctggaa ttgaaa
```

Rat Ab 1519 VL region with signal sequence underlined and italicised  SEQ ID NO: 9

*MMSPAQFLFL LMLWIQGTSG* DVVMTQTPLS LSVALGQPAS ISCKSSQSLV
GASGKTYLYW LFQRSGQSPK RLIYLVSTLD SGIPDRFSGS GAETDFTLKI
RRVEADDLGV YYCLQGTHFP HTFGAGTKLE LK

FIG. 1A

Rat Ab 1519 VL region with signal sequence underlined and italicised SEQ ID NO: 10
*atgatgagtc ctgcccagtt cctgtttctg ctgatgctct ggattcaggg*
*aaccagtggt* gatgttgtga tgacccagac tccactgtct tgtcggttg
ccttggaca accagcctcc atctcttgca agtcaagtca gagcctcgta
ggtgctagtg aaagacata tttgtattgg ttatttcaga ggtccggcca
gtctccaaag cgactaatct atctggtgtc cacactggac tctggaattc
ctgataggtt cagtggcagt ggagcagaga cagatttac tcttaaaatc
cgcagagtgg aagccgatga tttgggagtt tattactgct tgcaaggtac
acattttcct cacacgtttg gagctgggac caagctggaa ttgaaa Rat Ab 1519 VH region SEQ ID NO: 11
EVPLVESGGG SVQPGRSMKL SCVVSGFTFS NYGMVWVRQA PKKGLEWVAY
IDSDGDNTYY RDSVKGRFTI SRNNAKSTLY LQMDSLRSED TATYYCTTGI
VRPFLYWGQG TTVTVS Rat Ab 1519 VH region SEQ ID NO: 12
gaggtgccgc tggtggagtc tggggggcggc tcagtgcagc ctgggaggtc
catgaaactc tcctgtgtag tctcaggatt cactttcagt aattatggca
tggtctgggt ccgccaggct ccaaagaagg gtctggagtg ggtcgcatat
attgattctg atggtgataa tacttactac cgagattccg tgaagggccg
attcactatc tccagaaata atgcaaaaag caccctatat ttgcaaatgg
acagtctgag gtctgaggac acggccactt attactgtac aacagggatt
gtccggccct ttctctattg gggccaagga accacggtca ccgtctcg Rat Ab 1519 VH region with signal sequence underlined and italicised SEQ ID NO: 13

*MDISLSLAFL VLFIKGVRCE* VPLVESGGGS VQPGRSMKLS CVVSGFTFSN
YGMVWVRQAP KKGLEWVAYI DSDGDNTYYR DSVKGRFTIS RNNAKSTLYL
QMDSLRSEDT ATYYCTTGIV RPFLYWGQGT TVTVS

Rat Ab 1519 VH region with signal sequence underlined and italicised SEQ ID NO: 14

*atggacatca gtctcagctt ggctttcctt gtccttttca taaaaggtgt*
*ccggtgt*gag gtgccgctgg tggagtctgg gggcggctca gtgcagcctg
ggaggtccat gaaactctcc tgtgtagtct caggattcac tttcagtaat
tatggcatgg tctgggtccg ccaggctcca agaagggtc tggagtgggt
cgcatatatt gattctgatg gtgataatac ttactaccga gattccgtga
agggccgatt cactatctcc agaataatg caaaaagcac cctatatttg
caaatggaca gtctgaggtc tgaggacacg gccacttatt actgtacaac
agggattgtc cggccctttc tctattgggg ccaaggaacc acggtcaccg
tctcg

FIG. 1B

1519 gL20 V-region SEQ ID NO: 15
DIQMTQSPSS LSASVGDRVT ITCKSSQSLV GASGKTYLYW LFQKPGKAPK
RLIYLVSTLD SGIPSRFSGS GSGTEFTLTI SSLQPEDFAT YYCLQGTHFP
HTFGQGTKLE IK 1519 gL20 V-region (*E. coli* expression) SEQ ID NO: 16
gatatccaga tgacccagag tccaagcagt ctctccgcca gcgtaggcga
tcgtgtgact attacctgta aaagctccca gtccctggtg ggtgcaagcg
gcaaaaccta cctgtactgg ctcttccaga accgggcaa agctccgaaa
cgcctgatct atctggtgtc taccctggat agcggtattc cgtctcgttt
ctccggtagc ggtagcggta ccgaattcac gctgaccatt agctccctcc
agccggagga ctttgctacc tattactgcc tccagggcac tcattttccg
cacactttcg gccagggtac caaactggaa atcaaa 1519 gL20 V-region (mammalian expression) SEQ ID NO: 17
gatatccaga tgacccagag cccatctagc ttatccgctt ccgttggtga
tcgcgtgaca attacgtgta agagctccca atctctcgtg ggtgcaagtg
gcaagaccta tctgtactgg ctctttcaga agcctggcaa ggcaccaaaa
cggctgatct atctggtgtc taccttgac tctgggatac cgtcacgatt
ttccggatct gggagcggaa ctgagttcac actcacgatt tcatcgctgc
aacccgagga ctttgctacc tactactgcc tgcaaggcac tcatttccct
cacactttcg gccaggggac aaaactcgaa atcaaa 1519 gL20 V-region with signal sequence underlined and italicized (*E. coli* expression) SEQ
ID NO: 18
*MKKTAIAIAV ALAGFATVAQ A*DIQMTQSPS SLSASVGDRV TITCKSSQSL
VGASGKTYLY WLFQKPGKAP KRLIYLVSTL DSGIPSRFSG SGSGTEFTLT
ISSLQPEDFA TYYCLQGTHF PHTFGQGTKL EIK 1519 gL20 V-region with signal sequence underlined and italicized (*E. coli* expression) SEQ
ID NO: 19
*atgaaaaaga cagctatcgc aattgcagtg gccttggctg gtttcgctac
cgtagcgcaa gct*gatatcc agatgaccca gagtccaagc agtctctccg
ccagcgtagg cgatcgtgtg actattacct gtaaaagctc cagtccctg
gtgggtgcaa gcggcaaaac ctacctgtac tggctcttcc agaaaccggg
caaagctccg aaacgcctga tctatctggt gtctaccctg gatagcggta
ttccgtctcg ttttctccggt agcggtagcg gtaccgaatt cacgctgacc
attagctccc tccagccgga ggactttgct acctattact gcctccaggg
cactcatttt ccgcacactt tcggccaggg taccaaactg gaaatcaaa

FIG. 1C

1519 gL20 V-region with signal sequence underlined and italicized (mammalian expression)
SEQ ID NO: 20
*MSVPTQVLGL LLLWLTDARC* DIQMTQSPSS LSASVGDRVT ITCKSSQSLV
GASGKTYLYW LFQKPGKAPK RLIYLVSTLD SGIPSRFSGS GSGTEFTLTI
SSLQPEDFAT YYCLQGTHFP HTFGQGTKLE IK 1519 gL20 V-region with signal sequence underlined and italicized (mammalian expression)
SEQ ID NO: 21
*atgtctgtcc ccacccaagt cctcggactc ctgctactct ggcttacaga*
*tgccagatgc* gatatccaga tgacccagag cccatctagc ttatccgctt
ccgttggtga tcgcgtgaca attacgtgta agagctccca atctctcgtg
ggtgcaagtg gcaagaccta tctgtactgg ctctttcaga agcctggcaa
ggcaccaaaa cggctgatct atctggtgtc taccttgac tctggatac
cgtcacgatt ttccggatct gggagcggaa ctgagttcac actcacgatt
tcatcgctgc aacccgagga ctttgctacc tactactgcc tgcaaggcac
tcatttccct cacactttcg gccaggggac aaaactcgaa atcaaa 1519 gL20 light chain (V + constant) SEQ ID NO: 22
DIQMTQSPSS LSASVGDRVT ITCKSSQSLV GASGKTYLYW LFQKPGKAPK
RLIYLVSTLD SGIPSRFSGS GSGTEFTLTI SSLQPEDFAT YYCLQGTHFP
HTFGQGTKLE IKRTVAAPSV FIFPPSDEQL KSGTASVVCL LNNFYPREAK
VQWKVDNALQ SGNSQESVTE QDSKDSTYSL SSTLTLSKAD YEKHKVYACE
VTHQGLSSPV TKSFNRGEC 1519 gL20 light chain (V + constant, *E. coli* expression) SEQ ID NO: 23
gatatccaga tgacccagag tccaagcagt ctctccgcca gcgtaggcga
tcgtgtgact attacctgta aaagctccca gtccctggtg ggtgcaagcg
gcaaaaccta cctgtactgg ctcttccaga aaccgggcaa agctccgaaa
cgcctgatct atctggtgtc taccctggat agcggtattc cgtctcgttt
ctccggtagc ggtagcggta ccgaattcac gctgaccatt agctccctcc
agccggagga ctttgctacc tattactgcc tccaggcac tcatttccg
cacactttcg gccagggtac caaactggaa atcaaacgta cggtagcggc
cccatctgtc ttcatcttcc cgccatctga tgagcagttg aaatctggaa
ctgcctctgt tgtgtgcctg ctgaataact ctatcccag agaggccaaa
gtacagtgga aggtggataa cgcctccaa tcgggtaact cccaggagag
tgtcacagag caggacagca aggacagcac ctacagcctc agcagcaccc
tgacgctgag caaagcagac tacgagaaac acaaagtcta cgcctgcgaa
gtcacccatc agggcctgag ctcaccagta acaaaaagtt taatagagg ggagtgt

FIG. 1D

1519 gL20 light chain (V + constant, mammalian expression) SEQ ID NO: 24
```
gatatccaga tgacccagag tccaagcagt ctctccgcca gcgtaggcga
tcgtgtgact attacctgta aaagctccca gtccctggtg ggtgcaagcg
gcaaaaccta cctgtactgg ctcttccaga aaccgggcaa agctccgaaa
cgcctgatct atctggtgtc taccctggat agcggtattc cgtctcgttt
ctccggtagc ggtagcggta ccgaattcac gctgaccatt agctccctcc
agccggagga ctttgctacc tattactgcc tccagggcac tcattttccg
cacactttcg gccagggtac caaactggaa atcaaacgta cggtagcggc
cccatctgtc ttcatcttcc cgccatctga tgagcagttg aaatctggaa
ctgcctctgt tgtgtgcctg ctgaataact ctatcccag agaggccaaa
gtacagtgga aggtggataa cgcctccaa tcgggtaact cccaggagag
tgtcacagag caggacagca aggacagcac ctacagcctc agcagcaccc
tgacgctgag caaagcagac tacgagaaac acaaagtcta cgcctgcgaa
gtcacccatc agggcctgag ctcgcccgtc acaaagagct caacagggg agagtgt
```

1519 gL20 light chain with signal sequence underlined and italicized (*E. coli* expression) SEQ ID NO: 25
```
MKKTAIAIAV ALAGFATVAQ ADIQMTQSPS SLSASVGDRV TITCKSSQSL
VGASGKTYLY WLFQKPGKAP KRLIYLVSTL DSGIPSRFSG SGSGTEFTLT
ISSLQPEDFA TYYCLQGTHF PHTFGQGTKL EIKRTVAAPS VFIFPPSDEQ
LKSGTASVVC LLNNFYPREA KVQWKVDNAL QSGNSQESVT EQDSKDSTYS
LSSTLTLSKA DYEKHKVYAC EVTHQGLSSP VTKSFNRGEC
```

1519 gL20 light chain with signal sequence underlined and italicized (*E. coli* expression) SEQ ID NO: 26
```
atgaaaaaga cagctatcgc aattgcagtg gccttggctg gtttcgctac
cgtagcgcaa gctgatatcc agatgaccca gagtccaagc agtctctccg
ccagcgtagg cgatcgtgtg actattacct gtaaaagctc ccagtccctg
gtgggtgcaa gcggcaaaac ctacctgtac tggctcttcc agaaaccggg
caaagctccg aaacgcctga tctatctggt gtctaccctg gatagcggta
ttccgtctcg tttctccggt agcggtagcg gtaccgaatt cacgctgacc
attagctccc tccagccgga ggactttgct acctattact gcctccaggg
cactcatttt ccgcacactt tcggccaggg taccaaactg gaaatcaaac
gtacggtagc ggccccatct gtcttcatct tcccgccatc tgatgagcag
ttgaaatctg gaactgcctc tgttgtgtgc ctgctgaata acttctatcc
cagagaggcc aaagtacagt ggaaggtgga taacgccctc caatcgggta
actcccagga gagtgtcaca gagcaggaca gcaaggacag cacctacagc
ctcagcagca ccctgacgct gagcaaagca gactacgaga aacacaaagt
ctacgcctgc gaagtcaccc atcagggcct gagctcacca gtaacaaaaa
gtttaatag aggggagtgt
```

FIG. 1E 1519 gL20 light chain with signal sequence underlined and italicized (mammalian expression) SEQ ID NO: 27
*MSVPTQVLGL LLLWLTDARC* DIQMTQSPSS LSASVGDRVT ITCKSSQSLV
GASGKTYLYW LFQKPGKAPK RLIYLVSTLD SGIPSRFSGS GSGTEFTLTI
SSLQPEDFAT YYCLQGTHFP HTFGQGTKLE IKRTVAAPSV FIFPPSDEQL
KSGTASVVCL LNNFYPREAK VQWKVDNALQ SGNSQESVTE QDSKDSTYSL
SSTLTLSKAD YEKHKVYACE VTHQGLSSPV TKSFNRGEC 1519 gL20 light chain with signal sequence underlined and italicized (mammalian expression) SEQ ID NO: 28
*atgtctgtcc ccacccaagt cctcggactc ctgctactct ggcttacaga*
*tgccagatgc* gatatccaga tgacccagag cccatctagc ttatccgctt
ccgttggtga tcgcgtgaca attacgtgta agagctccca atctctcgtg
ggtgcaagtg gcaagaccta tctgtactgg ctctttcaga agcctggcaa
ggcaccaaaa cggctgatct atctggtgtc taccttgac tctgggatac
cgtcacgatt ttccggatct gggagcggaa ctgagttcac actcacgatt
tcatcgctgc aacccgagga ctttgctacc tactactgcc tgcaaggcac
tcatttccct cacactttcg gccaggggac aaaactcgaa atcaaacgta
cggtagcggc cccatctgtc ttcatcttcc cgccatctga tgagcagttg
aaatctggaa ctgcctctgt tgtgtgcctg ctgaataact tctatcccag
agaggccaaa gtacagtgga aggtggataa cgccctccaa tcgggtaact
cccaggagag tgtcacagag caggacagca aggacagcac ctacagcctc
agcagcaccc tgacgctgag caaagcagac tacgagaaac acaaagtcta
cgcctgcgaa gtcacccatc agggcctgag ctcgcccgtc acaaagagct
tcaacagggg agagtgt 1519 gH20 V-region SEQ ID NO: 29
EVPLVESGGG LVQPGGSLRL SCAVSGFTFS NYGMVWVRQA PGKGLEWVAY
IDSDGDNTYY RDSVKGRFTI SRDNAKSSLY LQMNSLRAED TAVYYCTTGI
VRPFLYWGQG TLVTVS 1519 gH20 V-region (*E. coli* expression) SEQ ID NO: 30
gaggttccgc tggtcgagtc tggaggcggg cttgtccagc ctggagggag
cctgcgtctc tcttgtgcag tatctggctt cacgttctcc aactacggta
tggtgtgggt tcgtcaggct ccaggtaaag gtctggaatg ggtggcgtat
attgactccg acggcgacaa cacctactat cgcgactctg tgaaaggtcg
cttcaccatt tcccgcgata cgccaaatc cagcctgtac ctgcagatga
acagcctgcg tgctgaagat actgcggtgt actattgcac cactggcatc
gtgcgtccgt ttctgtattg gggtcagggt accctcgtta ctgtctcg

FIG. 1F (signal sequences underlined and italicized)

1519 gH20 V-region (mammalian expression) SEQ ID NO: 31
```
gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg gtcttgaatg ggtggcctat
attgactctg acggggacaa cacctactat cgggattccg tgaaaggacg
cttcacaatc tcccgagata cgccaagag ctcactgtac ctgcagatga
atagcctgag agccgaggat actgccgtgt actattgcac aacgggaatc
gttaggcctt ttctgtactg gggacagggc accttggtta ctgtctcg
```

1519 gH20 V-region (*E. coli* expression) SEQ ID NO: 32
*MKKTAIAIAV ALAGFATVAQ A*EVPLVESGG GLVQPGGSLR LSCAVSGFTF
SNYGMVWVRQ APGKGLEWVA YIDSDGDNTY YRDSVKGRFT ISRDNAKSSL
YLQMNSLRAE DTAVYYCTTG IVRPFLYWGQ GTLVTVS 1519 gH20 V-region (*E. coli* expression) SEQ ID NO: 33
```
atgaagaaga ctgctatagc aattgcagtg gcgctagctg gtttcgccac
cgtggcgcaa gctgaggttc cgctggtcga gtctggaggc gggcttgtcc
agcctggagg gagcctgcgt ctctcttgtg cagtatctgg cttcacgttc
tccaactacg gtatggtgtg gttcgtcag gctccaggta aaggtctgga
atgggtggcg tatattgact ccgacggcga caacacctac tatcgcgact
ctgtgaaagg tcgcttcacc atttcccgcg ataacgccaa atccagcctg
tacctgcaga tgaacagcct gcgtgctgaa gatactgcgg tgtactattg
caccactggc atcgtgcgtc cgtttctgta ttggggtcag ggtaccctcg
ttactgtctc g
```

1519 gH20 V-region (mammalian expression) SEQ ID NO: 34
*MEWSWVFLFF LSVTTGVHSE* VPLVESGGGL VQPGGSLRLS CAVSGFTFSN
YGMVWVRQAP GKGLEWVAYI DSDGDNTYYR DSVKGRFTIS RDNAKSSLYL
QMNSLRAEDT AVYYCTTGIV RPFLYWGQGT LVTVS 1519 gH20 V-region with signal sequence underlined and italicized (mammalian expression) SEQ ID NO: 35
```
atggaatgga gctgggtctt tctcttcttc ctgtcagtaa ctacaggagt
ccattctgag gtaccacttg tggaaagcgg aggaggtctt gtgcagcctg
gaggaagttt acgtctctct tgtgctgtgt ctggcttcac cttctccaat
tacggaatgg tctgggtcag acaagcacct ggaagggtc ttgaatgggt
ggcctatatt gactctgacg gggacaacac ctactatcgg gattccgtga
aaggacgctt cacaatctcc cgagataacg ccaagagctc actgtacctg
cagatgaata gcctgagagc cgaggatact gccgtgtact attgcacaac
gggaatcgtt aggccttttc tgtactgggg acagggcacc ttggttactg tctcg
```

FIG. 1G

1519gH20 Fab' heavy chain (V + human gamma-1 CH1 + hinge) SEQ ID NO: 36
```
EVPLVESGGG LVQPGGSLRL SCAVSGFTFS NYGMVWVRQA PGKGLEWVAY
IDSDGDNTYY RDSVKGRFTI SRDNAKSSLY LQMNSLRAED TAVYYCTTGI
VRPFLYWGQG TLVTVSSAST KGPSVFPLAP SSKSTSGGTA ALGCLVKDYF
PEPVTVSWNS GALTSGVHTF PAVLQSSGLY SLSSVVTVPS SSLGTQTYIC
NVNHKPSNTK VDKKVEPKSC DKTHTCAA
```

1519gH20 Fab' heavy chain (V + human gamma-1 CH1 + hinge, *E.coli* expression) SEQ ID NO: 37
```
gaggttccgc tggtcgagtc tggaggcggg cttgtccagc ctggagggag
cctgcgtctc tcttgtgcag tatctggctt cacgttctcc aactacggta
tggtgtgggt cgtcaggct ccaggtaaag gtctggaatg ggtggcgtat
attgactccg acggcgacaa cacctactat cgcgactctg tgaaaggtcg
cttcaccatt tcccgcgata cgccaaatc cagcctgtac ctgcagatga
acagcctgcg tgctgaagat actgcggtgt actattgcac cactggcatc
gtgcgtccgt ttctgtattg ggtcaggt accctcgtta ctgtctcgag
cgcttctaca aagggccat cggtcttccc cctggcaccc tcctccaaga
gcacctctgg gggcacagcg ccctgggct gcctggtcaa ggactacttc
cccgaaccgg tgacggtgtc gtggaactca ggcgcctga ccagcggcgt
gcacccttc ccggctgtcc tacagtcctc aggactctac tccctcagca
gcgtggtgac cgtgccctcc agcagcttgg cacccagac ctacatctgc
aacgtgaatc acaagcccag caacaccaag gtcgacaaga aagttgagcc
caaatcttgt gacaaaactc acacatgcgc cgcg
```

1519gH20 Fab' heavy chain (V + human gamma-1 CH1 + hinge, mammalian expression) SEQ ID NO: 38
```
gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg tcttgaatg ggtggcctat
attgactctg acggggacaa cacctactat cgggattccg tgaaaggacg
cttcacaatc tcccgagata cgccaagag ctcactgtac ctgcagatga
atagcctgag agccgaggat actgccgtgt actattgcac aacgggaatc
gttaggcctt ttctgtactg gggacagggc accttggtta ctgtctcgag
cgcttctaca aagggccat cggtcttccc cctggcaccc tcctccaaga
gcacctctgg gggcacagcg ccctgggct gcctggtcaa ggactacttc
cccgaaccgg tgacggtgtc gtggaactca ggcgcctga ccagcggcgt
gcacccttc ccggctgtcc tacagtcctc aggactctac tccctcagca
gcgtggtgac cgtgccctcc agcagcttgg cacccagac ctacatctgc
aacgtgaatc acaagcccag caacaccaag gtcgacaaga aagttgagcc
caaatcttgt gacaaaactc acacatgcgc cgcg
```

FIG. 1H

1519 gH20 Fab' heavy chain with signal sequence underlined and italicized (*E. coli* expression) SEQ ID NO: 39

*MKKTAIAIAV ALAGFATVAQ* AEVPLVESGG GLVQPGGSLR LSCAVSGFTF
SNYGMVWVRQ APGKGLEWVA YIDSDGDNTY YRDSVKGRFT ISRDNAKSSL
YLQMNSLRAE DTAVYYCTTG IVRPFLYWGQ GTLVTVSSAS TKGPSVFPLA
PSSKSTSGGT AALGCLVKDY FPEPVTVSWN SGALTSGVHT FPAVLQSSGL
YSLSSVVTVP SSSLGTQTYI CNVNHKPSNT KVDKKVEPKS CDKTHTCAA 1519 gH20 Fab' heavy chain with signal sequence underlined and italicized (*E. coli* expression) SEQ ID NO: 40

*atgaagaaga ctgctatagc aattgcagtg gcgctagctg gtttcgccac*
*cgtggcgcaa gct*gaggttc cgctggtcga gtctggaggc gggcttgtcc
agcctggagg gagcctgcgt ctctcttgtg cagtatctgg cttcacgttc
tccaactacg gtatggtgtg ggttcgtcag gctccaggta aggtctgga
atgggtggcg tatattgact ccgacggcga caacacctac tatcgcgact
ctgtgaaagg tcgcttcacc atttccgcg ataacgccaa atccagcctg
tacctgcaga tgaacagcct gcgtgctgaa gatactgcgg tgtactattg
caccactggc atcgtcgtc cgtttctgta ttggggtcag ggtaccctcg
ttactgtctc gagcgcttct acaaagggcc atcggtctt ccccctggca
ccctcctcca agagcacctc tgggggcaca gcggccctgg gctgcctggt
caaggactac ttccccgaac cggtgacggt gtcgtggaac tcaggcgccc
tgaccagcgg cgtgcacacc ttcccggctg tcctacagtc ctcaggactc
tactccctca gcagcgtggt gaccgtgccc tccagcagct gggcaccca
gacctacatc tgcaacgtga atcacaagcc cagcaacacc aaggtcgaca
agaaagttga gcccaaatct tgtgacaaaa ctcacacatg cgccgcg 1519 gH20 Fab' heavy chain with signal sequence underlined and italicized (mammalian expression) SEQ ID NO: 41

*MEWSWVFLFF LSVTTGVHSE* VPLVESGGGL VQPGGSLRLS CAVSGFTFSN
YGMVWVRQAP GKGLEWVAYI DSDGDNTYYR DSVKGRFTIS RDNAKSSLYL
QMNSLRAEDT AVYYCTTGIV RPFLYWGQGT LVTVSSASTK GPSVFPLAPS
SKSTSGGTAA LGCLVKDYFP EPVTVSWNSG ALTSGVHTFP AVLQSSGLYS
LSSVVTVPSS SLGTQTYICN VNHKPSNTKV DKKVEPKSCD KTHTCAA

FIG. 1I

1519 gH20 Fab' heavy chain with signal sequence underlined and italicized (mammalian expression) SEQ ID NO: 42

*atggaatgga gctgggtctt tctcttcttc ctgtcagtaa ctacaggagt*
*ccattct*gag gtaccacttg tggaaagcgg aggaggtctt gtgcagcctg
gaggaagttt acgtctctct tgtgctgtgt ctggcttcac cttctccaat
tacggaatgg tctgggtcag acaagcacct ggaaagggtc ttgaatgggt
ggcctatatt gactctgacg gggacaacac ctactatcgg gattccgtga
aaggacgctt cacaatctcc cgagataacg ccaagagctc actgtacctg
cagatgaata gcctgagagc cgaggatact gccgtgtact attgcacaac
gggaatcgtt aggcctttc tgtactgggg acagggcacc ttggttactg
tctcgagcgc ttctacaaag ggcccatcgg tcttcccct ggcaccctcc
tccaagagca cctctggggg cacagcggcc ctgggctgcc tggtcaagga
ctacttcccc gaaccggtga cggtgtcgtg gaactcaggc gccctgacca
gcggcgtgca ccttcccg gctgtcctac agtcctcagg actctactcc
ctcagcagcg tggtgaccgt gccctccagc agcttgggca cccagaccta
catctgcaac gtgaatcaca agcccagcaa caccaaggtc gacaagaaag
ttgagcccaa atcttgtgac aaaactcaca catgcgccgc g 1519gH20 IgG4 heavy chain (V + human gamma-4P constant) SEQ ID NO: 43

EVPLVESGGG LVQPGGSLRL SCAVSGFTFS NYGMVWVRQA PGKGLEWVAY
IDSDGDNTYY RDSVKGRFTI SRDNAKSSLY LQMNSLRAED TAVYYCTTGI
VRPFLYWGQG TLVTVSSAST KGPSVFPLAP CSRSTSESTA ALGCLVKDYF
PEPVTVSWNS GALTSGVHTF PAVLQSSGLY SLSSVVTVPS SSLGTKTYTC
NVDHKPSNTK VDKRVESKYG PPCPPCPAPE FLGGPSVFLF PPKPKDTLMI
SRTPEVTCVV VDVSQEDPEV QFNWYVDGVE VHNAKTKPRE EQFNSTYRVV
SVLTVLHQDW LNGKEYKCKV SNKGLPSSIE KTISKAKGQP REPQVYTLPP
SQEEMTKNQV SLTCLVKGFY PSDIAVEWES NGQPENNYKT TPPVLDSDGS
FFLYSRLTVD KSRWQEGNVF SCSVMHEALH NHYTQKSLSL SLGK

FIG. 1J

1519gH20 IgG4 heavy chain (V + human gamma-4P constant, exons underlined) SEQ ID NO: 44 gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg gtcttgaatg ggtggcctat
attgactctg acggggacaa cacctactat cgggattccg tgaaaggacg
cttcacaatc tcccgagata cgccaagag ctcactgtac ctgcagatga
atagcctgag agccgaggat actgccgtgt actattgcac aacgggaatc
gttaggcctt ttctgtactg gggacagggc accttggtta ctgtctcgag
<u>cgcttctaca aagggcccat ccgtcttccc cctggcgccc tgctccagga
gcacctccga gagcacagcc gccctgggct gcctggtcaa ggactacttc
cccgaaccgg tgacggtgtc gtggaactca ggcgccctga ccagcggcgt
gcacaccttc ccggctgtcc tacagtcctc aggactctac tccctcagca
gcgtggtgac cgtgccctcc agcagcttgg gcacgaagac ctacacctgc
aacgtagatc acaagcccag caacaccaag gtggacaaga gagttggtga</u>
<u>gaggccagca cagggaggga gggtgtctgc tggaagccag gctcagccct
cctgctgga cgcaccccgg ctgtgcagcc cagcccagg gcagcaaggc
atgccccatc tgtctcctca cccggaggcc tctgaccacc ccactcatgc
ccagggagag ggtcttctgg attttccac caggctccgg gcagccacag
gctggatgcc cctaccccag gccctgcgca tacaggggca ggtgctgcgc
tcagacctgc caagagccat atccgggagg accctgcccc tgacctaagc
ccacccccaaa ggccaaactc tccactccct cagtcagac accttctctc
ctcccagatc tgagtaactc ccaatcttct ctctgcagag tccaaatatg
gtcccccatg cccaccatgc ccaggtaagc caacccaggc ctcgccctcc</u>
<u>agctcaaggc gggacaggtg ccctagagta gcctgcatcc agggacaggc
cccagccggg tgctgacgca tccacctcca tctcttcctc agcacctgag
ttcctggggg gaccatcagt cttcctgttc cccccaaaac ccaaggacac
tctcatgatc tcccggaccc ctgaggtcac gtgcgtggtg gtggacgtga
gccaggaaga ccccgaggtc cagttcaact ggtacgtgga tggcgtggag
gtgcataatg ccaagacaaa gccgcgggag gagcagttca acagcacgta
ccgtgtggtc agcgtcctca ccgtcctgca ccaggactgg ctgaacggca
aggagtacaa gtgcaaggtc tccaacaaag gcctcccgtc ctccatcgag</u>
<u>aaaaccatct ccaaagccaa aggtgggacc cacggggtgc gagggccaca
tggacagagg tcagctcggc ccaccctctg cctgggagt gaccgctgtg
ccaacctctg tccctacagg gcagcccga gagccacagg tgtacaccct
gccccatcc caggaggaga tgaccaagaa ccaggtcagc ctgacctgcc
tggtcaaagg cttctacccc agcgacatcg ccgtggagtg ggagagcaat
gggcagccgg agaacaacta caagaccacg cctcccgtgc tggactccga
cggctccttc ttcctctaca gcaggctaac cgtggacaag agcaggtggc
aggagggaa tgtcttctca tgctccgtga tgcatgaggc tctgcacaac
cactacacac agaagagcct ctccctgtct ctgggtaaa</u>

FIG. 1K

1519gH20 IgG4 heavy chain (V + human gamma-4P constant) with signal sequence underlined and italicised SEQ ID NO: 45

*atggaatgga gctgggtctt tctcttcttc ctgtcagtaa ctacaggagt*
*ccattctg*ag gtaccacttg tggaaagcgg aggaggtctt gtgcagcctg
gaggaagttt acgtctctct tgtgctgtgt ctggcttcac cttctccaat
tacggaatgg tctgggtcag acaagcacct ggaaagggtc ttgaatgggt
ggcctatatt gactctgacg gggacaacac ctactatcgg gattccgtga
aaggacgctt cacaatctcc cgagataacg ccaagagctc actgtacctg
cagatgaata gcctgagagc cgaggatact gccgtgtact attgcacaac
gggaatcgtt aggccttttc tgtactgggg acaggcacc ttggttactg
tctcgagcgc ttctacaaag ggcccatccg tcttcccct ggcgcctgc
tccaggagca cctccgagag cacagccgcc ctgggctgcc tggtcaagga
ctacttcccc gaaccggtga cggtgtcgtg aactcaggc gccctgacca
gcggcgtgca caccttcccg gctgtcctac agtcctcagg actctactcc
ctcagcagcg tggtgaccgt gccctccagc agcttgggca cgaagaccta
cacctgcaac gtagatcaca agcccagcaa caccaaggtg gacaagagag
ttggtgagag gccagcacag ggagggaggg tgtctgctgg aagccaggct
cagccctcct gcctggacgc accccggctg tgcagcccca gcccagggca
gcaaggcatg ccccatctgt ctcctcaccc ggaggcctct gaccacccca
ctcatgccca gggagagggt cttctggatt tttccaccag gctccgggca
gccacaggct ggatgcccct accccaggcc ctgcgcatac agggcaggt
gctgcgctca gacctgccaa gagccatatc cggaggacc ctgcccctga
cctaagccca ccccaaaggc caaactctcc actccctcag ctcagacacc
ttctctcctc ccagatctga gtaactccca atcttctctc tgcagagtcc
aaatatggtc ccccatgccc accatgccca ggtaagccaa cccaggcctc
gccctccagc tcaaggcggg acaggtgccc tagagtagcc tgcatccagg
gacaggcccc agccgggtgc tgacgcatcc acctccatct cttcctcagc
acctgagttc ctgggggac catcagtctt cctgttcccc ccaaaaccca
aggacactct catgatctcc cggacccctg aggtcacgtg cgtggtggtg
gacgtgagcc aggaagaccc cgaggtccag ttcaactggt acgtggatgg
cgtggaggtg cataatgcca agacaaagcc gcgggaggag cagttcaaca
gcacgtaccg tgtggtcagc gtcctcaccg tcctgcacca ggactggctg
aacggcaagg agtacaagtg caaggtctcc aacaaaggcc tcccgtcctc
catcgagaaa accatctcca aagccaaagg tgggacccac ggggtgcgag
ggccacatgg acagaggtca gctcggccca ccctctgccc tgggagtgac
cgctgtgcca acctctgtcc ctacaggca gccccgagag ccacaggtgt
acaccctgcc cccatcccag gaggagatga ccaagaacca ggtcagcctg
acctgcctgg tcaaaggctt ctaccccagc gacatcgccg tggagtggga
gagcaatggg cagccggaga caactacaa gaccacgcct cccgtgctgg
actccgacgg ctccttcttc ctctacagca ggctaaccgt ggacaagagc
aggtggcagg agggggaatgt cttctcatgc tccgtgatgc atgaggctct
gcacaaccac tacacacaga agagcctctc cctgtctctg ggtaaa

FIG._1L

1519gL20 FabFv light chain SEQ ID NO: 46
DIQMTQSPSS LSASVGDRVT ITCKSSQSLV GASGKTYLYW LFQKPGKAPK
RLIYLVSTLD SGIPSRFSGS GSGTEFTLTI SSLQPEDFAT YYCLQGTHFP
HTFGQGTKLE IKRTVAAPSV FIFPPSDEQL KSGTASVVCL LNNFYPREAK
VQWKVDNALQ SGNSQESVTE QDSKDSTYSL SSTLTLSKAD YEKHKVYACE
VTHQGLSSPV TKSFNRGECS GGGGSGGGGS GGGGSDIQMT QSPSSVSASV
GDRVTITCQS SPSVWSNFLS WYQQKPGKAP KLLIYEASKL TSGVPSRFSG
SGSGTDFTLT ISSLQPEDFA TYYCGGGYSS ISDTTFGCGT KVEIKRT 1519gL20 FabFv light chain SEQ ID NO: 47
gatatccaga tgacccagag cccatctagc ttatccgctt ccgttggtga
tcgcgtgaca attacgtgta agagctccca atctctcgtg ggtgcaagtg
gcaagaccta tctgtactgg ctctttcaga agcctggcaa ggcaccaaaa
cggctgatct atctggtgtc tacccttgac tctgggatac cgtcacgatt
ttccggatct gggagcggaa ctgagttcac actcacgatt tcatcgctgc
aacccgagga ctttgctacc tactactgcc tgcaaggcac tcatttccct
cacactttcg gccaggggac aaaactcgaa atcaaacgta cggtagcggc
cccatctgtc ttcatcttcc cgccatctga tgagcagttg aaatctggaa
ctgcctctgt tgtgtgcctg ctgaataact tctatcccag agaggccaaa
gtacagtgga aggtggataa cgccctccaa tcgggtaact cccaggagag
tgtcacagag caggacagca aggacagcac ctacagcctg agcagcaccc
tgacgctgtc taaagcagac tacgagaaac acaaagtgta cgcctgcgaa
gtcacccatc agggcctgag ctcaccagta acaaaaagtt ttaatagagg
ggagtgtagc ggtggcggtg gcagtggtgg gggaggctcc ggaggtggcg
gttcagacat acaaatgacc cagagtcctt catcggtatc cgcgtccgtt
ggcgataggg tgactattac atgtcaaagc tctcctagcg tctggagcaa
ttttctatcc tggtatcaac agaaaccggg gaaggctcca aaacttctga
tttatgaagc ctcgaaactc accagtggag ttccgtcaag attcagtggc
tctggatcag ggacagactt cacgttgaca atcagttcgc tgcaaccaga
ggactttgcg acctactatt gtggtggagg ttacagtagc ataagtgata
cgacatttgg gtgcggtact aaggtggaaa tcaaacgtac c 1519gL20 FabFv light chain with signal sequence underlined & italicised SEQ ID NO: 48
*MSVPTQVLGL LLLWLTDARC* DIQMTQSPSS LSASVGDRVT ITCKSSQSLV
GASGKTYLYW LFQKPGKAPK RLIYLVSTLD SGIPSRFSGS GSGTEFTLTI
SSLQPEDFAT YYCLQGTHFP HTFGQGTKLE IKRTVAAPSV FIFPPSDEQL
KSGTASVVCL LNNFYPREAK VQWKVDNALQ SGNSQESVTE QDSKDSTYSL
SSTLTLSKAD YEKHKVYACE VTHQGLSSPV TKSFNRGECS GGGGSGGGGS
GGGGSDIQMT QSPSSVSASV GDRVTITCQS SPSVWSNFLS WYQQKPGKAP
KLLIYEASKL TSGVPSRFSG SGSGTDFTLT ISSLQPEDFA TYYCGGGYSS
ISDTTFGCGT KVEIKRT

FIG. 1M

1519gL20 FabFv light chain with signal sequence underlined and italicised SEQ ID NO: 49

*atgtctgtcc ccacccaagt cctcggactc ctgctactct ggcttacaga*
*tgccagatgc* gatatccaga tgacccagag cccatctagc ttatccgctt
ccgttggtga tcgcgtgaca attacgtgta agagctccca atctctcgtg
ggtgcaagtg gcaagaccta tctgtactgg ctctttcaga agcctggcaa
ggcaccaaaa cggctgatct atctggtgtc tacccttgac tctgggatac
cgtcacgatt ttccggatct gggagcggaa ctgagttcac actcacgatt
tcatcgctgc aacccgagga ctttgctacc tactactgcc tgcaaggcac
tcatttccct cacactttcg gccagggac aaaactcgaa atcaaacgta
cggtagcggc cccatctgtc ttcatcttcc cgccatctga tgagcagttg
aaatctggaa ctgcctctgt tgtgtgcctg ctgaataact ctatcccag
agaggccaaa gtacagtgga aggtggataa cgccctccaa tcgggtaact
cccaggagag tgtcacagag caggacagca aggacagcac ctacagcctg
agcagcaccc tgacgctgtc taaagcagac tacgagaaac acaaagtgta
cgcctgcgaa gtcacccatc agggcctgag ctcaccagta acaaaaagtt
ttaatagagg ggagtgtagc ggtggcggtg gcagtggtgg gggaggctcc
ggaggtggcg gttcagacat acaaatgacc cagagtcctt catcggtatc
cgcgtccgtt ggcgataggg tgactattac atgtcaaagc tctcctagcg
tctggagcaa ttttctatcc tggtatcaac agaaaccggg gaaggctcca
aaacttctga tttatgaagc ctcgaaactc accagtggag ttccgtcaag
attcagtggc tctggatcag ggacagactt cacgttgaca atcagttcgc
tgcaaccaga ggactttgcg acctactatt gtggtggagg ttacagtagc
ataagtgata cgacatttgg gtgcggtact aaggtggaaa tcaaacgtac
c 1519gH20 FabFv heavy chain SEQ ID NO: 50

EVPLVESGGG LVQPGGSLRL SCAVSGFTFS NYGMVWVRQA PGKGLEWVAY
IDSDGDNTYY RDSVKGRFTI SRDNAKSSLY LQMNSLRAED TAVYYCTTGI
VRPFLYWGQG TLVTVSSAST KGPSVFPLAP SSKSTSGGTA ALGCLVKDYF
PEPVTVSWNS GALTSGVHTF PAVLQSSGLY SLSSVVTVPS SSLGTQTYIC
NVNHKPSNTK VDKKVEPKSC SGGGGSGGGG TGGGGSEVQL LESGGGLVQP
GGSLRLSCAV SGIDLSNYAI NWVRQAPGKC LEWIGIIWAS GTTFYATWAK
GRFTISRDNS KNTVYLQMNS LRAEDTAVYY CARTVPGYST APYFDLWGQG TLVTVSS

FIG. 1N

1519gH20 FabFv heavy chain SEQ ID NO: 51

```
gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg gtcttgaatg ggtggcctat
attgactctg acggggacaa cacctactat cgggattccg tgaaggacg
cttcacaatc tcccgagata cgccaagag ctcactgtac ctgcagatga
atagcctgag agccgaggat actgccgtgt actattgcac aacgggaatc
gttaggcctt ttctgtactg gggacaggc accttggtta ctgtctcgag
cgcgtccaca aagggcccat cggtcttccc cctggcaccc tcctccaaga
gcacctctgg gggcacagcg gccctgggct gcctggtcaa ggactacttc
cccgaaccag tgacggtgtc gtggaactca ggtgccctga ccagcggcgt
tcacaccttc ccggctgtcc tacagtcttc aggactctac tccctgagca
gcgtggtgac cgtgccctcc agcagcttgg cacccagac ctacatctgc
aacgtgaatc acaagcccag caacaccaag gtcgataaga aagttgagcc
caaatcttgt agtggaggtg gggctcagg tggaggcggg accggtggag
gtggcagcga ggttcaactg cttgagtctg gaggaggcct agtccagcct
ggagggagcc tgcgtctctc ttgtgcagta agcggcatcg acctgagcaa
ttacgccatc aactgggtga acaagctcc ggggaagtgt tagaatgga
tcggtataat atgggccagt gggacgacct tttatgctac atgggcgaaa
ggaaggttta caattagccg ggacaatagc aaaaacaccg tgtatctcca
aatgaactcc ttgcgagcag aggacacggc ggtgtactat tgtgctcgca
ctgtcccagg ttatagcact gcaccctact tcgatctgtg gggacaaggg
accctggtga ctgtttcaag t
```

1519gH20 FabFv heavy chain with signal sequence underlined and italicised SEQ ID NO: 52

*MEWSWVFLFF LSVTTGVHSE* VPLVESGGGL VQPGGSLRLS CAVSGFTFSN
YGMVWVRQAP GKGLEWVAYI DSDGDNTYYR DSVKGRFTIS RDNAKSSLYL
QMNSLRAEDT AVYYCTTGIV RPFLYWGQGT LVTVSSASTK GPSVFPLAPS
SKSTSGGTAA LGCLVKDYFP EPVTVSWNSG ALTSGVHTFP AVLQSSGLYS
LSSVVTVPSS SLGTQTYICN VNHKPSNTKV DKKVEPKSCS GGGGSGGGGT
GGGGSEVQLL ESGGGLVQPG GSLRLSCAVS GIDLSNYAIN WVRQAPGKCL
EWIGIIWASG TTFYATWAKG RFTISRDNSK NTVYLQMNSL RAEDTAVYYC
ARTVPGYSTA PYFDLWGQGT LVTVSS

FIG. 1P

1519gH20 FabFv heavy chain with signal sequence underlined & italicised SEQ ID NO: 53

*atggaatgga gctgggtctt tctcttcttc ctgtcagtaa ctacaggagt ccattct*gag gtaccacttg tggaaagcgg aggaggtctt gtgcagcctg gaggaagttt acgtctctct tgtgctgtgt ctggcttcac cttctccaat tacggaatgg tctgggtcag acaagcacct ggaaagggtc ttgaatggtt ggcctatatt gactctgacg ggacaacac ctactatcgg gattccgtga aggacgctt cacaatctcc cgagataacg ccaagagctc actgtacctg cagatgaata gcctgagagc cgaggatact gccgtgtact attgcacaac gggaatcgtt aggccttttc tgtactgggg acagggcacc ttggttactg tctcgagcgc gtccacaaag ggcccatcgg tcttcccct ggcaccctcc tccaagagca cctctggggg cacagcggcc ctgggctgcc tggtcaagga ctacttcccc gaaccagtga cggtgtcgtg gaactcaggt gccctgacca gcggcgttca caccttcccg gctgtcctac agtcttcagg actctactcc ctgagcagcg tggtgaccgt gccctccagc agcttgggca cccagaccta catctgcaac gtgaatcaca agcccagcaa caccaaggtc gataagaaag ttgagcccaa atcttgtagt ggaggtgggg gctcaggtgg aggcgggacc ggtggaggtg gcagcgaggt tcaactgctt gagtctggag gaggcctagt ccagcctgga gggagcctgc gtctctcttg tgcagtaagc ggcatcgacc tgagcaatta cgccatcaac tgggtgagac aagctccggg gaagtgttta gaatggatcg gtataatatg ggccagtggg acgacctttt atgctacatg ggcgaaagga aggtttacaa ttagccggga caatagcaaa aacaccgtgt atctccaaat gaactccttg cgagcagagg acacggcggt gtactattgt gctcgcactg tcccaggtta tagcactgca ccctacttcg atctgtgggg acaagggacc ctggtgactg tttcaagt Human VK1 2-1-(1) A30 JK2 acceptor framework SEQ ID NO: 54
DIQMTQSPSS LSASVGDRVT ITCRASQGIR NDLGWYQQKP GKAPKRLIYA
ASSLQSGVPS RFSGSGSGTE FTLTISSLQP EDFATYYCLQ HNSYPYTFGQ GTKLEIK Human VK1 2-1-(1) A30 JK2 acceptor framework SEQ ID NO: 55
gacatccaga tgacccagtc tccatcctcc ctgtctgcat ctgtaggaga cagagtcacc atcacttgcc gggcaagtca gggcattaga aatgatttag gctggtatca gcagaaacca gggaaagccc ctaagcgcct gatctatgct gcatccagtt tgcaaagtgg ggtcccatca aggttcagcg gcagtggatc tgggacagaa ttcactctca caatcagcag cctgcagcct gaagattttg caacttatta ctgtctacag cataatagtt acccttacac ttttggccag gggaccaagc tggagatcaa a

FIG. 1Q

Human VH3 1-3 3-07 JH4 acceptor framework SEQ ID NO: 56
EVQLVESGGG LVQPGGSLRL SCAASGFTFS SYWMSWVRQA PGKGLEWVAN
IKQDGSEKYY VDSVKGRFTI SRDNAKNSLY LQMNSLRAED TAVYYCARYF
DYWGQGTLVT VS Human VH3 1-3 3-07 JH4 acceptor framework SEQ ID NO: 57
gaggtgcagc tggtggagtc tgggggaggc ttggtccagc ctggggggtc
cctgagactc tcctgtgcag cctctggatt cacctttagt agctattgga
tgagctggt ccgccaggct ccagggaagg ggctggagtg ggtggccaac
ataaagcaag atggaagtga gaaatactat gtggactctg tgaagggccg
attcaccatc tccagagaca cgccaagaa ctcactgtat ctgcaaatga
acagcctgag agccgaggac acggctgtgt attactgtgc gagatacttt
gactactggg gccagggaac cctggtcacc gtctcc Rat Ab 1548 VL region SEQ ID NO: 58

DVVMTQTPLS LSVALGQPAS ISCKSSQSLV GASGKTYLYW LFQRSGQSPK
RLIYLVSTLD SGIPDRFSGS GAETDFTLKI RRVEADDLGV YYCLQGTHFP
HTFGAGTKLE IK

Rat Ab 1548 VL region SEQ ID NO: 59 gatgttgtga tgacccagac tccactgtct ttgtcggttg cccttggaca
accagcctcc atctcttgca agtcaagtca gagcctcgta ggtgctagtg
gaaagacata tttgtattgg ttatttcaga ggtccggcca gtctccaaag
cgactaatct atctggtgtc cacactggac tctggaattc ctgataggtt
cagtggcagt ggagcagaga cagatttac tcttaaaatc cgcagagtgg
aagccgatga tttgggagtt tattactgct tgcaaggtac acattttcct
cacacgtttg gagctgggac caagctggaa ataaaa Rat Ab 1548 VH region SEQ ID NO: 60

EVPLVESGGG SVQPGRSMKL SCVVSGFTFS NYGMVWVRQA PKKGLEWVAY
IDSDGDNTYY RDSVKGRFTI SRNNAKSTLY LQMDSLRSED TATYYCTTGI
VRPFLYWGQG VMVTVS

FIG. 1R

Rat Ab 1548 VH region SEQ ID NO: 61

```
gaggtgccgc tggtggagtc tgggggcggc tcagtgcagc ctggagggtc
catgaaactc tcctgtgtag tctcaggatt cactttcagt aattatggca
tggtctgggt ccgccaggct ccaaagaagg gtctggagtg ggtcgcatat
attgattctg atggtgataa tacttactac cgagattccg tgaagggccg
attcactatc tccagaaata atgcaaaaag caccctatat ttgcaaatgg
acagtctgag gtctgaggac acggccactt attactgtac aacagggatt
gtccggccct ttctctattg gggccaagga gtcatggtca cagtctcg
```

Rat Ab 1644 VL region SEQ ID NO: 62

```
DVVMTQTPLS LSVAIGQPAS ISCKSSQSLV GASGKTYLYW LFQRSGQSPK
RLIYLVSTLD SGIPDRFSGS GAETDFTLKI RRVEADDLGV YYCLQGTHFP
HTFGAGTKLE LK
```

Rat Ab 1644 VL region SEQ ID NO: 63

```
gatgttgtga tgacccagac tccactgtct ttgtcggttg ccattggaca
accagcctcc atctcttgca agtcaagtca gagcctcgta ggtgctagtg
gaaagacata tttgtattgg ttatttcaga ggtccggcca gtctccaaag
cgactaatct atctggtgtc cacactggac tctggaattc ctgataggtt
cagtggcagt ggagcagaga cagattttac tcttaaaatc cgcagagtgg
aagccgatga tttgggagtt tattactgct tgcaaggtac acattttcct
cacacgtttg gagctgggac caagctggaa ctgaaa
```

Rat Ab 1644 VH region SEQ ID NO: 64

```
EVPLVESGGG SVQPGRSTKL SCVVSGFTFS NYGMVWVRQA PKKGLEWVAY
IGSDGDNIYY RDSVKGRFTI SRNNAKSTLY LQMDSLRSED TATYYCTTGI
VRPFLYWGQG TTVTVS
```

Rat Ab 1644 VH region SEQ ID NO: 65

```
gaggtgccgc tggtggagtc tgggggcggc tcagtgcagc ctggagggtc
cacgaaactc tcctgtgtag tctcaggatt cactttcagt aactatggca
tggtctgggt ccgccaggct ccaaagaagg gtctggagtg ggtcgcatat
attggttctg atggtgataa tatttactac cgagattccg tgaagggtcg
attcactatc tccagaaata atgcaaaaag caccctatat ttgcaaatgg
acagtctgag gtctgaggac acggccactt attactgtac aacagggatt
gtccggccct ttctctactg gggccaagga accacggtca ccgtctcg
```

FIG. 1S

Rat Ab 1496 VK region SEQ ID NO: 66
DVVMTQTPLS LSVALGQPAS ISCKSSQSLV GASGKTYLYW LFQRSGQSPK
RLIYLVSTLD SGIPDRFSGS GAETDFTLKI RRVEADDLGV YYCLQGTHFP
HTFGAGTKLE LK Rat Ab 1496 VK region SEQ ID NO: 67
gatgttgtga tgacccagac tccactgtct tgtcggttg cccttggaca
accagcctcc atctcttgca agtcaagtca gagcctcgta ggtgctagtg
gaaagacata tttgtattgg ttatttcaga ggtccggcca gtctccaaag
cgactaatct atctggtgtc cacactggac tctggaattc ctgataggtt
cagtggcagt ggagcagaga cagatttac tcttaaaatc cgcagagtgg
aagccgatga tttgggagtt tattactgct tgcaaggtac acattttcct
cacacgtttg gagctgggac caagctggaa ctgaaa Rat Ab 1496 VH region SEQ ID NO: 68
EVLLVESGGG SVQPGRSMKL SCVVSGFTFS NYGMVWVRQA PKKGLEWVAY
IDSDGDNTYY RDSVKGRFTI SRNNAKSTLY LQMDSLRSED TATYYCTTGI
VRPFLYWGQG TMVTVS Rat Ab 1496 VH region SEQ ID NO: 69
gaggtgctgc tggtggagtc tgggggcggc tcagtgcagc ctgggaggtc
catgaaactc tcctgtgtag tctcaggatt cactttcagt aattatggca
tggtctgggt ccgccaggct ccaagaagg gtctggagtg ggtcgcatat
attgattctg atggtgataa tacttactac cgagattccg tgaagggccg
attcactatc tccagaaata atgcaaaaag caccctatat ttgcaaatgg
acagtctgag gtctgaggac acggccactt attactgtac aacagggatt
gtccggccct ttctctattg gggccaagga accatggtca ccgtctcg 1519gH20 IgG1 heavy chain (V + human gamma-1 constant) SEQ ID NO: 72

EVPLVESGGG LVQPGGSLRL SCAVSGFTFS NYGMVWVRQA PGKGLEWVAY IDSDGDNTYY
RDSVKGRFTI SRDNAKSSLY LQMNSLRAED TAVYYCTTGI VRPFLYWGQG TLVTVSSAST
KGPSVFPLAP SSKSTSGGTA ALGCLVKDYF PEPVTVSWNS GALTSGVHTF PAVLQSSGLY
SLSSVVTVPS SSLGTQTYIC NVNHKPSNTK VDKKVEPKSC DKTHTCPPCP APELLGGPSV
FLFPPKPKDT LMISRTPEVT CVVVDVSHED PEVKFNWYVD GVEVHNAKTK PREEQYNSTY
RVVSVLTVLH QDWLNGKEYK CKVSNKALPA PIEKTISKAK GQPREPQVYT LPPSRDELTK
NQVSLTCLVK GFYPSDIAVE WESNGQPENN YKTTPPVLDS DGSFFLYSKL TVDKSRWQQG
NVFSCSVMHE ALHNHYTQKS LSLSPGK

FIG. 1T

1519gH20 IgG1 heavy chain (V + human gamma-1 constant, exons underlined) SEQ ID NO: 73

<u>gaggtaccac ttgtggaaag cggaggaggt cttgtgcagc ctggaggaag tttacgtctc</u>
<u>tcttgtgctg tgtctggctt caccttctcc aattacggaa tggtctgggt cagacaagca</u>
<u>cctggaaagg gtcttgaatg ggtggcctat attgactctg acgggacaa cacctactat</u>
<u>cgggattccg tgaaaggacg cttcacaatc tcccgagata acgccaagag ctcactgtac</u>
<u>ctgcagatga atagcctgag agccgaggat actgccgtgt actattgcac aacgggaatc</u>
<u>gttaggcctt ttctgtactg gggacagggc accttggtta ctgtctcgag cgcttctaca</u>
<u>aagggcccat cggtcttccc cctggcaccc tcctccaaga gcacctctgg gggcacagcg</u>
<u>gccctgggct gcctggtcaa ggactacttc cccgaaccgg tgacggtgtc gtggaactca</u>
<u>ggcgccctga ccagcggcgt gcacaccttc ccggctgtcc tacagtcctc aggactctac</u>
<u>tccctcagca gcgtggtgac cgtgccctcc agcagcttgg gcacccagac ctacatctgc</u>
<u>aacgtgaatc acaagcccag caacaccaag gtcgacaaga agttggtga gaggccagca</u>
<u>cagggaggga gggtgtctgc tggaagccag gctcagcgct cctgcctgga cgcatcccgg</u>
<u>ctatgcagcc ccagtccagg gcagcaaggc aggccccgtc tgcctcttca cccggaggcc</u>
<u>tctgccccgcc ccactcatgc tcagggagag ggtcttctgg ctttttcccc aggctctggg</u>
<u>caggcacagg ctaggtgccc ctaacccagg ccctgcacac aaaggggcag gtgctgggct</u>
<u>cagacctgcc aagagccata tccgggagga ccctgcccct gacctaagcc cacccccaaag</u>
g<u>ccaaactct ccactccctc agctcggaca ccttctctcc tcccagatct gagtaactcc</u>
<u>caatcttctc tctgcagagc ccaaatcttg tgacaaaact cacacatgcc caccgtgccc</u>
<u>ag</u>gtaagcca gcccaggcct cgccctccag ctcaaggcgg gacaggtgcc ctagagtagc
ctgcatccag ggacaggccc cagccgggtg ctgacagtc cacctccatc tcttcctcag
<u>cacctgaact cctggggga ccgtcagtct tcctcttccc cccaaaaccc aaggacaccc</u>
<u>tcatgatctc ccggacccct gaggtcacat gcgtggtggt ggacgtgagc cacgaagacc</u>
<u>ctgaggtcaa gttcaactgg tacgtggacg gcgtggaggt gcataatgcc aagacaaagc</u>
<u>cgcgggagga gcagtacaac agcacgtacc gtgtggtcag cgtcctcacc gtcctgcacc</u>
<u>aggactggct gaatggcaag gagtacaagt gcaaggtctc caacaaagcc ctcccagccc</u>
<u>ccatcgagaa aaccatctcc aaagccaaag</u> gtgggacccg tggggtgcga gggccacatg
gacagaggcc ggctcggccc accctctgcc ctgagagtga ccgctgtacc aacctctgtc
cctacagggc agccccgaga accacaggtg tacaccctgc cccatcccg ggatgagctg
<u>accaagaacc aggtcagcct gacctgcctg gtcaaaggct tctatcccag cgacatcgcc</u>
<u>gtggagtggg agagcaatgg gcagccggag aacaactaca agaccacgcc tcccgtgctg</u>
<u>gactccgacg gctccttctt cctctacagc aagctcaccg tggacaagag caggtggcag</u>
<u>caggggaacg tcttctcatg ctccgtgatg catgaggctc tgcacaacca ctacacgcag</u>
<u>aagagcctct ccctgtctcc gggtaaa</u>

FIG. 1U

1519gH20 IgG1 heavy chain (V + human gamma-1 constant) with signal sequence underlined and italicized SEQ ID NO:74

*atggaatgga gctgggtctt tctcttcttc ctgtcagtaa ctacaggagt ccattctgag*
gtaccacttg tggaaagcgg aggaggtctt gtgcagcctg gaggaagttt acgtctctct
tgtgctgtgt ctggcttcac cttctccaat tacggaatgg tctgggtcag acaagcacct
ggaaagggtc ttgaatgggt ggcctatatt gactctgacg gggacaacac ctactatcgg
gattccgtga aggacgctt cacaatctcc cgagataacg ccaagagctc actgtacctg
cagatgaata gcctgagagc cgaggatact gccgtgtact attgcacaac gggaatcgtt
aggccttttc tgtactgggg acagggcacc ttggttactg tctcgagcgc ttctacaaag
ggcccatcgg tcttcccct ggcaccctcc tccaagagca cctctggggg cacagcggcc
ctgggctgcc tggtcaagga ctacttcccc gaaccggtga cggtgtcgtg gaactcaggc
gccctgacca gcggcgtgca caccttcccg gctgtcctac agtcctcagg actctactcc
ctcagcagcg tggtgaccgt gccctccagc agcttgggca cccagaccta catctgcaac
gtgaatcaca agcccagcaa caccaaggtc gacaagaaag ttggtgagag gccagcacag
ggagggaggg tgtctgctgg aagccaggct cagcgctcct gcctggacgc atcccggcta
tgcagcccca gtccaggca gcaggcagg cccgtctgc ctcttcaccc ggaggcctct
gcccgcccca ctcatgctca gggagagggt cttctggctt tttccccagg ctctgggcag
gcacaggcta ggtgcccta acccaggccc tgcacacaaa ggggcaggtg ctgggctcag
acctgccaag agccatatcc gggaggaccc tgcccctgac ctaagcccac cccaaaggcc
aaactctcca ctccctcagc tcggacacct tctctcctcc cagatctgag taactcccaa
tcttctctct gcagagccca atcttgtga caaaactcac acatgccac cgtgcccagg
taagccagcc caggcctcgc cctccagctc aaggcgggac aggtgcccta gagtagcctg
catccaggga caggccccag ccgggtgctg acacgtccac ctccatctct tcctcagcac
ctgaactcct gggggaccg tcagtcttcc tcttcccccc aaaacccaag gacaccctca
tgatctcccg gacccctgag gtcacatgcg tggtggtgga cgtgagccac gaagaccctg
aggtcaagtt caactggtac gtggacggcg tggaggtgca taatgccaag acaaagccgc
gggaggagca gtacaacagc acgtaccgtg tggtcagcgt cctcaccgtc ctgcaccagg
actggctgaa tggcaaggag tacaagtgca aggtctccaa caaagccctc ccagccccca
tcgagaaaac catctccaaa gccaaaggtg ggacccgtgg ggtgcgaggg ccacatggac
agaggccggc tcggcccacc ctctgccctg agagtgaccg ctgtaccaac ctctgtccct
acagggcagc cccgagaacc acaggtgtac accctgcccc catcccggga tgagctgacc
aagaaccagg tcagcctgac ctgcctggtc aaaggcttct atccagcga catcgccgtg
gagtgggaga gcaatgggca gccggagaac aactacaaga ccacgcctcc cgtgctggac
tccgacggct ccttcttcct ctacagcaag ctcaccgtgg acaagagcag gtggcagcag
gggaacgtct tctcatgctc cgtgatgcat gaggctctgc acaaccacta cacgcagaag
agcctctccc tgtctccggg taaa

FIG. 1V

1519 gL20 light chain (V + constant, mammalian expression alternative) SEQ ID NO: 75

```
gatatccaga tgacccagag cccatctagc ttatccgctt ccgttggtga
tcgcgtgaca attacgtgta agagctccca atctctcgtg ggtgcaagtg
gcaagaccta tctgtactgg ctctttcaga agcctggcaa ggcaccaaaa
cggctgatct atctggtgtc tacccttgac tctgggatac cgtcacgatt
ttccggatct gggagcggaa ctgagttcac actcacgatt tcatcgctgc
aacccgagga ctttgctacc tactactgcc tgcaaggcac tcatttccct
cacactttcg gccagggggac aaaactcgaa atcaaacgta cggtagcggc
cccatctgtc ttcatcttcc cgccatctga tgagcagttg aaatctggaa
ctgcctctgt tgtgtgcctg ctaataact tctatcccag agaggccaaa
gtacagtgga aggtggataa cgcctccaa tcgggtaact cccaggagag
tgtcacagag caggacagca aggacagcac ctacagcctc agcagcaccc
tgacgctgag caaagcagac tacgagaaac acaaagtcta cgcctgcgaa
gtcacccatc agggcctgag ctcgcccgtc acaaagagct caacagggg agagtgt
```

1519gH20 Fab' heavy chain (V + human gamma-1 CH1 + hinge, mammalian expression one base change from SEQ ID NO: 38) SEQ ID NO: 76

```
gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg gtcttgaatg ggtggcctat
attgactctg acggggacaa cacctactat cgggattccg tgaaaggacg
cttcacaatc tcccgagata cgccaagag ctcactgtac ctgcagatga
atagcctgag agccgaggat actgccgtgt actattgcac aacgggaatc
gttaggcctt ttctgtactg gggacagggc accttggtta ctgtctcgag
cgcttctaca aagggcccat cggtcttccc cctggcaccc tcctccaaga
gcacctctgg gggcacagcg gccctgggct gcctggtcaa ggactacttc
cccgaaccgg tgacggtgtc gtggaactca ggcgccctga ccagcggcgt
gcacaccttc ccggctgtcc tacagtcctc aggactctac tccctcagca
gcgtggtgac cgtgccctcc agcagcttgg gcacccagac ctacatctgc
aacgtgaatc acaagcccag caacaccaag gtggacaaga aagttgagcc
caaatcttgt gacaaaactc acacatgcgc cgcg
```

1519 gH20 Fab' heavy chain with signal sequence underlined and italicized (mammalian expression one base changed from SEQ ID NO: 42) SEQ ID NO: 77

```
atggaatgga gctgggtctt tctcttcttc ctgtcagtaa ctacaggagt
ccattctgag gtaccacttg tggaaagcgg aggaggtctt gtgcagcctg
gaggaagttt acgtctctct tgtgctgtgt ctggcttcac cttctccaat
tacggaatgg tctgggtcag acaagcacct ggaaagggtc ttgaatgggt
ggcctatatt gactctgacg gggacaacac ctactatcgg gattccgtga
aaggacgctt cacaatctcc cgagataacg ccaagagctc actgtacctg
cagatgaata gcctgagagc cgaggatact gccgtgtact attgcacaac
gggaatcgtt aggccttttc tgtactgggg acagggcacc ttggttactg
tctcgagcgc ttctacaaag gcccatcggt cttcccct ggcaccctcc
tccaagagca cctctggggg cacagcggcc ctgggctgcc tggtcaagga
ctacttcccc gaaccggtga cggtgtcgtg gaactcaggc gcctgacca
gcggcgtgca caccttcccg gctgtcctac agtcctcagg actctactcc
ctcagcagcg tggtgaccgt gccctccagc agcttgggca cccagaccta
catctgcaac gtgaatcaca gcccagcaa caccaaggtg gacaagaaag
ttgagcccaa atcttgtgac aaaactcaca catgcgccgc g
```

FIG. 1W

1519gL20 FabFv light chain (alternative sequence to SEQ ID NO: 46) SEQ ID NO: 78

```
DIQMTQSPSS LSASVGDRVT ITCKSSQSLV GASGKTYLYW LFQKPGKAPK
RLIYLVSTLD SGIPSRFSGS GSGTEFTLTI SSLQPEDFAT YYCLQGTHFP
HTFGQGTKLE IKRTVAAPSV FIFPPSDEQL KSGTASVVCL LNNFYPREAK
VQWKVDNALQ SGNSQESVTE QDSKDSTYSL SSTLTLSKAD YEKHKVYACE
VTHQGLSSPV TKSFNRGECG GGGSGGGGSG GGGSDIQMTQ SPSSVSASVG
DRVTITCQSS PSVWSNFLSW YQQKPGKAPK LLIYEASKLT SGVPSRFSGS
GSGTDFTLTI SSLQPEDFAT YYCGGGYSSI SDTTFGCGTK VEIKRT
```

1519gL20 FabFv light chain (alternative sequence to SEQ ID NO: 47) SEQ ID NO: 79

```
gacatccaga tgacccagtc ccctccagc ctgtccgcct ccgtgggcga
cagagtgacc atcacatgca agtcctccca gtccctggtc ggagcctccg
gcaagaccta cctgtactgg ctgttccaga agcccggcaa ggcccccaag
cggctgatct acctggtgtc taccctggac tccggcatcc cctcccggtt
ctccggctct ggctctggca ccgagttcac cctgaccatc tccagcctgc
agcccgagga cttcgccacc tactactgtc tgcaaggcac ccacttcccc
cacaccttcg gccagggcac caagctggaa atcaagcgga ccgtagcggc
cccatctgtc ttcatcttcc cgccatctga tgagcagttg aaatctggaa
ctgcctctgt tgtgtgcctg ctgaataact ctatcccag agaggccaaa
gtacagtgga aggtggataa cgcctccaa tcgggtaact cccaggagag
tgtcacagag caggacagca aggacagcac ctacagcctc agcagcaccc
tgacgctgag caaagcagac tacgagaaac acaaagtcta cgcctgcgaa
gtcacccatc agggcctgag ctcgcccgtc acaaagagct caacagggg
agagtgtggt ggaggtggct ctggcggtgg tggctccgga ggcggaggaa
gcgacatcca gatgacccag agcccttcct ctgtaagcgc cagtgtcgga
gacagagtga ctattacctg ccaaagctcc ccttcagtct ggtccaattt
tctatcctgg tatcagcaaa agcccggaaa ggctcctaaa ttgctgatct
acgaagcaag caaactcacc agcggcgtgc cagcaggtt cagcggcagt
gggtctggaa ctgactttac cctgacaatc tcctcactcc agcccgagga
cttcgccacc tattactgcg gtggaggtta cagtagcata agtgatacga
catttggatg cggcactaaa gtggaaatca agcgtacc
```

FIG. 1X

1519gH20 FabFv heavy chain (alternative sequence to SEQ ID NO: 51) SEQ ID NO: 80
```
gaggtgcccc tggtggaatc tggcggcgga ctggtgcagc ctggcggctc
cctgagactg tcttgcgccg tgtccggctt caccttctcc aactacggca
tggtctgggt ccgacaggct cctggcaagg gactggaatg ggtggcctac
atcgactccg acggcgacaa cacctactac cgggactccg tgaagggccg
gttcaccatc tcccgggaca cgccaagtc ctccctgtac ctgcagatga
actccctgcg ggccgaggac accgccgtgt actactgcac caccggcatc
gtgcggccct ttctgtactg gggccagggc accctggtca ccgtgtcctc
tgcttctaca aagggcccat cggtcttccc cctggcaccc tcctccaaga
gcacctctgg gggcacagcg ccctgggct gcctggtcaa ggactacttc
cccgaaccgg tgacggtgtc gtggaactca ggcgccctga ccagcggcgt
gcacacttc ccggctgtcc tacagtcctc tggactctac tccctcagca
gcgtggtgac cgtgccctcc agcagcttgg gcacccagac ctacatctgc
aacgtgaatc acaagcccag caacaccaag gtggacaaga agttgagcc
caaatcttgt tccggaggtg gcggttccgg aggtggcggt acaggtggcg
gtgggtccga agtccagctg cttgaatccg gaggcggact cgtgcagccc
ggaggcagtc ttcgcttgtc ctgcgctgta tctggaatcg acctgagcaa
ttacgccatc aactgggtga gacaggcacc tgggaaatgc ctcgaatgga
tcggcattat atgggctagt gggacgacct tttatgctac atgggcgaag
ggtagattca caatctcacg ggataatagt aagaacacag tgtacctgca
gatgaactcc ctgcgagcag aggataccgc cgtttactat tgtgctcgca
ctgtcccagg ttatagcact gcaccctact ttgatctgtg ggggcagggc
actctggtca ccgtctcgtc c
```

FIG. 1Y (signal sequences underlined and italicised)

Rat Ab 1548 VL region (alternative sequence to SEQ ID NO: 58) SEQ ID NO: 81
DVVMTQTPLS LSVAIGQPAS ISSKSSQSLV GAGGKTYLYW LLQRSGQSPK
RLIYLVSTLD SGIPDRFSGS GAETDFTLKI RRVEADDLGV YYCLQGTHFP
HTFGAGTNLE IK Rat Ab 1548 VL region (alternative sequence to SEQ ID NO: 59) SEQ ID NO: 82
gatgttgtga tgacccagac tccactgtct tgtcggttg ccattggaca
accagcctcc atctcttcta agtcaagtca gagcctcgta ggtgctggtg
gaaagacata tttgtattgg ttattacaga ggtccggcca gtctccaaag
cgactaatct atctggtgtc cacactggac tctggaattc ctgataggtt
cagtggcagt ggagcagaga cagatttac tcttaaaatc cgcagagtgg
aagccgatga tttgggagtt tattactgct tgcaaggtac acattttcct
cacacgtttg gagctggac caacctggaa ataaaa Rat Ab 1548 VH region (alternative sequence to SEQ ID NO: 60) SEQ ID NO: 83
EVPLVESGGG SVQPGRSMKL SCVVSGFTFS NYGMVWVRQA PKKGLEWVAY
IGSDGDNTYY RDSVKGRFTI SRNNAKSTLY LQMDSLRSED TATYYCTTGI
VRPFLYWGQG VMVTVS Rat Ab 1548 VH region (alternative sequence to SEQ IS NO: 61) SEQ ID NO: 84
gaggtgccgc tggtggagtc tgggggcggc tcagtgcagc ctgggaggtc
catgaaactc tcctgtgtag tctcaggatt cactttcagt aactatggca
tggtctgggt ccgccaggct ccaagaagg gtctggagtg ggtcgcatat
attggttctg atggtgataa tactactac cgagattccg tgaagggccg
attcactatc tccagaaata atgcaaaag cacctatat ttgcaaatgg
acagtctgag gtctgaggac acggccactt attactgtac aacagggatt
gtccggccct ttctctactg gggccaagga gtcatggtca cagtctcg

FIG. 1Z
1519gH20 IgG1 heavy chain (V + human gamma-1 constant, exons underlined one base change to SEQ ID NO: 71) SEQ ID NO: 85

<u>gaggtaccac ttgtggaaag cggaggaggt cttgtgcagc ctggaggaag tttacgtctc</u>
<u>tcttgtgctg tgtctggctt caccttctcc aattacggaa tggtctgggt cagacaagca</u>
<u>cctggaaagg gtcttgaatg ggtggcctat attgactctg acggggacaa cacctactat</u>
<u>cgggattccg tgaaaggacg cttcacaatc tcccgagata cgccaagag ctcactgtac</u>
<u>ctgcagatga atagcctgag agccgaggat actgccgtgt actattgcac aacgggaatc</u>
<u>gttaggcctt ttctgtactg gggacagggc accttggtta ctgtctcgag cgcttctaca</u>
<u>aagggcccat cggtcttccc cctggcaccc tcctccaaga gcacctctgg gggcacagcg</u>
<u>gccctgggct gcctggtcaa ggactacttc cccgaaccgg tgacggtgtc gtggaactca</u>
<u>ggcgccctga ccagcggcgt gcacaccttc ccggctgtcc tacagtcctc aggactctac</u>
<u>tccctcagca gcgtggtgac cgtgccctcc agcagcttgg gcacccagac ctacatctgc</u>
<u>aacgtgaatc acaagcccag caacaccaag gtggacaaga agttggtga gaggccagca</u>
caggagga gggtgtctgc tggaagccag gctcagcgct cctgcctgga cgcatcccgg
ctatgcagcc ccagtccagg gcagcaaggc aggccccgtc tgcctcttca cccggaggcc
tctgccccgcc ccactcatgc tcagggagag ggtcttctgg cttttccccc aggctctggg
caggcacagg ctaggtgccc ctaacccagg ccctgcacac aaaggggcag gtgctgggct
cagacctgcc aagagccata tccgggagga ccctgcccct gacctaagcc cacccccaaag
gccaaactct ccactccctc agctcggaca ccttctctcc tcccagatct gagtaactcc
caatcttctc tctgcagagc ccaaatcttg tgacaaaact cacacatgcc caccgtgccc
<u>a</u>ggtaagcca gcccaggcct cgccctccag ctcaaggcgg gacaggtgcc ctagagtagc
ctgcatccag ggacaggccc cagccgggtg ctgacacgtc cacctccatc tcttcctcag
<u>cacctgaact cctgggggga ccgtcagtct tcctcttccc cccaaaaccc aaggacaccc</u>
<u>tcatgatctc ccggaccccct gaggtcacat gcgtggtggt ggacgtgagc cacgaagacc</u>
<u>ctgaggtcaa gttcaactgg tacgtggacg gcgtggaggt gcataatgcc aagacaaagc</u>
<u>cgcgggagga gcagtacaac agcacgtacc gtgtggtcag cgtcctcacc gtcctgcacc</u>
<u>aggactggct gaatggcaag gagtacaagt gcaaggtctc caacaaagcc ctcccagccc</u>
<u>ccatcgagaa aaccatctcc aaagccaaag</u> gtgggacccg tggggtgcga gggccacatg
gacagaggcc ggctcggccc accctctgcc ctgagagtga ccgctgtacc aacctctgtc
cctacagggc agccccgaga accacaggtg tacaccctgc ccccatcccg ggatgagctg
<u>accaagaacc aggtcagcct gacctgcctg gtcaaaggct tctatcccag cgacatcgcc</u>
<u>gtggagtggg agagcaatgg gcagccggag aacaactaca agaccacgcc tcccgtgctg</u>
<u>gactccgacg gctccttctt cctctacagc aagctcaccg tggacaagag caggtggcag</u>
<u>caggggaacg tcttctcatg ctccgtgatg catgaggctc tgcacaacca ctacacgcag</u>
<u>aagagcctct ccctgtctcc gggtaaa</u>

FIG. 1AA

1519gH20 IgG1 heavy chain (V + human gamma-1 constant) with signal sequence underlined and italicized (one base change from SEQ ID NO:72) SEQ ID NO:86

*<u>atggaatgga gctgggtctt tctcttcttc ctgtcagtaa ctacaggagt ccattctgag</u>*
gtaccacttg tggaaagcgg aggaggtctt gtgcagcctg gaggaagttt acgtctctct
tgtgctgtgt ctggcttcac cttctccaat tacggaatgg tctgggtcag acaagcacct
ggaaagggtc ttgaatgggt ggcctatatt gactctgacg gggacaacac ctactatcgg
gattccgtga aggacgctt cacaatctcc cgagataacg ccaagagctc actgtacctg
cagatgaata gcctgagagc cgaggatact gccgtgtact attgcacaac gggaatcgtt
aggccttttc tgtactgggg acagggcacc ttggttactg tctcgagcgc ttctacaaag
ggcccatcgg tcttcccct ggcacctcc tccaagagca cctctggggg cacagcggcc
ctgggctgcc tggtcaagga ctacttcccc gaaccggtga cggtgtcgtg gaactcaggc
gccctgacca gcggcgtgca caccttcccg gctgtcctac agtcctcagg actctactcc
ctcagcagcg tggtgaccgt gccctccagc agcttgggca cccagaccta catctgcaac
gtgaatcaca agcccagcaa caccaaggtg gacaagaaag ttggtgagag gccagcacag
gggagggagg tgtctgctgg aagccaggct cagcgctcct gcctggacgc atcccggcta
tgcagcccca gtccagggca gcaaggcagg ccccgtctgc ctcttcaccc ggaggcctct
gcccgcccca ctcatgctca gggagagggt cttctggctt tttccccagg ctctgggcag
gcacaggcta ggtgcccta acccaggccc tgcacacaaa ggggcaggtg ctgggctcag
acctgccaag agccatatcc gggaggaccc tgcccctgac ctaagcccac ccaaaggcc
aaactctcca ctccctcagc tcggacacct tctctcctcc cagatctgag taactcccaa
tcttctctct gcagagccca atcttgtga caaaactcac acatgccac cgtgcccagg
taagccagcc caggcctcgc cctccagctc aaggcgggac aggtgcccta gagtagcctg
catccaggga caggccccag ccgggtgctg acacgtccac ctccatctct tcctcag<u>cac</u>
ctgaactcct gggggaccg tcagtcttcc tcttccccc aaaacccaag gacaccctca
tgatctcccg gaccctgag gtcacatgcg tggtggtgga cgtgagccac gaagaccctg
aggtcaagtt caactggtac gtggacggcg tggaggtgca taatgccaag acaaagccgc
gggaggagca gtacaacagc acgtaccgtg tggtcagcgt cctcaccgtc ctgcaccagg
actggctgaa tggcaaggag tacaagtgca aggtctccaa caaagcccctc ccagccccca
tcgagaaaac catctccaaa gccaaggtg ggacccgtgg ggtgcgaggg ccacatggac
agaggccggc tcggcccacc ctctgccctg agtgaccg ctgtaccaac ctctgtccct
acagggcagc cccgagaacc acaggtgtac accctgcccc catcccggga tgagctgacc
aagaaccagg tcagcctgac ctgcctggtc aaaggcttct atcccagcga catcgccgtg
gagtgggaga gcaatgggca gccggagaac aactacaaga ccacgcctcc cgtgctggac
tccgacggct ccttcttcct ctacagcaag ctcaccgtgg acaagagcag gtggcagcag
gggaacgtct tctcatgctc cgtgatgcat gaggctctgc acaaccacta cacgcagaag
agcctctccc tgtctccggg taaa

1519gH20 IgG4 heavy chain (V + human gamma-4 constant no P mutations) SEQ ID NO:87

EVPLVESGGG LVQPGGSLRL SCAVSGFTFS NYGMVWVRQA PGKGLEWVAY
IDSDGDNTYY RDSVKGRFTI SRDNAKSSLY LQMNSLRAED TAVYYCTTGI
VRPFLYWGQG TLVTVSSAST KGPSVFPLAP CSRSTSESTA ALGCLVKDYF
PEPVTVSWNS GALTSGVHTF PAVLQSSGLY SLSSVVTVPS SSLGTKTYTC
NVDHKPSNTK VDKRVESKYG PPCPSCPAPE FLGGPSVFLF PPKPKDTLMI
SRTPEVTCVV VDVSQEDPEV QFNWYVDGVE VHNAKTKPRE EQFNSTYRVV
SVLTVLHQDW LNGKEYKCKV SNKGLPSSIE KTISKAKGQP REPQVYTLPP
SQEEMTKNQV SLTCLVKGFY PSDIAVEWES NGQPENNYKT TPPVLDSDGS
FFLYSRLTVD KSRWQEGNVF SCSVMHEALH NHYTQKSLSL SLGK

FIG. 1BB

1519gH20 IgG4 heavy chain (V + human gamma-4 constant, exons underlined no P mutations) SEQ ID NO:88

```
gaggtaccac ttgtggaaag cggaggaggt cttgtgcagc ctggaggaag
tttacgtctc tcttgtgctg tgtctggctt caccttctcc aattacggaa
tggtctgggt cagacaagca cctggaaagg gtcttgaatg ggtggcctat
attgactctg acggggacaa cacctactat cgggattccg tgaaaggacg
cttcacaatc tcccgagata cgccaagag ctcactgtac ctgcagatga
atagcctgag agccgaggat actgccgtgt actattgcac aacgggaatc
gttaggcctt ttctgtactg gggacagggc accttggtta ctgtctcgag
cgcttctaca aagggcccat ccgtcttccc cctggcgccc tgctccagga
gcacctccga gagcacagcc gccctgggct gcctggtcaa ggactacttc
cccgaaccgg tgacggtgtc gtggaactca ggcgcctga ccagcggcgt
gcacaccttc ccggctgtcc tacagtcctc aggactctac tccctcagca
gcgtggtgac cgtgccctcc agcagcttgg gcacgaagac ctacacctgc
aacgtagatc acaagcccag caacaccaag gtggacaaga gagttggtga
gaggccagca cagggaggga gggtgtctgc tggaagccag gctcagccct
cctgcctgga cgcaccccgg ctgtgcagcc ccagcccagg gcagcaaggc
atgccccatc tgtctcctca cccggaggcc tctgaccacc ccactcatgc
ccagggagag ggtcttctgg attttccac caggctccgg gcagccacag
gctggatgcc cctaccccag gccctgcgca tacaggggca ggtgctgcgc
tcagacctgc caagagccat atccgggagg accctgcccc tgacctaagc
ccacccccaaa ggccaaactc tccactccct cagctcagac accttctctc
ctcccagatc tgagtaactc ccaatcttct ctctgcagag tccaaatatg
gtcccccatg cccatcatgc ccaggtaagc caacccaggc ctcgccctcc
agctcaaggc gggacaggtg ccctagagta gcctgcatcc agggacaggc
cccagccggg tgctgacgca tccacctcca tctcttcctc agcacctgag
ttcctggggg gaccatcagt cttcctgttc ccccaaaac caaggacac
tctcatgatc tcccggaccc ctgaggtcac gtgcgtggtg gtggacgtga
gccaggaaga ccccgaggtc cagttcaact ggtacgtgga tggcgtggag
gtgcataatg ccaagacaaa gccgcgggag gagcagttca acagcacgta
ccgtgtggtc agcgtcctca ccgtcctgca ccaggactgg ctgaacggca
aggagtacaa gtgcaaggtc tccaacaaag gcctcccgtc ctccatcgag
aaaaccatct ccaaagccaa aggtgggacc cacggggtgc gagggccaca
tggacagagg tcagctcggc ccaccctctg ccctgggagt gaccgctgtg
ccaacctctg tccctacagg gcagcccga gagccacagg tgtacaccct
gcccccatcc caggaggaga tgaccaagaa ccaggtcagc ctgacctgcc
tggtcaaagg cttctacccc agcgacatcg ccgtggagtg ggagagcaat
gggcagccgg agaacaacta caagaccacg cctcccgtgc tggactccga
cggctccttc ttcctctaca gcaggctaac cgtggacaag agcaggtggc
aggaggggaa tgtcttctca tgctccgtga tgcatgaggc tctgcacaac
cactacacac agaagagcct ctccctgtct ctgggtaaa
```

FIG. 1CC

1519gH20 IgG4 heavy chain (V + human gamma-4 constant) with signal sequence underlined and italicised– no P mutation SEQ ID NO:89

```
atggaatgga gctgggtctt tctcttcttc ctgtcagtaa ctacaggagt
ccattctgag gtaccacttg tggaaagcgg aggaggtctt gtgcagcctg
gaggaagttt acgtctctct tgtgctgtgt ctggcttcac cttctccaat
tacggaatgg tctgggtcag acaagcacct ggaaagggtc ttgaatgggt
ggcctatatt gactctgacg ggacaacac ctactatcgg gattccgtga
aaggacgctt cacaatctcc cgagataacg ccaagagctc actgtacctg
cagatgaata gcctgagagc cgaggatact gccgtgtact attgcacaac
gggaatcgtt aggccttttc tgtactgggg acagggcacc ttggttactg
tctcgagcgc ttctacaaag ggcccatccg tcttcccct ggcgcctgc
tccaggagca cctccgagag cacagccgcc ctgggctgcc tggtcaagga
ctacttcccc gaaccggtga cggtgtcgtg gaactcaggc gccctgacca
gcggcgtgca caccttcccg gctgtcctac agtcctcagg actctactcc
ctcagcagcg tggtgaccgt gccctccagc agcttgggca cgaagaccta
cacctgcaac gtagatcaca agcccagcaa caccaaggtg gacaagagag
ttggtgagag gccagcacag ggaggaggg tgtctgctgg aagccaggct
cagccctcct gcctggacgc accccggctg tgcagcccca gcccagggca
gcaaggcatg ccccatctgt ctcctcaccc ggaggcctct gaccacccca
ctcatgccca gggagagggt cttctggatt tttccaccag gctccgggca
gccacaggct ggatgcccct accccaggcc ctgcgcatac aggggcaggt
gctgcgctca gacctgccaa gagccatatc cggaggacc ctgcccctga
cctaagccca cccaaaggc caaactctcc actccctcag ctcagacacc
ttctctcctc ccagatctga gtaactccca atcttctctc tgcagagtcc
aaatatggtc ccccatgccc atcatgccca ggtaagccaa cccaggcctc
gccctccagc tcaaggcggg acaggtgccc tagagtagcc tgcatccagg
gacaggcccc agccgggtgc tgacgcatcc acctccatct cttcctcagc
acctgagttc ctgggggac catcagtctt cctgttcccc ccaaaaccca
aggacactct catgatctcc cggacccctg aggtcacgtg cgtggtggtg
gacgtgagcc aggaagaccc cgaggtccag ttcaactggt acgtggatgg
cgtggaggtg cataatgcca agacaaagcc gcgggaggag cagttcaaca
gcacgtaccg tgtggtcagc gtcctcaccg tcctgcacca ggactggctg
aacggcaagg agtacaagtg caaggtctcc aacaaaggcc tcccgtcctc
catcgagaaa accatctcca aagccaaagg tgggacccac ggggtgcgag
ggccacatgg acagaggtca gctcggccca ccctctgccc tgggagtgac
cgctgtgcca acctctgtcc ctacagggca gccccgagag ccacaggtgt
acaccctgcc cccatcccag gaggagatga ccaagaacca ggtcagcctg
acctgcctgg tcaaaggctt ctacccagc gacatcgccg tggagtggga
gagcaatggg cagccggaga acaactacaa gaccacgcct cccgtgctgg
actccgacgg ctccttcttc ctctacagca ggctaaccgt ggacaagagc
aggtggcagg aggggaatgt cttctcatgc tccgtgatgc atgaggctct
gcacaaccac tacacacaga agagcctctc cctgtctctg ggtaaa
```

FIG. 1DD

1519 gL20 V-region (mammalian expression alternative to SEQ ID NO: 17) SEQ ID NO:90

```
gacatccaga tgacccagtc cccctccagc ctgtccgcct ccgtgggcga
cagagtgacc atcacatgca agtcctccca gtccctggtc ggagcctccg
gcaagaccta cctgtactgg ctgttccaga agcccggcaa ggcccccaag
cggctgatct acctggtgtc taccctggac tccggcatcc cctcccggtt
ctccggctct ggctctggca ccgagttcac cctgaccatc tccagcctgc
agcccgagga cttcgccacc tactactgtc tgcaaggcac ccacttcccc
cacaccttcg gccagggcac caagctggaa atcaag
```

1519 gL20 light chain (V + constant, mammalian expression alternative to SEQ ID NO: 24) SEQ ID NO:91

```
gacatccaga tgacccagtc cccctccagc ctgtccgcct ccgtgggcga
cagagtgacc atcacatgca agtcctccca gtccctggtc ggagcctccg
gcaagaccta cctgtactgg ctgttccaga agcccggcaa ggcccccaag
cggctgatct acctggtgtc taccctggac tccggcatcc cctcccggtt
ctccggctct ggctctggca ccgagttcac cctgaccatc tccagcctgc
agcccgagga cttcgccacc tactactgtc tgcaaggcac ccacttcccc
cacaccttcg gccagggcac caagctggaa atcaagcgga ccgtggccgc
tcccctccgtg ttcatcttcc caccctccga cgagcagctg aagtccggca
ccgcctccgt cgtgtgcctg ctgaacaact ctacccccg cgaggccaag
gtgcagtgga aggtggacaa cgccctgcag tccggcaact cccaggaatc
cgtcaccgag caggactcca aggacagcac ctactccctg tcctccaccc
tgaccctgtc caaggccgac tacgagaagc acaaggtgta cgcctgcgaa
gtgacccacc agggcctgtc cagccccgtg accaagtcct tcaaccgggg
cgagtgc
```

FIG. 1EE

1519 gH20 V-region (mammalian expression alternative to SEQ ID NO: 31) SEQ ID NO:92

```
gaggtgcccc tggtggaatc tggcggcgga ctggtgcagc ctggcggctc
cctgagactg tcttgcgccg tgtccggctt caccttctcc aactacggca
tggtctgggt ccgacaggct cctggcaagg gactggaatg ggtggcctac
atcgactccg acggcgacaa cacctactac cgggactccg tgaagggccg
gttcaccatc tcccgggaca cgccaagtc ctccctgtac ctgcagatga
actccctgcg ggccgaggac accgccgtgt actactgcac caccggcatc
gtgcggccct ttctgtactg gggccagggc accctggtca ccgtgtcc
```

FIG. 1FF

1519gH20 IgG4 heavy chain (V + human gamma-4P constant alternative to SEQ ID NO: 44) SEQ ID NO:93

```
gaggtgcccc tggtggaatc tggcggcgga ctggtgcagc ctggcggctc
cctgagactg tcttgcgccg tgtccggctt caccttctcc aactacggca
tggtctgggt ccgacaggct cctggcaagg gactggaatg ggtggcctac
atcgactccg acggcgacaa cacctactac cgggactccg tgaagggccg
gttcaccatc tcccgggaca cgccaagtc ctccctgtac ctgcagatga
actccctgcg ggccgaggac accgccgtgt actactgcac caccggcatc
gtgcggccct tctgtactg gggccaggc accctggtca ccgtgtcctc
tgcctccacc aagggcccct ccgtgttccc tctggccct tgctcccggt
ccacctccga gtctaccgcc gctctgggct gcctggtcaa ggactacttc
cccgagcccg tgacagtgtc ctggaactct ggcgcctga cctccggcgt
gcacaccttc cctgccgtgc tgcagtcctc cggcctgtac tccctgtcct
ccgtcgtgac cgtgccctcc tccagcctgg caccaagac ctacacctgt
aacgtggacc acaagccctc caacaccaag gtggacaagc gggtggaatc
taagtacggc cctccctgcc cccctgccc tgccctgaa tttctgggcg
gaccttccgt gttcctgttc cccccaaagc ccaaggacac cctgatgatc
tcccggaccc ccgaagtgac ctgcgtggtg gtggacgtgt cccaggaaga
tcccgaggtc cagttcaatt ggtacgtgga cggcgtggaa gtgcacaatg
ccaagaccaa gcccagagag gaacagttca actccaccta ccgggtggtg
tccgtgctga ccgtgctgca ccaggactgg ctgaacggca agagtacaa
gtgcaaggtg tccaacaagg gcctgcctc cagcatcgaa aagaccatct
ccaaggccaa gggccagccc cgcgagcccc aggtgtacac cctgcccct
agccaggaag agatgaccaa gaaccaggtg tccctgacct gtctggtcaa
gggcttctac ccctccgaca ttgccgtgga atgggagtcc aacggccagc
ccgagaacaa ctacaagacc accccctg tgctggacag cgacggctcc
ttcttcctgt actctcggct gaccgtggac aagtcccggt ggcaggaagg
caacgtcttc tcctgctccg tgatgcacga ggccctgcac aaccactaca
cccagaagtc cctgtccctg agcctgggca ag
```

Human β2M (SEQ ID NO:95)
IQKTPQIQVYSRHPPENGKPNFLNCYVSQFHPPQIEIELLKNGKKIPNIEMSDLSFSKDWSFYILAHTEFTPTETDVYA
CRVKHVTLKEPKTVTWDRDM

FIG. 2A

LIGHT CHAIN Graft 1519

```
              1       5        10        15        20        25        30 abcde  35        40        45        50        55        60        65        70        75        80        85        90        95       100   105
Light 1519    DVVMTQTPLSLSVALGQPASISCKSSQSLVGASGKTYLYWLFQRSGQSPKRLIYLVSTLDSGIPDRFSGSGAETDFTLKIRRVEADDLGVYYCLQGTHFPHTFGAGTKLELK
              |||:||  ||:||:||:||||||||||||||||||||||||:|||:|||:|||||||||:|| |:||||:|| |:|||:|||||:||||:|||:|||||||||:|||||
VK1 2-1-(1) A30  DIQMTQSPSSLSASVGDRVTITCRASQGIRN-----DLGWYQQKPGKAPKRLLIYAASSLQSGVPSRFSGSGSGTEFTLTISSLQPEDFATYYCLQHNSYPYTFGQGTKLEIK
                                           |:|                    :|                                                  ::::|:|
1519 gL20     DIQMTQSPSSLSASVGDRVTITCKSSQSLVGASGKTYLYWLFQKPGKAPKRLIYLVSTLDSGIPSRFSGSGSGTEFTLTISSLQPEDFATYYCLQGTHFPHTFGQGTKLEIK
```

Legend

1519 = Rat variable light chain sequence
1519 gL20 = Humanized graft of 1519 variable light chain using VK1 2-1-(1) A30 human germline as the acceptor framework.

CDRs are shown in bold/underlined
Donor residues are shown in bold/italic and are highlighted: L36, F37 and I58

FIG. 2B

```
HEAVY CHAIN Graft 1519

1     5    10    15    20    25    30    35    40    a  45    50  a  55    60    65    70    75    80 abc 65    90    95   100   105   110
Heavy 1519    EVPLVESGGGSVQPEGRSMKLSCVVSGFTFSNYGMVWVRQAPKKGLEWVAYIDSDGDNTYYRDSVKGRFTISRNNAKSTLYLQMDSLRSEDTATYYCTTGIVRPFLYWGQGTTVTVS
                  |  ||        |||           |||||||||||||||         ||||||||||||||||         ||||        ||        ||||||||||||||||||
VH3 1-3 3-07  EVQLVESGGGLVQPGGSLRLSCAASGFTFSSYWMSWVRQAPGKGLEWVANIKQDGSEKYYVDSVKGRFTISRDNAKNSLYLQMNSLRAEDTAVYYCAR----YFDYWGQGTLVTVS
                                       |
1519gH20      EVPLVESGGGLVQPGGSLRLSCAVSGFTFSNYGMVWVRQAPGKGLEWVAYIDSDGDNTYYRDSVKGRFTISRDNAKSSLYLQMNSLRAEDTAVYYCTTGIVRPFLYWGQGTLVTVS
```

Legend

1519 = Rat variable heavy chain sequence

1519gH20 = Humanized graft of 1519 variable heavy chain using VH3 1-3 3-07 human germline as the acceptor framework.

CDRs are shown in bold/underlined

Donor residues are shown in bold/italic and are highlighted: P3, V24, S76, T93 and T94

FIG. 3A  CA170_01519.g57 Fab' binding on MDCK II clone 34 cells in acidic and neutral pH.

FIG. 3B  CA170_01519.g57 Fab'PEG binding on MDCK II clone 34 cells in acidic and neutral pH.

FIG. 4 CA170_01519.g57 inhibits IgG recycling in MDCK II clone 34 cells

FIG. 5 CA170_01519.g57 Fab'PEG inhibits apical to basolateral IgG transcytosis in MDCK II clone 34 cells FIG. 6A- CA170_01519.g57 Fab' binding on cynomolgus MDCK II (cm) cells in acidic and neutral pH FIG. 6B - CA170_01519.g57 Fab'PEG binding on cynomolgus MDCK II (cm) cells in acidic and neutral pH FIG. 7 CA170_01519.g57 inhibits IgG recycling in human and cynomolgus MDCK II clone 34 cells and MDCK II (cm) cells.

FIG. 8 Cynomolgus Monkey- single dose of 1519 Fab'PEG on Plasma IgG levels

FIG. 9 Cynomolgus Monkey 4 weekly doses of 1519 Fab'PEG on Plasma IgG Levels

FIG. 11  Flow Cytometry based human IgG blocking assay using purified gamma 1 IgG Antibodies FIG. 13  Fab'PEG: repeat IV doses in normal cyno- 4x 20 or 100 mg/Kg (top and bottom respectively) per week IgG pharmacodynamics (individual animals)

FIG. 14  Fab'PEG single/intermittent IV doses in normal cyno 20 mg/Kg and 100 mg/Kg days 1 and 67 IgG Pharmacodynamics FIG. 15 Change in plasma IgG levels in 4 cynomolgus monkeys after 2 IV doses of 20mg/Kg 1519.g57 Fab'PEG FIG. 17 Change in plasma IgG levels in 4 cynomolgus monkeys after 2 IV doses of 30 mg/Kg 1519.g57 IgG4P i.v FIG. 20 Increased clearance of IV hIgG in plasma of hFcRn transgenic mice treated with CA170_01519.g57 Fab'PEG or PBS IV FIG. 21 Increased clearance of IV hIgG in plasma of hFcRn transgenic mice treated with CA170_01519.g57 IgG1 or IgG4 or PBS IV FIG. 22  Increased clearance of IV hIgG in plasma of hFcRn transgenic mice treated with CA170_01519.g57 Fab'-human serum albumin or PBS IV FIG. 23 Increased clearance of IV hIgG in plasma of hFcRn transgenic mice treated with CA170_01519.g57 FabFv or PBS IV FIG. 24  Increased clearance of IV hIgG in plasma of hFcRn transgenic mice treated with CA170_01519.g57 Fab or Fab'PEG or PBS IV

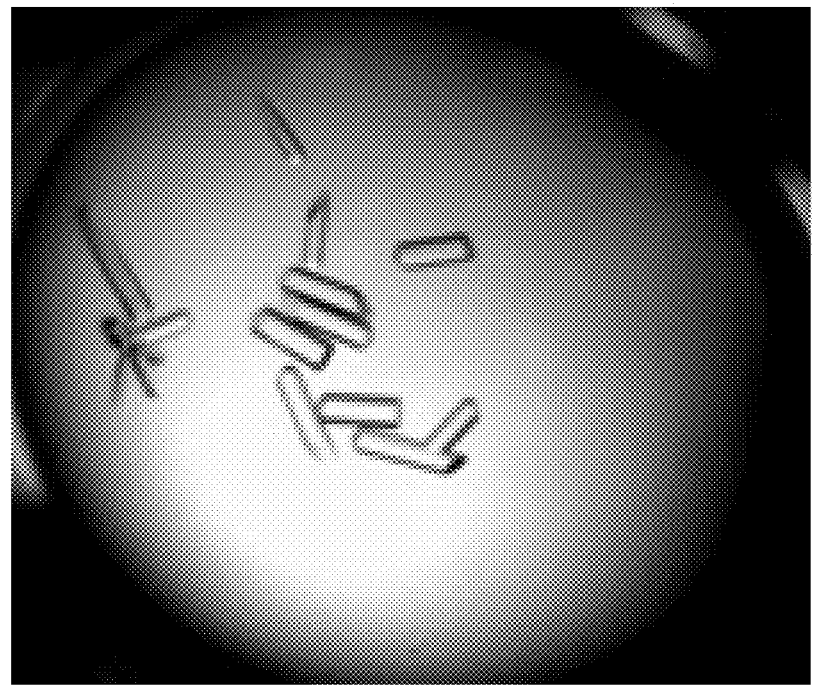
Picture of crystal in drop
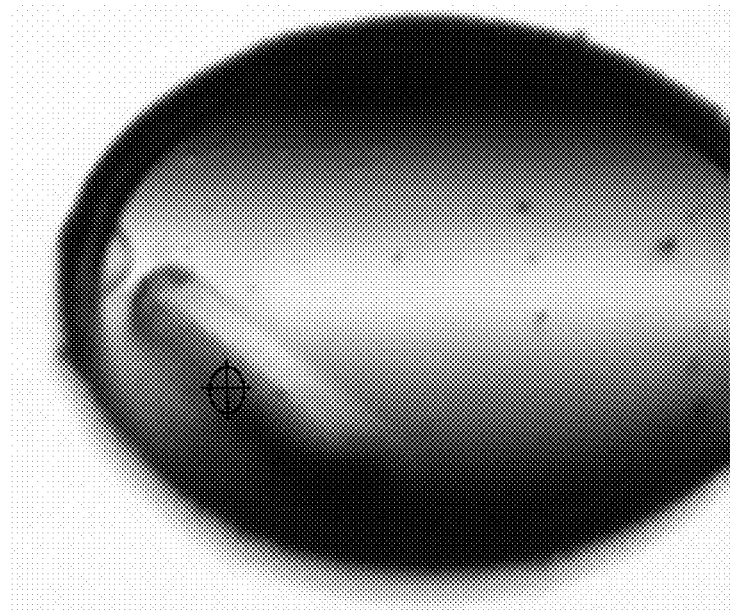
Pictures of crystal frozen in the loop
(target mark is X-ray beam)
FIG. 26

ANTI-FCRN ANTIBODIES

CROSS-REFERENCE TO RELATED APPLICATIONS

The present application is a Divisional Application under 35 U.S.C. § 120 of U.S. application Ser. No. 14/400,812, filed Nov. 13, 2014, which is the U.S. National Phase under 35 U.S.C. § 371 of PCT International Application No. PCT/EP2013/059802, filed May 13, 2013, which claims the benefit of priority under 35 U.S.C. § 119(a) of British Application No. 1208370.5, filed May 14, 2012, all of which are incorporated herein by reference in their entirety.

The disclosure relates to antibodies specific to FcRn, formulations comprising the same, use of each in therapy, processes for expressing and optionally formulating said antibody, DNA encoding the antibodies and hosts comprising said DNA.

FcRn is a non-covalent complex of membrane protein FcRn a chain and β2 microglobulin (β2M). In adult mammals FcRn plays a key role in maintaining serum antibody levels by acting as a receptor that binds and salvages antibodies of the IgG isotype. IgG molecules are endocytosed by endothelial cells, and if they bind to FcRn, are recycled transcytosed out into, for example circulation. In contrast, IgG molecules that do not bind to FcRn enter the cells and are targeted to the lysosomal pathway where they are degraded. A variant IgG1 in which His435 is mutated to alanine results in the selective loss of FcRn binding and a significantly reduced serum half-life (Firan et al. 2001, International Immunology 13:993).

It is hypothesised that FcRn is a potential therapeutic target for certain autoimmune disorders caused at least in part by autoantibodies. The current treatment for certain such disorders includes plasmapheresis. Sometimes the plasmapheresis is employed along with immunosuppressive therapy for long-term management of the disease. Plasma exchange offers the quickest short-term answer to removing harmful autoantibodies. However, it may also be desirable to suppress the production of autoantibodies by the immune system for example by the use of medications such as prednisone, cyclophosphamide, cyclosporine, mycophenolate mofetil, rituximab or a mixture of these.

Examples of diseases that can be treated with plasmapheresis include: Guillain-Barré syndrome; Chronic inflammatory demyelinating polyneuropathy; Goodpasture's syndrome; hyperviscosity syndromes; cryoglobulinemia; paraproteinemia; Waldenstrom macroglobulinemia; myasthenia gravis; thrombotic thrombocytopenic purpura (TTP)/hemolytic uremic syndrome; Wegener's granulomatosis; Lambert-Eaton Syndrome; antiphospholipid antibody syndrome (APS or APLS); microscopic polyangiitis; recurrent focal and segmental glomerulosclerosis in the transplanted kidney; HELLP syndrome; PANDAS syndrome; Refsum disease; Behcet syndrome; HIV-related neuropathy; Graves' disease in infants and neonates; pemphigus vulgaris; multiple sclerosis, rhabdomyolysis and alloimune diseases.

Plasmapheresis is sometimes used as a rescue therapy for removal of Fc containing therapeutics, for example in emergencies to reduced serious side effects.

Though plasmapheresis is helpful in certain medical conditions there are potential risks and complications associated with the therapy. Insertion of a rather large intravenous catheter can lead to bleeding, lung puncture (depending on the site of catheter insertion), and, if the catheter is left in too long, it can lead to infection and/or damage to the veins giving limited opportunity to repeat the procedure.

The procedure has further complications associated with it, for example when a patient's blood is outside of the body passing through the plasmapheresis instrument, the blood has a tendency to clot. To reduce this tendency, in one common protocol, citrate is infused while the blood is running through the circuit. Citrate binds to calcium in the blood, calcium being essential for blood to clot. Citrate is very effective in preventing blood from dotting; however, its use can lead to life-threateningly low calcium levels. This can be detected using the Chvostek's sign or Trousseau's sign. To prevent this complication, calcium is infused intravenously while the patient is undergoing the plasmapheresis; in addition, calcium supplementation by mouth may also be given.

Other complications of the procedure include: hypotension; potential exposure to blood products, with risk of transfusion reactions or transfusion transmitted diseases, suppression of the patient's immune system and bleeding or hematoma from needle placement.

Additionally facilities that provide plasmapheresis are limited and the procedure is very expensive.

An alternative to plasmapheresis is intravenous immunoglobulin (IVIG), which is a blood product containing pooled polyclonal IgG extracted from the plasma of over one thousand blood donors. The therapy is administered intravenously and lasts in the region of 2 weeks to 3 months.

Complications of the IVIG treatment include headaches, dermatitis, viral infection from contamination of the therapeutic product, for example HIV or hepatitis, pulmonary edema, allergic reactions, acute renal failure, venous thrombosis and aseptic meningitis.

Thus there is a significant unmet need for therapies for autoimmune disorders which are less invasive and which expose the patients to less medical complications.

Thus there is a significant unmet need for therapies for immunological disorders and/or autoimmune disorders which are less invasive and which expose the patients to less medical complications.

Accordingly agents that block or reduce the binding of IgG to FcRn may be useful in the treatment or prevention of such autoimmune and inflammatory diseases. Anti-FcRn antibodies have been described previously in WO2009/131702, WO2007/087289 and WO2006/118772.

However, there remains a need for improved anti-FcRn antibodies.

SUMMARY OF THE DISCLOSURE

Thus in one aspect there is provided an anti-FcRn antibody or binding fragment thereof comprising a heavy chain or heavy chain fragment having a variable region, wherein said variable region comprises one, two or three CDRs independently selected from SEQ ID NO: 1, SEQ ID NO: 2 and SEQ ID NO: 3, for example wherein CDR H1 is SEQ ID NO: 1, CDR H2 is SEQ ID NO: 2 and CDR H3 is SEQ ID NO: 3.

In another aspect there is provided an antibody or fragment comprising a sequence or combinations of sequences as defined herein, for example a cognate pair variable region.

The antibodies of the disclosure block binding of IgG to FcRn and are thought to be useful in reducing one or more biological functions of FcRn, including reducing half-life of circulating antibodies. This may be beneficial in that it allows the patient to more rapidly clear antibodies, such as autoantibodies.

Importantly the antibodies of the present invention are able to bind human FcRn at both pH6 and pH7.4 with comparable and high binding affinity. Advantageously therefore the antibodies are able to continue to bind FcRn even within the endosome, thereby maximising the blocking of FcRn binding to IgG, see FIG. 10 for an illustration of the mechanism.

In one embodiment the antibodies or binding fragments according to the present disclosure comprise a light chain or light chain fragment having a variable region, for example comprising one, two or three CDRs independently selected from SEQ ID NO: 4, SEQ ID NO: 5 and SEQ ID NO: 6, in particular wherein CDR L1 is SEQ ID NO: 4, CDR L2 is SEQ ID NO: 5 and CDR L3 is SEQ ID NO: 6.

In one embodiment the antibodies or binding fragments according to the present disclosure comprise CDR sequences of SEQ ID NOs: 1 to 6, for example wherein CDR H1 is SEQ ID NO: 1, CDR H2 is SEQ ID NO: 2, CDR H3 is SEQ ID NO: 3, CDR L1 is SEQ ID NO: 4, CDR L2 is SEQ ID NO: 5 and CDR L3 is SEQ ID NO: 6.

The disclosure also extends to a polynucleotide, such as DNA, encoding an antibody or fragment as described herein.

Also provided is a host cell comprising said polynucleotide.

Methods of expressing an antibody or fragment are provided herein as are methods of conjugating an antibody or fragment to a polymer, such as PEG.

The present disclosure also relates to pharmaceutical compositions comprising said antibodies and fragments.

In one embodiment there is provided a method of treatment comprising administering a therapeutically effective amount of an antibody, fragment or composition as described herein.

The present disclosure also extends to an antibody, fragment or composition according to the present disclosure for use in treatment, particularly in the treatment of an immunological and/or autoimmune disorder.

Thus the present disclosure provides antibodies, fragments thereof and methods for removal of pathogenic IgG, which is achieved by accelerating the body's natural mechanism for catabolising IgG.

In essence the antibodies and fragments according to the disclosure block the system that recycles IgG in the body.

The present therapy is likely to provide a replacement or supplement for certain diseases where plasmapheresis is a therapy or IVIg therapy, which is advantageous for patients.

BRIEF DESCRIPTION OF THE FIGURES

FIGS. 1 and 1A-1FF shows certain amino acid and polynucleotide sequences.

FIG. 26 shows pictures of the crystals in a drop and frozen.

DETAILS OF THE DISCLOSURE

Figure 1:
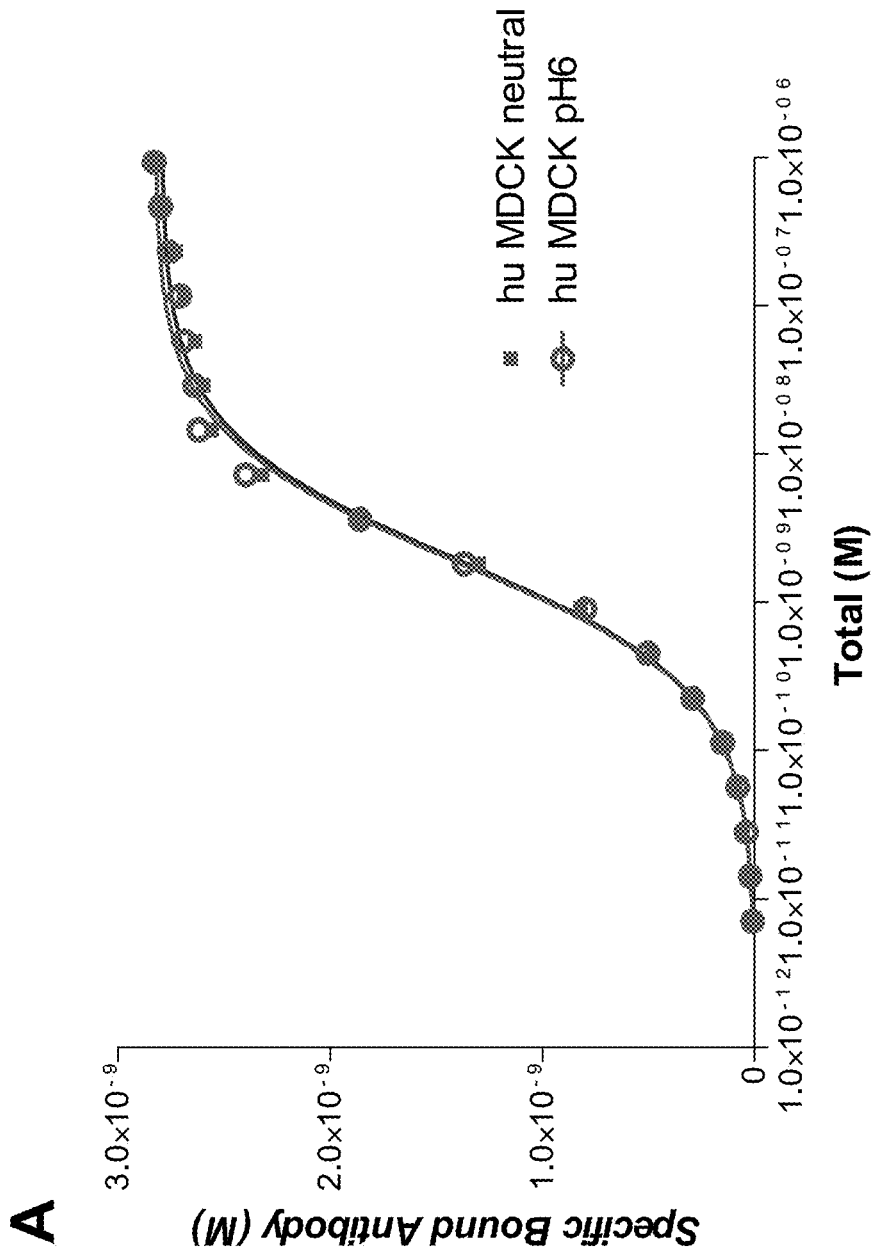

FcRn as employed herein refers to the non-covalent complex between the human IgG receptor alpha chain, also known as the neonatal Fc receptor, the amino acid sequence of which is in UniProt under number P55899 together with β2 microglobulin (β2M), the amino acid sequence of which is in UniProt under number P61769.

Antibody molecule as employed herein refers to an antibody or binding fragment thereof.

The term 'antibody' as used herein generally relates to intact (whole) antibodies i.e. comprising the elements of two heavy chains and two light chains. The antibody may comprise further additional binding domains for example as per the molecule DVD-Ig as disclosed in WO 2007/024715, or the so-called (FabFv)$_2$Fc described in WO2011/030107. Thus antibody as employed herein includes bi, tri or tetra-valent full length antibodies.

Binding fragments of antibodies include single chain antibodies (i.e. a full length heavy chain and light chain); Fab, modified Fab, Fab', modified Fab', F(ab')$_2$, Fv, Fab-Fv, Fab-dsFv, single domain antibodies (e.g. VH or VL or VHH), scFv, bi, tri or tetra-valent antibodies, Bis-scFv, diabodies, tribodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilised versions thereof, the Fab-dsFv was first disclosed in WO2010/035012, see also FIG. 25 herein. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

A typical Fab' molecule comprises a heavy and a light chain pair in which the heavy chain comprises a variable region V$_H$, a constant domain C$_H$1 and a natural or modified hinge region and the light chain comprises a variable region V$_L$ and a constant domain C$_L$.

In one embodiment there is provided a dimer of a Fab' according to the present disclosure to create a F(ab')$_2$ for example dimerisation may be through the hinge.

In one embodiment the antibody or binding fragment thereof comprises a binding domain. A binding domain will generally comprises 6 CDRs, three from a heavy chain and three from a light chain. In one embodiment the CDRs are in a framework and together form a variable region. Thus in one embodiment an antibody or binding fragment comprises a binding domain specific for antigen comprising a light chain variable region and a heavy chain variable region.

It will be appreciated that one or more (for example 1, 2, 3 or 4) amino acid substitutions, additions and/or deletions may be made to the CDRs or other sequences (e.g variable domains) provided by the present invention without significantly altering the ability of the antibody to bind to FcRn. The effect of any amino acid substitutions, additions and/or deletions can be readily tested by one skilled in the art, for example by using the methods described herein, in particular in the Examples, to determine FcRn.

In one or more (for example 1, 2, 3 or 4) amino acid substitutions, additions and/or deletions may be made to the framework region employed in the antibody or fragment provided by the present invention and wherein binding affinity to FcRn is retained or increased.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies and fragments of the present disclosure block FcRn and may thereby prevent it functioning in the recycling of IgG. Blocking as employed herein refers to physically blocking such as occluding the receptor but will also include where the antibody or fragments binds an epitope that causes, for example a conformational change which means that the natural ligand to the receptor no longer binds. Antibody molecules of the present invention bind to FcRn and thereby decrease or prevent (e.g. inhibit) FcRn binding to an IgG constant region.

In one embodiment the antibody or fragment thereof binds FcRn competitively with respect to IgG.

In one example the antibody or binding fragment thereof functions as a competitive inhibitor of human FcRn binding to human IgG. In one example the antibody or binding fragment thereof binds to the IgG binding site on FcRn. In one example the antibody or binding fragment thereof does not bind β2M.

Antibodies for use in the present disclosure may be obtained using any suitable method known in the art. The FcRn polypeptide/protein including fusion proteins, cells (recombinantly or naturally) expressing the polypeptide (such as activated T cells) can be used to produce antibodies which specifically recognise FcRn. The polypeptide may be the 'mature' polypeptide or a biologically active fragment or derivative thereof. The human protein is registered in Swiss-Prot under the number P55899. The extracellular domain of human FcRn alpha chain is provided in SEQ ID NO:94. The sequence of β2M is provided in SEQ ID NO:95.

In one embodiment the antigen is a mutant form of FcRn which is engineered to present FcRn on the surface of a cell, such that there is little or no dynamic processing where the FcRn is internalised in the cell, for example this can be achieved by making a mutation in the cytoplasmic tail of the FcRn alpha chain, wherein di-leucine is mutated to di-alanine as described in Ober et al 2001 Int. Immunol. 13, 1551-1559.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The FcRn polypeptide may in some instances be part of a larger protein such as a fusion protein for example fused to an affinity tag or similar.

Antibodies generated against the FcRn polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to human FcRn and/or assays to measure the ability to block IgG binding to the receptor. An example of a binding assay is an ELISA, in particular, using a fusion protein of human FcRn and human Fc, which is immobilised on plates, and employing a secondary antibody to detect anti-FcRn antibody bound to the fusion protein. Examples of suitable antagonistic and blocking assays are described in the Examples herein.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived. The latter are often referred to as donor residues.

Specific as employed herein is intended to refer to an antibody that only recognises the antigen to which it is specific or an antibody that has significantly higher binding affinity to the antigen to which it is specific compared to binding to antigens to which it is non-specific, for example at least 5, 6, 7, 8, 9, 10 times higher binding affinity. Binding affinity may be measured by techniques such as BIAcore as described herein below. In one example the antibody of the present invention does not bind β2 microglobulin (β2M). In one example the antibody of the present invention binds cynomolgus FcRn. In one example the antibody of the present invention does not bind rat or mouse FcRn.

The amino acid sequences and the polynucleotide sequences of certain antibodies according to the present disclosure are provided in the Figures.

In one embodiment the antibody or fragments according to the disclosure are humanised.

As used herein, the term 'humanised antibody molecule' refers to an antibody molecule wherein the heavy and/or light chain contains one or more CDRs (including, if desired, one or more modified CDRs) from a donor antibody (e.g. a non-human antibody such as a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions.

Suitably, the humanised antibody according to the present invention has a variable domain comprising human acceptor framework regions as well as one or more of the CDRs provided specifically herein. Thus, provided in one embodiment is blocking humanised antibody which binds human FcRn wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: vbase.mrc-cpe.cam.ac.uk/

In a humanised antibody of the present invention, the acceptor heavy and light chains do not necessarily need to be derived from the same antibody and may, if desired, comprise composite chains having framework regions derived from different chains.

One such suitable framework region for the heavy chain of the humanised antibody of the present invention is derived from the human sub-group VH3 sequence 1-3 3-07 together with JH4 (SEQ ID NO: 56).

Accordingly, in one example there is provided a humanised antibody comprising the sequence given in SEQ ID NO: 1 for CDR-H1, the sequence given in SEQ ID NO: 2 for CDR-H2 and the sequence given in SEQ ID NO: 3 for CDRH3, wherein the heavy chain framework region is derived from the human subgroup VH3 sequence 1-3 3-07 together with JH4.

The sequence of human JH4 is as follows: (YFDY) WGQGTLVTVS (Seq ID No: 70). The YFDY motif is part of CDR-H3 and is not part of framework 4 (Ravetch, J V. et al., 1981, Cell, 27, 583-591).

In one example the heavy chain variable domain of the antibody comprises the sequence given in SEQ ID NO: 29.

A suitable framework region for the light chain of the humanised antibody of the present invention is derived from the human germline sub-group VK1 sequence 2-1-(1) A30 together with JK2 (SEQ ID NO: 54).

Accordingly, in one example there is provided a humanised antibody comprising the sequence given in SEQ ID NO: 4 for CDR-L1, the sequence given in SEQ ID NO: 5 for CDR-L2 and the sequence given in SEQ ID NO: 6 for CDRL3, wherein the light chain framework region is derived from the human subgroup VK1 sequence 2-1-(1) A30 together with JK2.

The JK2 sequence is as follows: (YT)FGQGTKLEIK (Seq ID No: 71). The YT motif is part of CDR-L3 and is not part of framework 4 (Hieter, P A., et al., 1982, J. Biol. Chem., 257, 1516-1522).

In one example the light chain variable domain of the antibody comprises the sequence given in SEQ ID NO: 15.

In a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Thus in one embodiment 1, 2, 3, 4, or 5 residues in the framework are replaced with an alternative amino acid residue.

Accordingly, in one example there is provided a humanised antibody, wherein at least the residues at each of positions 3, 24, 76, 93 and 94 of the variable domain of the heavy chain (Kabat numbering) are donor residues, see for example the sequence given in SEQ ID NO:
29.

In one embodiment residue 3 of the heavy chain variable domain is replaced with an alternative amino acid, for example glutamine.

In one embodiment residue 24 of the heavy chain variable domain is replaced with an alternative amino acid, for example alanine.

In one embodiment residue 76 of the heavy chain variable domain is replaced with an alternative amino acid, for example asparagine.

In one embodiment residue 93 of the heavy chain is replaced with an alternative amino acid, for example alanine.

In one embodiment residue 94 of the heavy chain is replaced with an alternative amino acid, for example arginine.

In one embodiment residue 3 is glutamine, residue 24 is alanine, residue 76 is aspargine, residue 93 is alanine and residue 94 is arginine in the humanised heavy chain variable region according to the present disclosure.

Accordingly, in one example there is provided a humanised antibody, wherein at least the residues at each of positions 36, 37 and 58 of the variable domain of the light chain (Kabat numbering) are donor residues, see for example the sequence given in SEQ ID NO: 15

In one embodiment residue 36 of the light chain variable domain is replaced with an alternative amino acid, for example tyrosine.

In one embodiment residue 37 of the light chain variable domain is replaced with an alternative amino acid, for example glutamine.

In one embodiment residue 58 of the light chain variable domain is replaced with an alternative amino acid, for example valine.

In one embodiment residue 36 is tyrosine, residue 37 is glutamine and residue 58 is valine, in the humanised heavy chain variable region according to the present disclosure.

In one embodiment the disclosure provides an antibody sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment the relevant sequence is SEQ ID NO: 15. In one embodiment the relevant sequence is SEQ ID NO: 29.

In one embodiment, the present invention provides an antibody molecule which binds human FcRn comprising a heavy chain, wherein the variable domain of the heavy chain comprises a sequence having at least 80%, 85%, 90%, 91%, 92%, 93%, 94%, 95% 96%, 97%, 98% or 99% identity or similarity to the sequence given in SEQ ID NO:29.

In one embodiment, the present invention provides an antibody molecule which binds human FcRn comprising a light chain, wherein the variable domain of the light chain comprises a sequence having at least 80%, 85%, 90%, 91%, 92%, 93%, 94%, 95% 96%, 97%, 98% or 99% identity or similarity to the sequence given in SEQ ID NO:15.

In one embodiment the present invention provides an antibody molecule which binds human FcRn wherein the antibody has a heavy chain variable domain which is at least 90%, 91%, 92%, 93%, 94%, 95% 96%, 97%, 98% or 99% similar or identical to the sequence given in SEQ ID NO:29 but wherein the antibody molecule has the sequence given in SEQ ID NO: 1 for CDR-H1, the sequence given in SEQ ID NO: 2 for CDR-H2 and the sequence given in SEQ ID NO: 3 for CDR-H3.

In one embodiment the present invention provides an antibody molecule which binds human FcRn wherein the antibody has a light chain variable domain which is at least 90%, 91%, 92%, 93%, 94%, 95% 96%, 97%, 98% or 99% similar or identical to the sequence given in SEQ ID NO:15 but wherein the antibody molecule has the sequence given in SEQ ID NO: 4 for CDR-L1, the sequence given in SEQ ID NO: 5 for CDR-L2 and the sequence given in SEQ ID NO:6 for CDR-L3.

In one embodiment the present invention provides an antibody molecule which binds human FcRn wherein the antibody has a heavy chain variable domain which is at least 90%, 91%, 92%, 93%, 94%, 95% 96%, 97%, 98% or 99% similar or identical to the sequence given in SEQ ID NO:29 and a light chain variable domain which is at least 90%, 91%, 92%, 93%, 94%, 95% 96%, 97%, 98% or 99% similar or identical to the sequence given in SEQ ID NO:15 but wherein the antibody molecule has the sequence given in SEQ ID NO: 1 for CDR-H1, the sequence given in SEQ ID NO: 2 for CDR-H2, the sequence given in SEQ ID NO: 3 for CDR-H3, the sequence given in SEQ ID NO: 4 for CDR-L1, the sequence given in SEQ ID NO: 5 for CDR-L2 and the sequence given in SEQ ID NO:6 for CDR-L3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities e.g bispecific or may be monospecific (see for example WO 92/22853, WO05/113605, WO2009/040562 and WO2010/035012).

In one embodiment the antibody molecule of the present disclosure is an antibody Fab' fragment comprising the variable regions shown in SEQ ID NOs: 15 and 29 for example for the light and heavy chain respectively. In one embodiment the antibody molecule has a light chain comprising the sequence given in SEQ ID NO:22 and a heavy chain comprising the sequence given in SEQ ID NO:36.

In one embodiment the antibody molecule of the present disclosure is a full length IgG1 antibody comprising the variable regions shown in SEQ ID NOs: 15 and 29 for example for the light and heavy chain respectively. In one embodiment the antibody molecule has a light chain comprising the sequence given in SEQ ID NO:22 and a heavy chain comprising the sequence given in SEQ ID NO:72.

In one embodiment the antibody molecule of the present disclosure is a full length IgG4 format comprising the variable regions shown in SEQ ID NOs: 15 and 29 for example for the light and heavy chain respectively. In one embodiment the antibody molecule has a light chain comprising the sequence given in SEQ ID NO:22 and a heavy chain comprising the sequence given in SEQ ID NO:87.

In one embodiment the antibody molecule of the present disclosure is a full length IgG4P format comprising the variable regions shown in SEQ ID NOs: 15 and 29 for example for the light and heavy chain respectively. In one embodiment the antibody molecule has a light chain comprising the sequence given in SEQ ID NO:22 and a heavy chain comprising the sequence given in SEQ ID NO:43.

IgG4P as employed herein is a mutation of the wild-type IgG4 isotype where amino acid 241 is replaced by proline see for example where serine at position 241 has been changed to proline as described in Angal et al., Molecular Immunology, 1993, 30 (1), 105-108.

In one embodiment the antibody according to the present disclosure is provided as FcRn binding antibody fusion protein which comprises an immunoglobulin moiety, for example a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

Figure 25:
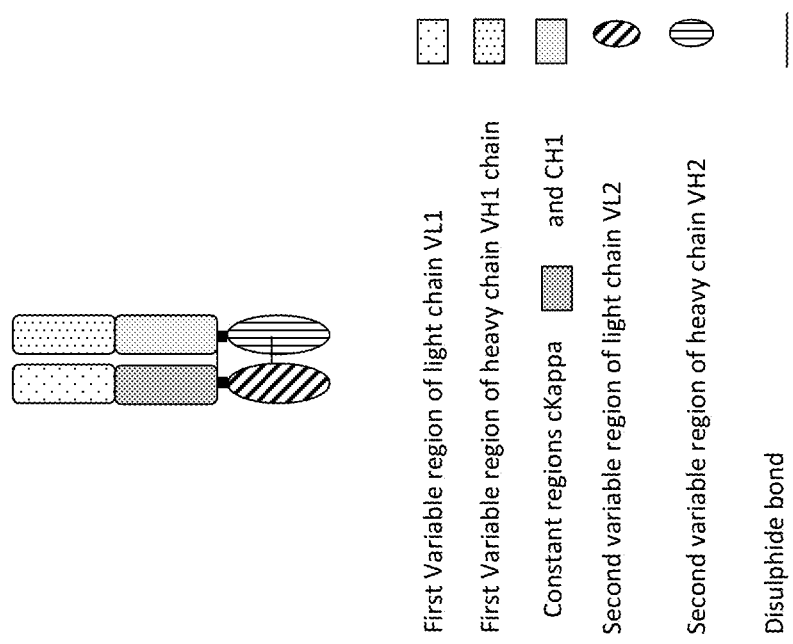
FIG. 25 shows a bispecific antibody fusion protein of the present invention, referred to as a Fab-dsFv.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site. In one such embodiment the heavy chain comprises the sequence given in SEQ ID NO:50 and the light chain comprises the sequence given in SEQ ID NO:46 or SEQ ID NO:78. This Fab-dsFv format is illustrated in FIG. 25 herein.

In one embodiment the Fab or Fab' according to the present disclosure is conjugated to a PEG molecule or human serum albumin.

CA170_01519g57 and 1519 and 1519.g57 are employed inchangeably herein and are used to refer to a specific pair of antibody variable regions which may be used in a number of different formats. These variable regions are the heavy chain sequence given in SEQ ID NO:29 and the light chain sequence given in SEQ ID NO:15 (FIG. 1).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705: 129-134, 1995). Accordingly, the C-terminal lysine of the antibody heavy chain may be absent.

In one embodiment the antibody heavy chain comprises a CH1 domain and the antibody light chain comprises a CL domain, either kappa or lambda.

In one embodiment the light chain has the sequence given in SEQ ID NO:22 and the heavy chain has the sequence given in SEQ ID NO:43.

In one embodiment the light chain has the sequence given in SEQ ID NO:22 and the heavy chain has the sequence given in SEQ ID NO:72.

In one embodiment a C-terminal amino acid from the antibody molecule is cleaved during post-translation modifications.

In one embodiment an N-terminal amino acid from the antibody molecule is cleaved during post-translation modifications.

Also provided by the present invention is a specific region or epitope of human FcRn which is bound by an antibody provided by the present invention, in particular an antibody comprising the heavy chain sequence gH20 (SEQ ID NO:29) and/or the light chain sequence gL20 (SEQ ID NO:15).

This specific region or epitope of the human FcRn polypeptide can be identified by any suitable epitope mapping method known in the art in combination with any one of the antibodies provided by the present invention. Examples of such methods include screening peptides of varying lengths derived from FcRn for binding to the antibody of the present invention with the smallest fragment that can specifically bind to the antibody containing the sequence of the epitope recognised by the antibody. The FcRn peptides may be produced synthetically or by proteolytic digestion of the FcRn polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

In one embodiment the antibody of the present disclosure binds the human FcRn alpha chain extracellular sequence as shown below:

```
                                          (SEQ ID NO: 94)
AESHLSLLYH LTAVSSPAPG TPAFWVSGWL GPQQYLSYNS

LRGEAEPCGA WVWENQVSWY WEKETTDLRI KEKLFLEAFK

ALGGKGPYTL QGLLGCELGP DNTSVPTAKF ALNGEEFMNF

DLKQGTWGGD WPEALAISQR WQQQDKAANK ELTFLLFSCP

HRLREHLERG RGNLEWKEPP SMRLKARPSS PGFSVLTCSA
```

-continued

```
FSFYPPELQL RFLRNGLAAG TGQGDFGPNS DGSFHASSSL

TVKSGDEHHY CCIVQHAGLA QPLRVELESPAKSS.
```

The residues underlined are those known to be critical for the interaction of human FcRn with the Fc region of human IgG and those residues highlighted in bold are those involved in the interaction of FcRn with the 1519 antibody of the present disclosure comprising the heavy chain sequence gH20 (SEQ ID NO:29) and the light chain sequence gL20 (SEQ ID NO:15).

In one example, the present invention provides an anti-FcRn antibody molecule which binds an epitope of human FcRn which comprises at least one amino acid selected from the group consisting of residues V105, P106, T107, A108 and K109 of SEQ ID NO:94 and at least one residue, for example at least 2, 3, 4, 5, 6, 7, 8, 9 or 10 residues selected from the group consisting of P100, E115, E116, F117, M118, N119, F120, D121, L122, K123, Q124, G128, G129, D130, W131, P132 and E133 of SEQ ID NO:94.

In one example the epitope of the antibody molecule is determined by X-ray crystallography using the FcRn alpha chain extracellular sequence (SEQ ID NO:94) in complex with β2M.

In one example, the present invention provides an anti-FcRn antibody molecule which binds an epitope of human FcRn which comprises at least one amino acid selected from the group consisting of residues V105, P106, T107, A108 and K109 of SEQ ID NO:94 and at least one residue, for example at least 2, 3, 4, 5, 6, 7, 8, 9 or 10 residues, selected from the group consisting of E115, E116, F117, M118, N119, F120, D121, L122, K123 and Q124 of SEQ ID NO:94.

In one example, the present invention provides an anti-FcRn antibody molecule which binds an epitope of human FcRn which comprises at least two, three, four or five amino acids selected from the group consisting of residues V105, P106, T107, A108 and K109 of SEQ ID NO:94 and at least one residue selected from the group consisting of E115, E116, F117, M118, N119, F120, D121, L122, K123 and Q124 of SEQ ID NO:94.

In one example, the present invention provides an anti-FcRn antibody molecule which binds an epitope of human FcRn which comprises at least one amino acid selected from the group consisting of residues V105, P106, T107, A108 and K109 of SEQ ID NO:94 and at least one residue selected from the group consisting of P100, E115, E116, F117, M118, N119, F120, D121, L122, K123, Q124, G128, G129, D130, W131, P132 and E133 of SEQ ID NO:94.

In one example, the present invention provides an anti-FcRn antibody molecule which binds an epitope of human FcRn which comprises at least one amino acid selected from the group consisting of residues V105, P106, T107, A108 and K109 of SEQ ID NO:94 and at least one residue selected from the group consisting of P100, M118, N119, F120, D121, L122, K123, Q124 and G128 of SEQ ID NO:94.

In one example, the present invention provides an anti-FcRn antibody molecule which binds an epitope of human FcRn which comprises residues V105, P106, T107, A108 and K109 of SEQ ID NO:94 and at least one residue selected from the group consisting of P100, M118, N119, F120, D121, L122, K123, Q124 and G128 of SEQ ID NO:94.

In one example, the present invention provides an anti-FcRn antibody molecule which binds an epitope of human FcRn which comprises residues V105, P106, T107, A108 and K109 of SEQ ID NO:94 and at least one residue selected from the group consisting of P100, E115, E116, F117, M118, N119, F120, D121, L122, K123, Q124, G128, G129, D130, W131, P132 and E133 of SEQ ID NO:94.

In one example, the present invention provides an anti-FcRn antibody molecule which binds an epitope of human FcRn which comprises residues P100, V105, P106, T107, A108 and K109 of SEQ ID NO:94 and at least one residue selected from the group consisting of E115, E116, F117, M118, N119, F120, D121, L122, K123, Q124, G128, G129, D130, W131, P132 and E133 of SEQ ID NO:94.

In one example 'at least one residue' may be 1, 2, 3, 4, 5, 6, 7, 8, 9, 10, 11, 12, 13, 14, 15 or 16 residues.

In one example the present invention provides an anti-FcRn antibody molecule which binds an epitope of human FcRn which comprises or consists of residues 100, 105 to 109, 115 to 124 and 129 to 133 of SEQ ID NO: 94.

Antibodies which cross-block the binding of an antibody molecule according to the present invention in particular, an antibody molecule comprising the heavy chain sequence given in SEQ ID NO:29 and the light chain sequence given in SEQ ID NO:15 may be similarly useful in blocking FcRn activity. Accordingly, the present invention also provides an anti-FcRn antibody molecule, which cross-blocks the binding of any one of the antibody molecules described herein above to human FcRn and/or is cross-blocked from binding human FcRn by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above.

Cross-blocking antibodies can be identified using any suitable method in the art, for example by using competition ELISA or BIAcore assays where binding of the cross blocking antibody to human FcRn prevents the binding of an antibody of the present invention or vice versa. Such cross blocking assays may use isolated natural or recombinant FcRn or a suitable fusion protein/polypeptide. In one example binding and cross-blocking is measured using recombinant human FcRn extracellular domain (SEQ ID NO:94). In one example the recombinant human FcRn alpha chain extracellular domain is used in a complex with β2 microglobulin (β2M) (SEQ ID NO:95).

In one embodiment there is provided an anti-FcRn antibody molecule which blocks FcRn binding to IgG and which cross-blocks the binding of an antibody whose heavy chain comprises the sequence given in SEQ ID NO:29 and whose light chain comprises the sequence given in SEQ ID NO:15 to human FcRn. In one embodiment the cross-blocking antibodies provided by the present invention inhibit the binding of an antibody comprising the heavy chain sequence given in SEQ ID NO:29 and the light chain sequence given in SEQ ID NO:15 by greater than 80%, for example by greater than 85%, such as by greater than 90%, in particular by greater than 95%.

Alternatively or in addition, anti-FcRn antibodies according to this aspect of the invention may be cross-blocked from binding to human FcRn by an antibody comprising the heavy chain sequence given in SEQ ID NO:29 and the light chain sequence given in SEQ ID NO:15. Also provided therefore is an anti-FcRn antibody molecule which blocks FcRn binding to IgG and which is cross-blocked from binding human FcRn by an antibody comprising the heavy chain sequence given in SEQ ID NO:29 and the light chain sequence given in SEQ ID NO:15. In one embodiment the anti-FcRn antibodies provided by this aspect of the invention are inhibited from binding human FcRn by an antibody comprising the heavy chain sequence given in SEQ ID NO:29 and the light chain sequence given in SEQ ID NO:15 by greater than 80%, for example by greater than 85%, such as by greater than 90%, in particular by greater than 95%.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human FcRn of 100 pM or less. In one embodiment the cross-blocking antibodies provided by the present invention have an affinity for human FcRn of 50 pM or less. Affinity can be measured using the methods described herein below.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the FcRn antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised FcRn antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY www.expasy.ch/tools/pi_tool.html, and
www.iut-arles.up.univ-mrs.fr/w3bb/d_abim/compo-p.html, may be used to predict the isoelectric point of the antibody or fragment.

The antibody molecules of the present invention suitably have a high binding affinity, in particular in the nanomolar range. Affinity may be measured using any suitable method known in the art, including BIAcore, as described in the Examples herein, using isolated natural or recombinant FcRn or a suitable fusion protein/polypeptide. In one example affinity is measured using recombinant human FcRn extracellular domain as described in the Examples herein (SEQ ID NO:94). In one example affinity is measured using the recombinant human FcRn alpha chain extracellular domain (SEQ ID NO:94) in association with β2 microglobulin (β2M) (SEQ ID NO:95). Suitably the antibody molecules of the present invention have a binding affinity for isolated human FcRn of about 1 nM or lower. In one embodiment the antibody molecule of the present invention has a binding affinity of about 500 pM or lower (i.e. higher affinity). In one embodiment the antibody molecule of the present invention has a binding affinity of about 250 pM or lower. In one embodiment the antibody molecule of the present invention has a binding affinity of about 200 pM or lower. In one embodiment the present invention provides an anti-FcRn antibody with a binding affinity of about 100 pM or lower. In one embodiment the present invention provides a humanised anti-FcRn antibody with a binding affinity of about 100 pM or lower. In one embodiment the present invention provides an anti-FcRn antibody with a binding affinity of 50 pM or lower.

Importantly the antibodies of the present invention are able to bind human FcRn at both pH6 and pH7.4 with comparable binding affinity. Advantageously therefore the antibodies are able to continue to bind FcRn even within the endosome, thereby maximising the blocking of FcRn binding to IgG, see FIG. 10 for an illustration of the mechanism.

In one embodiment the present invention provides an anti-FcRn antibody with a binding affinity of 100 pM or lower when measured at pH6 and pH7.4.

The affinity of an antibody or binding fragment of the present invention, as well as the extent to which a binding agent (such as an antibody) inhibits binding, can be determined by one of ordinary skill in the art using conventional techniques, for example those described by Scatchard et al. (Ann. K Y. Acad. Sci. 51:660-672 (1949)) or by surface plasmon resonance (SPR) using systems such as BIAcore. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In the present invention affinity of the test antibody molecule is typically determined using SPR as follows. The test antibody molecule is captured on the solid phase and human FcRn alpha chain extracellular domain in non-covalent complex with β2M is run over the captured antibody in the mobile phase and affinity of the test antibody molecule for human FcRn determined. The test antibody molecule may be captured on the solid phase chip surface using any appropriate method, for example using an anti-Fc or anti Fab' specific capture agent. In one example the affinity is determined at pH6. In one example the affinity is determined at pH7.4.

It will be appreciated that the affinity of antibodies provided by the present invention may be altered using any suitable method known in the art. The present invention therefore also relates to variants of the antibody molecules of the present invention, which have an improved affinity for FcRn. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention block human FcRn activity. Assays suitable for determining the ability of an antibody to block FcRn are described in the Examples herein. Suitable assays for determining whether antibodies block FcRn interaction with circulating IgG molecules as described in the Examples herein. A suitable assay for determining the ability of an antibody molecule to block IgG recycling in vitro is described herein below.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

In one embodiment a half-life provided by an effector molecule which is independent of FcRn is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

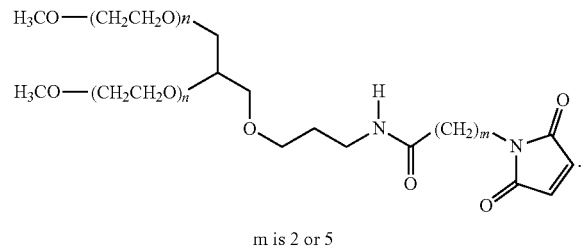

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl) amino]propyloxy} hexane (the 2 arm branched PEG, —CH₂)₃NHCO(CH₂)₅-MAL, Mw 40,000 known as SUNBRIGHT GL2-400MA3.

Further alternative PEG effector molecules of the following type:

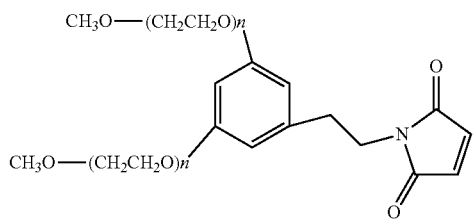

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering), for example amino acid 226 of SEQ ID NO:36.

In one embodiment the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one example the present invention provides a method treating a disease ameliorated by blocking human FcRn comprising administering a therapeutically effective amount of an anti-FcRn antibody or binding fragment thereof wherein the antibody or binding fragment thereof has a half life that is independent of Fc binding to FcRn.

In one embodiment there is provided a Fab' conjugated to a polymer, such as a PEG molecule, a starch molecule or an albumin molecule.

In one embodiment there is provided a scFv conjugated to a polymer, such as a PEG molecule, a starch molecule or an albumin molecule.

In one embodiment the antibody or fragment is conjugated to a starch molecule, for example to increase the half life. Methods of conjugating starch to a protein as described in U.S. Pat. No. 8,017,739 incorporated herein by reference.

In one embodiment there is provided an anti-FcRn binding molecule which:
Causes 70% reduction of plasma IgG concentration,
With not more than 20% reduction of plasma albumin concentration, and/or
With the possibility of repeat dosing to achieve long-term maintenance of low plasma IgG concentration.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in herein.

Examples of suitable DNA sequences encoding the 1519 light chain variable region are provided in SEQ ID NO:16, SEQ ID NO:17 and SEQ ID NO:90. Examples of suitable DNA sequences encoding the 1519 heavy chain variable region are provided in SEQ ID NO:30, SEQ ID NO:31 and SEQ ID NO:92.

Examples of suitable DNA sequences encoding the 1519 light chain (variable and constant) are provided in SEQ ID NO:23, SEQ ID NO:75 and SEQ ID NO:91.

Examples of suitable DNA sequences encoding the 1519 heavy chain (variable and constant, depending on format) are provided in SEQ ID NOs:37, 38 and 76 (Fab'), SEQ ID NO:72 or 85 (IgG1), SEQ ID NO: 44 or 93 (IgG4P) and SEQ ID:88 (IgG4).

Accordingly in one example the present invention provides an isolated DNA sequence encoding the heavy chain of an antibody Fab' fragment of the present invention which comprises the sequence given in SEQ ID NO:37. Also provided is an isolated DNA sequence encoding the light chain of an antibody Fab' fragment of the present invention which comprises the sequence given in SEQ ID NO:23.

In one example the present invention provides an isolated DNA sequence encoding the heavy chain and the light chain of an IgG4(P) antibody of the present invention in which the DNA encoding the heavy chain comprises the sequence given in SEQ ID NO:44 or SEQ ID NO:93 and the DNA encoding the light chain comprises the sequence given in SEQ ID NO:75 or SEQ ID NO:91.

In one example the present invention provides an isolated DNA sequence encoding the heavy chain and the light chain of a Fab-dsFv antibody of the present invention in which the DNA encoding the heavy chain comprises the sequence given in SEQ ID NO:51 or SEQ ID NO:80 and the DNA encoding the light chain comprises the sequence given in SEQ ID NO:47 or SEQ ID NO:79.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are conducive to commercial processing.

Thus there is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising the steps: performing anion exchange chromatography in non-binding mode such that the impurities are retained on the column and the antibody is eluted.

In one embodiment the purification employs affinity capture on an FcRn column.

In one embodiment the purification employs cibacron blue or similar for purification of albumin fusion or conjugate molecules.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filtration steps, such as a diafiltration step.

Thus in one embodiment there is provided a purified anti-FcRn antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

The antibody molecule of the present invention may also be used in diagnosis, for example in the in vivo diagnosis and imaging of disease states involving FcRn.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody molecule of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable excipient.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients or non-antibody ingredients such as steroids or other drug molecules, in particular drug molecules whose half-life is independent of FcRn binding.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Therapeutic doses of the antibodies according to the present disclosure show no apparent toxicology effects in vivo.

In one embodiment of an antibody or fragment according to the invention a single dose may provide up to a 70% reduction in circulating IgG levels.

The maximal therapeutic reduction in circulating IgG may be observed about 1 week after administration of the relevant therapeutic dose. The levels of IgG may recover over about a six week period if further therapeutic doses are not delivered.

Advantageously, the levels of IgG in vivo may be maintained at an appropriately low level by administration of sequential doses of the antibody or fragments according to the disclosure.

Compositions may be administered individually to a patient or may be administered in combination (e.g. simultaneously, sequentially or separately) with other agents, drugs or hormones.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) and/or long lasting pharmacodynamics (PD) profile it may only be necessary to give a dosage once per day, once per week or even once every 1 or 2 months.

In one embodiment the dose is delivered bi-weekly, i.e. twice a month.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pI of the protein is in the range 8-9 or above then a formulation pH of 7 may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solutionbuffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of autoimmune diseases, for example Acute Disseminated Encephalomyelitis (ADEM), Acute necrotizing hemorrhagic leukoencephalitis, Addison's disease, Agammaglobulinemia, Alopecia areata, Amyloidosis, ANCA-associated vasculitis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticarial, Axonal & nal neuropathies, Balo disease, Behcet's disease, Bullous pemphigoid, Cardiomyopathy, Castleman disease, Celiac disease, Chagas disease, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Dilated cardiomyopathy, Discoid lupus, Dressler's syndrome, Endometriosis, Eosinophilic angiocentric fibrosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Granulomatosis with Polyangiitis (GPA) see Wegener's, Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic hypocomplementemic tubulointestitial nephritis, Idiopathic thrombocytopenic purpura (ITP), IgA nephropathy, IgG4-related disease, IgG4-related sclerosing disease, Immunoregulatory lipoproteins, Inflammatory aortic aneurysm, Inflammatory pseudotumour, Inclusion body myositis, Insulin-dependent diabetes (type1), Interstitial cystitis, Juvenile arthritis, Juvenile diabetes, Kawasaki syndrome, Kuttner's tumour, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Mediastinal fibrosis, Meniere's disease, Microscopic polyangiitis, Mikulicz's syndrome, Mixed connective tissue disease (MCTD), Mooren's ulcer, Mucha-Habermann disease, Multifocal fibrosclerosis, Multiple sclerosis, Myasthenia gravis, Myositis, Narcolepsy, Neuromyelitis optica (Devic's), Neutropenia, Ocular cicatricial pemphigoid, Optic neuritis, Ormond's disease (retroperitoneal fibrosis), Palindromic rheumatism, PANDAS (Pediatric Autoimmune Neuropsychiatric Disorders Associated with *Streptococcus*), Paraneoplastic cerebellar degeneration, Paraproteinemic polyneuropathies, Paroxysmal nocturnal hemoglobinuria (PNH), Parry Romberg syndrome, Parsonnage-Turner syndrome, Pars planitis (peripheral uveitis), Pemphigus vulgaris, Periaortitis, Periarteritis, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis (Ormond's disease), Rheumatic fever, Rheumatoid arthritis, Riedel's thyroiditis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombotic, thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, Waldenstrom Macroglobulinaemia, Warm idiopathic haemolytic anaemia and Wegener's granulomatosis (now termed Granulomatosis with Polyangiitis (GPA).

In one embodiment the antibodies or fragments according to the disclosure are employed in the treatment or prophylaxis of epilepsy or seizures.

In one embodiment the antibodies or fragments according to the disclosure are employed in the treatment or prophylaxis of multiple sclerosis.

In embodiment the antibodies and fragments of the disclosure are employed in alloimmune disease/indications which includes:

Transplantation donor mismatch due to anti-HLA antibodies

Foetal and neonatal alloimmune thrombocytopenia, FNAIT (or neonatal alloimmune thrombocytopenia, NAITP or NAIT or NAT, or foeto-maternal alloimmune thrombocytopenia, FMAITP or FMAIT).

Additional indications include: rapid clearance of Fc-containing biopharmaceutical drugs from human patients and combination of anti-FcRn therapy with other therapies—IVIg, Rituxan, plasmapheresis. For example anti-FcRn therapy may be employed following Rituxan therapy.

In embodiment the antibodies and fragments of the disclosure are employed in a neurology disorder such as:
Chronic inflammatory demyelinating polyneuropathy (CIDP)
Guillain-Barre syndrome
Paraproteinemic polyneuropathies
Neuromyelitis optica (NMO, NMO spectrum disorders or NMO spectrum diseases), and
Myasthenia gravis.

In embodiment the antibodies and fragments of the disclosure are employed in a dermatology disorder such as:
Bullous pemphigoid
Pemphigus vulgaris
ANCA-associated vasculitis
Dilated cardiomyopathy In embodiment the antibodies and fragments of the disclosure are employed in an Immunology, haematology disorder such as:
Idiopathic thrombocytopenic purpura (ITP)
Thrombotic thrombocytopenic purpura (TTP)
Warm idiopathic haemolytic anaemia
Goodpasture's syndrome
Transplantation donor mismatch due to anti-HLA antibodies In one embodiment the disorder is selected from Myasthenia Gravis, Neuro-myelitis Optica, CIDP, Guillaume-Barre Syndrome, Para-proteinemic Poly neuropathy, Refractory Epilepsy, ITP/TTP, Hemolytic Anemia, Goodpasture's Syndrome, ABO mismatch, Lupus nephritis, Renal Vasculitis, Sclero-derma, Fibrosing alveolitis, Dilated cardiomyopathy, Grave's Disease, Type 1 diabetes, Auto-immune diabetes, Pemphigus, Sclero-derma, Lupus, ANCA vasculitis, Dermato-myositis, Sjogren's Disease and Rheumatoid Arthritis.

In one embodiment the disorder is selected from autoimmune polyendocrine syndrome types 1 (APECED or Whitaker's Syndrome) and 2 (Schmidt's Syndrome); alopecia universalis; myasthenic crisis; thyroid crisis; thyroid associated eye disease; thyroid ophthalmopathy; autoimmune diabetes; autoantibody associated encephalitis and/or encephalopathy; pemphigus foliaceus; epidermolysis bullosa; dermatitis herpetiformis; Sydenham's chorea; acute motor axonal neuropathy (AMAN); Miller-Fisher syndrome; multifocal motor neuropathy (MMN); opsoclonus; inflammatory myopathy; Isaac's syndrome (autoimmune neuromyotonia), Paraneoplastic syndromes and Limbic encephalitis.

The antibodies and fragments according to the present disclosure may be employed in treatment or prophylaxis.

The present invention also provides a method of reducing the concentration of undesired antibodies in an individual comprising the steps of administering to an individual a therapeutically effective dose of an anti-FcRn antibody or binding fragment thereof described herein.

In one embodiment the present disclosure comprises use of antibodies or fragments thereof as a reagent for diagnosis, for example conjugated to a reporter molecule. Thus there is provided antibody or fragment according to the disclosure which is labelled. In one aspect there is provided a column comprising an antibody or fragment according to the disclosure.

Thus there is provided an anti-FcRn antibody or binding fragment for use as a reagent for such uses as:
1) purification of FcRn protein (or fragments thereof)—being conjugated to a matrix and used as an affinity column, or (as a modified form of anti-FcRn) as a precipitating agent (e.g. as a form modified with a domain recognised by another molecule, which may be modified by addition of an Fc (or produced as full length IgG), which is optionally precipitated by an anti-Fc reagent)

2) detection and/or quantification of FcRn on cells or in cells, live or fixed (cells in vitro or in tissue or cell sections). Uses for this may include quantification of FcRn as a biomarker, to follow the effect of anti-FcRn treatment. For these purposes, the candidate might be used in a modified form (e.g. by addition of an Fc domain, as in full length IgG, or some other moiety, as a genetic fusion protein or chemical conjugate, such as addition of a fluorescent tag used for the purposes of detection).

3) purification or sorting of FcRn-bearing cells labeled by binding to candidate modified by ways exemplified in (1) and (2).

Also provided by the present invention is provided an assay suitable for assessing the ability of a test molecule such as an antibody molecule to block FcRn activity and in particular the ability of the cells to recycle IgG. Such an assay may be useful for identifying inhibitors of FcRn activity, such as antibody molecules or small molecules and as such may also be useful as a batch release assay in the production of such an inhibitor.

In one aspect there is provided an assay suitable for assessing the ability of a test molecule such as an antibody molecule to block human FcRn activity and in particular the ability of human FcRn to recycle IgG, wherein the method comprises the steps of:
a) coating onto a surface non-human mammalian cells recombinantly expressing human FcRn alpha chain and human β2 microglobulin (β2M),
b) contacting the cells under mildly acidic conditions such as about pH5.9 with a test molecule and an IgG to be recycled by the cell for a period of time sufficient to allow binding of both the test molecule and the IgG to FcRn, optionally adding the test molecule before the IgG to be recycled and incubating for a period of time sufficient to allow binding of the test molecule to FcRn.
c) washing with a slightly acidic buffer, and
d) detecting the amount of IgG internalised and/or recycled by the cells.

In one aspect there is provided an assay suitable for assessing the ability of a test molecule such as an antibody molecule to block human FcRn activity and in particular the ability of human FcRn to recycle IgG, wherein the method comprises the steps of:
a) coating onto a surface non-human mammalian cells recombinantly expressing human FcRn alpha chain and human β2 microglobulin (β2M),
b) contacting the cells under mildly acidic conditions such as about pH5.9 with a test antibody molecule and an IgG to be recycled by the cell for a period of time sufficient to allow binding of both the test antibody molecule and the IgG to FcRn, optionally adding the test antibody molecule before the IgG to be recycled and incubating for a period of time sufficient to allow binding of the test antibody molecule to FcRn.
c) washing with a slightly acidic buffer to remove unbound IgG and test antibody molecule, and
d) detecting the amount of IgG recycled by the cells.

In one aspect there is provided an assay suitable for assessing the ability of a test molecule such as an antibody molecule to block human FcRn activity and in particular the ability of human FcRn to recycle IgG, wherein the method comprises the steps of:
- a) coating onto a surface non-human mammalian cells recombinantly expressing human FcRn alpha chain and human β2 microglobulin (β2M),
- b) contacting the cells under mildly acidic conditions such as about pH5.9 with a test antibody molecule and an IgG to be recycled by the cell for a period of time sufficient to allow binding of both the test antibody molecule and IgG to FcRn, optionally adding the test antibody molecule before the IgG to be recycled and incubating for a period of time sufficient to allow binding of the test antibody molecule to FcRn.
- c) washing with a slightly acidic buffer to remove unbound IgG and test antibody molecule,
- d) incubating the cells in a neutral buffer such as about pH 7.2
- e) detecting the amount of IgG recycled by the cells by determining the amount of IgG released into the supernatant.

Suitable cells include Madin-Darby Canine Kidney (MDCK) II cells. Transfection of MDCKII cells with human FcRn alpha chain and humanβ2 microglobulin (β2M) has previously been described by Claypool et al., 2002, Journal of Biological Chemistry, 277, 31, 28038-28050. This paper also describes recycling of IgG by these transfected cells.

Media for supporting the cells during testing includes complete media comprising MEM (Gibco #21090-022), 1× non-essential amino acids (Gibco 11140-035), 1× sodium pyruvate (Gibco #11360-039), and L-glutamine (Gibco #25030-024).

Acidic wash can be prepared by taking HBSS+(PAA #H15-008) and adding 1M MES until a pH 5.9+/−0.5 is reached. BSA about 1% may also be added (Sigma #A9647).

A neutral wash can be prepared by taking HBSS+(PAA #H15-008) and adding 10M Hepes pH 7.2+/−0.5 is reached. BSA about 1% may also be added (Sigma #A9647).

Washing the cells with acidic buffer removes the unbound test antibody and unbound IgG and allows further analysis to be performed. Acidic conditions used in step (b) encourage the binding of the IgG to FcRn and internalisation and recycling of the same.

The amount of test antibody or fragment and IgG on only the surface of the cells may be determined by washing the cells with neutral wash and analysing the supernatant/washings to detect the quantity of test antibody or IgG. Importantly a lysis buffer is not employed. To determine the amount of IgG internalised by the cells the antibody may first be removed from the surface of the cell with a neutral wash and the cells lysed by a lysis buffer and then the internal contents analysed. To determine the amount of IgG recycled by the cells the cells are incubated under neutral conditions for a suitable period of time and the surrounding buffer analysed for IgG content. If the surface and internal antibody content of the cell is required then the cell can be washed with acid wash to maintain the antibody presence on the cell surface, followed by cell lysis and analysis of the combined material.

Where it is desired to measure both internalisation and recycling of the IgG samples are run in duplicate and testing for internalisation and recycling conducted separately.

A suitable lysis buffer includes 150 mM NaCl, 20 mM Tris, pH 7.5, 1 mM EDTA, 1 mM EGTA, 1% Triton-X 100, for each 10 ml add protease inhibitors/phosphate inhibitors as described in manufacturer's guidelines.

Typically the IgG to be recycled is labelled, in one example a biotinylated human IgG may be used. The IgG can then be detected employing, for example a streptavidin sulfo-tag detection antibody (such as MSD #r32ad-5) 25 mL at 0.2 ug/mL of MSD blocking buffer. Blocking buffer may comprise 500 mM Tris, pH7.5. 1.5M NaCl and 0.2% Tween-20 and 1.5% BSA.

Alternatively the IgG may be pre-labelled with a fluorophore or similar label.

In one embodiment a suitable surface is a plastic plate or well such as a 96 well plate or similar, a glass slide or a membrane. In one example cells are coated onto the surface at a density that results in the formation of a monolayer.

In one embodiment the assay described herein is not a measurement of transcytosis of an antibody top to bottom across a membrane with a pH gradient there-across, for example acid conditions one side of the membrane and neutral conditions on the underside of the membrane.

In one example the test antibody or fragment and IgG may be incubated with the cells in step (b) for about 1 hour for example at ambient temperature under acidic conditions to allow binding.

In one example the test antibody or fragment may be incubated with the cells in step (b) for about 1 hour for example at ambient temperature under acidic conditions to allow binding before addition of the IgG to be recycled. Subsequently the IgG to be recycled by the cell may be incubated with the cells in step (b) for about 1 hour for example at ambient temperature under acidic conditions to allow binding.

Neutral conditions facilitate release of the IgG into the supernatant.

Comprising in the context of the present specification is intended to meaning including. Where technically appropriate embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

The present invention is further described by way of illustration only in the following examples, which refer to the accompanying Figures, in which:

FIG. 1 shows certain amino acid and polynucleotide sequences.

Figure 2:
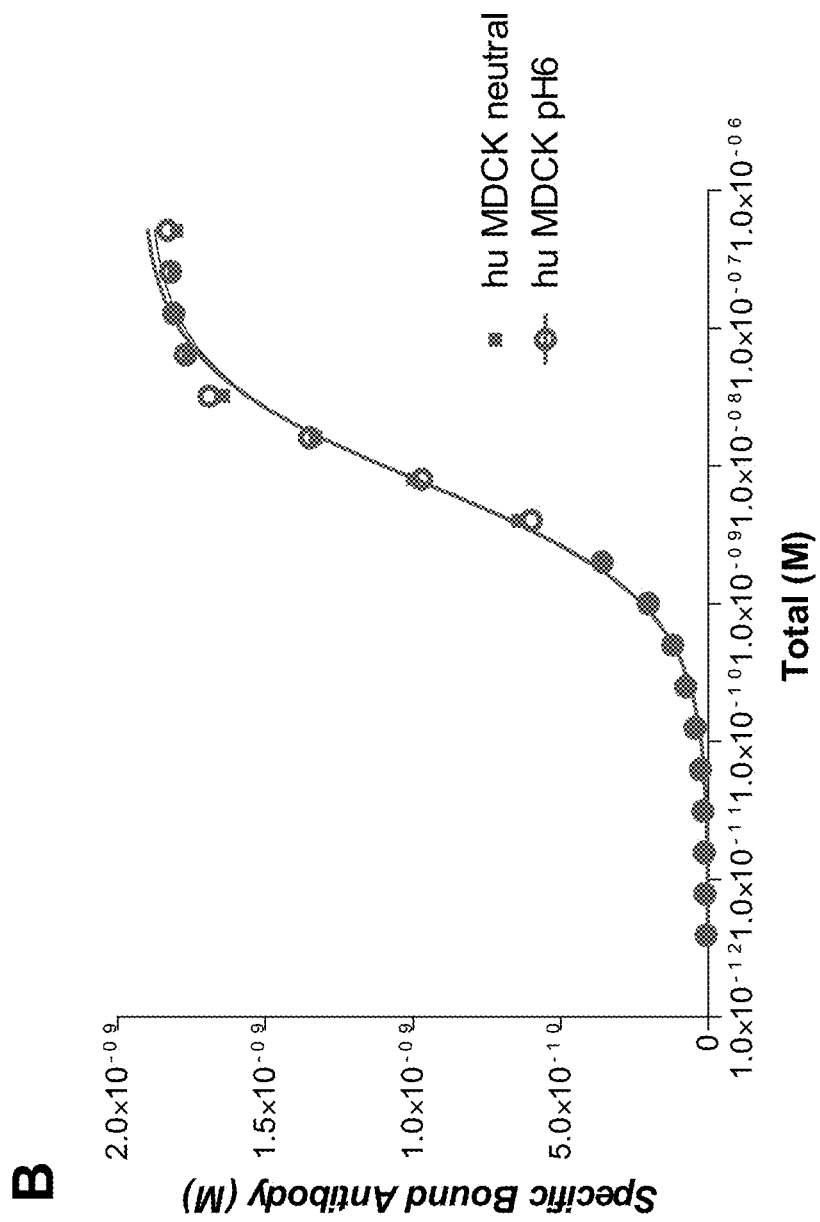
FIGS. 2A-2B shows alignments of certain sequences.

FIG. 2 shows alignments of certain sequences.

Figure 3:
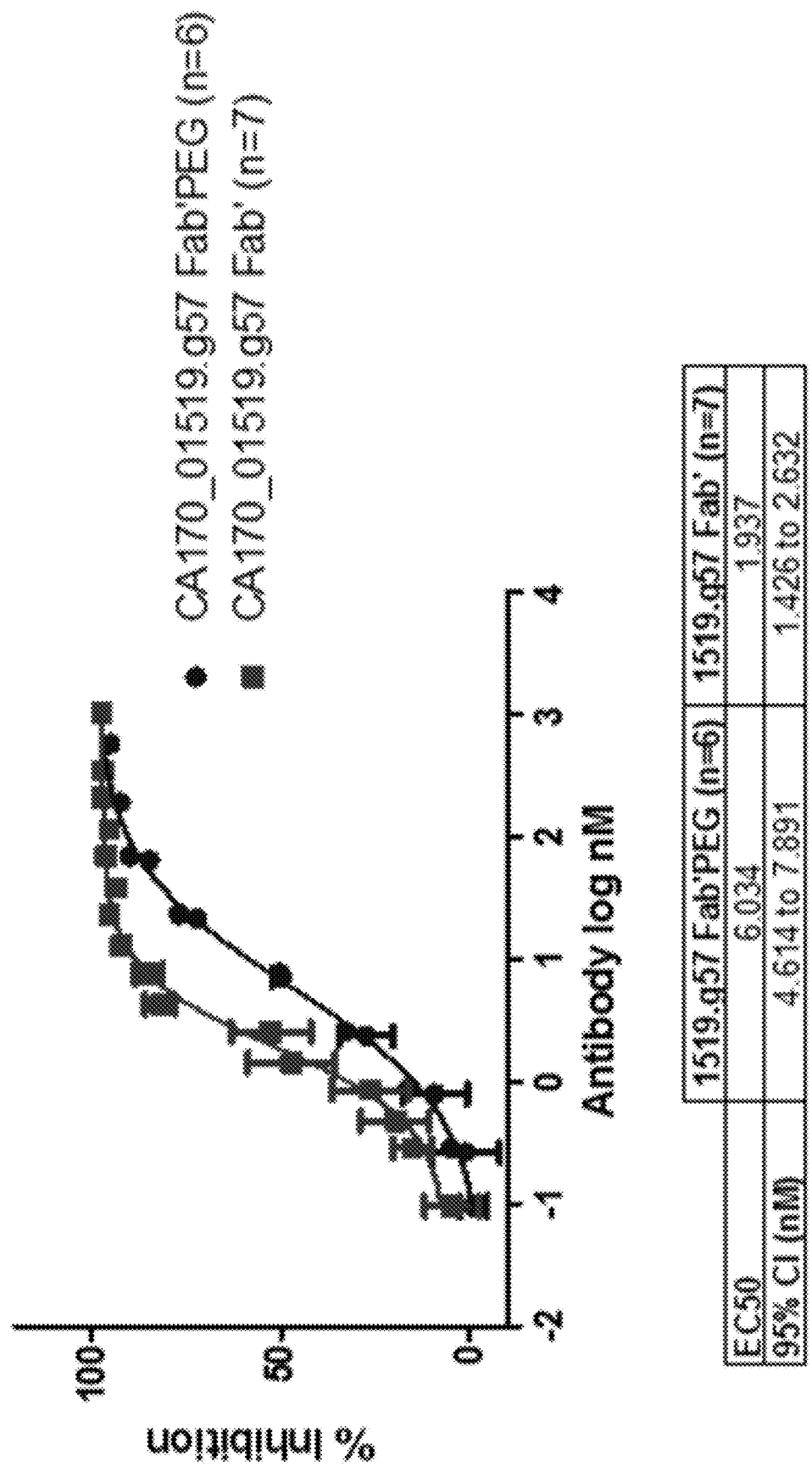
FIGS. 3A-3B shows a comparison of binding on human MDCK II for a Fab' fragment according to the present disclosure and a PEGylated version thereof
Figure 4:
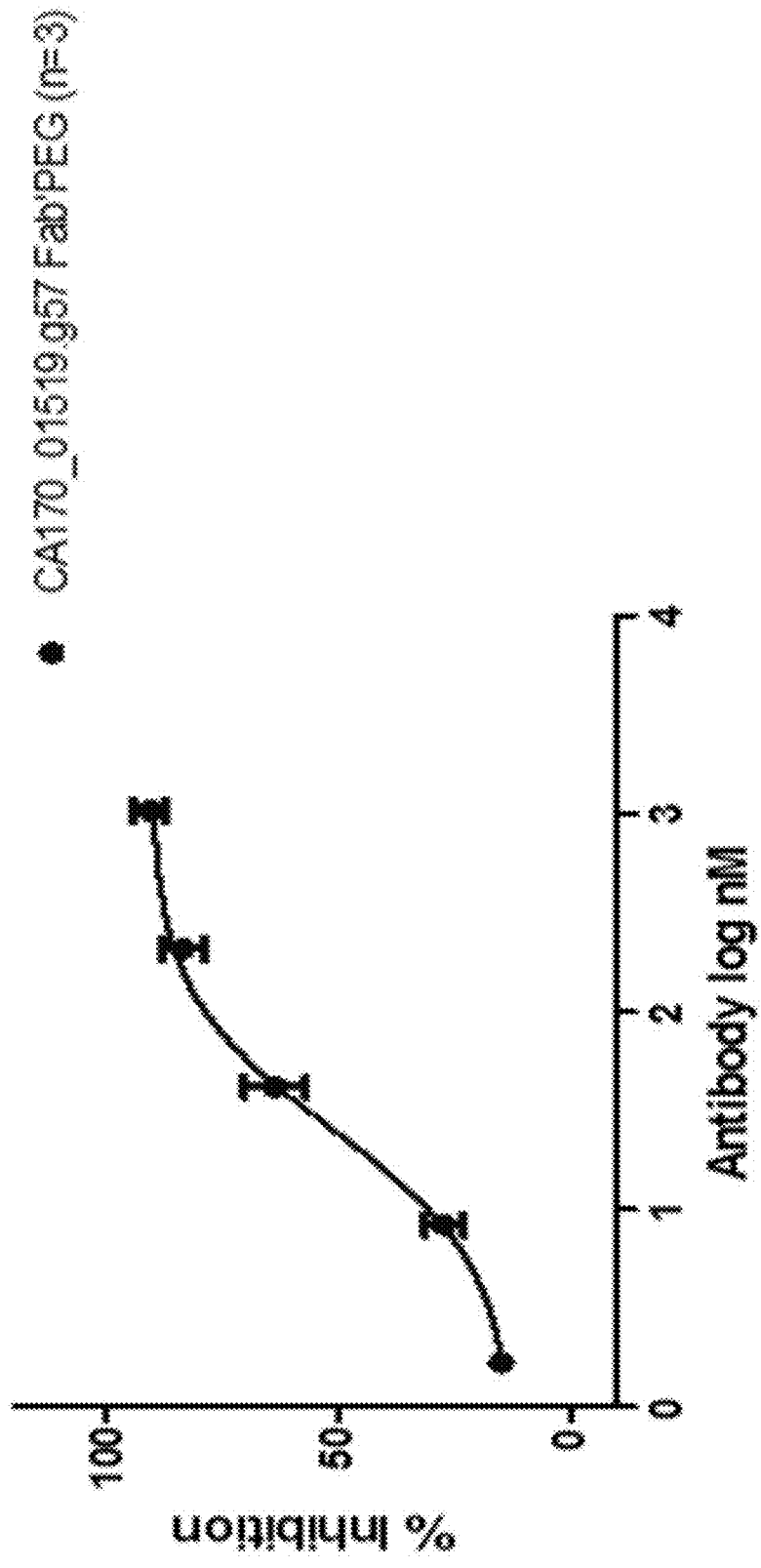
FIG. 4 shows a Fab' fragment according to the present disclosure and a PEGylated version thereof inhibiting IgG recycling on MDCK II cells
Figure 5:
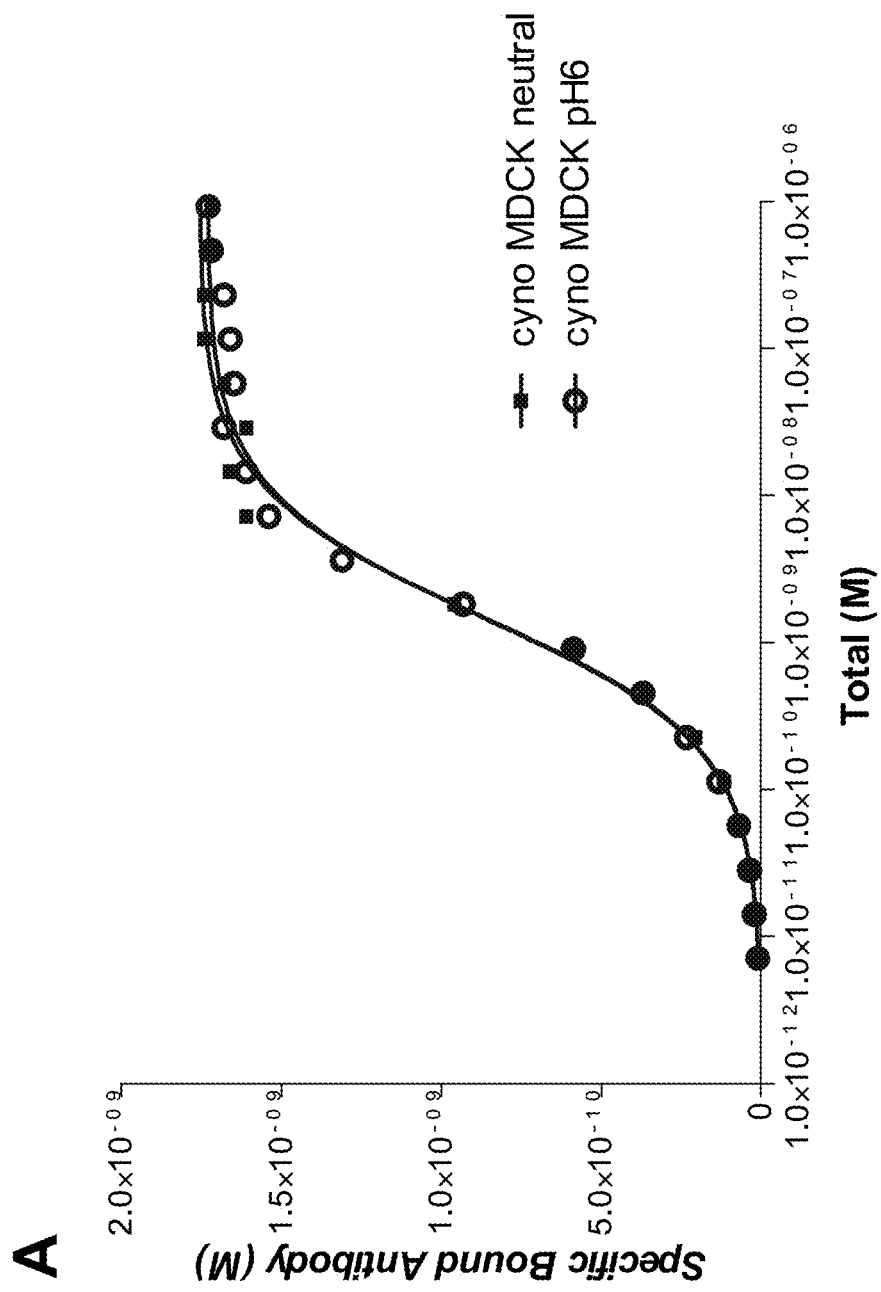
FIG. 5 shows a PEGylated Fab' fragment according to the present disclosure inhibits apical to basolateral IgG trancytosis in MDCK II cells
Figure 6:
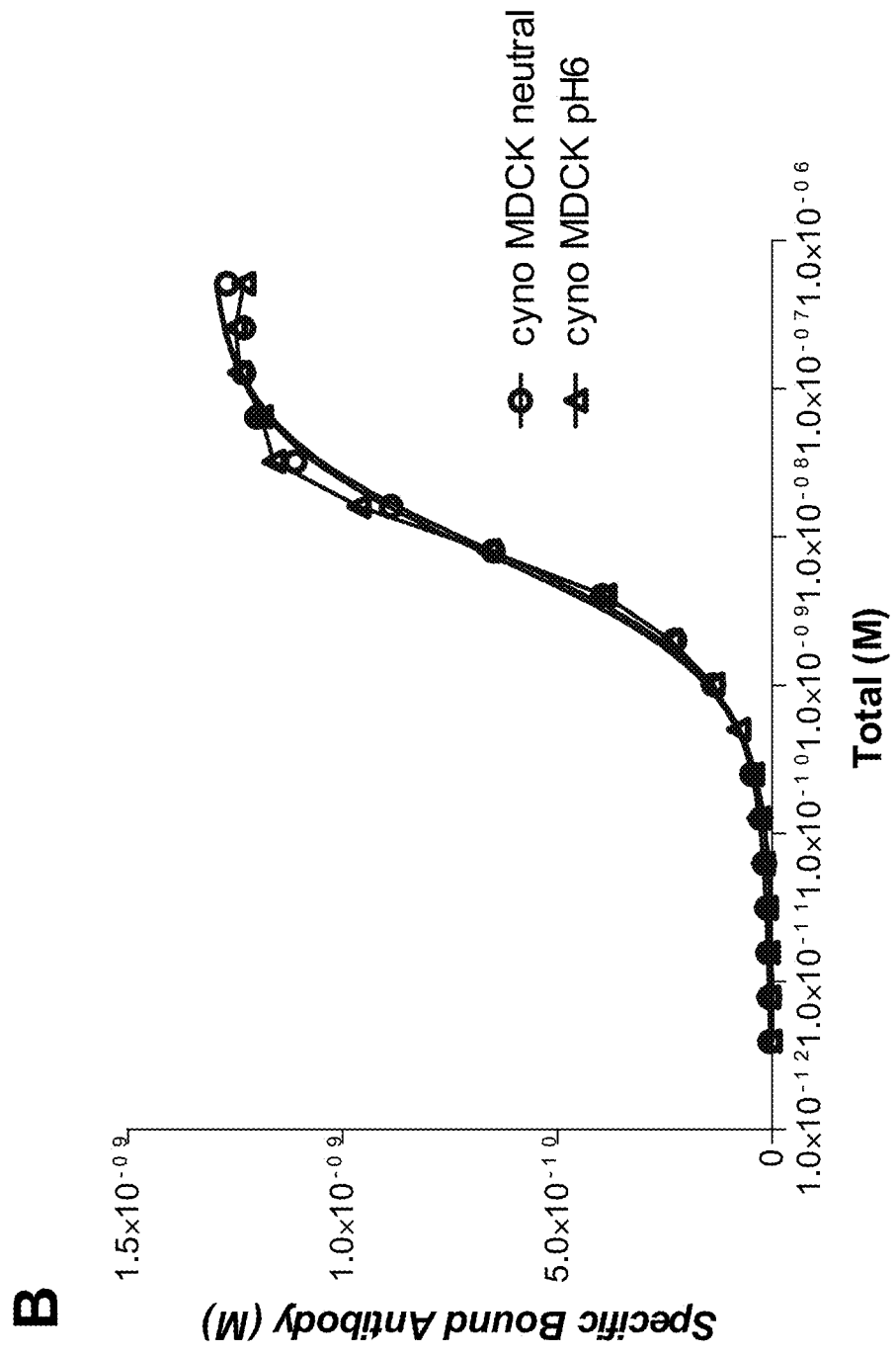
FIGS. 6A-6B shows a comparison of binding of cyno monkey MDCK II for a Fab' fragment according to the present disclosure and a PEGylated version thereof
Figure 7:
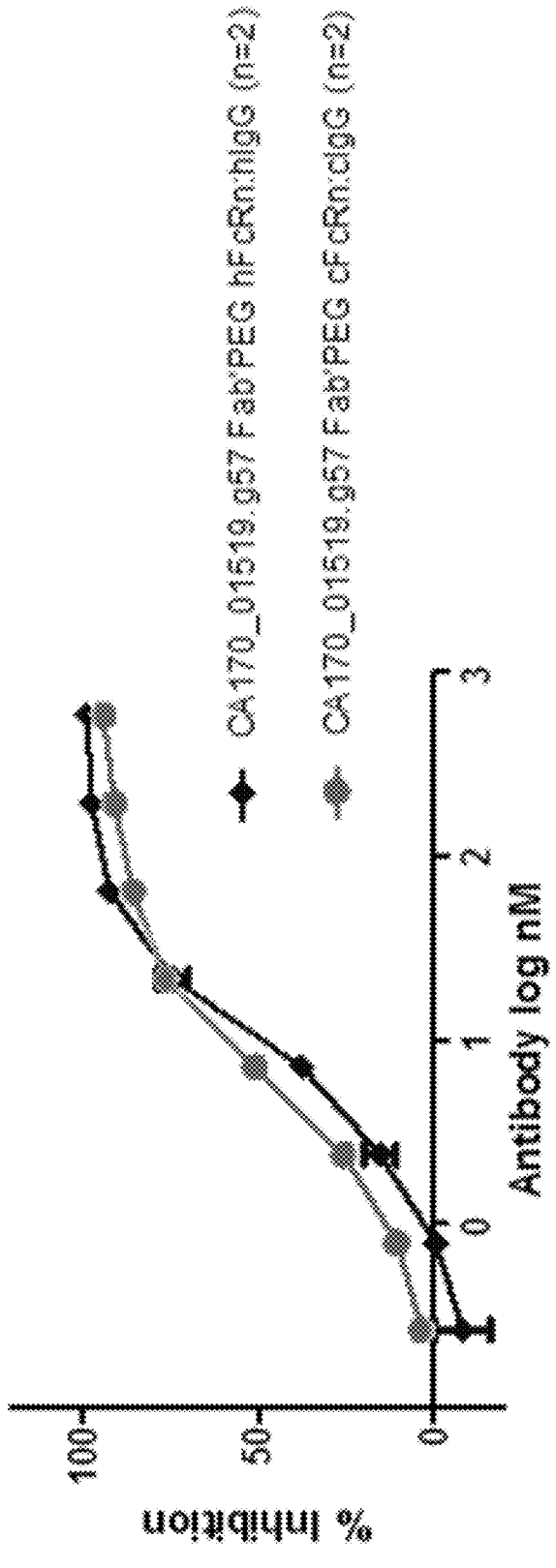
FIG. 7 shows a PEGylated Fab' fragment according to the present inhibiting IgG recycling on MDCK II cells for human and cyno monkey versions thereof
Figure 8:
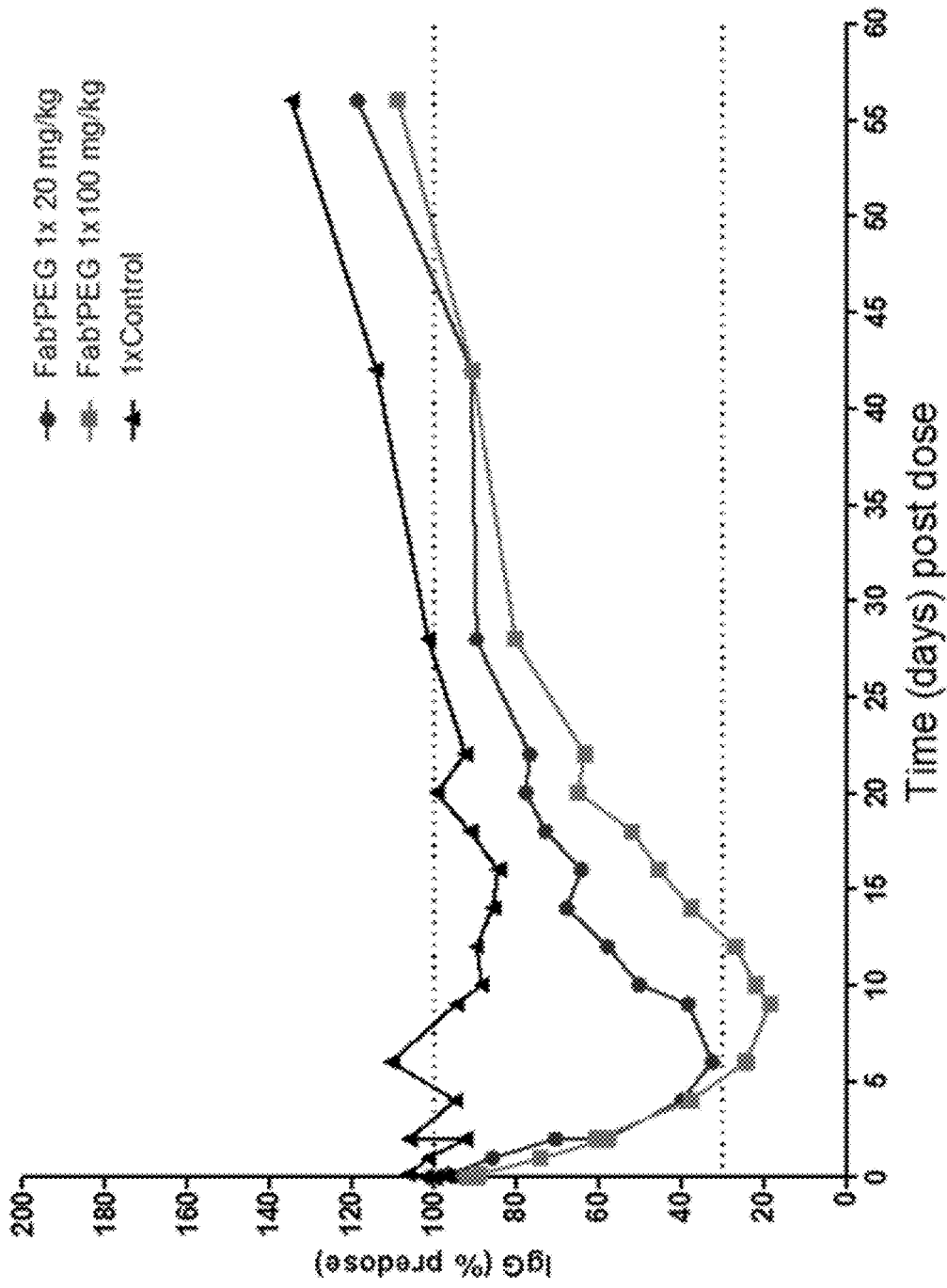
FIG. 8 shows the effect of a single dose of a PEGylated Fab' molecule according to the disclosure on plasma IgG levels in cynomolgus monkeys
Figure 9:
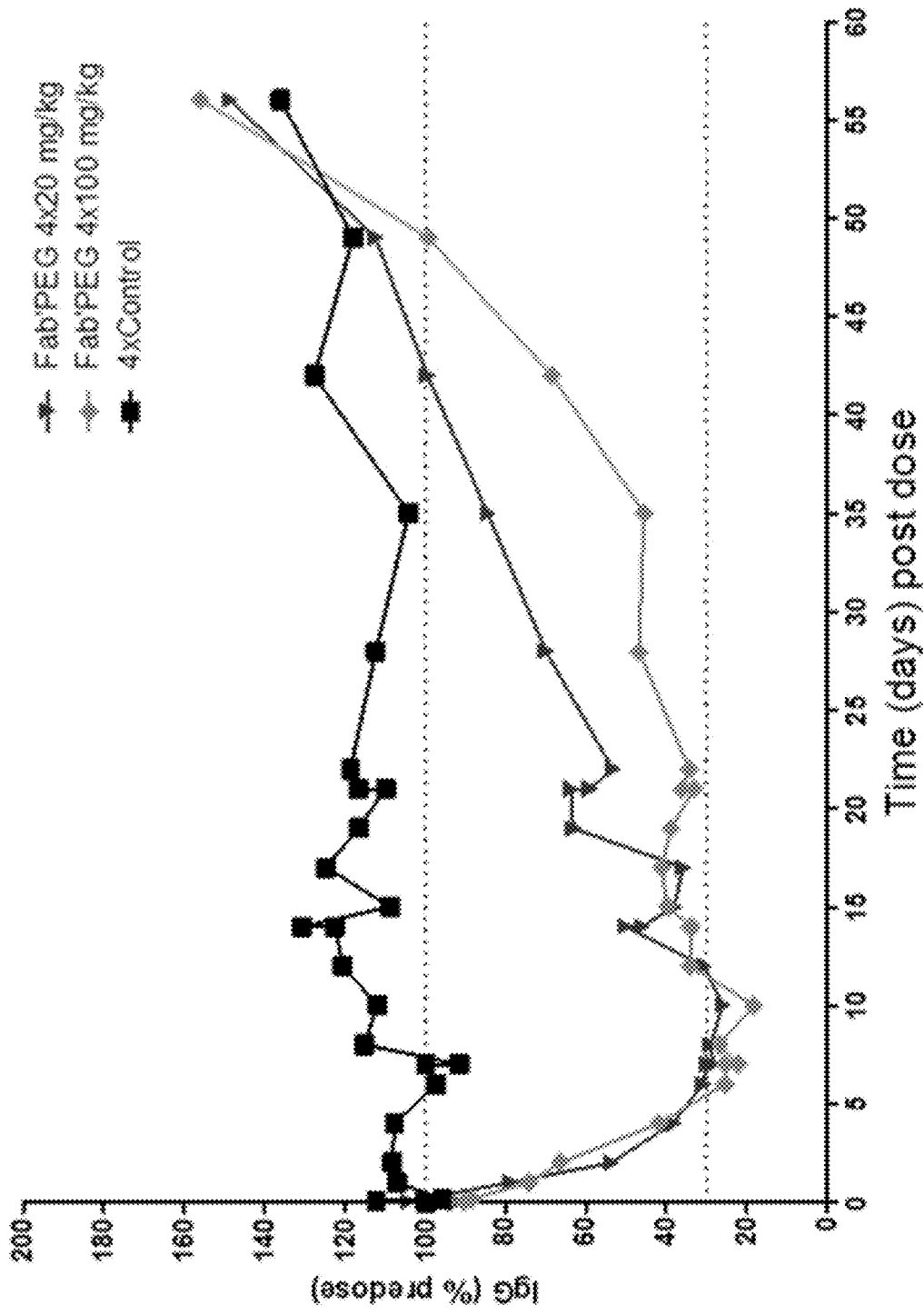
FIG. 9 shows the effect of four weekly doses of a PEGylated Fab' molecule according to the disclosure on plasma IgG levels
Figure 10:
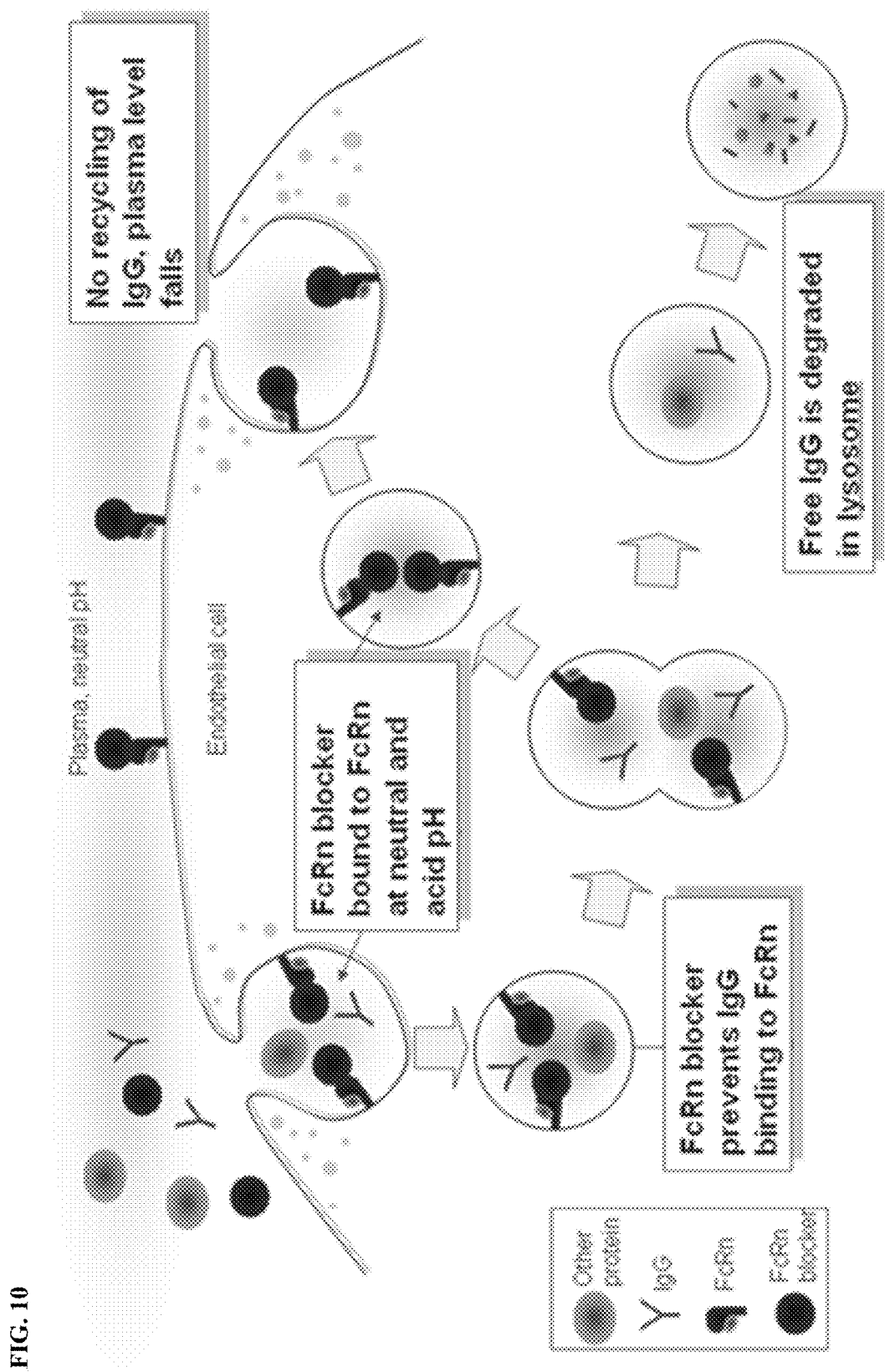
FIG. 10 shows a diagrammatic representation of antibody recycling function of FcRn inhibited by a blocking protein
Figure 11:
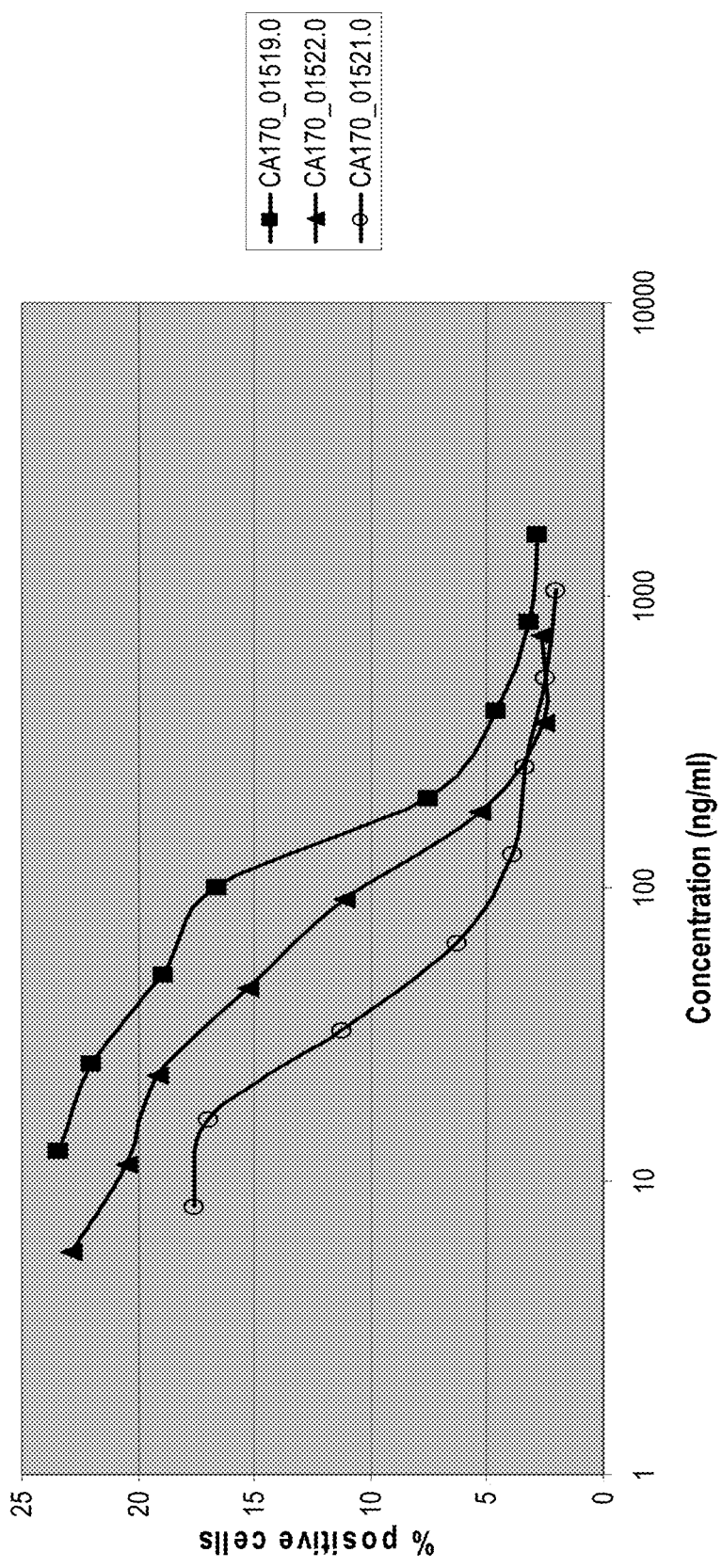
FIG. 11 shows flow cytometry based human IgG blocking assay using purified gamma 1 IgG antibodies
Figure 12:
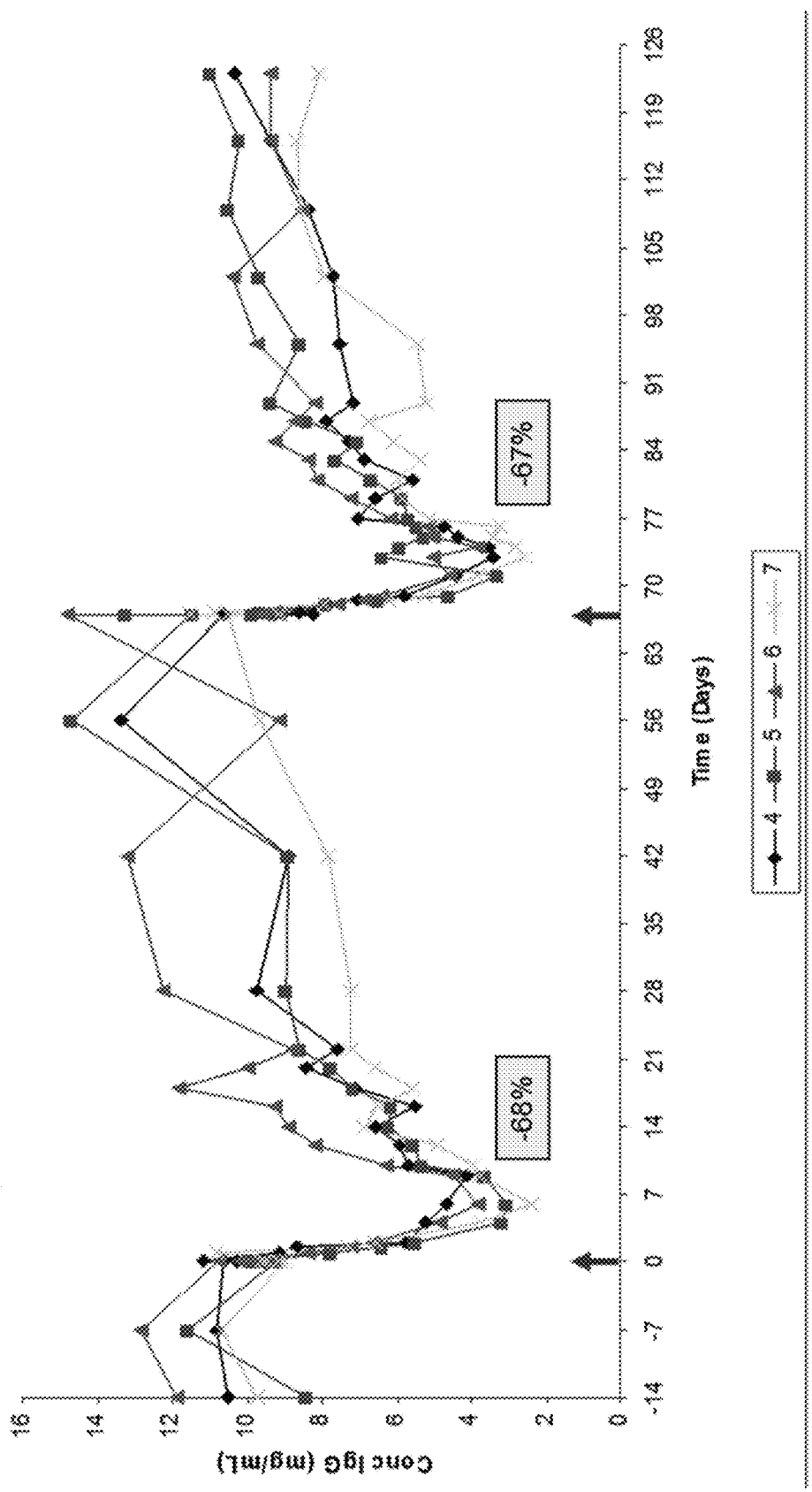
FIG. 12 shows Fab'PEG single/intermittent IV doses in normal cyno 20 mg/Kg days 1 and 67 IgG pharmacodynamics
Figure 13:
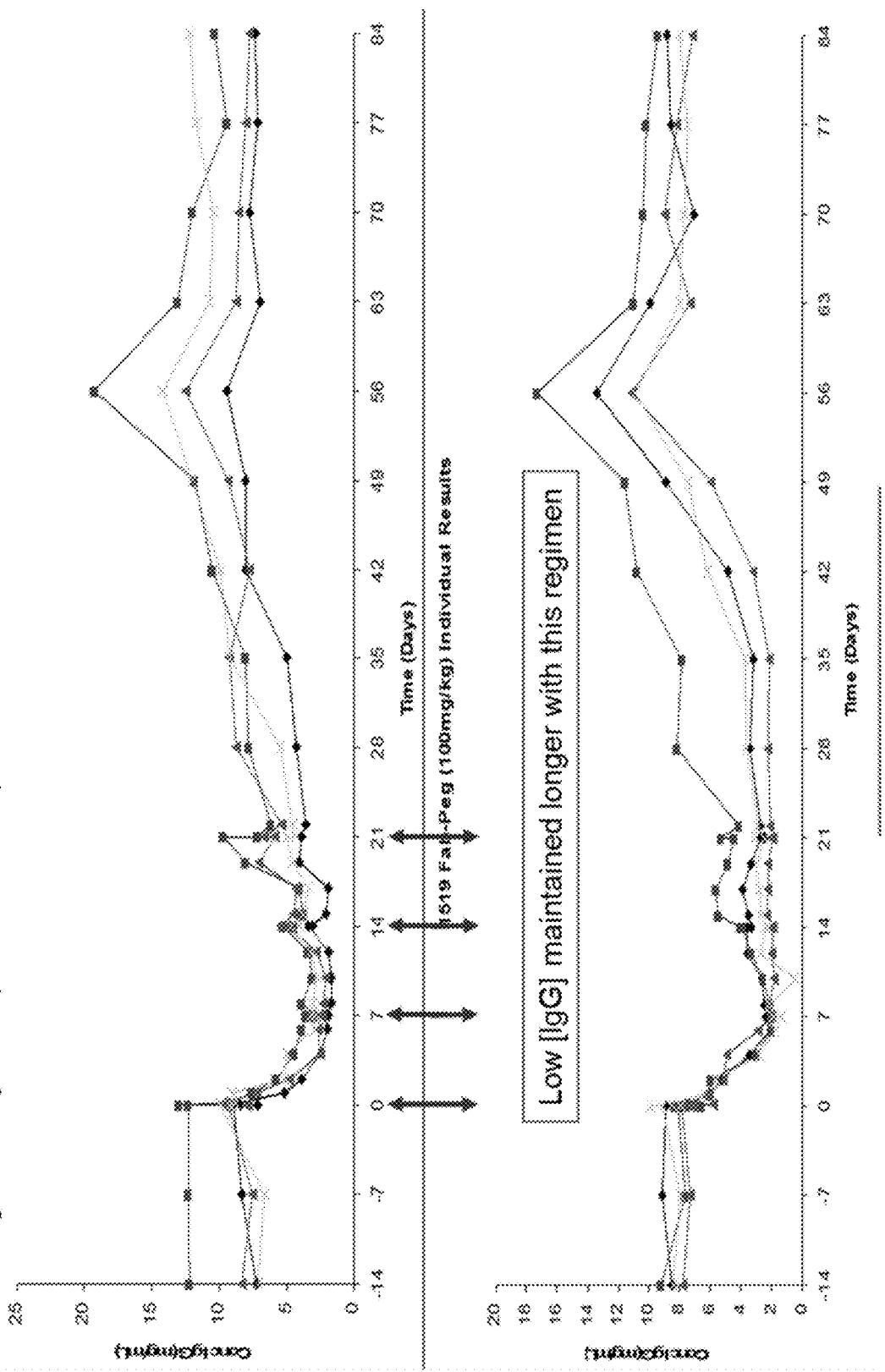
FIG. 13 shows Fab'PEG: repeat IV doses in normal cyno-4×20 or 100 mg/Kg per week IgG pharmacodynamics
Figure 14:
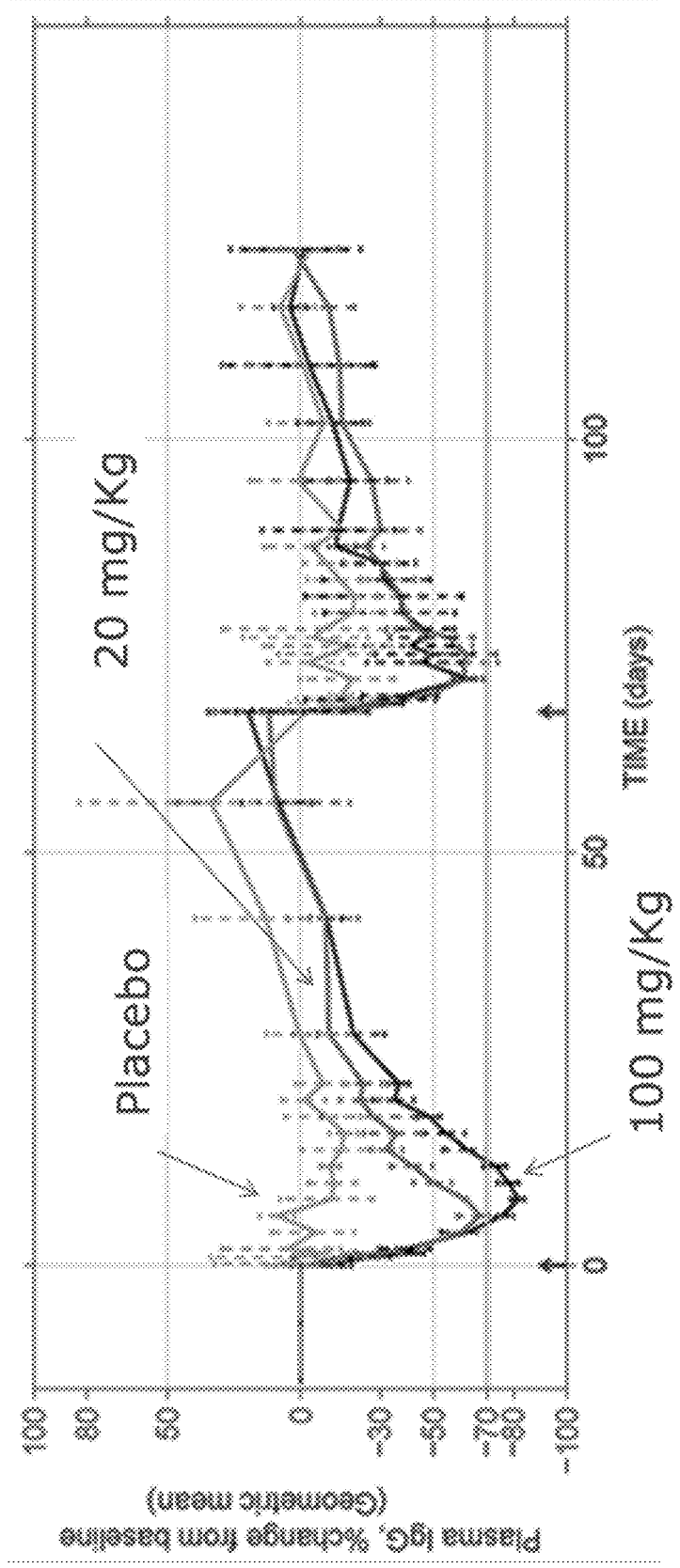
FIG. 14 shows Fab'PEG single/intermittent IV doses in normal cyno –20 mg/Kg and 100 mg/Kg days 1 and 67 IgG Pharmacodynamics
Figure 15:
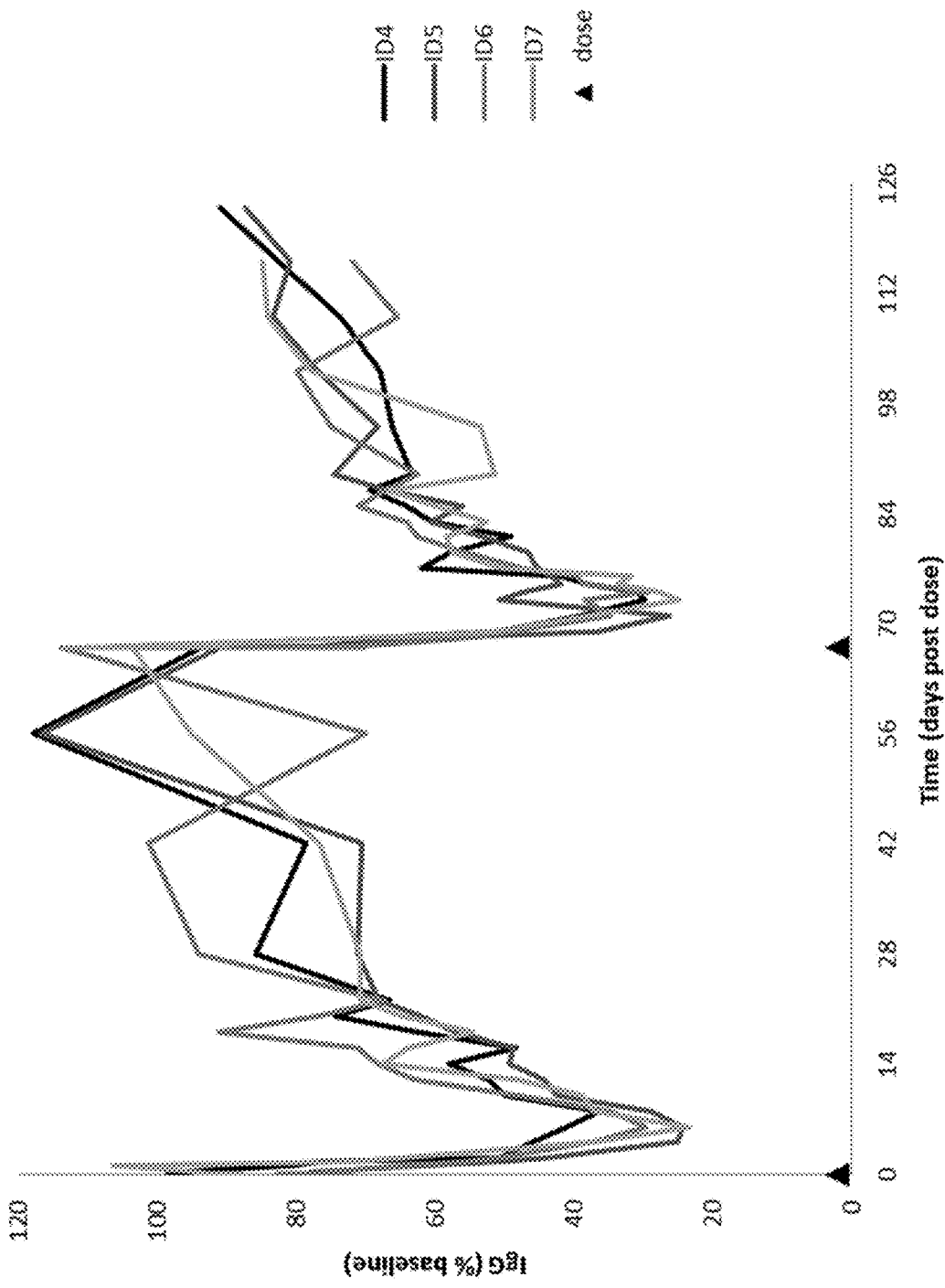
FIG. 15 shows plasma IgG levels in 4 cynomolgus monkeys after 2 IV doses of 20 mg/Kg 1519.g57 Fab'PEG
Figure 16:
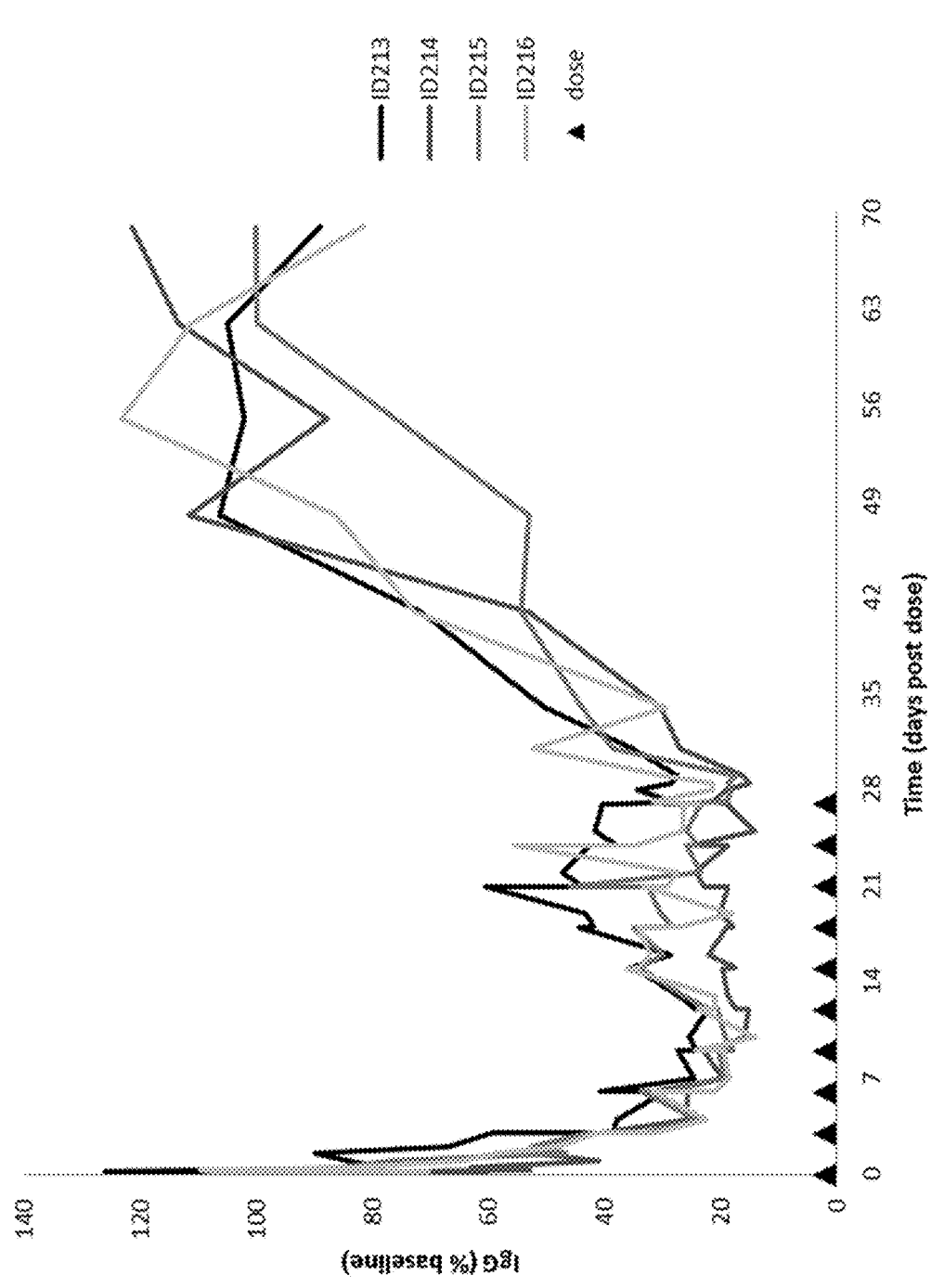
FIG. 16 shows plasma IgG levels in 4 cynomolgus monkeys receiving 10 IV doses of 20 mg/Kg 1519.g57 Fab'PEG, one every 3 days
Figure 17:
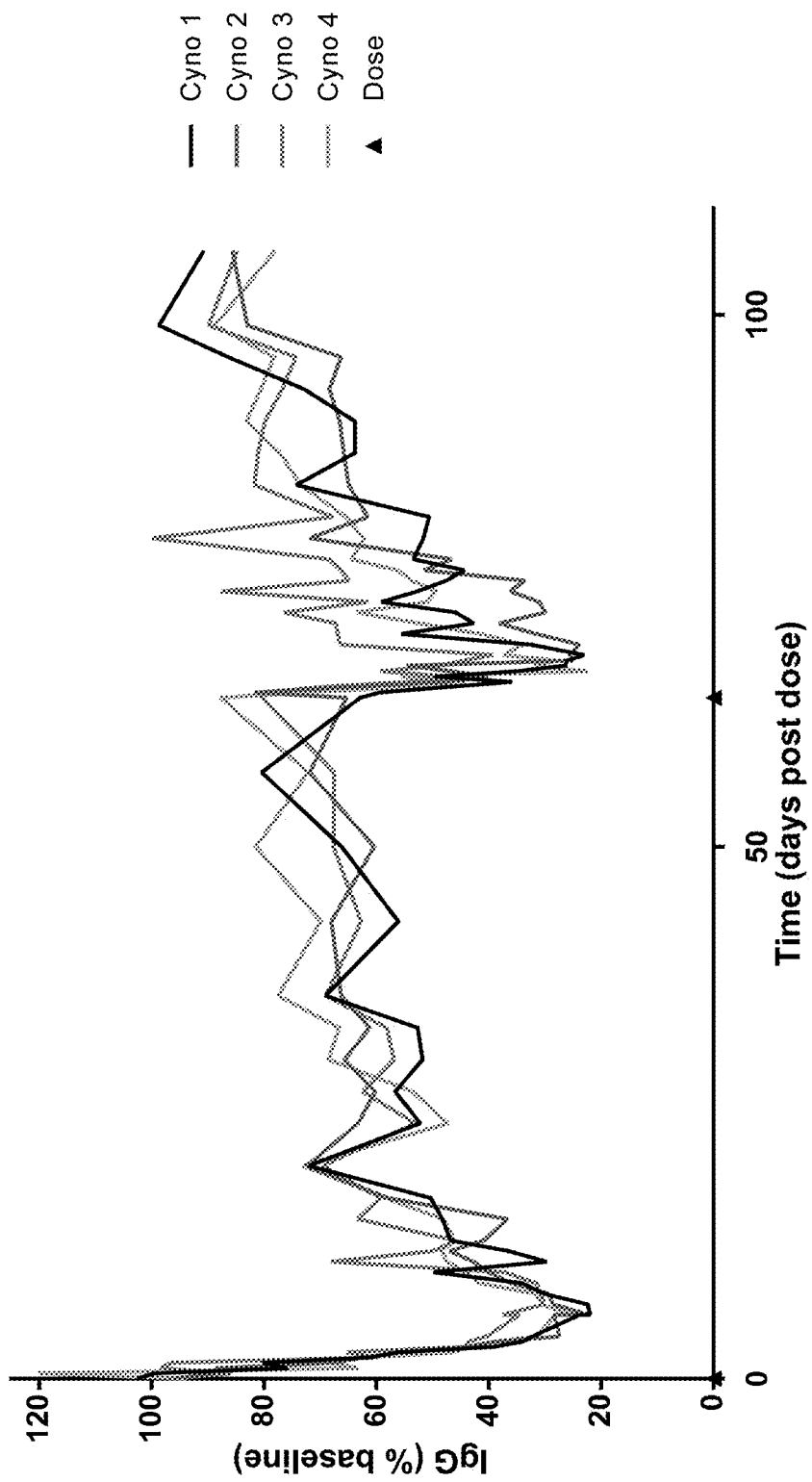
FIG. 17 shows the effect of two 30 mg/Kg IV doses of 1519.g57 IgG4P on the endogenous plasma IgG in cynomolgus monkeys
Figure 18:
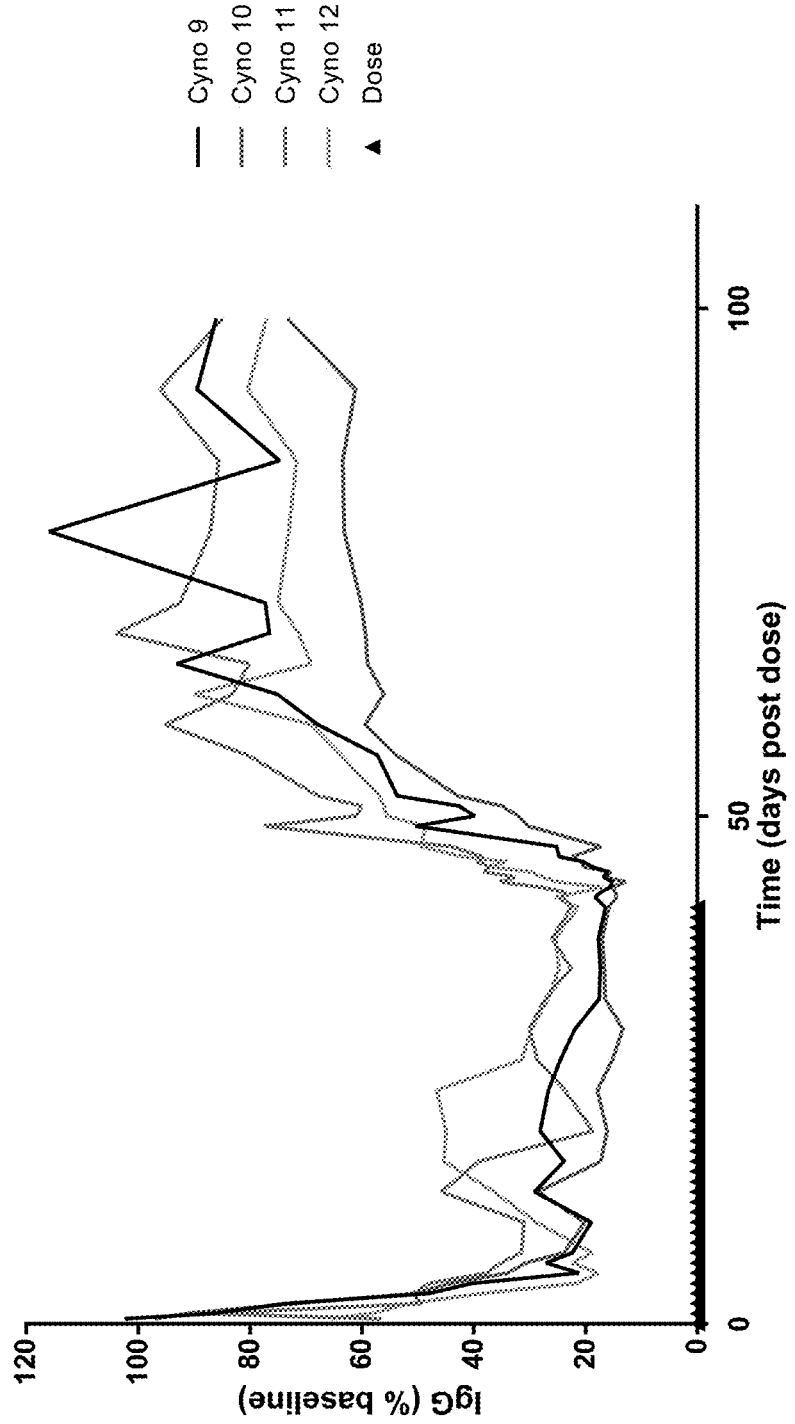
FIG. 18 shows the effect of 30 mg/Kg if followed by 41 daily doses of 5 mg/Kg 1519.g57 IgG4P on plasma IgG in cynomolgus monkeys
Figure 19:
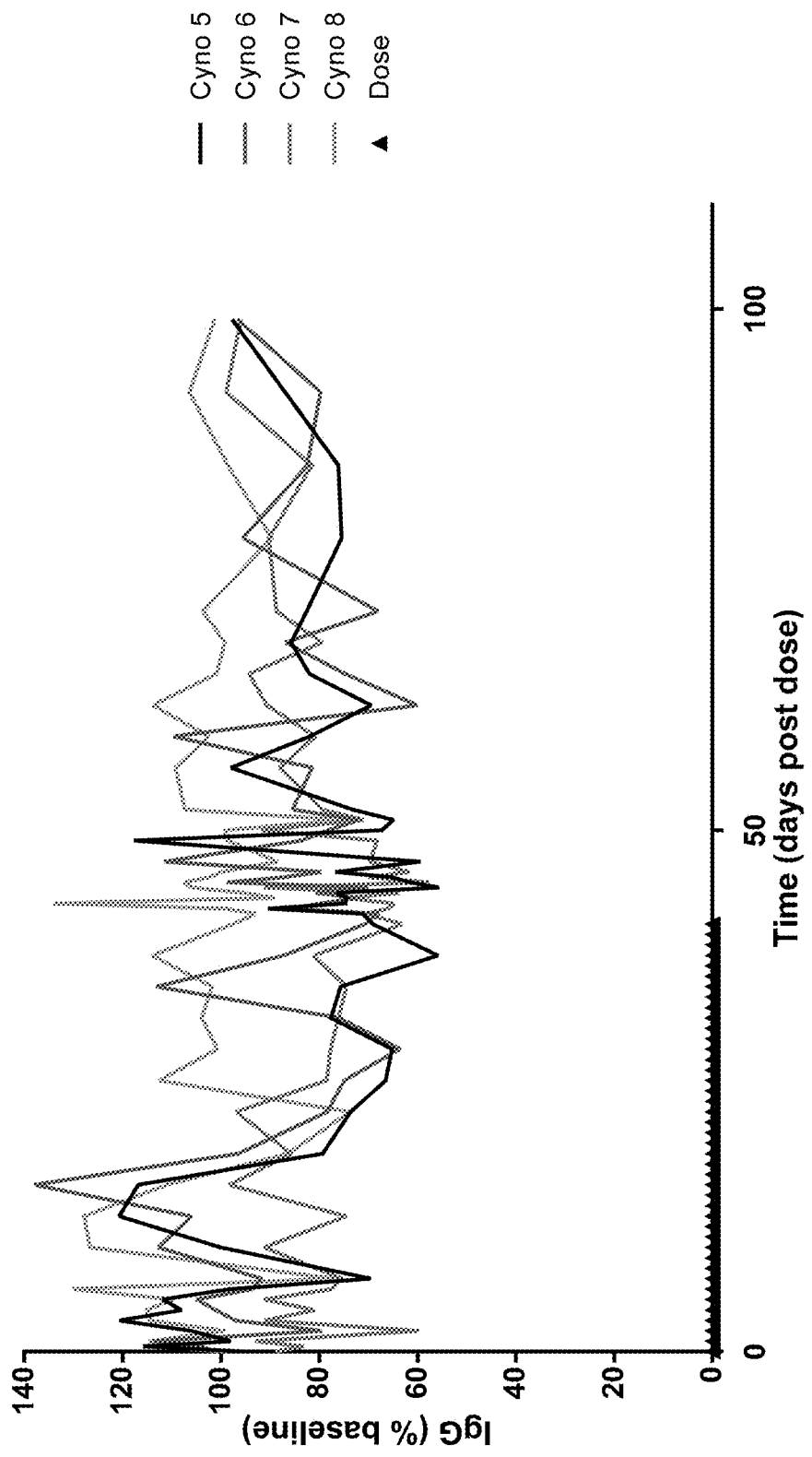
FIG. 19 shows the result of daily dosing with vehicle on the plasma IgG in cynomolgus monkeys
Figure 20:
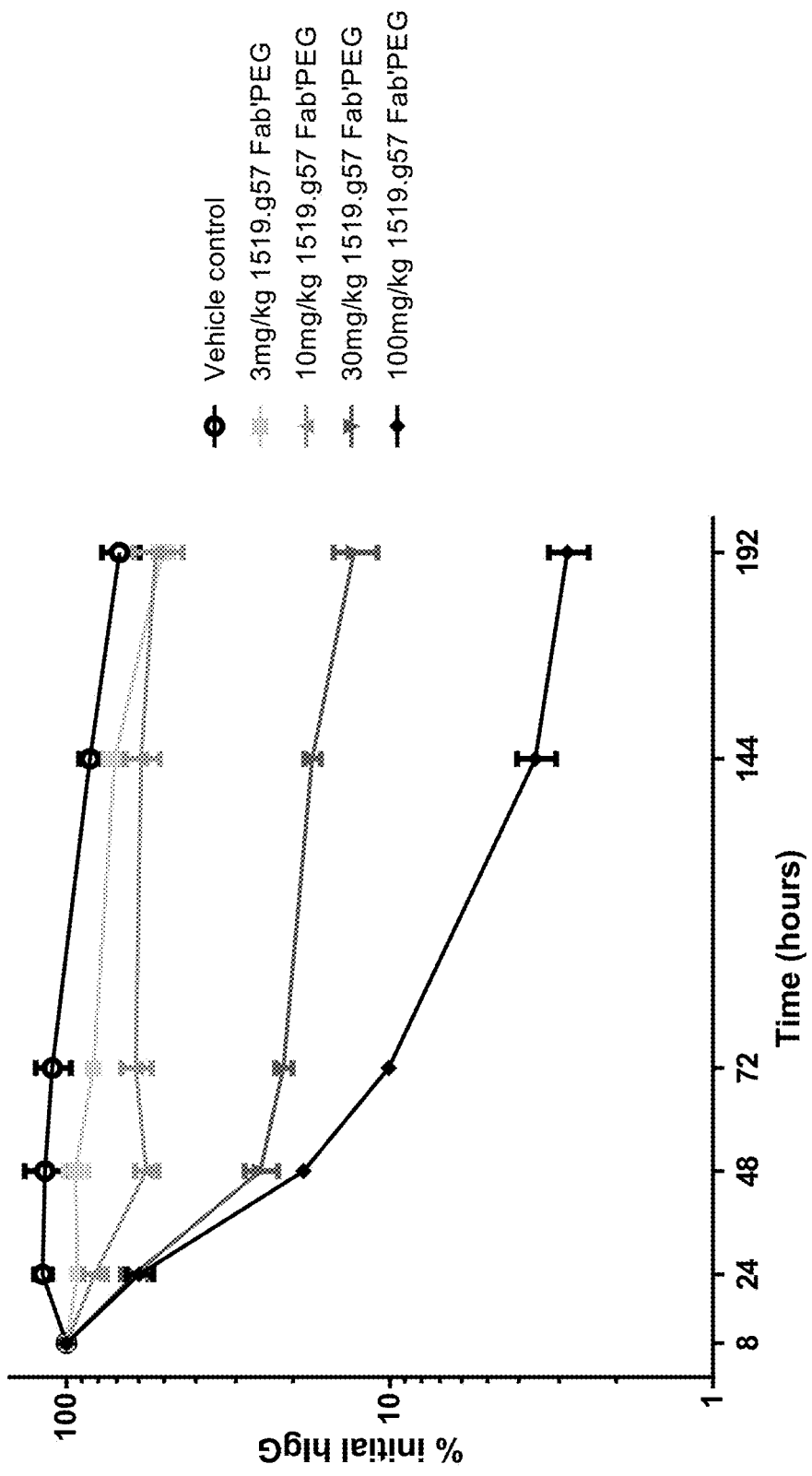
FIG. 20 shows the increased clearance of IV hIgG in plasma of hFcRn transgenic mice treated with CA170_01519.g57 Fab'PEG or PBS IV
Figure 21:
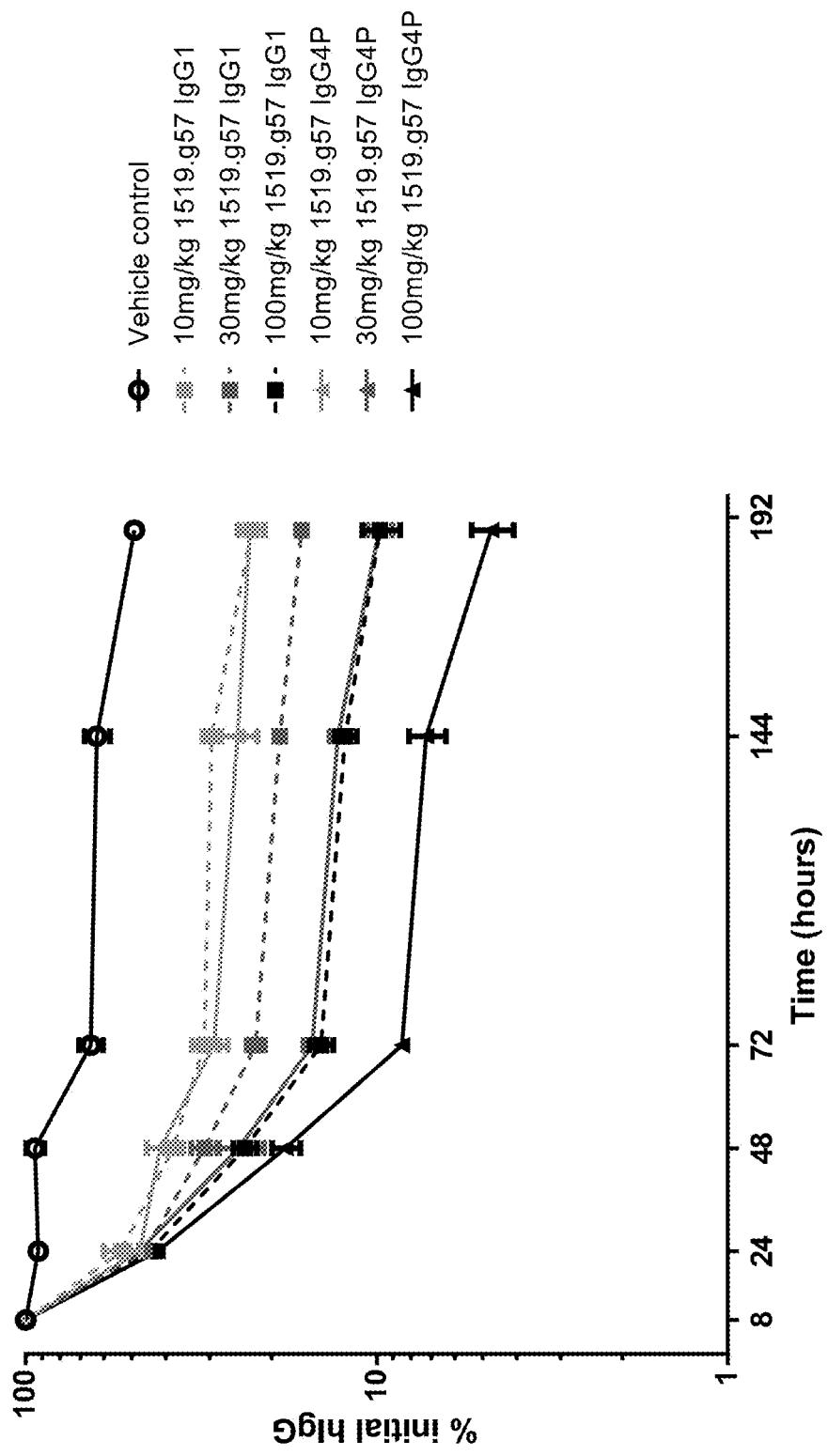
FIG. 21 shows the increased clearance of IV hIgG in plasma of hFcRn transgenic mice treated with CA170_01519.g57 IgG1 or IgG4 or PBS IV
Figure 22:
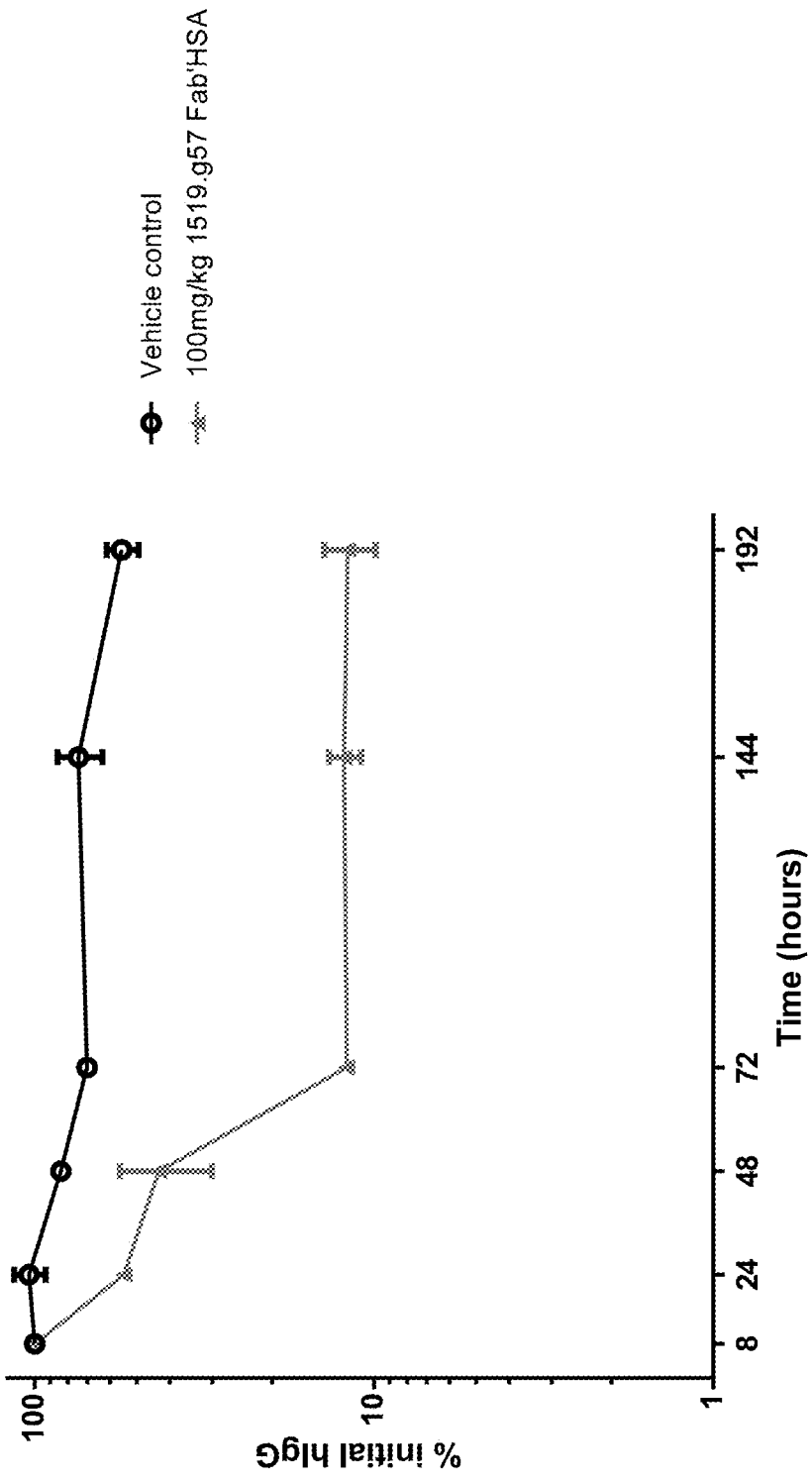
FIG. 22 shows the increased clearance of IV hIgG in plasma of hFcRn transgenic mice treated with CA170_01519.g57 Fab'-human serum albumin or PBS IV
Figure 23:
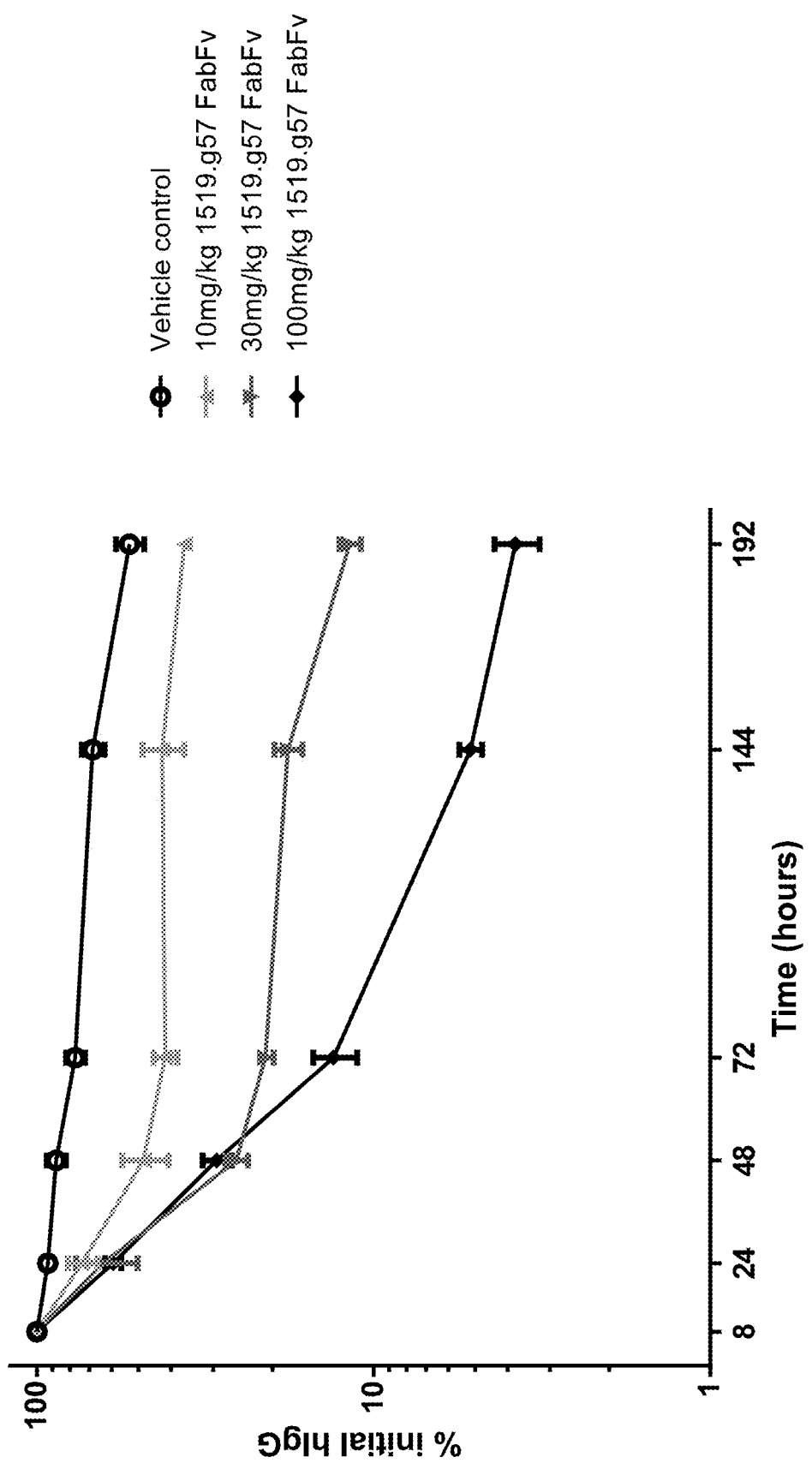
FIG. 23 shows the increased clearance of IV hIgG in plasma of hFcRn transgenic mice treated with CA170_01519.g57 FabFv or PBS IV
Figure 24:
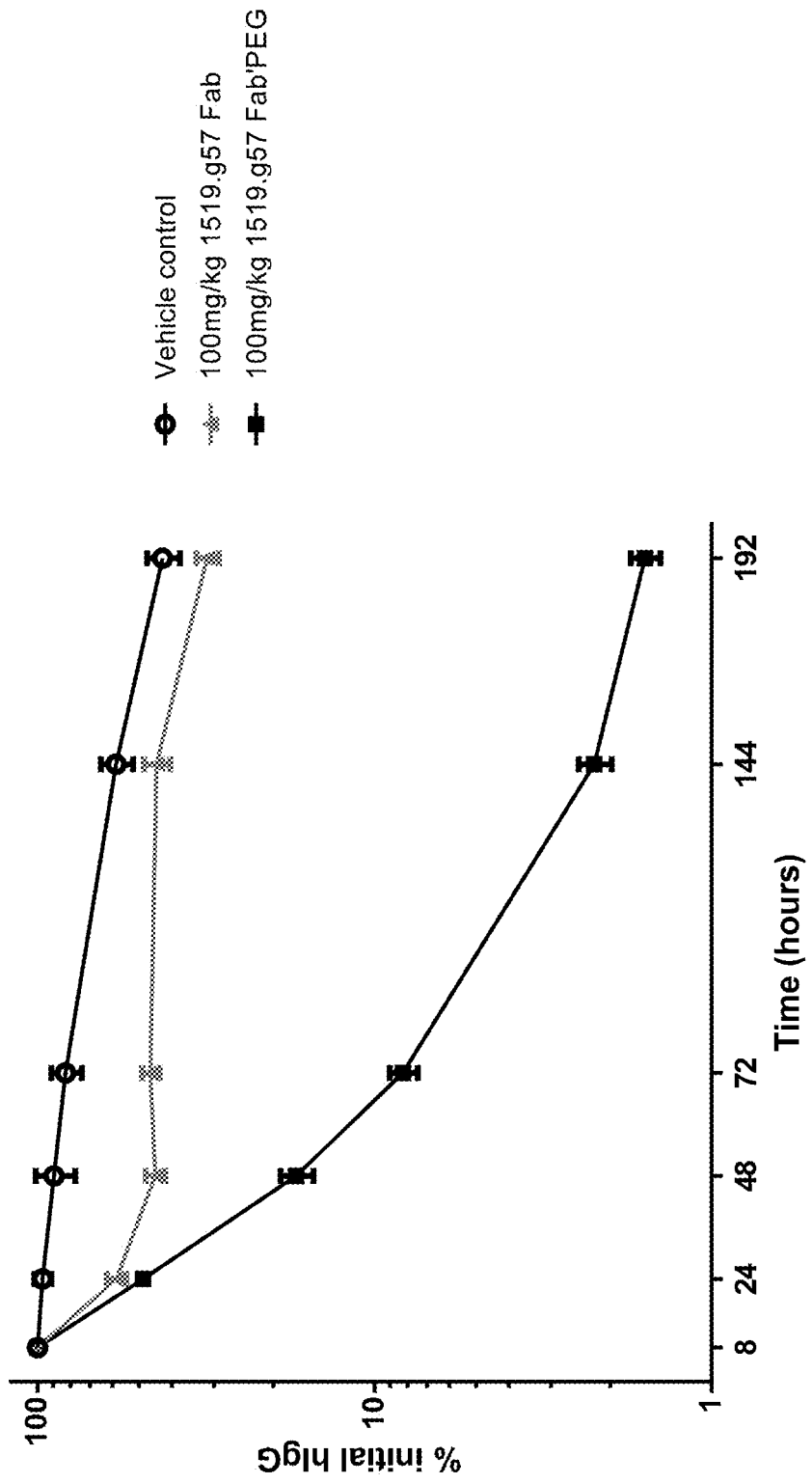
FIG. 24 shows the increased clearance of IV hIgG in plasma of hFcRn transgenic mice treated with CA170_01519.g57 Fab or Fab'PEG or PBS IV

FIG. 3 shows a comparison of binding on human MDCK II for a Fab' fragment according to the present disclosure and a PEGylated version thereof FIG. 4 shows a Fab' fragment according to the present disclosure and a PEGylated version thereof inhibiting IgG recycling on MDCK II cells FIG. 5 shows a PEGylated Fab' fragment according to the present disclosure inhibits apical to basolateral IgG trancytosis in MDCK II cells FIG. 6 shows a comparison of binding of cyno monkey MDCK II for a Fab' fragment according to the present disclosure and a PEGylated version thereof FIG. 7 shows a PEGylated Fab' fragment according to the present inhibiting IgG recycling on MDCK II cells for human and cyno monkey versions thereof FIG. 8 shows the effect of a single dose of a PEGylated Fab' molecule according to the disclosure on plasma IgG levels in cynomolgus monkeys FIG. 9 shows the effect of four weekly doses of a PEGylated Fab' molecule according to the disclosure on plasma IgG levels FIG. 10 shows a diagrammatic representation of antibody recycling function of FcRn inhibited by a blocking protein FIG. 11 shows flow cytometry based human IgG blocking assay using purified gamma 1 IgG antibodies FIG. 12 shows Fab'PEG single/intermittent IV doses in normal cyno 20 mg/Kg days 1 and 67 IgG pharmacodynamics FIG. 13 shows Fab'PEG: repeat IV doses in normal cyno-4×20 or 100 mg/Kg per week IgG pharmacodynamics FIG. 14 shows Fab'PEG single/intermittent IV doses in normal cyno –20 mg/Kg and 100 mg/Kg days 1 and 67 IgG Pharmacodynamics FIG. 15 shows plasma IgG levels in 4 cynomolgus monkeys after 2 IV doses of 20 mg/Kg 1519.g57 Fab'PEG FIG. 16 shows plasma IgG levels in 4 cynomolgus monkeys receiving 10 IV doses of 20 mg/Kg 1519.g57 Fab'PEG, one every 3 days FIG. 17 shows the effect of two 30 mg/Kg IV doses of 1519.g57 IgG4P on the endogenous plasma IgG in cynomolgus monkeys FIG. 18 shows the effect of 30 mg/Kg if followed by 41 daily doses of 5 mg/Kg 1519.g57 IgG4P on plasma IgG in cynomolgus monkeys FIG. 19 shows the result of daily dosing with vehicle on the plasma IgG in cynomolgus monkeys FIG. 20 shows the increased clearance of IV hIgG in plasma of hFcRn transgenic mice treated with CA170_01519.g57 Fab'PEG or PBS IV FIG. 21 shows the increased clearance of IV hIgG in plasma of hFcRn transgenic mice treated with CA170_01519.g57 IgG1 or IgG4 or PBS IV FIG. 22 shows the increased clearance of IV hIgG in plasma of hFcRn transgenic mice treated with CA170_01519.g57 Fab'-human serum albumin or PBS IV FIG. 23 shows the increased clearance of IV hIgG in plasma of hFcRn transgenic mice treated with CA170_01519.g57 FabFv or PBS IV FIG. 24 shows the increased clearance of IV hIgG in plasma of hFcRn transgenic mice treated with CA170_01519.g57 Fab or Fab'PEG or PBS IV FIG. 25 shows a bispecific antibody fusion protein of the present invention, referred to as a Fab-dsFv.

EXAMPLES

The following immunizations were performed in order to generate material for B cell culture and antibody screening:

Sprague Dawley rats were immunized with three shots of NIH3T3 mouse fibroblasts co-expressing mutant human FcRn (L320A; L321A) (Ober et al., 2001 Int. Immunol. 13, 1551-1559) and mouse β2M with a fourth final boost of human FcRn extracellular domain. Sera were monitored for both binding to mutant FcRn on HEK-293 cells and for its ability to prevent binding of Alexafluor 488-labelled human IgG. Both methods were performed by flow cytometry. For binding, phycoerythrin (PE)-labelled anti mouse or rat Fc specific secondary reagents were used to reveal binding of IgG in sera.

B cell cultures were prepared using a method similar to that described by Zubler et al. (1985). Briefly, B cells at a density of approximately 5000 cells per well were cultured in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 2-5% activated rabbit splenocyte culture supernatant and gamma-irradiated EL-4-B5 murine thymoma cells ($5 \times 10^4$/well) for seven days at 37° C. in an atmosphere of 5% $CO_2$.

The presence of FcRn-specific antibodies in B cell culture supernatants was determined using a homogeneous fluorescence-based binding assay using HEK-293 cells transiently transfected with mutant FcRn (surface-stabilised) as a source of target antigen. 10 ul of supernatant was transferred from barcoded 96-well tissue culture plates into barcoded 384-well black-walled assay plates containing 5000 transfected HEK-293 cells per well using a Matrix Platemate liquid handler. Binding was revealed with a goat anti-rat or mouse IgG Fcγ-specific Cy-5 conjugate (Jackson). Plates were read on an Applied Biosystems 8200 cellular detection system. From 3800×96-well culture plates, representing 38 different immunized animals, 9800 anti-human FcRn binders were identified. It was estimated that this represented the screening of approximately 2.5 billion B cells.

Following primary screening, positive supernatants were consolidated on 96-well bar-coded master plates using an Aviso Onyx hit-picking robot and B cells in cell culture plates frozen at –80 C. Master plates were then screened in a Biacore assay in order to identify wells containing antibodies of high affinity and those which inhibited the binding of human IgG to FcRn (see below).

Biomolecular interaction analysis using surface plasmon resonance technology (SPR) was performed on a BIAcore T200 system (GE Healthcare). Goat anti-rat IgG, Fc gamma (Chemicon International Inc.) in 10 mM NaAc, pH 5 buffer was immobilized on a CM5 Sensor Chip via amine coupling chemistry to a capture level of approx. 19500 response units (RU) using HBS-EP+ as the running buffer. 50 mM Phosphate, pH6+150 mM NaCl was used as the running buffer for the affinity and blocking assay. B cell culture supernatants were diluted 1 in 5 in 200 mM Phosphate, pH6+150 mM NaCl. A 600 s injection of diluted B cell supernatant at 5 μl/min was used for capture by the immobilized anti-rat IgG,Fc. Human FcRn at 100 nM was injected over the captured B cell culture supernatant for 180 s at 30 μl/min followed by 360 s dissociation. Human IgG (Jackson ImmunoResearch) was injected over for 60 s with 180 s dissociation at 30 μl/min.

The data was analysed using T200 evaluation software (version 1.0) to determine affinity constants ($K_D$) of antibodies and determine those which blocked IgG binding.

As an alternative assay, master plate supernatants were also screened in a cell-based human IgG blocking assay. 25 ul of B cell culture supernatant from master plates were added to 96 well U-bottomed polypropylene plate. Mutant hFcRn-transfected HEK-293 cells (50,000 cells per well in 25 ul PBS pH6/1% FCS) were then added to each well and incubated for 1 hour at 4° C. Cells were washed twice with 150 ul of PBS media. Cells were then resuspended in 50 ul/well PBS/FCS media containing human IgG labelled with Alexafluor 488 or 649 at 7.5 ug/ml and incubated 1 hour at 4° C. Cells were then washed twice with 150 ul of media and then resuspended in 35 ul/well of PBS/FCS media containing 1% formaldehyde as fixative. Plates were then read on a FACS Canto 2 flow cytometer. Example data is given in FIG. 11.

To allow recovery of antibody variable region genes from a selection of wells of interest, a deconvolution step had to be performed to enable identification of the antigen-specific B cells in a given well that contained a heterogeneous population of B cells. This was achieved using the Fluorescent foci method. Briefly, Immunoglobulin-secreting B cells from a positive well were mixed with streptavidin beads (New England Biolabs) coated with biotinylated human FcRn and a 1:1200 final dilution of a goat anti-rat or mouse Fcγ fragment-specific FITC conjugate (Jackson). After static incubation at 37° C. for 1 hour, antigen-specific B cells could be identified due to the presence of a fluorescent halo surrounding that B cell. These individual B cells, identified using an Olympus microscope, were then picked with an Eppendorf micromanipulator and deposited into a PCR tube. Fluorescent foci were generated from 268 selected wells.

Antibody variable region genes were recovered from single cells by reverse transcription polymerase chain reaction (RT)-PCR using heavy and light chain variable region-specific primers. Two rounds of PCR were performed on an Aviso Onyx liquid handling robot, with the nested 2° PCR incorporating restriction sites at the 3' and 5' ends allowing cloning of the variable regions into a mouse γ1 IgG (VH) or mouse kappa (VL) mammalian expression vector. Paired heavy and light chain constructs were co-transfected into HEK-293 cells using Fectin 293 (Invitrogen) and cultured in 48-well plates in a volume of 1 ml. After 5-7 days expression, supernatants were harvested and antibody subjected to further screening. PCR successfully recovered heavy and light chain cognate pairs from single B cells from 156 of the selected wells. DNA sequence analysis of the cloned variable region genes identified a number of unique families of recombinant antibody. Following expression, transient supernatants were interrogated in both human IgG FACS blocking (described above) and IgG recycling assays. In some cases, purified mouse γ1 IgG was produced and tested (data labeled accordingly).

The recycling assay used MDCK II cells (clone 34 as described in Examples 4 and 5 below) over-expressing human FcRn and beta 2 microglobulin plated out at 25,000 cells per well of a 96 well plate. These were incubated overnight at 37° C., 5% $CO_2$. The cells were washed with HBSS+Ca/Mg pH 7.2+1% BSA and then incubated with 50 μl of varying concentrations of HEK-293 transient supernatant or purified antibody for 1 hour at 37° C., 5% $CO_2$. The supernatant was removed and 500 ng/ml of biotinylated human IgG (Jackson) in 50 μl of HBSS+Ca/Mg pH 5.9+1% BSA was added to the cells and incubated for 1 hour at 37° C., 5% $CO_2$. The cells were then washed three times in HBSS+Ca/Mg pH 5.9 and 100 μl of HBSS+Ca/Mg pH 7.2 added to the cells and incubated at 37° C., 5% $CO_2$ for 2 hours. The supernatant was removed from the cells and analysed for total IgG using an MSD assay with an anti-human IgG capture antibody (Jackson) and a streptavidin-sulpho tag reveal antibody (MSD). The inhibition curve was analysed by non-linear regression to determine IC50 values. Based on performance in these assays a family of antibodies was selected comprising the six CDRs given in SEQ ID NOs 1 to 6. Antibody CA170_01519 had the best activity and was selected for humanisation.

Example 1 Humanisation Method

Antibody CA170_01519 was humanised by grafting the CDRs from the rat antibody V-regions onto human germline antibody V-region frameworks. In order to recover the activity of the antibody, a number of framework residues from the rat V-regions were also retained in the humanised sequence. These residues were selected using the protocol outlined by Adair et al. (1991) (Humanised antibodies. WO91/09967). Alignments of the rat antibody (donor) V-region sequences with the human germline (acceptor) V-region sequences are shown in FIGS. 2A and 2B, together with the designed humanised sequences. The CDRs grafted from the donor to the acceptor sequence are as defined by Kabat (Kabat et al., 1987), with the exception of CDR-H1 where the combined Chothia/Kabat definition is used (see Adair et al., 1991 Humanised antibodies. WO91/09967). Human V-region VK1 2-1-(1) A30 plus JK2 J-region (V BASE, vbase.mrc-cpe.cam.ac.uk/) was chosen as the acceptor for the light chain CDRs. Human V-region VH3 1-3 3-07 plus JH4 J-region (V BASE, vbase.mrc-cpe.cam.ac.uk/) was chosen as the acceptor for the heavy chain CDRs.

Genes encoding a number of variant heavy and light chain V-region sequences were designed and these were constructed by an automated synthesis approach by Entelechon GmbH. Further variants of both heavy and light chain V-regions were created by modifying the VH and VK genes by oligonucleotide-directed mutagenesis. These genes were cloned into a number of vectors to enable expression of humanised 1519 Fab' in mammalian and E. coli cells. The variant chains, and combinations thereof, were assessed for their expression in E. coli, their potency relative to the parent antibody, their biophysical properties and suitability for downstream processing, leading to the selection of the gL20 light chain graft and gH20 heavy chain graft. The final selected gL20 and gH20 graft sequences are shown in FIGS. 2A and 2B, respectively. This V-region pairing was named 1519.g57.

The light chain framework residues in graft gL20 are all from the human germline gene, with the exception of residues 36, 37 and 58 (Kabat numbering), where the donor residues Leucine (L36), Phenylalanine (F37) and Isoleucine (I58) were retained, respectively. Retention of these three residues was essential for full potency of the humanised Fab'. The heavy chain framework residues in graft gH20 are all from the human germline gene, with the exception of residues 3, 24, 76, 93 and 94 (Kabat numbering), where the donor residues Proline (P3), Valine (V24), Serine (S76), Threonine (T93) and Threonine (T94) were retained, respectively. Retention of these five residues was important for full potency of the humanised Fab'

For expression in E. coli, the humanised heavy and light chain V-region genes were cloned into the UCB expression vector pTTOD, which contains DNA encoding the human C-kappa constant region (K1m3 allotype) and the human gamma-1 CH1-hinge region (G1m17 allotype). The E. coli FkpA gene was also introduced into the expression plasmid, as co-expression of this chaperone protein was found to improve the yield of the humanised Fab' in E. coli strain MXE016 (disclosed in WO2011/086136) during batch-fed fermentation, using IPTG to induce Fab' expression. The 1519 Fab' light and heavy chains and FkpA polypeptide were all expressed from a single multi-cistron under the control of the IPTG-inducible tac promoter.

For expression in mammalian cells, the humanised light chain V-region genes were cloned into the UCB-Celltech human light chain expression vector pMhCK, which contains DNA encoding the human Kappa chain constant region (Km3 allotype). The humanised heavy chain V-region genes were cloned into the UCB-Celltech human gamma-4 heavy chain expression vector pMhg4P FL, which contains DNA encoding the human gamma-4 heavy chain constant region with the hinge stabilising mutation S241P (Angal et al., Mol Immunol. 1993, 30(1):105-8). Co-transfection of light and heavy chain vectors into HEK293 suspension cells was achieved using 293 Fectin (12347-019 Invitrogen), and gave expression of the humanised, recombinant 1519 antibodies.

Example 1A Preparation of 1519.g57 Fab'-PEG Conjugate

Fab' expressed in the periplasm of E. coli was extracted from cells by heat extraction. Fab' purified by Protein G affinity purification with an acid elution. Fab' reduced and PEGylated with 40 kDa PEG (SUNBRIGHT GL2-400MA3). PEG is covalently linked via a maleimide group to one or more thiol groups in the antibody fragment. PEGylation efficiency was confirmed by SE-HPLC. Fab'PEG was separated from un-PEGylated Fab' and diFab' by cation exchange chromatography. Fractions analyzed by SE-HPLC and SDS-PAGE. Pooling carried out to minimize levels of impurities. Final sample concentrated and diafiltered into desired buffer.

Example 1B Preparation of 1519.g57 Fab' (Anti Human FcRn) Conjugated with Human Serum Albumin Anti human FcRn Fab' 1519.g57 was chemically conjugated with human serum albumin (recombinant derived) which was then used for animal studies.

Human serum albumin: Recombumin from Novozyme (Cat No: 200-010) presented as 20% w/v solution produced recombinantly in Saccharomyces cerevisiae.

1519.g57Fab': 30 mg/ml presented in 0.1M Sodium Phosphate, 2 mM EDTA, pH6.0 (reduction buffer)

1,6-Bismaleimidohexane (BMH) from Thermofisher (Cat No. 22330)

Reduction of Albumin:

Albumin was reduced using freshly prepared cysteamine hydrochloride (Sigma cat no: 30078) which was prepared in reduction buffer. To the albumin solution cysteamine hydrochloride was added at 10 fold molar excess and then incubated at 37° C. water bath for 30 minutes. Following reduction the solution was desalted using PD10 columns (GE Healthcare Cat. No: 17-0851-01) to remove any excess reducing agent.

Addition of BMH Linker:

A stock solution of 1,6-bismaleimidohexane was prepared in glass vial using dimethylformamide. The solution was vortexed to ensure complete dissolution of BMH. BMH solution was added to the desalted reduced albumin solution at 10 fold molar excess with respect to albumin concentration. The solution was then incubated at 37° C. for 30 minutes followed by overnight incubation at room temperature on a roller to ensure proper mixing. A white precipitate was seen which was spun down using bench top centrifuge. After the completion of the reaction the solution was desalted using PD10 columns.

Reduction of 1519.g57 Fab'

1519.g57 Fab' was reduced using freshly prepared cysteamine hydrochloride (Sigma cat no: 30078) which was prepared in reduction buffer. To the 1519.g57 Fab' solution cysteamine hydrochloride was added at 10 fold molar excess and then incubated at 37° C. water bath for 30 minutes. Following reduction the solution was desalted using PD10 columns (from GE Healthcare Cat. No: 17-0851-01) to remove any excess reducing agent.

Mixing of Reduced Fab and Albumin-BMH

Equal amounts (in molar terms) of the reduced Fab' and albumin-linker was added and incubated at room temperature overnight on a roller mixer.

Affinity Purification:

The above mix was then affinity purified using Blue Sepharose which bound to albumin-Fab conjugate and free albumin. Purification was carried out according to manufacturer's instruction which is briefly described here:

Blue sepharose was reconstituted in DPBS pH7.4 and washed thrice with PBS. Following washing the mixture of Fab and linker linked albumin was added and incubated at room temperature for 1 hour on a roller mixer. After incubation the matrix was washed again with PBS to remove any unbound materials and then eluted with PBS7.4 containing 2M KCl.

Size Exclusion Purification:

The affinity purified material contained albumin conjugated to Fab along with some unreacted HSA. This required further clean-up and this was achieved using size exclusion chromatography (S200 16X60 from GE Healthcare). The final pooled fractions were presented in DPBS pH7.4.

The final 1519.g57Fab-HSA conjugate was concentrated up to 20 mg/ml in DPBS pH7.4 and analyzed on analytical size exclusion chromatography (Agilent Zorbax GF250 and GF450 in tandem) and was found to be predominantly monomeric conjugate. Endotoxin assay was also carried out and the sample was found to be below the specified lower limit of endotoxin content.

Example 2 Screening of Fab' & Fab'PEG Candidate Molecules in the IgG Recycling Assay To determine the ability of the candidate Fab'PEG molecules to block FcRn activity in a functional cell assay, the molecules were screened in the IgG recycling assay (described in more detail in Example 5). Briefly, MDCK II clone 34 cells were pre-incubated with candidate Fab' or Fab'PEG before addition of biotinylated human IgG in an acidic buffer. The cells were washed to remove all excess IgG and then incubated in a neutral pH buffer to facilitate release of IgG into the supernatant. The amount of IgG released into the supernatant was measured by MSD assay and $EC_{50}$ values calculated. The $EC_{50}$ values of humanised Fab' and Fab'PEG candidate molecules that inhibit IgG recycling are shown in the table below. Upon PEGylation there is a loss of potency for all candidate antibodies, however the extent of this varies depending on candidate.

TABLE 1

| Antibody | Fab' $EC_{50}$ (nM) | (n) | Fab'PEG $EC_{50}$ (nM) | (n) | Fold Change in $EC_{50}$ after pegylation |
|---|---|---|---|---|---|
| CA170_0519.g63 | 1.91 | 3 | 5.25 | 3 | 2.7 |
| CA170_0519.g57 | 2.06 | 7 | 6.64 | 6 | 3.2 |
| CA170_0519.g2 | 4.22 | 2 | 11.01 | 4 | 2.6 |

Mean $EC_{50}$ Values for Fab' and Fab'PEG Molecules in the IgG Recycling Assay.

MDCK II clone 34 cells stably transfected with human FcRn and beta 2 microglobulin were at 25,000 cells per well in a 96 well plate and incubated overnight at 37° C., 5% $CO_2$. The cells were incubated with candidate Fab' or Fab'PEG in HBSS+ (Ca/Mg) pH 5.9+1% BSA for 1 hour at 37° C., 5% $CO_2$ before addition of 500 ng/ml of biotinylated human IgG (Jackson) and incubation for a further 1 hour. The cells were washed with HBSS+ pH 5.9 and then incubated at 37° C., 5% $CO_2$ for 2 hours in HBSS+ pH 7.2. The supernatant was removed from the cells and analysed for total IgG using an MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. Table 1 represents combined data from 2 to 7 experiments.

Example 3 Affinity for hFcRn Binding

Biomolecular interaction analysis using surface plasmon resonance technology (SPR) was performed on a Biacore T200 system (GE Healthcare) and binding to human FcRn extracellular domain determined. Human FcRn extracellular domain was provided as a non-covalent complex between the human FcRn alpha chain extracellular domain (SEQ ID NO:94) and β2 microglobulin (β2M) (SEQ ID NO:95). Affinipure F(ab')$_2$ fragment goat anti-human IgG, F(ab')$_2$ fragment specific (for Fab'-PEG capture) or Fc fragment specific (for IgG1 or IgG4 capture) (Jackson ImmunoResearch Lab, Inc.) in 10 mM NaAc, pH 5 buffer was immobilized on a CM5 Sensor Chip via amine coupling chemistry to a capture level between 4000-5000 response units (RU) using HBS-EP+ (GE Healthcare) as the running buffer.

50 mM Phosphate, pH6+150 mM NaCl+0.05% P20 or HBS-P, pH7.4 (GE Healthcare) was used as the running buffer for the affinity assay. The relevant antibody, either anti-hFcRn Fab'-PEG, IgG1 or IgG4P was diluted to 5 µg/ml (Fab'-PEG), 0.3 µg/ml (IgG1) or 4 µg/ml (IgG4) in running buffer. A 60 s injection of Fab'-PEG or IgG1 or IgG4 at 10 µl/min was used for capture by the immobilized anti-human IgG, F(ab')$_2$. Human FcRn extracellular domain was titrated from 20 nM to 1.25 nM over the captured anti-FcRn antibody (Fab'-PEG, IgG1 or IgG4) for 300 s at 30 µl/min followed by 1200 s dissociation. The surface was regenerated by 2×60 s 50 mM HCl at 10 µl/min.

The data was analysed using T200 evaluation software (version 1.0).

TABLE 2

Affinity data for anti-hFcRn 1519.g57 Fab'-PEG at pH 6

| 1519.g57Fab'-PEG | ka ($M^{-1}s^{-1}$) | kd ($s^{-1}$) | KD (M) |
|---|---|---|---|
| 1 | 4.37E+05 | 1.59E-05 | 3.63E-11 |
| 2 | 4.20E+05 | 2.01E-05 | 4.78E-11 |
| 3 | 4.35E+05 | 1.43E-05 | 3.29E-11 |
| 4 | 4.37E+05 | 2.75E-05 | 6.30E-11 |
| 5 | 4.33E+05 | 1.28E-05 | 2.97E-11 |
|   | 4.32E+05 | 1.81E-05 | 4.19E-11 |

TABLE 3

Affinity data for anti-hFcRn 1519.g57 Fab'-PEG at pH 7.4

| 1519.g57Fab'-PEG | ka ($M^{-1}s^{-1}$) | kd ($s^{-1}$) | $K_D$ (M) |
|---|---|---|---|
| 1 | 3.40E+05 | 1.87E-05 | 5.49E-11 |
| 2 | 3.31E+05 | 1.85E-05 | 5.58E-11 |
| 3 | 3.25E+05 | 1.99E-05 | 6.13E-11 |
| 4 | 3.23E+05 | 1.52E-05 | 4.70E-11 |
| 5 | 3.20E+05 | 1.99E-05 | 6.21E-11 |
|   | 3.28E+05 | 1.84E-05 | 5.62E-11 |

In these experiments the Fab'PEG had an average affinity of around 42 pM at pH6 and around 56 pM at pH7.4.

TABLE 3A

Affinity data for anti-hFcRn 1519.g57 as IgG1 and IgG4P at pH 7.4 (average of three experiments) pH 7.4

| 1519.g57 | ka ($M^{-1}s^{-1}$) | kd ($s^{-1}$) | KD (M) | KD (pM) |
|---|---|---|---|---|
| IgG1 | 3.80E+05 | 1.25E-05 | 3.29E-11 | 33 |
| IgG4P | 3.68E+05 | 1.26E-05 | 3.43E-11 | 34 |

TABLE 3B

Affinity data for anti-hFcRn 1519.g57 as IgG1 and IgG4P at pH 6 (average of three experiments) pH 6

| 1519.g57 | ka ($M^{-1}s^{-1}$) | kd ($s^{-1}$) | KD (M) | KD (pM) |
|---|---|---|---|---|
| IgG1 | 4.56E+05 | 1.01E-05 | 2.21E-11 | 22 |
| IgG4P | 4.43E+05 | 1.00E-05 | 2.26E-11 | 23 |

Tables 3A and 3B show the affinity of the full length antibodies is consistent with that observed for the Fab'-PEG at both pH6 and pH7.4.

Example 4 Cell-Based Potency

Cell-based assays were performed using Madin-Darby Canine Kidney (MDCK) II cells which had been stably transfected with a human FcRn and human B2M double gene vector with a Geneticin selection marker. A stable cell clone was selected that was able to recycle and transcytose human IgG and this was used for all subsequent studies. It will be referred to as MDCK II clone 34.

Cell based Affinity of CA170_01519.g57 Fab'PEG for human FcRn Quantitative flow cytometry experiments were performed using MDCK II clone 34 cells and AlexaFluor 488-labelled CA170_01519.g57 Fab' or CA170_01519.g57 Fab'PEG. Specific binding of antibody to FcRn across a range of antibody concentrations was used to determine $K_D$. The analyses were performed in both neutral and acidic buffers to determine whether environmental pH comparable to that found in blood plasma (pH7.4) or endosomes (pH6) had any effect on the antibody binding.

FIG. 3 shows representative binding curves for CA170_01519.g57 Fab'(FIG. 3A) and Fab'PEG (FIG. 3B). The mean $K_D$ values (n=2 or 3) were 1.66 nM and 6.5 nM in neutral buffer, and 1.59 nM and 5.42 nM in acidic buffer, respectively (see Table 4).

TABLE 4

Mean $K_D$ values (nM) for CA170_01519.g57 Fab' and Fab'PEG on MDCK II clone 34 cells.

| Antibody format | Human FcRnpH 7.4 | Human FcRnpH 6.0 |
|---|---|---|
| 1519.g57 Fab' | 1.66 | 1.59 |
| 1519.g57 Fab'PEG | 6.5 | 5.42 |

FIG. 3 shows CA170_01519.g57 Fab' (A) and CA170_01519.g57 Fab'PEG (B) binding on MDCK II clone 34 cells in acidic and neutral pH.

MDCK II clone 34 cells were incubated in Facs buffer (PBS with 0.2% w/v BSA, 0.09% w/v NaN3) for 30 mins prior to the addition of Alexa-fluor 488-labelled CA170_01519.g57 Fab' or Fab'PEG for 1 hour in Facs buffer at either pH 7.4 or pH 6. The final antibody concentrations ranged from 931 nM to 0.002 nM. The cells were washed in ice cold Facs buffer then analysed by flow cytometry using a Guava flow cytometer (Millipore, UK). Titration data sets were also produced for isotype control antibodies for each antibody format to determine non-specific binding. The number of moles of bound antibody was calculated using interpolated values from a standard curve generated from beads comprised of differing amounts of fluorescent dye. Geometric mean fluorescence values were determined in the flow cytometric analyses of cells and beads. Non-specific binding was subtracted from the anti-FcRn antibody values and the specific binding curve generated was analysed by non-linear regression using a one-site binding equation (Graphpad Prism®) to determine the $K_D$. Data is representative of 2 or 3 experiments.

CA170_01519.g57 Fab'PEG can bind human FcRn expressed on cells at both acidic and neutral pH and the determined $K_D$ values are approximately 3.5 to 4 fold below the equivalent Fab' molecule.

Example 5 Functional Cell Based Assays

CA170_01519.g57 Fab'PEG inhibits the recycling of human IgG FcRn expression is primarily intracellular (Borvak J et al. 1998, Int. Immunol., 10 (9) 1289-98 and Cauza K et al. 2005, J. Invest. Dermatol., 124 (1), β2-139), and associated with endosomal and lysosomal membranes. The Fc portion of IgG binds to FcRn at acidic pH (<6.5), but not at a neutral physiological pH (7.4) (Rhagavan M et al. 1995) and this pH-dependency facilitates the recycling of IgG.

Once it is taken up by pinocytosis and enters the acidic endosome, IgG bound to FcRn will be recycled along with the FcRn to the cell surface, whereas at the physiologically neutral pH the IgG will be released. (Ober R J et al. 2004, The Journal of Immunology, 172, 2021-2029). Any IgG not bound to FcRn will enter the lysosomal degradative pathway.

An in vitro assay was established to examine the ability of CA170_01519.g57 Fab'PEG or Fab' to inhibit the IgG recycling capabilities of FcRn. Briefly, MDCK II clone 34 cells were incubated in the presence or absence of CA170_01519.g57 Fab' or CA170_01519.g57 Fab'PEG before addition of biotinylated human IgG in an acidic buffer (pH 5.9) to allow binding to FcRn. All excess antibody was removed and the cells incubated in a neutral pH buffer (pH 7.2) which allows release of surface-exposed, bound IgG into the supernatant. The inhibition of FcRn was followed using an MSD assay to detect the amount of IgG recycled and thus released into the supernatant.

FIG. 4 shows CA170_01519.g57 inhibits IgG recycling in MDCK II clone 34 cells. MDCK II clone 34 cells were plated at 25,000 cells per well in a 96 well plate and incubated overnight at 37° C., 5% $CO_2$. The cells were incubated with CA170_01519.g57 Fab' or Fab'PEG in HBSS$^+$ (Ca/Mg) pH 5.9+1% BSA for 1 hour at 37° C., 5% $CO_2$ before addition of 500 ng/ml of biotinylated human IgG (Jackson) and incubation for a further 1 hour. The cells were washed with HBSS$^+$ pH 5.9 then incubated at 37° C., 5% $CO_2$ for 2 hours in HBSS$^+$ pH 7.2. The supernatant was removed from the cells and analysed for total IgG using an MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. The graph represents combined data from 6 or 7 experiments.

As shown in FIG. 4 CA170_01519.g57 Fab' and CA170_01519.g57 Fab'PEG inhibit IgG recycling in a concentration dependent manner with mean $EC_{50}$ values (n=6 or 7) of 1.937 nM and 6.034 nM respectively. Hence the CA170_01519.g57 Fab'PEG is approximately 3 fold less potent than CA170_01519.g57 Fab' in inhibiting IgG recycling.

CA170_01519.g57 Fab'PEG Inhibits the Transcytosis of Human IgG

FcRn can traffic IgG across polarised epithelial cell layers in both the apical to basolateral and basolateral to apical directions and thus plays an important role in permitting IgG to move between the circulation and lumen at mucosal barriers (Claypool et al. 2004 Mol Biol Cell 15(4):1746-59).

An in vitro assay was established to examine the ability of CA170_01519.g57 Fab'PEG to inhibit FcRn dependent IgG transcytosis. Briefly, MDCK II clone 34 cells were plated in a 24 well transwell plate and allowed to form monolayers over 3 days. The cells were then pre-incubated with CA170_01519.g57 Fab'PEG on the apical surface before the addition of biotinylated human IgG in an acidic buffer which facilitates binding to FcRn. The human IgG is transcytosed through the cells from the apical to basolateral side and released into a neutral buffer in the lower chamber. Levels of IgG on the basolateral side were then measured using an MSD assay.

FIG. 5 shows CA170_01519.g57 Fab'PEG inhibits apical to basolateral IgG transcytosis in MDCK II clone 34 cells.

MDCK II clone 34 cells were plated at 500,000 cells per well of a 24 well transwell plate and incubated for 3 days at 37° C., 5% $CO_2$ until monolayers were formed. The pH of the apical compartment was adjusted to 5.9 and the basolateral side to 7.2 in a HBSS$^+$ (Ca/Mg) buffer+1% BSA. Cells on the apical compartment were pre-incubated with CA170_01519.g57 Fab'PEG for 1 hour before addition of 2.5 µg/ml biotinylated human IgG (Jackson) at the indicated concentrations for 4 hours at 37° C., 5% $CO_2$. The basolateral medium was then collected and total IgG measured by MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. The graph represents combined data from 3 experiments.

In summary FIG. 5 shows that CA170_01519.g57 Fab'PEG can inhibit the apical to basolateral transcytosis of human IgG in a concentration dependent manner with an $EC_{50}$ value of 25.5 nM (n=3).

Summary of In Vitro Effects of CA170_01519.g57 Fab'PEG

CA170_01519.g57 Fab'PEG inhibits both IgG recycling and transcytosis. The $EC_{50}$ of 6 nM achieved in the IgG recycling assay is comparable to the cell affinity binding data in which $K_D$ values of 6.5 nM in neutral buffer and 5.42 nM in acidic buffer were obtained. CA170_01519.g57 Fab'PEG does show a slight reduction in potency compared to the Fab' alone, but compared to many of the other candidate molecules assessed showed the lowest drop in potency between the two formats (see supra). In the IgG transcytosis assay an $EC_{50}$ of 25.5 nM was obtained.

The data in this section have clearly shown that CA170_01519.g57 Fab'PEG can inhibit human FcRn function.

Example 6 Cross Reactivity of CA170_01519.g57 Fab'PEG with Non-Human Primate FcRn To validate the use of CA170_01519.g57 Fab'PEG in a non-human primate PK/PD study and pre-clinical toxicology, its relative affinity and functional potency with cynomolgus macaque FcRn was examined. MDCK II cells stably transfected with cynomolgus macaque FcRn and B2M (MDCKII (cm)) were used for the following studies alongside the previously described MDCK II cells stably transfected with human FcRn and B2M (MDCK II clone 34).

Cell Based Affinity of CA170_01519.g57 Fab'PEG for Cynomolgus Monkey FcRn

To determine the cell based binding affinity of CA170_01519.g57 Fab'PEG for cynomolgus monkey FcRn, quantitative flow cytometry experiments were performed using MDCK II (cm) cells and AlexaFluor 488-labelled CA170_01519.g57 Fab' or Fab'PEG. Specific binding of antibody to cynomolgus macaque FcRn across a range of antibody concentrations was used to determine $K_D$. Antibody binding was performed in both neutral and acidic pH to determine the effect of binding FcRn in neutral blood plasma or acidic endosomes and to therefore determine any effect pH may have on CA170_01519.g57 binding to cynomolgus macaque FcRn.

FIG. 6—shows CA170_01519.g57 Fab' (A) and CA170_01519.g57 Fab'PEG (B) binding on MDCK II (cm) cells in acidic and neutral pH.

MDCK II (cm) cells were incubated in Facs buffer (PBS with 0.2% w/v BSA, 0.09% w/v NaN3) for 30 mins prior to the addition of Alexa-fluor 488 labelled CA170_01519.g57 Fab' or Fab'PEG for 1 hour in Facs buffer at either pH 7.4 or pH 6. The final antibody concentrations ranged from 931 nM to 0.002 nM. The cells were washed in ice cold Facs buffer then analysed by flow cytometry using a Guava flow cytometer (Millipore, UK). Titration data sets were also produced for isotype control antibodies for each antibody format to determine non specific binding. The number of moles of bound antibody was calculated by using interpolated values from a standard curve generated from beads carrying varying amounts of fluorescent dye. Geometric mean fluorescence values were determined in the flow cytometric analyses of cells and beads. Non-specific binding was subtracted from the anti-FcRn antibody values and the specific binding curve generated was analysed by non-linear regression using a one-site binding equation (Graphpad Prism®) to determine the $K_D$. Data is representative of between 2 and 3 experiments.

TABLE 5

Mean $K_D$ values (nM) for CA170_01519.g57 Fab' & Fab'PEG on MDCK II (cm) cells.

| Antibody format | Cyno FcRnpH 7.4 | Cyno FcRnpH 6.0 |
| --- | --- | --- |
| 1519.g57 Fab' | 1.16 | 1.09 |
| 1519.g57 Fab'PEG | 8.15 | 5.01 |

FIG. 6 shows representative binding curves for CA17001519.g57 Fab' (FIG. 6A) and Fab'PEG (FIG. 6B) binding to cynomolgus macaque FcRn. The mean $K_D$ values obtained for CA17001519.g57 Fab' and Fab'PEG are shown in Table 5. These values are comparable to the $K_D$ values obtained for CA170_01519.g57 Fab' and Fab'PEG binding to human FcRn (see table 4)

CA170_01519.g57 Fab'PEG Inhibits the Recycling of Cynomolgus Monkey IgG

To determine if CA170_01519.g57 Fab'PEG is functionally active in blocking cynomolgus monkey FcRn, MDCK II (cm) cells were used to examine the ability of CA170_01519.g57 Fab'PEG to inhibit the recycling of cynomolgus macaque IgG as described previously for the human FcRn assay. The assay was run alongside representative human assays to allow for a comparison between the two.

Briefly, MDCK II cells (clone 34 or cm) were pre-incubated with CA170_01519.g57 Fab'PEG before addition of biotinylated human (h) or cynomolgus macaque (c) IgG in an acidic buffer to allow binding to FcRn. All excess CA170_01519.g57 Fab'PEG and biotinylated IgG were removed and the cells incubated in a neutral pH buffer to allow release of IgG into the supernatant. The inhibition of FcRn was assessed by detecting the amount of IgG present in the supernatant by MSD assay and percent inhibition calculated.

As shown in FIG. 7, CA170_01519.g57 Fab'PEG can inhibit both human and cynomolgus macaque IgG recycling in a concentration dependent manner, with $EC_{50}$ values of 8.448 nM and 5.988 nM respectively. Inhibition of FcRn by CA170_01519.g57 Fab'PEG in the human and cynomolgus macaque assays are comparable, although it appears slightly more potent against the cynomolgus FcRn.

TABLE 6

|  | 1519.g57 Fab'PEG hFcRn:hIgG | 1519.g57 Fab'PEG cFcRn:cIgG |
| --- | --- | --- |
| EC50 (nM) | 8.446 | 5.988 |
| 95% CI (nM) | 6.560 to 10.88 | 5.383 to 6.661 |

FIG. 7 shows CA170_01519.g57 inhibits IgG recycling in MDCK II clone 34 cells & MDCK II (cm) cells.

MDCK II clone 34 and MDCK II (cm) cells were plated at 25,000 cells per well in a 96 well plate and incubated overnight at 37° C., 5% $CO_2$. The cells were pre-incubated with CA170_01519.g57 Fab' or Fab'PEG in HBSS+ (Ca/Mg) pH 5.9+1% BSA for 1 hour at 37° C., 5% $CO_2$ before addition of 500 ng/ml of biotinylated human or cyno IgG and incubated for a further 1 hour. The cells were then washed with HBSS+ pH 5.9 and incubated at 37° C., 5% $CO_2$ for 2 hours in HBSS+ pH 7.2. The supernatant was removed from the cells and analysed for total IgG using an MSD assay (using an anti-human IgG capture antibody (Jackson) and a streptavidin-sulpho tag reveal antibody (MSD)). The inhibition curve was analysed by non-linear regression (Graphpad Prism®) to determine the $EC_{50}$. The graph represents combined data from 2 experiments.

Example 7 Effect of 01519g Fab PEG in Cynomolgus Monkey

This was a study of the effect of the administration of 01519g Fab PEG in cynomolgus monkeys, in single, intermittent or repeated dosing regimens. 01519g Fab PEG was administered by intravenous infusion, as a single dose or in repeat doses to groups of four cynomolgus monkeys as indicated in Table 7. Plasma IgG and the pharmacokinetics of the 01519g Fab PEG were monitored by immunoassay (see Table 7A for immunoassay methods) and LC-MS/MS. Assay of plasma albumin was conducted at Covance.

TABLE 7

Dose groups in study NCD2241. Dosing was by intravenous infusion. The redose was the same as the first dose in each case. Repeat doses (4 of) were weekly.

| Phase | Group | Antibody | Dose (mg/kg) | Dosing Regimen | Comments |
|---|---|---|---|---|---|
| I | 1 | Control | 0 | Single Dose | Redose at 67 days |
|  | 2 | Fab PEG | 20 | Single Dose | Redose at 67 days |
|  | 3 | Fab PEG | 100 | Single Dose | Redose at 67 days |
| II | 4 | Control | 0 | Repeat Dose |  |
|  | 5 | Fab PEG | 20 | Repeat Dose |  |
|  | 6 | Fab PEG | 100 | Repeat Dose |  |

TABLE 7A

Plasma IgG, PK and ADA immunoassay methods

| Assay type | Immunoassay | Method |
|---|---|---|
| PD | Total plasma IgG | 1) Coat immunoassay plate with F(ab')$_2$ goat anti-human Fcγ<br>2) Incubate with sample.<br>3) Reveal with horseradish peroxidase conjugated F(ab')$_2$, goat anti-human IgG F(ab')$_2$ & the addition of TMB substrate. |
| PK | Fab PEG PK | 1) Coat immunoassay plate with FcRn.<br>2) Incubate with sample.<br>3) Reveal with biotin conjugated murine IgG1 anti-PEG/.Streptavidin-horseradish peroxidase conjugate & the addition of TMB substrate alternatively reveal with MSD sulfo-tagged goat anti-human kappa & the addition of MSD read buffer |

Effect on Plasma IgG Concentration

Immunoassay and LC-MS/MS plasma IgG data were in good agreement. Plasma IgG was reduced by the administration of Fab PEG (see FIG. 12 and FIG. 14). For both Phase I dose groups, a single dose of Fab PEG reduced plasma IgG by approximately 70-80%, reaching a nadir at approximately 7 days and returning to pre-dosing levels by day 63. Redosing at day 67 achieved similar results.

For both Phase II dose groups, 4 weekly doses of the Fab PEG reduced plasma IgG by approximately 70-80%, again reaching a nadir at about 7 days after the first dose. The results are shown in FIG. 13.

Example 8 Effect of CA170_01519.g57 Fab'PEG and CA170_01519.g57 IgG4P in Cynomolgus Monkeys The ASCII text file named "CELL0017-100-DIV-1 Sequence Listing," created on Feb. 8, 2019, comprising 127 kilobytes, is hereby incorporated by reference in its entirety.

The effects of CA170_01519g.57 Fab'PEG and CA170_01519g.57 IgG4P on endogenous plasma IgG were determined in cynomolgus monkeys. Animals were dosed as indicated in Table 8, with 4 animals per treatment group. Plasma IgG and the pharmacokinetics of the anti-FcRn entities were monitored by immunoassay (see Table 8A for immunoassay methods) and LC-MS/MS.

TABLE 8

Treatment regimens in cynomolgus monkeys.

| Anti-FcRn | Dose (mg/kg) | Dosing Regimen | Route | FIG. |
|---|---|---|---|---|
| Fab'PEG | 20 | Day 0 & 65 | i.v. | 15 |
| Fab'PEG | 20 | Every 3 days, day 0-27 | i.v. | 16 |
| IgG4P | 30 | Day 0 & 63 | i.v. | 17 |
| IgG4P | 30 & 5 | 30 mg/kg on day 0, 5 mg/kg daily day 1-41 | i.v. | 18 |
| Control | 0 | Daily day 0-41 | i.v. | 19 |

TABLE 8A

Plasma IgG and PK immunoassay methods

| Assay type | Immunoassay | Method |
|---|---|---|
| PD | Total plasma IgG | 1) Coat immunoassay plate with F(ab')$_2$ Goat anti-human Fcγ.<br>2) Incubate with sample.<br>3) Reveal with horseradish peroxidase conjugated F(ab')$_2$, goat anti-human IgG F(ab')$_2$ and the addition of TMB substrate. |
| PK | Fab'PEG PK | 1) Coat MSD streptavidin plate with biotinylated FcRn.<br>2) Incubate with sample.<br>3) Reveal with MSD sulfo-tagged goat anti-human kappa and the addition of MSD read buffer. |

Effect on Plasma IgG Concentration.

Immunoassay and LC-MS/MS plasma IgG data were in good agreement. Plasma IgG was reduced by the administration of anti-FcRn Fab'PEG or anti-FcRn IgG4P (see FIGS. 15 and 16 and FIGS. 17 and 18 respectively; see FIG. 19 for control). For both anti-FcRn entities, a single dose reduced plasma IgG by approximately 70-80%, reaching a nadir at approximately 7 days and returning to pre-dosing levels by day 62. Redosing at day 63 or day 65, as described achieved similar results.

Repeated dosing of anti-FcRn Fab'PEG or IgG4P reduced plasma IgG by approximately 60-80% and maintained the level of IgG for the duration of the dose period. Again, the nadir was reached at about 7 days after the first dose. The results are shown in FIGS. 16 and 18.

Example 9 Effect of CA170_01519.g57 Fab'PEG, CA170_01519.g57 IgG1, CA170_01519.g57 IgG4P, CA170_01519.g57 Fab'HSA, CA170_01519.g57 FabFv and CA170_01519.g57 Fab in hFcRn Transgenic Mice The effect of various different formats of antibody CA170_01519.g57 on the clearance of human IVIG was determined in human FcRn transgenic mice. The formats tested were CA170_01519.g57 Fab'PEG, CA170_01519.g57 IgG1, CA170_01519.g57 IgG4P, CA170_01519.g57 Fab'HSA, CA170_01519.g57 FabFv and CA170_01519.g57 Fab and the results and are shown in FIGS. 20, 21, 22, 23 and 24 respectively. The single doses of active compound were as shown in the Figures. In order to detect their effects on the clearance of human IgG (IVIG), the mice were injected with 500 mg/kg human IVIG which was quantified by LCMSMS in serial plasma samples withdrawn from the tails of the mice at intervals. Blocking of hFcRn by each of the different antibody formats tested resulted in accelerated clearance of hIVIG and lower concentrations of total IgG were observed compared to control mice.

Anti-FcRn Treatment Enhances the Clearance of hIgG in hFcRn Transgenic Mice

Humanised FcRn transgenic mice (B6.Cg-Fcgrt$^{tm1Dcr}$Tg (FCGRT)32Dcr/DcrJ, JAX Mice) were infused intravenously with 500 mg/kg human IgG (Human IgI 10% Gamunex-c, Talecris Biotherapeutics). 24 hours later animals were dosed with vehicle control (PBS) or anti-FcRn intravenously as a single dose. Tail tip blood samples were taken at −24, 8, 24, 48, 72, 144 and 192 hours relative to anti-FcRn treatment. Serum levels of human IgG in the hFcRn mouse and the pharmacokinetics of FcRn inhibitors were determined by LC-MS/MS. Data presented in FIGS. 20 to 24 are mean±SEM with 3-6 mice per treatment group.

Quantification of Human IgG, Endogenous Cynomolgus IgG and FcRn Inhibitors by LC-MS/MS Human IgG, cynomolgus IgG and FcRn inhibitors (1519.g57 Fab'PEG, 1519.g57 IgG4P, 1519.g57 IgG1, 1519.g57 FabFv, 1519.g57 Fab and 1519.g57 Fab'HAS) were quantified using liquid chromatography tandem mass spectrometry (LC-MS/MS) analysis following tryptic digestion.

Quantitation was achieved by comparison to authentic standard material spiked at known concentrations into blank matrix, with spiked horse myoglobin used as the internal standard. Unique ("proteotypic") peptides for all analytes of interest investigated were selected and both samples and calibration samples were typically digested as outlined below. In brief, tryptic digest of 5 μl serum samples was performed overnight using Sequencing Grade Modified Trypsin (Promega, Southampton, UK) following denaturation with acetonitrile/tris (2-carboxyethyl) phosphine and carbamido-methylation with iodoacetamide (all from Sigma-Aldrich, Poole, UK).

Analytes were separated using an Onyx Monolithic C18 column (100×4.6 mm, Phenomenex, Macclesfield, UK) with a gradient of 2 to 95% (v/v) water/acetonitrile (0.1% formic acid) delivered at 1.5 mL/min over 6 minutes.

The injection volume was 10 μL; all of the eluent was introduced into the mass spectrometer source.

The source temperature of the mass spectrometer was maintained at 600° C. and other source parameters (e.g. collision energy, declustering potential, curtain gas pressure etc.) were optimized to achieve maximum sensitivity for each peptides of interest. Selective transitions for each proteotypic peptide of interest were monitored.

Example 10: Crystallography and Binding Epitope

The crystal structure of 1519g57 Fab' and deglycosylated human FcRn extracellular domain (alpha chain extracellular domain (SEQ ID NO:94) in association with beta2 microglobulin SEQ ID NO:95) was determined, with the FcRn oligsaccharide excluded in order to facilitate crystallization. 1519.g57 Fab' was reacted with 10-fold molar excess of N-ethyl maleimide to prevent formation of diFab' and any existing diFab' removed by SEC (S200 on Akta FPLC). Human FcRn extracellular domain was treated by PNGaseF to remove N-linked sugars. For this, the FcRn sample concentration was adjusted using PBS (pH7.4) to 5 mg/ml and a total volume of 1 ml. 200 units of PNGaseF (Roche) was added to this solution of human FcRn. This was incubated at 37° C. for ~18 hours, following which the extent of deglycosylation was checked using SDS PAGE. Upon completion of the reaction the deglycosylated FcRn was buffer exchanged into 50 mM Sodium Acetate, 125 mM NaCl, pH6.0.

The complex was formed by incubation of a mixture of reagents (Fab':FcRn::1.2:1, w/w) at room temperature for 60 minutes, and then purified using SEC (S200 using Akta FPLC). Screening was performed using the various conditions that were available from Qiagen (approximately 2000 conditions). The incubation and imaging was performed by Formulatrix Rock Imager 1000 (for a total incubation period of 21 days). The result of screening is shown in Tables 9, 10 and 11 (see FIG. 26).

TABLE 9

The result of crystallisation screening, showing the crystal used for X-ray analysis.

| | |
|---|---|
| Crystallization experiment type | Sitting drop, vapour diffusion |
| Crystallization condition | 0.1M Sodium citrate pH 5.5, 11% PEG6000 |
| Protein concentration | 10 mg/ml   Drop volume/ratio   0.4 ul Protein + 0.4 ul Reservoir |
| Crystal growth time | 8-21 days |
| Cryoprotection | Crystals were harvested from the drop, transferred to cryoprotection buffer (70% reservoir + 30% ethylene glycol) and flash-frozen in liquid nitrogen (−180° C.) within 10 seconds. |

TABLE 10

Conditions for collection and processing of X-ray analysis data.

| | | | |
|---|---|---|---|
| X-ray source | Diamond Light Source, Beamline I04 | | |
| Experiment Type | Single-wavelength | Wavelength | 0.9795 Å |
| Processing Software | Mosflm/Scala | | |
| Resolution Limits | 35.00-2.90 | Space group | P3$_2$ 2 1 |
| Unit Cell parameters | a = 150.10 Å  α = 90.00° | b = 150.10 Å  β = 90.00° | c = 89.15 Å  γ = 120.00° |
| Completeness | 99.9% (100.0%) | Multiplicity | 6.7 (6.8) |
| I/σ(I) | 13.4 (4.8) | R$_{merge}$ | 9.2% (36.3%) |
| Number of reflections | 172724 (25602) | Number of unique reflections | 25967 (3760) |
| Comments | | | |

Note:
Numbers in parenthesis refer to the outer resolution shell

TABLE 11

Structure determination and refinement.

| | | | |
|---|---|---|---|
| Structure determination method | Molecular Replacement | Program(s) used | Phaser |
| Structure template | Structure FcRn receptor from PDB 3M17 and previously solved Fab-3DVN | | |

TABLE 11-continued

Structure determination and refinement.

| Structure determination method | Molecular Replacement | Program(s) used | Phaser |
|---|---|---|---|
| Refinement program | Refmac5 | Resolution limits | 30.00-2.9 |
| R factor | 23.2% | Free R factor | 28.4% |
| Number of non-hydrogen atoms | | 6125 protein atoms 2 Acetate ions (4 atoms each) 27 waters in AU 2 Cl⁻ ions 2 Na⁺ ions | |
| RMSD bond length | 0.009 Å | RMSD bond angle | 1.338° |
| Ramachandran allowed | 98.6% | Ramachandran outliers | 1.4% |
| Comments | Rebuilt using CCP4/Coot. | | |

There was no obvious change in FcRn structure upon binding of 1519g57 Fab' (comparing this complex with published structures of FcRn). From the crystal structure it the secondary structure content was calculated to be: α-helix 9.4%; β-sheet 45.2%; 3-10 turn 2.5%.

The residues interacting with 1519g57 Fab' were all in the FcRn a chain (not β2M) and are indicated below in bold. The residues concerned encompass all but 1 of the residues critical for binding Fc. 1519g57 binds in a region that overlays the Fc-binding region, suggesting that blockade of FcRn by 1519g57 Fab' is by simple competition, the anti-FcRn being effective by virtue of its superior affinity.

```
                                                (SEQ ID NO: 94)
AESHLSLLYH LTAVSSPAPG TPAFWVSGWL GPQQYLSYNS

LRGEAEPCGA WVWENQVSWY WEKETTDLRI KEKLFLEAFK

ALGGKGPYTL QGLLGCELGP DNTSVPTAKF ALNGEEFMNF

DLKQGTWGGD WPEALAISQR WQQQDKAANK ELTFLLFSCP

HRLREHLERG RGNLEWKEPP SMRLKARPSS PGFSVLTCSA

FSFYPPELQL RFLRNGLAAG TGQGDFGPNS DGSFHASSSL

TVKSGDEHHY CCIVQHAGLA QPLRVELESPAKSS
```

The FcRn a chain sequence, showing residues involved in interaction with 1519g57 Fab' (bold) and residues critical for interaction with Fc of IgG (underlined). All but 1 of the latter are included in the former.

---

The invention claimed is:

1. A method of treating a patient for an autoimmune disease comprising administering a therapeutically effective amount of an anti-FcRn antibody or binding fragment thereof, wherein the antibody or binding fragment comprises a heavy chain or heavy chain fragment having a variable region, wherein said variable region comprises three CDRs, wherein CDR H1 has the sequence given in SEQ ID NO: 1, CDR H2 has the sequence given in SEQ ID NO: 2 and CDR H3 has the sequence given in SEQ ID NO: 3, and comprising a light chain or light chain fragment having a variable region comprising three CDRs, wherein CDR L1 has the sequence given in SEQ ID NO: 4, CDR L2 has the sequence given in SEQ ID NO: 5 and CDR L3 has the sequence given in SEQ ID NO: 6.

2. The method according to claim 1, wherein the anti-FcRn antibody or binding fragment thereof is humanized.

3. The method according to claim 1, wherein the anti-FcRn antibody or binding fragment thereof has a heavy chain comprising the sequence given in SEQ ID NO:29 and a light chain comprising the sequence given in SEQ ID NO:15.

4. The method according to claim 1 wherein the antibody or binding fragment binds to human FcRn, and wherein the variable region of the heavy chain comprises a sequence having at least 90% identity to the sequence given in SEQ ID NO:29 and wherein the variable region of the light chain comprises a sequence having at least 90% identity to the sequence given in SEQ ID NO:15.

5. The method according to claim 1, wherein the anti-FcRn binding fragment thereof is a scFv, Fv, Fab or Fab' fragment.

6. The method according to claim 5, wherein the Fab' fragment has a heavy chain comprising the sequence given in SEQ ID NO:36 and a light chain comprising the sequence given in SEQ ID NO:22.

7. The method according to claim 1, wherein the anti-FcRn antibody or binding fragment thereof is conjugated to a polymer selected from starch, albumin and polyethylene glycol.

8. The method according to claim 7, wherein the polymer is PEG, with a molecular weight in the range of from 5 to 50 kDa.

9. The method according to claim 1, wherein the antibody is a full length antibody.

10. The method according to claim 9 wherein the full length antibody is selected from the group consisting of an IgG1, IgG4 and IgG4P.

11. The method according to claim 9, wherein the anti-FcRn antibody has a heavy chain comprising the sequence given in SEQ ID NO:72 or SEQ ID NO:87 or SEQ ID NO:43 and a light chain comprising the sequence given in SEQ ID NO:22.

12. The method according to claim 1, wherein the anti-FcRn antibody or binding fragment thereof is a Fab-dsFv having a heavy chain comprising the sequence given in SEQ ID NO:50 and a light chain comprising the sequence given in SEQ ID NO:46 or SEQ ID NO:78.

13. The method according to claim 1, wherein the anti-FcRn antibody or binding fragment thereof binds human FcRn.

14. The method according to claim 13, wherein the anti-FcRn antibody or binding fragment thereof blocks binding of human IgG to human FcRn.

15. The method according to claim 1, wherein the anti-FcRn antibody or binding fragment thereof does not bind (32 microglobulin.

16. The method according to claim 1, wherein the autoimmune disease is selected from the group consisting of myasthenia gravis, Pemphigus vulgaris, Neuromyelitis optica, Guillain-Barré syndrome, lupus, idiopathic thrombocytopenic purpura, thrombotic thrombocytopenic purpura, antiphospholipid syndrome (APS), autoimmune urticaria, chronic inflammatory demyelinating polyneuropathy (CIDP), Goodpasture's syndrome, Graves' disease, neutropenia, paraneoplastic cerebellar degeneration, paraproteinemic polyneuropathies, primary biliary cirrhosis, stiff person syndrome, vitiligo and warm idiopathic haemolytic anaemia.

\* \* \* \* \*

SEQUENCE LISTING

```
<160> NUMBER OF SEQ ID NOS: 95

<210> SEQ ID NO 1
<211> LENGTH: 10
<212> TYPE: PRT
<213> ORGANISM: Artificial
<220> FEATURE:
<223> OTHER INFORMATION: CA170_1519 CDRH1

<400> SEQUENCE: 1

Gly Phe Thr Phe Ser Asn Tyr Gly Met Val
1               5                   10

<210> SEQ ID NO 2
<211> LENGTH: 17
<212> TYPE: PRT
<213> ORGANISM: Artificial
<220> FEATURE:
<223> OTHER INFORMATION: CA170_1519 CDRH2

<400> SEQUENCE: 2

Tyr Ile Asp Ser Asp Gly Asp Asn Thr Tyr Tyr Arg Asp Ser Val Lys
1               5                   10                  15

Gly

<210> SEQ ID NO 3
<211> LENGTH: 8
<212> TYPE: PRT
<213> ORGANISM: Artificial
<220> FEATURE:
<223> OTHER INFORMATION: CA170_1519 CDRH3

<400> SEQUENCE: 3

Gly Ile Val Arg Pro Phe Leu Tyr
1               5

<210> SEQ ID NO 4
<211> LENGTH: 16
<212> TYPE: PRT
<213> ORGANISM: Artificial
```

<220> FEATURE:
<223> OTHER INFORMATION: CA170_1519 CDRL1

<400> SEQUENCE: 4

Lys Ser Ser Gln Ser Leu Val Gly Ala Ser Gly Lys Thr Tyr Leu Tyr
1               5                   10                  15

<210> SEQ ID NO 5
<211> LENGTH: 7
<212> TYPE: PRT
<213> ORGANISM: Artificial
<220> FEATURE:
<223> OTHER INFORMATION: CA170_1519 CDRL2

<400> SEQUENCE: 5

Leu Val Ser Thr Leu Asp Ser
1               5

<210> SEQ ID NO 6
<211> LENGTH: 9
<212> TYPE: PRT
<213> ORGANISM: Artificial
<220> FEATURE:
<223> OTHER INFORMATION: CA170_1519 CDRL3

<400> SEQUENCE: 6

Leu Gln Gly Thr His Phe Pro His Thr
1               5

<210> SEQ ID NO 7
<211> LENGTH: 112
<212> TYPE: PRT
<213> ORGANISM: Artificial
<220> FEATURE:
<223> OTHER INFORMATION: Rat Ab 1519 VL region

<400> SEQUENCE: 7

Asp Val Val Met Thr Gln Thr Pro Leu Ser Leu Ser Val Ala Leu Gly
1               5                   10                  15

Gln Pro Ala Ser Ile Ser Cys Lys Ser Ser Gln Ser Leu Val Gly Ala
            20                  25                  30

Ser Gly Lys Thr Tyr Leu Tyr Trp Leu Phe Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Lys Leu Glu Leu Lys
            100                 105                 110

<210> SEQ ID NO 8
<211> LENGTH: 336
<212> TYPE: DNA
<213> ORGANISM: Artificial
<220> FEATURE:
<223> OTHER INFORMATION: Rat Ab 1519 VL region

<400> SEQUENCE: 8
gatgttgtga tgacccagac tccactgtct ttgtcggttg cccttggaca accagcctcc     60
atctcttgca agtcaagtca gagcctcgta ggtgctagtg gaaagacata tttgtattgg    120

```
ttatttcaga ggtccggcca gtctccaaag cgactaatct atctggtgtc cacactggac    180
tctggaattc ctgataggtt cagtggcagt ggagcagaga cagattttac tcttaaaatc    240
cgcagagtgg aagccgatga tttgggagtt tattactgct tgcaaggtac acatttttcct   300 cacacgtttg gagctgggac caagctggaa ttgaaa                              336
```

<210> SEQ ID NO 9
<211> LENGTH: 132
<212> TYPE: PRT
<213> ORGANISM: Artificial
<220> FEATURE:
<223> OTHER INFORMATION: Rat Ab 1519 VL region with signal sequence

<400> SEQUENCE: 9

```
Met Met Ser Pro Ala Gln Phe Leu Phe Leu Leu Met Leu Trp Ile Gln
1               5                   10                  15

Gly Thr Ser Gly Asp Val Val Met Thr Gln Thr Pro Leu Ser Leu Ser
            20                  25                  30

Val Ala Leu Gly Gln Pro Ala Ser Ile Ser Cys Lys Ser Ser Gln Ser
        35                  40                  45

Leu Val Gly Ala Ser Gly Lys Thr Tyr Leu Tyr Trp Leu Phe Gln Arg
    50                  55                  60

Ser Gly Gln Ser Pro Lys Arg Leu Ile Tyr Leu Val Ser Thr Leu Asp
65                  70                  75                  80

Ser Gly Ile Pro Asp Arg Phe Ser Gly Ser Gly Ala Glu Thr Asp Phe
                85                  90                  95

Thr Leu Lys Ile Arg Arg Val Glu Ala Asp Asp Leu Gly Val Tyr Tyr
            100                 105                 110

Cys Leu Gln Gly Thr His Phe Pro His Thr Phe Gly Ala Gly Thr Lys
        115                 120                 125

Leu Glu Leu Lys
    130
```

<210> SEQ ID NO 10
<211> LENGTH: 396
<212> TYPE: DNA
<213> ORGANISM: Artificial
<220> FEATURE:
<223> OTHER INFORMATION: Rat Ab 1519 VL region with signal sequence

<400> SEQUENCE: 10

```
atgatgagtc ctgcccagtt cctgtttctg ctgatgctct ggattcaggg aaccagtggt     60
gatgttgtga tgacccagac tccactgtct ttgtcggttg cccttggaca accagcctcc    120
atctcttgca agtcaagtca gagcctcgta ggtgctagtg gaaagacata tttgtattgg    180
ttatttcaga ggtccggcca gtctccaaag cgactaatct atctggtgtc cacactggac    240
tctggaattc ctgataggtt cagtggcagt ggagcagaga cagattttac tcttaaaatc    300
cgcagagtgg aagccgatga tttgggagtt tattactgct tgcaaggtac acatttttcct   360 cacacgtttg gagctgggac caagctggaa ttgaaa                              396
```

<210> SEQ ID NO 11
<211> LENGTH: 116
<212> TYPE: PRT
<213> ORGANISM: Artificial
<220> FEATURE:
<223> OTHER INFORMATION: Rat Ab 1519 VH region

<400> SEQUENCE: 11

```
Glu Val Pro Leu Val Glu Ser Gly Gly Ser Val Gln Pro Gly Arg
1               5                   10                  15

Ser Met Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
                35                  40                  45

Ala Tyr Ile Asp Ser Asp Gly Asp Asn Thr Tyr Tyr Arg Asp Ser Val
        50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Thr Thr
                100                 105                 110

Val Thr Val Ser
            115
```

```
<210> SEQ ID NO 12
<211> LENGTH: 348
<212> TYPE: DNA
<213> ORGANISM: Artificial
<220> FEATURE:
<223> OTHER INFORMATION: Rat Ab 1519 VH region

<400> SEQUENCE: 12
gaggtgccgc tggtggagtc tgggggcggc tcagtgcagc ctggagggtc catgaaactc      60
tcctgtgtag tctcaggatt cactttcagt aattatggca tggtctgggt ccgccaggct    120
ccaaagaagg gtctggagtg ggtcgcatat attgattctg atggtgataa tacttactac    180
cgagattccg tgaagggccg attcactatc tccagaaata atgcaaaaag cacccttatt     240
ttgcaaatgg acagtctgag gtctgaggac acggccactt attactgtac aacagggatt    300
gtccggccct ttctctattg gggccaagga accacggtca ccgtctcg                 348
```

```
<210> SEQ ID NO 13
<211> LENGTH: 135
<212> TYPE: PRT
<213> ORGANISM: Artificial
<220> FEATURE:
<223> OTHER INFORMATION: Rat Ab 1519 VH region with signal sequence

<400> SEQUENCE: 13

Met Asp Ile Ser Leu Ser Leu Ala Phe Leu Val Leu Phe Ile Lys Gly
1               5                   10                  15

Val Arg Cys Glu Val Pro Leu Val Glu Ser Gly Gly Gly Ser Val Gln
                20                  25                  30

Pro Gly Arg Ser Met Lys Leu Ser Cys Val Val Ser Gly Phe Thr Phe
            35                  40                  45

Ser Asn Tyr Gly Met Val Trp Val Arg Gln Ala Pro Lys Lys Gly Leu
        50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asn Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Thr Thr Gly Ile Val Arg Pro Phe Leu Tyr Trp Gly Gln
            115                 120                 125
```

Gly Thr Thr Val Thr Val Ser
    130             135

<210> SEQ ID NO 14
<211> LENGTH: 405
<212> TYPE: DNA
<213> ORGANISM: Artificial
<220> FEATURE:
<223> OTHER INFORMATION: Rat Ab 1519 VH region with signal sequence

<400> SEQUENCE: 14
atggacatca gtctcagctt ggctttcctt gtccttttca taaaaggtgt ccggtgtgag    60
gtgccgctgg tggagtctgg gggcggctca gtgcagcctg ggaggtccat gaaactctcc   120
tgtgtagtct caggattcac tttcagtaat tatggcatgg tctgggtccg ccaggctcca   180
aagaagggtc tggagtgggt cgcatatatt gattctgatg gtgataatac ttactaccga   240
gattccgtga agggccgatt cactatctcc agaaataatg caaaaagcac cctatatttg   300
caaatggaca gtctgaggtc tgaggacacg gccacttatt actgtacaac agggattgtc   360 cggcccttc tctattgggg ccaaggaacc acggtcaccg tctcg                    405

<210> SEQ ID NO 15
<211> LENGTH: 112
<212> TYPE: PRT
<213> ORGANISM: Artificial
<220> FEATURE:
<223> OTHER INFORMATION: 1519 gL20 V-region

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

<210> SEQ ID NO 16
<211> LENGTH: 336
<212> TYPE: DNA
<213> ORGANISM: Artificial
<220> FEATURE:
<223> OTHER INFORMATION: 1519 gL20 V-region (E. coli expression)

<400> SEQUENCE: 16
gatatccaga tgacccagag tccaagcagt ctctccgcca gcgtaggcga tcgtgtgact    60
attacctgta aaagctccca gtccctggtg ggtgcaagcg gcaaaaccta cctgtactgg   120
ctcttccaga aaccgggcaa agctccgaaa cgcctgatct atctggtgtc taccctggat   180
agcggtattc cgtctcgttt ctccggtagc ggtagcggta ccgaattcac gctgaccatt   240
agctccctcc agccggagga ctttgctacc tattactgcc tccagggcac tcattttccg   300

```
cacactttcg gccagggtac caaactggaa atcaaa                                 336
```

<210> SEQ ID NO 17
<211> LENGTH: 336
<212> TYPE: DNA
<213> ORGANISM: Artificial
<220> FEATURE:
<223> OTHER INFORMATION: 1519 gL20 V-region (mammalian expression)

<400> SEQUENCE: 17

```
gatatccaga tgacccagag cccatctagc ttatccgctt ccgttggtga tcgcgtgaca    60
attacgtgta agagctccca atctctcgtg ggtgcaagtg gcaagaccta tctgtactgg   120
ctctttcaga agcctggcaa ggcaccaaaa cggctgatct atctggtgtc taccctttgac  180
tctgggatac cgtcacgatt ttccggatct gggagcggaa ctgagttcac actcacgatt  240
tcatcgctgc aacccgagga ctttgctacc tactactgcc tgcaaggcac tcatttccct  300
cacactttcg gcaggggac aaaactcgaa atcaaa                              336
```

<210> SEQ ID NO 18
<211> LENGTH: 133
<212> TYPE: PRT
<213> ORGANISM: Artificial
<220> FEATURE:
<223> OTHER INFORMATION: 1519 gL20 V-region with signal sequence (E.
      coli expression)

<400> SEQUENCE: 18

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Val Gly Ala Ser Gly Lys Thr Tyr Leu Tyr Trp Leu Phe Gln
    50                  55                  60

Lys Pro Gly Lys Ala Pro Lys Arg Leu Ile Tyr Leu Val Ser Thr Leu
65                  70                  75                  80

Asp Ser Gly Ile Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

Tyr Cys Leu Gln Gly Thr His Phe Pro His Thr Phe Gly Gln Gly Thr
        115                 120                 125

Lys Leu Glu Ile Lys
    130
```

<210> SEQ ID NO 19
<211> LENGTH: 399
<212> TYPE: DNA
<213> ORGANISM: Artificial
<220> FEATURE:
<223> OTHER INFORMATION: 1519 gL20 V-region with signal sequence (E.
      coli expression)

<400> SEQUENCE: 19

```
atgaaaaaga cagctatcgc aattgcagtg gccttggctg gtttcgctac cgtagcgcaa    60
gctgatatcc agatgaccca gagtccaagc agtctctccg ccagcgtagg cgatcgtgtg   120
actattacct gtaaaagctc ccagtccctg gtgggtgcaa gcggcaaaac ctacctgtac   180
```

```
tggctcttcc agaaaccggg caaagctccg aaacgcctga tctatctggt gtctacccctg    240 gatagcggta ttccgtctcg tttctccggt agcggtagcg gtaccgaatt cacgctgacc    300
attagctccc tccagccgga ggactttgct acctattact gcctccaggg cactcatttt    360
ccgcacactt tcggccaggg taccaaactg gaaatcaaa                           399
```

```
<210> SEQ ID NO 20
<211> LENGTH: 132
<212> TYPE: PRT
<213> ORGANISM: Artificial
<220> FEATURE:
<223> OTHER INFORMATION: 1519 gL20 V-region with signal sequence
      (mammalian expression)

<400> SEQUENCE: 20
```

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Val Gly Ala Ser Gly Lys Thr Tyr Leu Tyr Trp Leu Phe Gln Lys
    50                  55                  60

Pro Gly Lys Ala Pro Lys Arg Leu Ile Tyr Leu Val Ser Thr Leu Asp
65                  70                  75                  80

Ser Gly Ile Pro Ser Arg Phe Ser Gly Ser Gly Ser Gly Thr Glu Phe
                85                  90                  95

Thr Leu Thr Ile Ser Ser Leu Gln Pro Glu Asp Phe Ala Thr Tyr Tyr
            100                 105                 110

Cys Leu Gln Gly Thr His Phe Pro His Thr Phe Gly Gln Gly Thr Lys
        115                 120                 125

Leu Glu Ile Lys
    130

```
<210> SEQ ID NO 21
<211> LENGTH: 396
<212> TYPE: DNA
<213> ORGANISM: Artificial
<220> FEATURE:
<223> OTHER INFORMATION: 1519 gL20 V-region with signal sequence
      (mammalian expression)

<400> SEQUENCE: 21
atgtctgtcc ccacccaagt cctcggactc ctgctactct ggcttacaga tgccagatgc     60
gatatccaga tgacccagag cccatctagc ttatccgctt ccgttggtga tcgcgtgaca    120
attacgtgta agagctccca atctctcgtg ggtgcaagtg gcaagaccta tctgtactgg    180
ctctttcaga agcctggcaa ggcaccaaaa cggctgatct atctggtgtc tacccttgac    240
tctgggatac cgtcacgatt ttccggatct gggagcggaa ctgagttcac actcacgatt    300
tcatcgctgc aacccgagga ctttgctacc tactactgcc tgcaaggcac tcatttccct    360
cacactttcg gccagggac aaaactcgaa atcaaa                               396
```

```
<210> SEQ ID NO 22
<211> LENGTH: 219
<212> TYPE: PRT
<213> ORGANISM: Artificial
<220> FEATURE:
<223> OTHER INFORMATION: 1519 gL20 light chain (V + constant)
```

<400> SEQUENCE: 22

```
Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Val Gly Ala
            20                  25                  30
Ser Gly Lys Thr Tyr Leu Tyr Trp Leu Phe Gln Lys Pro Gly Lys Ala
        35                  40                  45
Pro Lys Arg Leu Ile Tyr Leu Val Ser Thr Leu Asp Ser Gly Ile Pro
    50                  55                  60
Ser Arg Phe Ser Gly Ser Gly Ser Gly Thr Glu Phe Thr Leu Thr Ile
65                  70                  75                  80
Ser Ser Leu Gln Pro Glu Asp Phe Ala Thr Tyr Tyr Cys Leu Gln Gly
                85                  90                  95
Thr His Phe Pro His Thr Phe Gly Gln Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 23
<211> LENGTH: 657
<212> TYPE: DNA
<213> ORGANISM: Artificial
<220> FEATURE:
<223> OTHER INFORMATION: 1519 gL20 light chain (V + constant, E. coli expression)

<400> SEQUENCE: 23

```
gatatccaga tgacccagag tccaagcagt ctctccgcca gcgtaggcga tcgtgtgact    60
attacctgta aaagctccca gtccctggtg ggtgcaagcg gcaaaaccta cctgtactgg   120
ctcttccaga accgggcaa agctccgaaa cgcctgatct atctggtgtc taccctggat   180
agcggtattc cgtctcgttt ctccggtagc ggtagcggta ccgaattcac gctgaccatt   240
agctccctcc agccggagga ctttgctacc tattactgcc tccagggcac tcattttccg   300
cacactttcg gccagggtac caaactggaa atcaaacgta cggtagcggc cccatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcaccagta acaaaaagtt ttaatagagg ggagtgt       657
```

<210> SEQ ID NO 24

<211> LENGTH: 657
<212> TYPE: DNA
<213> ORGANISM: Artificial
<220> FEATURE:
<223> OTHER INFORMATION: 1519 gL20 light chain (V + constant, mammalian expression)

<400> SEQUENCE: 24

```
gatatccaga tgacccagag tccaagcagt ctctccgcca gcgtaggcga tcgtgtgact      60
attacctgta aaagctccca gtccctggtg ggtgcaagcg gcaaaaccta cctgtactgg     120
ctcttccaga aaccgggcaa agctccgaaa cgcctgatct atctggtgtc taccctggat     180
agcggtattc cgtctcgttt ctccggtagc ggtagcggta ccgaattcac gctgaccatt     240
agctccctcc agccggagga ctttgctacc tattactgcc tccagggcac tcatttccg      300
cacactttcg gccagggtac caaactggaa atcaaacgta cggtagcggc cccatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 25
<211> LENGTH: 240
<212> TYPE: PRT
<213> ORGANISM: Artificial
<220> FEATURE:
<223> OTHER INFORMATION: 1519 gL20 light chain with signal sequence (E. coli expression)

<400> SEQUENCE: 25

```
Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Val Gly Ala Ser Gly Lys Thr Tyr Leu Tyr Trp Leu Phe Gln
    50                  55                  60

Lys Pro Gly Lys Ala Pro Lys Arg Leu Ile Tyr Leu Val Ser Thr Leu
65                  70                  75                  80

Asp Ser Gly Ile Pro Ser Arg Phe Ser Gly Ser Gly Ser Gly Thr Glu
                85                  90                  95

Phe Thr Leu Thr Ile Ser Ser Leu Gln Pro Glu Asp Phe Ala Thr Tyr
            100                 105                 110

Tyr Cys Leu Gln Gly Thr His Phe Pro His Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
```

Lys Ala Asp Tyr Glu Lys His Lys Val Tyr Ala Cys Glu Val Thr His
    210             215                 220

Gln Gly Leu Ser Ser Pro Val Thr Lys Ser Phe Asn Arg Gly Glu Cys
225                 230                 235                 240

<210> SEQ ID NO 26
<211> LENGTH: 720
<212> TYPE: DNA
<213> ORGANISM: Artificial
<220> FEATURE:
<223> OTHER INFORMATION: 1519 gL20 light chain with signal sequence (E.
      coli expression)

<400> SEQUENCE: 26
atgaaaaaga cagctatcgc aattgcagtg gccttggctg gtttcgctac cgtagcgcaa        60
gctgatatcc agatgaccca gagtccaagc agtctctccg ccagcgtagg cgatcgtgtg       120
actattacct gtaaaagctc ccagtccctg gtgggtgcaa gcggcaaaac ctacctgtac       180
tggctcttcc agaaaccggg caaagctccg aaacgcctga tctatctggt gtctaccctg       240
gatagcggta ttccgtctcg tttctccggt agcggtagcg gtaccgaatt cacgctgacc       300
attagctccc tccagccgga ggactttgct acctattact gcctccaggg cactcatttt       360
ccgcacactt tcggccaggg taccaaactg gaaatcaaac gtacggtagc ggccccatct       420
gtcttcatct tcccgccatc tgatgagcag ttgaaatctg gaactgcctc tgttgtgtgc       480
ctgctgaata acttctatcc cagagaggcc aaagtacagt ggaaggtgga taacgccctc       540
caatcgggta actcccagga gagtgtcaca gagcaggaca gcaaggacag cacctacagc       600
ctcagcagca ccctgacgct gagcaaagca gactacgaga aacacaaagt ctacgcctgc       660
gaagtcaccc atcagggcct gagctcacca gtaacaaaaa gttttaatag aggggagtgt       720

<210> SEQ ID NO 27
<211> LENGTH: 239
<212> TYPE: PRT
<213> ORGANISM: Artificial
<220> FEATURE:
<223> OTHER INFORMATION: 1519 gL20 light chain with signal sequence
      (mammalian expression)

<400> SEQUENCE: 27

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Val Gly Ala Ser Gly Lys Thr Tyr Leu Tyr Trp Leu Phe Gln Lys
    50                  55                  60

Pro Gly Lys Ala Pro Lys Arg Leu Ile Tyr Leu Val Ser Thr Leu Asp
65                  70                  75                  80

Ser Gly Ile Pro Ser Arg Phe Ser Gly Ser Gly Ser Gly Thr Glu Phe
                85                  90                  95

Thr Leu Thr Ile Ser Ser Leu Gln Pro Glu Asp Phe Ala Thr Tyr Tyr
            100                 105                 110

Cys Leu Gln Gly Thr His Phe Pro His Thr Phe Gly Gln Gly Thr Lys
        115                 120                 125

Leu Glu Ile Lys Arg Thr Val Ala Ala Pro Ser Val Phe Ile Phe Pro

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 28
<211> LENGTH: 717
<212> TYPE: DNA
<213> ORGANISM: Artificial
<220> FEATURE:
<223> OTHER INFORMATION: 1519 gL20 light chain with signal sequence
      (mammalian expression)

<400> SEQUENCE: 28
atgtctgtcc ccacccaagt cctcggactc ctgctactct ggcttacaga tgccagatgc      60
gatatccaga tgacccagag cccatctagc ttatccgctt ccgttggtga tcgcgtgaca     120
attacgtgta gagctcccca atctctcgtg ggtgcaagtg caagacccta tctgtactgg     180
ctctttcaga agcctggcaa ggcaccaaaa cggctgatct atctggtgtc taccettgac     240
tctgggatac cgtcacgatt ttccggatct gggagcggaa ctgagttcac actcacgatt     300
tcatcgctgc aacccgagga ctttgctacc tactactgcc tgcaaggcac tcatttccct     360
cacactttcg gccaggggac aaaactcgaa atcaaacgta cggtagcggc ccatctgtc      420
ttcatcttcc cgccatctga tgagcagttg aaatctggaa ctgcctctgt tgtgtgcctg     480
ctgaataact ctatcccag agaggccaaa gtacagtgga aggtggataa cgccctccaa      540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct caacagggga gagtgt         717

<210> SEQ ID NO 29
<211> LENGTH: 116
<212> TYPE: PRT
<213> ORGANISM: Artificial
<220> FEATURE:
<223> OTHER INFORMATION: 1519 gH20 V-region

<400> SEQUENCE: 29

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
            85                  90                  95

Thr Thr Gly Ile Val Arg Pro Phe Leu Tyr Trp Gly Gln Gly Thr Leu
            100                 105                 110

Val Thr Val Ser
        115

<210> SEQ ID NO 30
<211> LENGTH: 348
<212> TYPE: DNA
<213> ORGANISM: Artificial
<220> FEATURE:
<223> OTHER INFORMATION: 1519 gH20 V-region (E. coli expression)

<400> SEQUENCE: 30
gaggttccgc tggtcgagtc tggaggcggg cttgtccagc ctggaggag cctgcgtctc    60 tcttgtgcag tatctggctt cacgttctcc aactacggta tggtgtgggt tcgtcaggct   120
ccaggtaaag gtctggaatg ggtggcgtat attgactccg acggcgacaa cacctactat   180
cgcgactctg tgaaaggtcg cttcaccatt tcccgcgata cgccaaatc cagcctgtac    240 ctgcagatga cagcctgcg tgctgaagat actgcggtgt actattgcac cactggcatc    300
gtgcgtccgt ttctgtattg gggtcagggt accctcgtta ctgtctcg               348

<210> SEQ ID NO 31
<211> LENGTH: 348
<212> TYPE: DNA
<213> ORGANISM: Artificial
<220> FEATURE:
<223> OTHER INFORMATION: 1519 gH20 V-region (mammalian expression)

<400> SEQUENCE: 31
gaggtaccac ttgtggaaag cggaggaggt cttgtgcagc ctggaggaag tttacgtctc    60
tcttgtgctg tgtctggctt caccttctcc aattacggaa tggtctgggt cagacaagca   120
cctggaaagg gtcttgaatg ggtggcctat attgactctg acggggacaa cacctactat   180
cgggattccg tgaaaggacg cttcacaatc tcccgagata cgccaagag ctcactgtac    240 ctgcagatga atagcctgag agccgaggat actgccgtgt actattgcac aacgggaatc   300
gttaggcctt ttctgtactg gggacagggc accttggtta ctgtctcg               348

<210> SEQ ID NO 32
<211> LENGTH: 137
<212> TYPE: PRT
<213> ORGANISM: Artificial
<220> FEATURE:
<223> OTHER INFORMATION: 1519 gH20 V-region (E. coli expression)

<400> SEQUENCE: 32

Met Lys Lys Thr Ala Ile Ala Ile Ala Val Ala Leu Ala Gly Phe Ala
1               5                   10                  15

Thr Val Ala Gln Ala Glu Val Pro Leu Val Glu Ser Gly Gly Gly Leu
            20                  25                  30

Val Gln Pro Gly Gly Ser Leu Arg Leu Ser Cys Ala Val Ser Gly Phe
        35                  40                  45

Thr Phe Ser Asn Tyr Gly Met Val Trp Val Arg Gln Ala Pro Gly Lys
    50                  55                  60

Gly Leu Glu Trp Val Ala Tyr Ile Asp Ser Asp Gly Asp Asn Thr Tyr
65                  70                  75                  80

```
Tyr Arg Asp Ser Val Lys Gly Arg Phe Thr Ile Ser Arg Asp Asn Ala
                 85                  90                  95

Lys Ser Ser Leu Tyr Leu Gln Met Asn Ser Leu Arg Ala Glu Asp Thr
            100                 105                 110

Ala Val Tyr Tyr Cys Thr Thr Gly Ile Val Arg Pro Phe Leu Tyr Trp
        115                 120                 125

Gly Gln Gly Thr Leu Val Thr Val Ser
    130                 135
```

<210> SEQ ID NO 33
<211> LENGTH: 411
<212> TYPE: DNA
<213> ORGANISM: Artificial
<220> FEATURE:
<223> OTHER INFORMATION: 1519 gH20 V-region (E. coli expression)

<400> SEQUENCE: 33

```
atgaagaaga ctgctatagc aattgcagtg gcgctagctg gtttcgccac cgtggcgcaa     60
gctgaggttc cgctggtcga gtctggaggc gggcttgtcc agcctggagg gagcctgcgt    120
ctctcttgtg cagtatctgg cttcacgttc tccaactacg gtatggtgtg ggttcgtcag    180
gctccaggta aaggtctgga atgggtggcg tatattgact ccgacggcga caacacctac    240
tatcgcgact ctgtgaaagg tcgcttcacc atttcccgcg ataacgccaa atccagcctg    300
tacctgcaga tgaacagcct gcgtgctgaa gatactgcgg tgtactattg caccactggc    360
atcgtgcgtc cgtttctgta ttggggtcag ggtaccctcg ttactgtctc g             411
```

<210> SEQ ID NO 34
<211> LENGTH: 135
<212> TYPE: PRT
<213> ORGANISM: Artificial
<220> FEATURE:
<223> OTHER INFORMATION: 1519 gH20 V-region (mammalian expression)

<400> SEQUENCE: 34

```
Met Glu Trp Ser Trp Val Phe Leu Phe Phe Leu Ser Val Thr Thr Gly
1               5                   10                  15

Val His Ser Glu Val Pro Leu Val Glu Ser Gly Gly Gly Leu Val Gln
            20                  25                  30

Pro Gly Gly Ser Leu Arg Leu Ser Cys Ala Val Ser Gly Phe Thr Phe
        35                  40                  45

Ser Asn Tyr Gly Met Val Trp Val Arg Gln Ala Pro Gly Lys Gly Leu
    50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Arg Ala Glu Asp Thr Ala Val
            100                 105                 110

Tyr Tyr Cys Thr Thr Gly Ile Val Arg Pro Phe Leu Tyr Trp Gly Gln
        115                 120                 125

Gly Thr Leu Val Thr Val Ser
    130                 135
```

<210> SEQ ID NO 35
<211> LENGTH: 405
<212> TYPE: DNA
<213> ORGANISM: Artificial
<220> FEATURE:

<223> OTHER INFORMATION: 1519 gH20 V-region with signal sequence
       (mammalian expression)

<400> SEQUENCE: 35

```
atggaatgga gctgggtctt tctcttcttc ctgtcagtaa ctacaggagt ccattctgag    60
gtaccacttg tggaaagcgg aggaggtctt gtgcagcctg aggaagtttt acgtctctct   120
tgtgctgtgt ctggcttcac cttctccaat tacggaatgg tctgggtcag acaagcacct   180
ggaaagggtc ttgaatgggt ggcctatatt gactctgacg gggacaacac ctactatcgg   240
gattccgtga aggacgcttc acaatctccc gagataacg ccaagagctc actgtacctg    300
cagatgaata gcctgagagc cgaggatact gccgtgtact attgcacaac gggaatcgtt   360
aggccttttc tgtactgggg acagggcacc ttggttactg tctcg                   405
```

<210> SEQ ID NO 36
<211> LENGTH: 228
<212> TYPE: PRT
<213> ORGANISM: Artificial
<220> FEATURE:
<223> OTHER INFORMATION: 1519gH20 Fab' heavy chain (V + human gamma-1
       CH1 + hinge)

<400> SEQUENCE: 36

```
Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Ala Ala
225
```

<210> SEQ ID NO 37
<211> LENGTH: 684
<212> TYPE: DNA

<213> ORGANISM: Artificial
<220> FEATURE:
<223> OTHER INFORMATION: 1519gH20 Fab' heavy chain (V + human gamma-1 CH1 + hinge, E.coli expression)

<400> SEQUENCE: 37

```
gaggttccgc tggtcgagtc tggaggcggg cttgtccagc ctggagggag cctgcgtctc    60
tcttgtgcag tatctggctt cacgttctcc aactacggta tggtgtgggt cgtcaggct   120
ccaggtaaag gtctgaatg gtggcgtat attgactccg acggcgacaa cacctactat   180
cgcgactctg tgaaaggtcg cttcaccatt tcccgcgata cgccaaatc agcctgtac   240
ctgcagatga cagcctgcg tgctgaagat actgcggtgt actattgcac cactggcatc   300
gtgcgtccgt ttctgtattg gggtcagggt accctcgtta ctgtctcgag cgcttctaca   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtcgacaaga agttgagcc caaatcttgt   660
gacaaaactc acacatgcgc cgcg                                         684
```

<210> SEQ ID NO 38
<211> LENGTH: 684
<212> TYPE: DNA
<213> ORGANISM: Artificial
<220> FEATURE:
<223> OTHER INFORMATION: 1519gH20 Fab' heavy chain (V + human gamma-1 CH1 + hinge, mammalian expression)

<400> SEQUENCE: 38

```
gaggtaccac ttgtggaaag cggaggaggt cttgtgcagc ctggaggaag tttacgtctc    60
tcttgtgctg tgtctggctt cacctttctcc aattacggaa tggtctgggt cagacaagca   120
cctggaaagg gtcttgaatg gtggccctat attgactctg acggggacaa cacctactat   180
cgggattccg tgaaaggacg cttcacaatc tcccgagata cgccaagag ctcactgtac   240
ctgcagatga atagcctgag agccgaggat actgccgtgt actattgcac aacgggaatc   300
gttaggcctt ttctgtactg gggacagggc accttggtta ctgtctcgag cgcttctaca   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtcgacaaga agttgagcc caaatcttgt   660
gacaaaactc acacatgcgc cgcg                                         684
```

<210> SEQ ID NO 39
<211> LENGTH: 249
<212> TYPE: PRT
<213> ORGANISM: Artificial
<220> FEATURE:
<223> OTHER INFORMATION: 1519 gH20 Fab' heavy chain with signal sequence (E. coli expression)

<400> SEQUENCE: 39

```
Met Lys Lys Thr Ala Ile Ala Ile Ala Val Ala Leu Ala Gly Phe Ala
1               5                   10                  15
```

```
Thr Val Ala Gln Ala Glu Val Pro Leu Val Glu Ser Gly Gly Gly Leu
             20                  25                  30
Val Gln Pro Gly Gly Ser Leu Arg Leu Ser Cys Ala Val Ser Gly Phe
         35                  40                  45
Thr Phe Ser Asn Tyr Gly Met Val Trp Val Arg Gln Ala Pro Gly Lys
     50                  55                  60
Gly Leu Glu Trp Val Ala Tyr Ile Asp Ser Asp Gly Asp Asn Thr Tyr
 65                  70                  75                  80
Tyr Arg Asp Ser Val Lys Gly Arg Phe Thr Ile Ser Arg Asp Asn Ala
                 85                  90                  95
Lys Ser Ser Leu Tyr Leu Gln Met Asn Ser Leu Arg Ala Glu Asp Thr
            100                 105                 110
Ala Val Tyr Tyr Cys Thr Thr Gly Ile Val Arg Pro Phe Leu Tyr Trp
        115                 120                 125
Gly Gln Gly Thr Leu Val Thr Val Ser Ser Ala Ser Thr Lys Gly Pro
130                 135                 140
Ser Val Phe Pro Leu Ala Pro Ser Ser Lys Ser Thr Ser Gly Gly Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
            180                 185                 190
Ala Val Leu Gln Ser Ser Gly Leu Tyr Ser Leu Ser Ser Val Val Thr
        195                 200                 205
Val Pro Ser Ser Ser Leu Gly Thr Gln Thr Tyr Ile Cys Asn Val Asn
    210                 215                 220
His Lys Pro Ser Asn Thr Lys Val Asp Lys Lys Val Glu Pro Lys Ser
225                 230                 235                 240
Cys Asp Lys Thr His Thr Cys Ala Ala
                245
```

<210> SEQ ID NO 40
<211> LENGTH: 747
<212> TYPE: DNA
<213> ORGANISM: Artificial
<220> FEATURE:
<223> OTHER INFORMATION: 1519 gH20 Fab' heavy chain with signal sequence
      (E. coli expression)

<400> SEQUENCE: 40

```
atgaagaaga ctgctatagc aattgcagtg gcgctagctg gtttcgccac cgtggcgcaa      60
gctgaggttc cgctggtcga gtctggaggc gggcttgtcc agcctggagg gagcctgcgt     120
ctctcttgtg cagtatctgg cttcacgttc tccaactacg gtatggtgtg ggttcgtcag     180
gctccaggta aggtctggaa tgggtggcg tatattgact ccgacggcga caacacctac     240
tatcgcgact ctgtgaaagg tcgcttcacc atttcccgcg ataacgccaa atccagcctg     300
tacctgcaga tgaacagcct gcgtgctgaa gatactgcgg tgtactattg caccactggc     360
atcgtgcgtc cgtttctgta ttggggtcag ggtaccctcg ttactgtctc gagcgcttct     420
acaaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcaccca gacctacatc     660
```

```
tgcaacgtga atcacaagcc cagcaacacc aaggtcgaca agaaagttga gcccaaatct    720
tgtgacaaaa ctcacacatg cgccgcg                                        747
```

<210> SEQ ID NO 41
<211> LENGTH: 247
<212> TYPE: PRT
<213> ORGANISM: Artificial
<220> FEATURE:
<223> OTHER INFORMATION: 1519 gH20 Fab' heavy chain with signal sequence
      (mammalian expression)

<400> SEQUENCE: 41

```
Met Glu Trp Ser Trp Val Phe Leu Phe Phe Leu Ser Val Thr Thr Gly
1               5                   10                  15

Val His Ser Glu Val Pro Leu Val Glu Ser Gly Gly Gly Leu Val Gln
            20                  25                  30

Pro Gly Gly Ser Leu Arg Leu Ser Cys Ala Val Ser Gly Phe Thr Phe
        35                  40                  45

Ser Asn Tyr Gly Met Val Trp Val Arg Gln Ala Pro Gly Lys Gly Leu
    50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Arg Ala Glu Asp Thr Ala Val
            100                 105                 110

Tyr Tyr Cys Thr Thr Gly Ile Val Arg Pro Phe Leu Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Ala Ala
                245
```

<210> SEQ ID NO 42
<211> LENGTH: 741
<212> TYPE: DNA
<213> ORGANISM: Artificial
<220> FEATURE:
<223> OTHER INFORMATION: 1519 gH20 Fab' heavy chain with signal sequence
      (mammalian expression)

<400> SEQUENCE: 42

```
atggaatgga gctgggtctt tctcttcttc ctgtcagtaa ctacaggagt ccattctgag    60
gtaccacttg tggaaagcgg aggaggtctt gtgcagcctg gaggaagttt acgtctctct   120
tgtgctgtgt ctggcttcac cttctccaat tacggaatgg tctgggtcag acaagcacct   180
```

-continued

```
ggaaagggtc ttgaatgggt ggcctatatt gactctgacg gggacaacac ctactatcgg    240
gattccgtga aaggacgctt cacaatctcc cgagataacg ccaagagctc actgtacctg    300
cagatgaata gcctgagagc cgaggatact gccgtgtact attgcacaac gggaatcgtt    360 aggcctttc  tgtactgggg acagggcacc ttggttactg tctcgagcgc ttctacaaag    420
ggcccatcgg tcttccccct ggcaccctcc tccaagagca cctctggggg cacagcggcc    480
ctgggctgcc tggtcaagga ctacttcccc gaaccggtga cggtgtcgtg aactcaggc     540 gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtc gacaagaaag ttgagcccaa atcttgtgac    720
aaaactcaca catgcgccgc g                                              741
```

<210> SEQ ID NO 43
<211> LENGTH: 444
<212> TYPE: PRT
<213> ORGANISM: Artificial
<220> FEATURE:
<223> OTHER INFORMATION: 1519gH20 IgG4 heavy chain (V + human gamma-4P constant)

<400> SEQUENCE: 43

```
Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

```
Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 44
<211> LENGTH: 1939
<212> TYPE: DNA
<213> ORGANISM: Artificial
<220> FEATURE:
<223> OTHER INFORMATION: 1519gH20 IgG4 heavy chain (V + human gamma-4P
      constant with exons)

<400> SEQUENCE: 44
gaggtaccac ttgtggaaag cggaggaggt cttgtgcagc ctggaggaag tttacgtctc    60
tcttgtgctg tgtctggctt caccttctcc aattacggaa tggtctgggt cagacaagca   120
cctggaaagg gtcttgaatg ggtggcctat attgactctg acggggacaa cacctactat   180
cgggattccg tgaaaggacg cttcacaatc tcccgagata cgccaagag ctcactgtac    240 ctgcagatga atagcctgag agccgaggat actgccgtgt actattgcac aacgggaatc   300
gttaggcctt ttctgtactg gggacagggc accttggtta ctgtctcgag cgcttctaca   360
aagggcccat ccgtcttccc cctggcgccc tgctccagga gcacctccga gagcacagcc   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacgaagac ctacacctgc   600
aacgtagatc acaagcccag caacaccaag gtggacaaga gagttggtga gaggccagca   660
cagggaggga gggtgtctgc tggaagccag gctcagccct cctgcctgga cgcaccccgg   720
ctgtgcagcc ccagcccagg gcagcaaggc atgccccatc tgtctcctca cccggaggcc   780
tctgaccacc ccactcatgc ccagggagag gtcttctgg atttttccac caggctccgg   840
gcagccacag gctggatgcc cctacccag gccctgcgca tagggggca ggtgctgcgc    900 tcagacctgc caagagccat atccgggagg accctgcccc tgacctaagc ccaccccaaa   960
```

```
ggccaaactc tccactccct cagctcagac accttctctc ctcccagatc tgagtaactc    1020
ccaatcttct ctctgcagag tccaaatatg gtcccccatg cccaccatgc ccaggtaagc    1080
caacccaggc ctcgccctcc agctcaaggc gggacaggtg ccctagagta gcctgcatcc    1140
agggacaggc cccagccggg tgctgacgca tccacctcca tctcttcctc agcacctgag    1200
ttcctggggg gaccatcagt cttcctgttc ccccaaaac caaggacac tctcatgatc    1260 tcccggaccc ctgaggtcac gtgcgtggtg gtggacgtga gccaggaaga ccccgaggtc    1320
cagttcaact ggtacgtgga tggcgtggag gtgcataatg ccaagacaaa gccgcgggag    1380
gagcagttca acagcacgta ccgtgtggtc agcgtcctca ccgtcctgca ccaggactgg    1440
ctgaacggca aggagtacaa gtgcaaggtc tccaacaaag gcctcccgtc ctccatcgag    1500
aaaaccatct ccaaagccaa aggtgggacc cacggggtgc gagggccaca tggacagagg    1560
tcagctcggc ccaccctctg ccctgggagt gaccgctgtg ccaacctctg tccctacagg    1620
gcagccccga gagccacagg tgtacaccct gcccccatcc caggaggaga tgaccaagaa    1680
ccaggtcagc ctgacctgcc tggtcaaagg cttctacccc agcgacatcg ccgtggagtg    1740
ggagagcaat gggcagccgg agaacaacta caagaccacg cctcccgtgc tggactccga    1800
cggctccttc ttcctctaca gcaggctaac cgtggacaag agcaggtggc aggaggggaa    1860
tgtcttctca tgctccgtga tgcatgaggc tctgcacaac cactacacac agaagagcct    1920
ctccctgtct ctgggtaaa                                                 1939

<210> SEQ ID NO 45
<211> LENGTH: 1996
<212> TYPE: DNA
<213> ORGANISM: Artificial
<220> FEATURE:
<223> OTHER INFORMATION: 1519gH20 IgG4 heavy chain (V + human gamma-4P
      constant) with signal sequence

<400> SEQUENCE: 45
atggaatgga gctgggtctt tctcttcttc ctgtcagtaa ctacaggagt ccattctgag      60
gtaccacttg tggaaagcgg aggaggtctt gtgcagcctg gaggaagttt acgtctctct    120
tgtgctgtgt ctggcttcac cttctccaat tacggaatgg tctgggtcag acaagcacct    180
ggaaagggtc ttgaatgggt ggcctatatt gactctgacg gggacaacac ctactatcgg    240
gattccgtga aggacgcttt cacaatctcc cgagataacg ccaagagctc actgtacctg    300
cagatgaata gcctgagagc cgaggatact gccgtgtact attgcacaac gggaatcgtt    360
aggccttttc tgtactgggg acagggcacc ttggttactg tctcgagcgc ttctacaaag    420
ggcccatccg tcttccccct ggcgccctgc tccaggagca cctccgagag cacagccgcc    480
ctgggctgcc tggtcaagga ctacttcccc gaaccggtga cggtgtcgtg gaactcaggc    540
gccctgacca gcggcgtgca caccttcccg gctgtcctac agtcctcagg actctactcc    600
ctcagcagcg tggtgaccgt gccctccagc agcttgggca cgaagaccta cacctgcaac    660
gtagatcaca agcccagcaa caccaaggtg gacaagagag ttggtgagag gccagcacag    720
ggagggaggg tgtctgctgg aagccaggct cagccctcct gcctggacgc accccggctg    780
tgcagcccca gcccagggca gcaaggcatg cccatctgt ctcctcaccc ggaggcctct    840
gaccacccca ctcatgccca gggagagggt cttctggatt tttccaccag gctccgggca    900
gccacaggct ggatgcccct accccaggcc ctgcgcatac aggggcaggt gctgcgctca    960
gacctgccaa gagccatatc cgggaggacc ctgcccctga cctaagccca cccaaaggc    1020
```

```
caaactctcc actccctcag ctcagacacc ttctctcctc ccagatctga gtaactccca    1080
atcttctctc tgcagagtcc aaatatggtc cccatgccc accatgccca ggtaagccaa     1140
cccaggcctc gccctccagc tcaaggcggg acaggtgccc tagagtagcc tgcatccagg    1200
gacaggccca gccgggtgc tgacgcatcc acctccatct cttcctcagc acctgagttc     1260 ctgggggac catcagtctt cctgttcccc ccaaaaccca aggacactct catgatctcc     1320
cggacccctg aggtcacgtg cgtggtggtg gacgtgagcc aggaagaccc cgaggtccag    1380
ttcaactggt acgtggatgg cgtggaggtg cataatgcca agacaaagcc gcgggaggag    1440
cagttcaaca gcacgtaccg tgtggtcagc gtcctcaccg tcctgcacca ggactggctg    1500
aacggcaagg agtacaagtg caaggtctcc aacaaaggcc tcccgtcctc catcgagaaa    1560
accatctcca aagccaaagg tgggacccac ggggtgcgag ggccacatgg acagaggtca    1620
gctcggccca cctctgccc tgggagtgac cgctgtgcca acctctgtcc ctacagggca    1680
gccccgagag ccacaggtgt acaccctgcc cccatcccag gaggagatga ccaagaacca    1740
ggtcagcctg acctgcctgg tcaaaggctt ctaccccagc gacatcgccg tggagtggga    1800
gagcaatggg cagccggaga acaactacaa gaccacgcct cccgtgctgg actccgacgg    1860
ctccttcttc ctctacagca ggctaaccgt ggacaagagc aggtggcagg aggggaatgt    1920
cttctcatgc tccgtgatgc atgaggctct gcacaaccac tacacacaga gagcctctc    1980 cctgtctctg ggtaaa                                                    1996
```

<210> SEQ ID NO 46
<211> LENGTH: 347
<212> TYPE: PRT
<213> ORGANISM: Artificial
<220> FEATURE:
<223> OTHER INFORMATION: 1519gL20 FabFv light chain

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                180             185             190
Lys His Lys Val Tyr Ala Cys Glu Val Thr His Gln Gly Leu Ser Ser
                195             200             205
Pro Val Thr Lys Ser Phe Asn Arg Gly Glu Cys Ser Gly Gly Gly Gly
            210             215             220
Ser Gly Gly Gly Gly Ser Gly Gly Gly Ser Asp Ile Gln Met Thr
225             230             235             240
Gln Ser Pro Ser Ser Val Ser Ala Ser Val Gly Asp Arg Val Thr Ile
                245             250             255
Thr Cys Gln Ser Ser Pro Ser Val Trp Ser Asn Phe Leu Ser Trp Tyr
            260             265             270
Gln Gln Lys Pro Gly Lys Ala Pro Lys Leu Leu Ile Tyr Glu Ala Ser
            275             280             285
Lys Leu Thr Ser Gly Val Pro Ser Arg Phe Ser Gly Ser Gly Ser Gly
            290             295             300
Thr Asp Phe Thr Leu Thr Ile Ser Ser Leu Gln Pro Glu Asp Phe Ala
305             310             315             320
Thr Tyr Tyr Cys Gly Gly Tyr Ser Ser Ile Ser Asp Thr Thr Phe
            325             330             335
Gly Cys Gly Thr Lys Val Glu Ile Lys Arg Thr
            340             345
```

<210> SEQ ID NO 47
<211> LENGTH: 1041
<212> TYPE: DNA
<213> ORGANISM: Artificial
<220> FEATURE:
<223> OTHER INFORMATION: 1519gL20 FabFv light chain

<400> SEQUENCE: 47

```
gatatccaga tgacccagag cccatctagc ttatccgctt ccgttggtga tcgcgtgaca      60
attacgtgta agagctccca atctctcgtg ggtgcaagtg caagaccta tctgtactgg     120
ctctttcaga gcctggcaa ggcaccaaaa cggctgatct atctggtgtc tacccttgac     180
tctgggatac cgtcacgatt ttccggatct gggagcggaa ctgagttcac actcacgatt    240
tcatcgctgc aacccgagga cttttgctacc tactactgcc tgcaaggcac tcatttccct   300
cacactttcg gccagggac aaaactcgaa atcaaacgta cggtagcggc ccatctgtc     360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctg    540
agcagcaccc tgacgctgtc taaagcagac tacgagaaac acaaagtgta cgcctgcgaa    600
gtcacccatc agggcctgag ctcaccagta acaaaaagtt ttaatagagg ggagtgtagc    660
ggtggcggtg gcagtggtgg gggaggctcc ggaggtggcg gttcagacat acaaatgacc    720
cagagtcctt catcggtatc cgcgtccgtt ggcgatggg tgactattac atgtcaaagc    780
tctcctagcg tctggagcaa ttttctatcc tggtatcaac agaaaccggg gaaggctcca    840
aaacttctga tttatgaagc ctcgaaactc accgtggga ttccgtcaag attcagtggc    900
tctggatcag ggacagactt cacgttgaca atcagttcgc tgcaaccaga ggactttgcg    960
acctactatt gtggtggagg ttacagtagc ataagtgata cgacatttgg gtgcggtact   1020
aaggtggaaa tcaaacgtac c                                             1041
```

<210> SEQ ID NO 48
<211> LENGTH: 367
<212> TYPE: PRT
<213> ORGANISM: Artificial
<220> FEATURE:
<223> OTHER INFORMATION: 1519gL20 FabFv light chain with signal sequence

<400> SEQUENCE: 48

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
        35                  40                  45

Leu Val Gly Ala Ser Gly Lys Thr Tyr Leu Tyr Trp Leu Phe Gln Lys
    50                  55                  60

Pro Gly Lys Ala Pro Lys Arg Leu Ile Tyr Leu Val Ser Thr Leu Asp
65                  70                  75                  80

Ser Gly Ile Pro Ser Arg Phe Ser Gly Ser Gly Ser Gly Thr Glu Phe
                85                  90                  95

Thr Leu Thr Ile Ser Ser Leu Gln Pro Glu Asp Phe Ala Thr Tyr Tyr
            100                 105                 110

Cys Leu Gln Gly Thr His Phe Pro His Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Ser
225                 230                 235                 240

Gly Gly Gly Gly Ser Gly Gly Gly Ser Gly Gly Gly Gly Ser Asp
                245                 250                 255

Ile Gln Met Thr Gln Ser Pro Ser Ser Val Ser Ala Ser Val Gly Asp
            260                 265                 270

Arg Val Thr Ile Thr Cys Gln Ser Ser Pro Ser Val Trp Ser Asn Phe
        275                 280                 285

Leu Ser Trp Tyr Gln Gln Lys Pro Gly Lys Ala Pro Lys Leu Leu Ile
    290                 295                 300

Tyr Glu Ala Ser Lys Leu Thr Ser Gly Val Pro Ser Arg Phe Ser Gly
305                 310                 315                 320

Ser Gly Ser Gly Thr Asp Phe Thr Leu Thr Ile Ser Ser Leu Gln Pro
                325                 330                 335

Glu Asp Phe Ala Thr Tyr Tyr Cys Gly Gly Tyr Ser Ser Ile Ser
            340                 345                 350

Asp Thr Thr Phe Gly Cys Gly Thr Lys Val Glu Ile Lys Arg Thr
        355                 360                 365

<210> SEQ ID NO 49
<211> LENGTH: 1101
<212> TYPE: DNA
<213> ORGANISM: Artificial
<220> FEATURE:
<223> OTHER INFORMATION: 1519gL20 FabFv light chain with signal sequence

<400> SEQUENCE: 49

```
atgtctgtcc ccacccaagt cctcggactc ctgctactct ggcttacaga tgccagatgc      60
gatatccaga tgacccagag cccatctagc ttatccgctt ccgttggtga tcgcgtgaca     120
attacgtgta agagctccca atctctcgtg ggtgcaagtg caagaccta tctgtactgg      180
ctctttcaga agcctggcaa ggcaccaaaa cggctgatct atctggtgtc tacccttgac     240
tctgggatac cgtcacgatt ttccggatct gggagcggaa ctgagttcac actcacgatt     300
tcatcgctgc aacccgagga ctttgctacc tactactgcc tgcaaggcac tcatttccct     360
cacactttcg gccaggggac aaaactcgaa atcaaacgta cggtagcggc ccatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctg     600
agcagcaccc tgacgctgtc taaagcagac tacgagaaac acaaagtgta cgcctgcgaa     660
gtcacccatc agggcctgag ctcaccagta acaaaaagtt ttaatagagg ggagtgtagc     720
ggtggcggtg gcagtggtgg gggaggctcc ggaggtggcg gttcagacat acaaatgacc     780
cagagtcctt catccgtatc cgcgtccgtt ggcgatagg tgactattac atgtcaaagc     840
tctcctagcg tctggagcaa ttttctatcc tggtatcaac agaaaccggg gaaggctcca     900
aaacttctga tttatgaagc ctcgaaactc accgtggag ttccgtcaag attcagtggc     960
tctggatcag ggacagactt cacgttgaca atcagttcgc tgcaaccaga ggactttgcg    1020
acctactatt gtggtggagg ttacagtagc ataagtgata cgacatttgg gtgcggtact    1080
aaggtggaaa tcaaacgtac c                                              1101
```

<210> SEQ ID NO 50
<211> LENGTH: 357
<212> TYPE: PRT
<213> ORGANISM: Artificial
<220> FEATURE:
<223> OTHER INFORMATION: 1519gH20 FabFv heavy chain

<400> SEQUENCE: 50

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu

```
            115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
210                 215                 220

Gly Ser Gly Gly Gly Gly Thr Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285

Ala Ser Gly Thr Thr Phe Tyr Ala Thr Trp Ala Lys Gly Arg Phe Thr
290                 295                 300

Ile Ser Arg Asp Asn Ser Lys Asn Thr Val Tyr Leu Gln Met Asn Ser
305                 310                 315                 320

Leu Arg Ala Glu Asp Thr Ala Val Tyr Tyr Cys Ala Arg Thr Val Pro
                325                 330                 335

Gly Tyr Ser Thr Ala Pro Tyr Phe Asp Leu Trp Gly Gln Gly Thr Leu
            340                 345                 350

Val Thr Val Ser Ser
        355

<210> SEQ ID NO 51
<211> LENGTH: 1071
<212> TYPE: DNA
<213> ORGANISM: Artificial
<220> FEATURE:
<223> OTHER INFORMATION: 1519gH20 FabFv heavy chain

<400> SEQUENCE: 51
gaggtaccac ttgtggaaag cggaggaggt cttgtgcagc tggaggaag tttacgtctc    60 tcttgtgctg tgtctggctt caccttctcc aattacggaa tggtctgggt cagacaagca   120
cctggaaagg gtcttgaatg ggtggcctat attgactctg acggggacaa cacctactat   180
cgggattccg tgaaaggacg cttcacaatc tcccgagata cgccaagag ctcactgtac    240 ctgcagatga atagcctgag agccgaggat actgccgtgt actattgcac aacgggaatc   300
gttaggcctt ttctgtactg gggacagggc accttggtta ctgtctcgag cgcgtccaca   360
aagggcccat cggtcttccc cctggcaccc tcctccaaga gcacctctgg gggcacagcg   420
gccctgggct gcctggtcaa ggactacttc cccgaaccag tgacggtgtc gtggaactca   480
ggtgccctga ccagcggcgt tcacaccttc ccggctgtcc tacagtcttc aggactctac   540
tccctgagca gcgtggtgac cgtgccctcc agcagcttgg gcacccagac ctacatctgc   600
aacgtgaatc acaagcccag caacaccaag gtcgataaga agttgagcc caaatcttgt    660
```

```
agtggaggtg ggggctcagg tggaggcggg accggtggag gtggcagcga ggttcaactg    720
cttgagtctg gaggaggcct agtccagcct ggagggagcc tgcgtctctc ttgtgcagta    780
agcggcatcg acctgagcaa ttacgccatc aactgggtga acaagctcc ggggaagtgt     840 ttagaatgga tcggtataat atgggccagt gggacgacct tttatgctac atgggcgaaa    900
ggaaggttta caattagccg ggacaatagc aaaaacaccg tgtatctcca aatgaactcc    960
ttgcgagcag aggacacggc ggtgtactat tgtgctcgca ctgtcccagg ttatagcact   1020
gcaccctact tcgatctgtg gggacaaggg accctggtga ctgtttcaag t            1071
```

<210> SEQ ID NO 52
<211> LENGTH: 376
<212> TYPE: PRT
<213> ORGANISM: Artificial
<220> FEATURE:
<223> OTHER INFORMATION: 1519gH20 FabFv heavy chain with signal sequence

<400> SEQUENCE: 52

```
Met Glu Trp Ser Trp Val Phe Leu Phe Leu Ser Val Thr Thr Gly
1               5                   10                  15

Val His Ser Glu Val Pro Leu Val Glu Ser Gly Gly Gly Leu Val Gln
            20                  25                  30

Pro Gly Gly Ser Leu Arg Leu Ser Cys Ala Val Ser Gly Phe Thr Phe
        35                  40                  45

Ser Asn Tyr Gly Met Val Trp Val Arg Gln Ala Pro Gly Lys Gly Leu
    50                  55                  60

Glu Trp Val Ala Tyr Ile Asp Ser Asp Gly Asp Asn Thr Tyr Tyr Arg
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Arg Ala Glu Asp Thr Ala Val
            100                 105                 110

Tyr Tyr Cys Thr Thr Gly Ile Val Arg Pro Phe Leu Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Ser
225                 230                 235                 240

Gly Gly Gly Gly Ser Gly Gly Gly Thr Gly Gly Gly Ser Glu
                245                 250                 255

Val Gln Leu Leu Glu Ser Gly Gly Gly Leu Val Gln Pro Gly Gly Ser
            260                 265                 270

Leu Arg Leu Ser Cys Ala Val Ser Gly Ile Asp Leu Ser Asn Tyr Ala
        275                 280                 285

Ile Asn Trp Val Arg Gln Ala Pro Gly Lys Cys Leu Glu Trp Ile Gly
```

```
                290                 295                 300

Ile Ile Trp Ala Ser Gly Thr Thr Phe Tyr Ala Thr Trp Ala Lys Gly
305                 310                 315                 320

Arg Phe Thr Ile Ser Arg Asp Asn Ser Lys Asn Thr Val Tyr Leu Gln
                325                 330                 335

Met Asn Ser Leu Arg Ala Glu Asp Thr Ala Val Tyr Tyr Cys Ala Arg
            340                 345                 350

Thr Val Pro Gly Tyr Ser Thr Ala Pro Tyr Phe Asp Leu Trp Gly Gln
        355                 360                 365

Gly Thr Leu Val Thr Val Ser Ser
        370                 375

<210> SEQ ID NO 53
<211> LENGTH: 1128
<212> TYPE: DNA
<213> ORGANISM: Artificial
<220> FEATURE:
<223> OTHER INFORMATION: 1519gH20 FabFv heavy chain with signal sequence

<400> SEQUENCE: 53
atggaatgga gctgggtctt tctcttcttc ctgtcagtaa ctacaggagt ccattctgag      60
gtaccacttg tggaaagcgg aggaggtctt gtgcagcctg aggaagtttt acgtctctct     120
tgtgctgtgt ctggcttcac cttctccaat tacggaatgg tctgggtcag acaagcacct     180
ggaaagggtc ttgaatgggt ggcctatatt gactctgacg gggacaacac ctactatcgg     240
gattccgtga aggacgcttt cacaatctcc cgagataacg ccaagagctc actgtacctg     300
cagatgaata gcctgagagc cgaggatact gccgtgtact attgcacaac gggaatcgtt     360 aggcctttc tgtactgggg acagggcacc ttggttactg tctcgagcgc gtccacaaag     420
ggcccatcgg tcttccccct ggcacccctcc tccaagagca cctctggggg cacagcggcc     480
ctgggctgcc tggtcaagga ctacttcccc gaaccagtga cggtgtcgtg aactcaggt     540 gccctgacca gcggcgttca ccttcccg gctgtcctac agtcttcagg actctactcc     600
ctgagcagcg tggtgaccgt gccctccagc agcttgggca cccagaccta catctgcaac     660
gtgaatcaca gcccagcaa caccaaggtc gataagaaag ttgagcccaa atcttgtagt     720
ggaggtgggg gctcaggtgg aggcgggacc ggtggaggtg gcagcgaggt tcaactgctt     780
gagtctggag gaggcctagt ccagcctgga gggagcctgc gtctctcttg tgcagtaagc     840
ggcatcgacc tgagcaatta cgccatcaac tgggtgagac aagctccggg gaagtgttta     900
gaatggatcg gtataatatg gccagtggga cgacctttt atgctacatg gcgaaagga     960 aggtttacaa ttagccggga caatagcaaa acaccgtgt atctccaaat gaactccttg    1020
cgagcagagg acacggcggt gtactattgt gctcgcactg tcccaggtta tagcactgca    1080
ccctacttcg atctgtgggg acaagggacc ctggtgactg tttcaagt                 1128

<210> SEQ ID NO 54
<211> LENGTH: 107
<212> TYPE: PRT
<213> ORGANISM: Artificial
<220> FEATURE:
<223> OTHER INFORMATION: Human VK1 2-1-(1) A30 JK2 acceptor framework

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

```
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Tyr
                 85                  90                  95

Thr Phe Gly Gln Gly Thr Lys Leu Glu Ile Lys
                100                 105
```

<210> SEQ ID NO 55
<211> LENGTH: 321
<212> TYPE: DNA
<213> ORGANISM: Artificial
<220> FEATURE:
<223> OTHER INFORMATION: Human VK1 2-1-(1) A30 JK2 acceptor framework

<400> SEQUENCE: 55

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccttacac ttttggccag   300
gggaccaagc tggagatcaa a                                             321
```

<210> SEQ ID NO 56
<211> LENGTH: 112
<212> TYPE: PRT
<213> ORGANISM: Artificial
<220> FEATURE:
<223> OTHER INFORMATION: Human VH3 1-3 3-07 JH4 acceptor framework

<400> SEQUENCE: 56

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Phe Asp Tyr Trp Gly Gln Gly Thr Leu Val Thr Val Ser
                100                 105                 110
```

<210> SEQ ID NO 57
<211> LENGTH: 336
<212> TYPE: DNA
<213> ORGANISM: Artificial
<220> FEATURE:
<223> OTHER INFORMATION: Human VH3 1-3 3-07 JH4 acceptor framework

<400> SEQUENCE: 57

```
gaggtgcagc tggtggagtc tgggggaggc ttggtccagc ctgggggggtc cctgagactc      60 tcctgtgcag cctctggatt cacctttagt agctattgga tgagctgggt ccgccaggct     120
ccagggaagg ggctggagtg ggtggccaac ataaagcaag atggaagtga aaatactat      180 gtggactctg tgaagggccg attcaccatc tccagagaca cgccaagaa ctcactgtat      240 ctgcaaatga acagcctgag agccgaggac acggctgtgt attactgtgc gagatacttt     300
gactactggg gccagggaac cctggtcacc gtctcc                               336
```

<210> SEQ ID NO 58
<211> LENGTH: 112
<212> TYPE: PRT
<213> ORGANISM: Artificial
<220> FEATURE:
<223> OTHER INFORMATION: Rat Ab 1548 VL region

<400> SEQUENCE: 58

```
Asp Val Val Met Thr Gln Thr Pro Leu Ser Leu Ser Val Ala Leu Gly
1               5                   10                  15

Gln Pro Ala Ser Ile Ser Cys Lys Ser Ser Gln Ser Leu Val Gly Ala
            20                  25                  30

Ser Gly Lys Thr Tyr Leu Tyr Trp Leu Phe Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Lys Leu Glu Ile Lys
            100                 105                 110
```

<210> SEQ ID NO 59
<211> LENGTH: 336
<212> TYPE: DNA
<213> ORGANISM: Artificial
<220> FEATURE:
<223> OTHER INFORMATION: Rat Ab 1548 VL region

<400> SEQUENCE: 59

```
gatgttgtga tgacccagac tccactgtct ttgtcggttg cccttggaca accagcctcc      60
atctcttgca agtcaagtca gagcctcgta ggtgctagtg gaaagacata tttgtattgg     120
ttatttcaga ggtccggcca gtctccaaag cgactaatct atctggtgtc cacactggac     180
tctggaattc ctgataggtt cagtggcagt ggagcagaga cagatttttac tcttaaaatc     240 cgcagagtgg aagccgatga tttgggagtt tattactgct tgcaaggtac acatttttcct    300 cacacgtttg gagctgggac caagctggaa ataaaa                               336
```

<210> SEQ ID NO 60
<211> LENGTH: 116
<212> TYPE: PRT
<213> ORGANISM: Artificial
<220> FEATURE:
<223> OTHER INFORMATION: Rat Ab 1548 VH region

<400> SEQUENCE: 60

```
Glu Val Pro Leu Val Glu Ser Gly Gly Gly Ser Val Gln Pro Gly Arg
1               5                   10                  15
```

```
Ser Met Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Val Met
            100                 105                 110

Val Thr Val Ser
        115
```

<210> SEQ ID NO 61
<211> LENGTH: 348
<212> TYPE: DNA
<213> ORGANISM: Artificial
<220> FEATURE:
<223> OTHER INFORMATION: Rat Ab 1548 VH region

<400> SEQUENCE: 61

```
gaggtgccgc tggtggagtc tgggggcggc tcagtgcagc ctggagggtc catgaaactc      60
tcctgtgtag tctcaggatt cactttcagt aattatggca tggtctgggt ccgccaggct     120
ccaaagaagg gtctggagtg gtcgcatat attgattctg atggtgataa tacttactac     180
cgagattccg tgaagggccg attcactatc tccagaaata tgcaaaaag caccctatat      240 ttgcaaatgg acagtctgag gtctgaggac acggccactt attactgtac aacagggatt     300 gtccggcct ttctctattg gggccaagga gtcatggtca cagtctcg              348
```

<210> SEQ ID NO 62
<211> LENGTH: 112
<212> TYPE: PRT
<213> ORGANISM: Artificial
<220> FEATURE:
<223> OTHER INFORMATION: Rat Ab 1644 VL region

<400> SEQUENCE: 62

```
Asp Val Val Met Thr Gln Thr Pro Leu Ser Leu Ser Val Ala Ile Gly
1               5                   10                  15

Gln Pro Ala Ser Ile Ser Cys Lys Ser Ser Gln Ser Leu Val Gly Ala
            20                  25                  30

Ser Gly Lys Thr Tyr Leu Tyr Trp Leu Phe Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Lys Leu Glu Leu Lys
            100                 105                 110
```

<210> SEQ ID NO 63
<211> LENGTH: 336
<212> TYPE: DNA
<213> ORGANISM: Artificial

<220> FEATURE:
<223> OTHER INFORMATION: Rat Ab 1644 VL region

<400> SEQUENCE: 63

```
gatgttgtga tgacccagac tccactgtct ttgtcggttg ccattggaca accagcctcc    60
atctcttgca agtcaagtca gagcctcgta ggtgctagtg aaagacata tttgtattgg    120
ttatttcaga ggtccggcca gtctccaaag cgactaatct atctggtgtc cacactggac    180
tctggaattc ctgataggtt cagtggcagt ggagcagaga cagattttac tcttaaaatc    240
cgcagagtgg aagccgatga tttgggagtt tattactgct tgcaaggtac acattttcct    300
cacacgtttg gagctgggac caagctggaa ctgaaa                              336
```

<210> SEQ ID NO 64
<211> LENGTH: 116
<212> TYPE: PRT
<213> ORGANISM: Artificial
<220> FEATURE:
<223> OTHER INFORMATION: Rat Ab 1644 VH region

<400> SEQUENCE: 64

```
Glu Val Pro Leu Val Glu Ser Gly Gly Gly Ser Val Gln Pro Gly Arg
1               5                   10                  15

Ser Thr Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
        35                  40                  45

Ala Tyr Ile Gly Ser Asp Gly Asp Asn Ile Tyr Tyr Arg Asp Ser Val
    50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Thr Thr
            100                 105                 110

Val Thr Val Ser
        115
```

<210> SEQ ID NO 65
<211> LENGTH: 348
<212> TYPE: DNA
<213> ORGANISM: Artificial
<220> FEATURE:
<223> OTHER INFORMATION: Rat Ab 1644 VH region

<400> SEQUENCE: 65

```
gaggtgccgc tggtggagtc tgggggcggc tcagtgcagc ctggagaggtc cacgaaactc    60
tcctgtgtag tctcaggatt cactttcagt aactatggca tggtctgggt ccgccaggct   120
ccaaagaagg gtctggagtg ggtcgcatat attggttctg atggtgataa tatttactac   180
cgagattccg tgaagggtcg attcactatc tccagaaata tgcaaaaag cacccctatat   240
ttgcaaatgg acagtctgag gtctgaggac acggccactt attactgtac aacagggatt   300
gtccggcccct ttctctactg gggccaagga accacggtca ccgtctcg               348
```

<210> SEQ ID NO 66
<211> LENGTH: 112
<212> TYPE: PRT
<213> ORGANISM: Artificial
<220> FEATURE:

<223> OTHER INFORMATION: Rat Ab 1496 VK region

<400> SEQUENCE: 66

```
Asp Val Val Met Thr Gln Thr Pro Leu Ser Leu Ser Val Ala Leu Gly
1               5                   10                  15

Gln Pro Ala Ser Ile Ser Cys Lys Ser Ser Gln Ser Leu Val Gly Ala
            20                  25                  30

Ser Gly Lys Thr Tyr Leu Tyr Trp Leu Phe Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Lys Leu Glu Leu Lys
            100                 105                 110
```

<210> SEQ ID NO 67
<211> LENGTH: 336
<212> TYPE: DNA
<213> ORGANISM: Artificial
<220> FEATURE:
<223> OTHER INFORMATION: Rat Ab 1496 VK region

<400> SEQUENCE: 67

```
gatgttgtga tgacccagac tccactgtct ttgtcggttg cccttggaca accagcctcc    60
atctcttgca agtcaagtca gagcctcgta ggtgctagtg gaaagacata tttgtattgg   120
ttatttcaga ggtccggcca gtctccaaag cgactaatct atctggtgtc cacactggac   180
tctggaattc ctgataggtt cagtggcagt ggagcagaga cagattttac tcttaaaatc   240
cgcagagtgg aagccgatga tttgggagtt tattactgct tgcaaggtac acattttcct   300
cacacgtttg gagctgggac caagctggaa ctgaaa                             336
```

<210> SEQ ID NO 68
<211> LENGTH: 116
<212> TYPE: PRT
<213> ORGANISM: Artificial
<220> FEATURE:
<223> OTHER INFORMATION: Rat Ab 1496 VH region

<400> SEQUENCE: 68

```
Glu Val Leu Leu Val Glu Ser Gly Gly Gly Ser Val Gln Pro Gly Arg
1               5                   10                  15

Ser Met Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Thr Met
            100                 105                 110

Val Thr Val Ser
```

<210> SEQ ID NO 69
<211> LENGTH: 348
<212> TYPE: DNA
<213> ORGANISM: Artificial
<220> FEATURE:
<223> OTHER INFORMATION: Rat Ab 1496 VH region

<400> SEQUENCE: 69

```
gaggtgctgc tggtggagtc tgggggcggc tcagtgcagc ctggagggtc catgaaactc      60
tcctgtgtag tctcaggatt cactttcagt aattatggca tggtctgggt ccgccaggct     120
ccaaagaagg gtctggagtg ggtcgcatat attgattctg atggtgataa tacttactac     180
cgagattccg tgaagggccg attcactatc tccagaaata atgcaaaaag caccctatat     240
ttgcaaatgg acagtctgag gtctgaggac acggccactt attactgtac aacagggatt     300
gtccggccct ttctctattg gggccaagga accatggtca ccgtctcg                  348
```

<210> SEQ ID NO 70
<211> LENGTH: 14
<212> TYPE: PRT
<213> ORGANISM: Artificial
<220> FEATURE:
<223> OTHER INFORMATION: framework

<400> SEQUENCE: 70

Tyr Phe Asp Tyr Trp Gly Gln Gly Thr Leu Val Thr Val Ser
1               5                   10

<210> SEQ ID NO 71
<211> LENGTH: 12
<212> TYPE: PRT
<213> ORGANISM: Artificial
<220> FEATURE:
<223> OTHER INFORMATION: framework

<400> SEQUENCE: 71

Tyr Thr Phe Gly Gln Gly Thr Lys Leu Glu Ile Lys
1               5                   10

<210> SEQ ID NO 72
<211> LENGTH: 447
<212> TYPE: PRT
<213> ORGANISM: Artificial
<220> FEATURE:
<223> OTHER INFORMATION: 1519gH20 IgG1 heavy chain (V + human gamma-1
      constant)

<400> SEQUENCE: 72

Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
                20                  25                  30

Gly Met Val Trp Val Arg Gln Ala Pro Gly Lys Gly Leu Glu Trp Val
            35                  40                  45

Ala Tyr Ile Asp Ser Asp Gly Asp Asn Thr Tyr Tyr Arg Asp Ser Val
        50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

```
Thr Thr Gly Ile Val Arg Pro Phe Leu Tyr Trp Gly Gln Gly Thr Leu
                100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 73
<211> LENGTH: 1947
<212> TYPE: DNA
<213> ORGANISM: Artificial
<220> FEATURE:
<223> OTHER INFORMATION: 1519gH20 IgG1 heavy chain (V + human gamma-1
      constant with exons)

<400> SEQUENCE: 73
gaggtaccac ttgtggaaag cggaggaggt cttgtgcagc ctggaggaag tttacgtctc    60
```

```
tcttgtgctg tgtctggctt caccttctcc aattacggaa tggtctgggt cagacaagca    120
cctggaaagg gtcttgaatg ggtggcctat attgactctg acggggacaa cacctactat    180
cgggattccg tgaaaggacg cttcacaatc tcccgagata cgccaagag  ctcactgtac    240
ctgcagatga atagcctgag agccgaggat actgccgtgt actattgcac aacgggaatc    300
gttaggcctt ttctgtactg gggacagggc accttggtta ctgtctcgag cgcttctaca    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtcgacaaga agttggtga  gaggccagca    660
cagggaggga gggtgtctgc tggaagccag gctcagcgct cctgcctgga cgcatcccgg    720
ctatgcagcc ccagtccagg gcagcaaggc aggccccgtc tgcctcttca cccggaggcc    780
tctgcccgcc ccactcatgc tcaggagag  ggtcttctgg cttttccc  aggctctggg    840
caggcacagg ctaggtgccc ctaacccagg ccctgcacac aaaggggcag gtgctgggct    900
cagacctgcc aagagccata tccggggagga ccctgccct  gacctaagcc accccaaag    960
gccaaactct ccactccctc agctcggaca ccttctctcc tcccagatct gagtaactcc    1020
caatcttctc tctgcagagc ccaaatcttg tgacaaaact cacacatgcc caccgtgccc    1080
aggtaagcca gcccaggcct cgccctccag ctcaaggcgg gacaggtgcc ctagagtagc    1140
ctgcatccag ggacaggccc cagccgggtg ctgacacgtc cacctccatc tcttcctcag    1200
cacctgaact cctggggga  ccgtcagtct tcctcttccc cccaaaaccc aaggacaccc    1260
tcatgatctc ccggacccct gaggtcacat gcgtggtggt ggacgtgagc cacgaagacc    1320
ctgaggtcaa gttcaactgg tacgtggacg gcgtggaggt gcataatgcc aagacaaagc    1380
cgcgggagga gcagtacaac agcacgtacc gtgtggtcag cgtcctcacc gtcctgcacc    1440
aggactggct gaatggcaag gagtacaagt gcaaggtctc caacaaagcc ctcccagccc    1500
ccatcgagaa aaccatctcc aaagccaaag gtgggaccccg tggggtgcga gggccacatg    1560
gacagaggcc ggctcggccc accctctgcc ctgagagtga ccgctgtacc aacctctgtc    1620
cctacagggc agccccgaga accacaggtg tacaccctgc ccccatcccg ggatgagctg    1680
accaagaacc aggtcagcct gacctgcctg gtcaaaggct tctatcccag cgacatcgcc    1740
gtggagtggg agagcaatgg gcagccggag aacaactaca agaccacgcc tcccgtgctg    1800
gactccgacg gctccttctt cctctacagc aagctcaccg tggacaagag caggtggcag    1860
caggggaacg tcttctcatg ctccgtgatg catgaggctc tgcacaacca ctacacgcag    1920
aagagcctct ccctgtctcc gggtaaa                                       1947
```

<210> SEQ ID NO 74
<211> LENGTH: 2004
<212> TYPE: DNA
<213> ORGANISM: Artificial
<220> FEATURE:
<223> OTHER INFORMATION: 1519gH20 IgG1 heavy chain (V + human gamma-1
      constant) with signal sequence

<400> SEQUENCE: 74

```
atggaatgga gctgggtctt tctcttcttc ctgtcagtaa ctacaggagt ccattctgag     60
gtaccacttg tggaaagcgg aggaggtctt gtgcagcctg gaggaagttt acgtctctct    120
```

```
tgtgctgtgt ctggcttcac cttctccaat tacggaatgg tctgggtcag acaagcacct      180
ggaaagggtc ttgaatgggt ggcctatatt gactctgacg gggacaacac ctactatcgg      240
gattccgtga aggacgcttc acaatctcc cgagataacg ccaagagctc actgtacctg       300
cagatgaata gcctgagagc cgaggatact gccgtgtact attgcacaac gggaatcgtt      360 aggcctttc tgtactgggg acagggcacc ttggttactg tctcgagcgc ttctacaaag       420
ggcccatcgg tcttccccct ggcaccctcc tccaagagca cctctggggg cacagcggcc      480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtc gacaagaaag ttggtgagag gccagcacag      720
ggagggaggg tgtctgctgg aagccaggct cagcgctcct gcctggacgc atcccggcta      780
tgcagcccca gtccagggca gcaaggcagg ccccgtctgc ctcttcaccc ggaggcctct      840
gcccgcccca ctcatgctca gggagagggt cttctggctt tttccccagg ctctgggcag      900
gcacaggcta ggtgccccta acccaggccc tgcacacaaa ggggcaggtg ctgggctcag      960
acctgccaag agccatatcc gggaggaccc tgccctgac ctaagcccac cccaaaggcc      1020
aaactctcca ctccctcagc tcggacacct tctctcctcc cagatctgag taactcccaa      1080
tcttctctct gcagagccca aatcttgtga caaaactcac acatgcccac cgtgcccagg      1140
taagccagcc caggcctcgc cctccagctc aaggcgggac aggtgcccta gagtagcctg      1200
catccaggga caggccccag ccgggtgctg acacgtccac ctccatctct tcctcagcac      1260
ctgaactcct gggggaccg tcagtcttcc tcttccccc aaaacccaag gacaccctca       1320
tgatctcccg gaccctgag gtcacatgcg tggtggtgga cgtgagccac gaagaccctg      1380
aggtcaagtt caactggtac gtggacggcg tggaggtgca taatgccaag acaaagccgc      1440
gggaggagca gtacaacagc acgtaccgtg tggtcagcgt cctcaccgtc ctgcaccagg      1500
actggctgaa tggcaaggag tacaagtgca aggtctccaa caaagccctc ccagccccca      1560
tcgagaaaac catctccaaa gccaaaggtg ggacccgtgg ggtgcgaggg ccacatggac      1620
agaggccggc tcggcccacc ctctgccctg agagtgaccg ctgtaccaac ctctgtccct      1680
acagggcagc cccgagaacc acaggtgtac accctgcccc catcccggga tgagctgacc      1740
aagaaccagg tcagcctgac ctgcctggtc aaaggcttct atcccagcga catcgccgtg      1800
gagtgggaga gcaatgggca gccggagaac aactacaaga ccacgcctcc cgtgctggac      1860
tccgacggct ccttcttcct ctacagcaag ctcaccgtgg acaagagcag gtggcagcag      1920
gggaacgtct tctcatgctc cgtgatgcat gaggctctgc acaaccacta cacgcagaag      1980
agcctctccc tgtctccggg taaa                                             2004
```

<210> SEQ ID NO 75
<211> LENGTH: 657
<212> TYPE: DNA
<213> ORGANISM: Artificial
<220> FEATURE:
<223> OTHER INFORMATION: 1519 gL20 light chain (V + constant, mammalian expression alternative)

<400> SEQUENCE: 75

```
gatatccaga tgacccagag cccatctagc ttatccgctt ccgttggtga tcgcgtgaca       60
attacgtgta agagctccca atctctcgtg ggtgcaagtg gcaagaccta tctgtactgg      120
```

```
ctctttcaga agcctggcaa ggcaccaaaa cggctgatct atctggtgtc taccctttgac    180 tctgggatac cgtcacgatt ttccggatct gggagcggaa ctgagttcac actcacgatt    240
tcatcgctgc aacccgagga ctttgctacc tactactgcc tgcaaggcac tcatttccct    300
cacactttcg gccaggggac aaaactcgaa atcaaacgta cggtagcggc ccatctgtc     360 ttcatcttcc cgccatctga tgagcagttg aaatctggaa ctgcctctgt tgtgtgcctg    420
ctgaataact ctatcccag agaggccaaa gtacagtgga aggtggataa cgccctccaa     480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacaggggg agagtgt      657
```

<210> SEQ ID NO 76
<211> LENGTH: 684
<212> TYPE: DNA
<213> ORGANISM: Artificial
<220> FEATURE:
<223> OTHER INFORMATION: 1519gH20 Fab' heavy chain (V + human gamma-1 CH1 + hinge, mammalian expression one base change from SEQ ID NO: 38)

<400> SEQUENCE: 76

```
gaggtaccac ttgtggaaag cggaggaggt cttgtgcagc ctggaggaag tttacgtctc    60
tcttgtgctg tgtctggctt caccttctcc aattacggaa tggtctgggt cagacaagca    120
cctggaaagg gtcttgaatg ggtggcctat attgactctg acggggacaa cacctactat    180
cgggattccg tgaaaggacg cttcacaatc tcccgagata cgccaagag ctcactgtac     240 ctgcagatga atagcctgag agccgaggat actgccgtgt actattgcac aacgggaatc    300
gttaggcctt ttctgtactg gggacagggc accttggtta ctgtctcgag cgcttctaca    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgcgc cgcg                                           684
```

<210> SEQ ID NO 77
<211> LENGTH: 741
<212> TYPE: DNA
<213> ORGANISM: Artificial
<220> FEATURE:
<223> OTHER INFORMATION: 1519 gH20 Fab' heavy chain with signal sequence (mammalian expression one base changed from SEQ ID NO: 42)

<400> SEQUENCE: 77

```
atggaatgga gctgggtctt tctcttcttc ctgtcagtaa ctacaggagt ccattctgag    60
gtaccacttg tggaaagcgg aggaggtctt gtgcagcctg aggaagtttt acgtctctct    120
tgtgctgtgt ctggcttcac cttctccaat tacggaatgg tctgggtcag acaagcacct    180
ggaaagggtc ttgaatgggt ggcctatatt gactctgacg ggacaacac ctactatcgg      240 gattccgtga aggacgctt cacaatctcc cgagataacg ccaagagctc actgtacctg      300
cagatgaata gcctgagagc cgaggatact gccgtgtact attgcacaac gggaatcgtt    360
aggccttttc tgtactgggg acagggcacc ttggttactg tctcgagcgc ttctacaaag    420
```

```
ggcccatcgg tcttcccct ggcaccctcc tccaagagca cctctggggg cacagcggcc      480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtg gacaagaaag ttgagcccaa atcttgtgac      720
aaaactcaca catgcgccgc g                                                 741
```

<210> SEQ ID NO 78
<211> LENGTH: 346
<212> TYPE: PRT
<213> ORGANISM: Artificial
<220> FEATURE:
<223> OTHER INFORMATION: 1519gL20 FabFv light chain (alternative
      sequence to SEQ ID NO: 46)

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Gly Gly Gly Ser Asp Ile Gln Met Thr Gln
225                 230                 235                 240

Ser Pro Ser Ser Val Ser Ala Ser Val Gly Asp Arg Val Thr Ile Thr
                245                 250                 255

Cys Gln Ser Ser Pro Ser Val Trp Ser Asn Phe Leu Ser Trp Tyr Gln
            260                 265                 270

Gln Lys Pro Gly Lys Ala Pro Lys Leu Leu Ile Tyr Glu Ala Ser Lys
        275                 280                 285

Leu Thr Ser Gly Val Pro Ser Arg Phe Ser Gly Ser Gly Ser Gly Thr
    290                 295                 300
```

Asp Phe Thr Leu Thr Ile Ser Ser Leu Gln Pro Glu Asp Phe Ala Thr
305                 310                 315                 320

Tyr Tyr Cys Gly Gly Tyr Ser Ser Ile Ser Asp Thr Thr Phe Gly
                325                 330                 335

Cys Gly Thr Lys Val Glu Ile Lys Arg Thr
                340                 345

<210> SEQ ID NO 79
<211> LENGTH: 1038
<212> TYPE: DNA
<213> ORGANISM: Artificial
<220> FEATURE:
<223> OTHER INFORMATION: 1519gL20 FabFv light chain (alternative
      sequence to SEQ ID NO: 47)

<400> SEQUENCE: 79

| | | | | | |
|---|---|---|---|---|---|
| gacatccaga | tgacccagtc | ccctccagc | ctgtccgcct | ccgtgggcga | cagagtgacc | 60 |
| atcacatgca | gtcctccca | gtccctggtc | ggagcctccg | gcaagaccta | cctgtactgg | 120 |
| ctgttccaga | agcccggcaa | ggcccccaag | cggctgatct | acctggtgtc | taccctggac | 180 |
| tccggcatcc | cctcccggtt | ctccggctct | ggctctggca | ccgagttcac | cctgaccatc | 240 |
| tccagcctgc | agcccgagga | cttcgccacc | tactactgtc | tgcaaggcac | ccacttcccc | 300 |
| cacaccttcg | gccagggcac | caagctggaa | atcaagcgga | cctagcggc | cccatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagggg | agagtgtggt | 660 |
| ggaggtggct | ctggcggtgg | tggctccgga | ggcggaggaa | gcgacatcca | gatgacccag | 720 |
| agcccttcct | ctgtaagcgc | cagtgtcgga | gacagagtga | ctattacctg | ccaaagctcc | 780 |
| ccttcagtct | ggtccaattt | tctatcctgg | tatcagcaaa | agcccggaaa | ggctcctaaa | 840 |
| ttgctgatct | acgaagcaag | caaactcacc | agcggcgtgc | cagcaggtt | cagcggcagt | 900 |
| gggtctggaa | ctgactttac | cctgacaatc | tcctcactcc | agcccgagga | cttcgccacc | 960 |
| tattactgcg | gtggaggtta | cagtagcata | agtgatacga | catttggatg | cggcactaaa | 1020 |
| gtggaaatca | agcgtacc | | | | | 1038 |

<210> SEQ ID NO 80
<211> LENGTH: 1071
<212> TYPE: DNA
<213> ORGANISM: Artificial
<220> FEATURE:
<223> OTHER INFORMATION: 1519gH20 FabFv heavy chain (alternative
      sequence to SEQ ID NO: 51)

<400> SEQUENCE: 80

| | | | | | |
|---|---|---|---|---|---|
| gaggtgcccc | tggtggaatc | tggcggcgga | ctggtgcagc | ctggcggctc | cctgagactg | 60 |
| tcttgcgccg | tgtccggctt | caccttctcc | aactacggca | tggtctgggt | ccgacaggct | 120 |
| cctggcaagg | gactggaatg | ggtggcctac | atcgactccg | acggcgacaa | cacctactac | 180 |
| cgggactccg | tgaagggccg | gttcaccatc | tcccgggaca | acgccaagtc | ctccctgtac | 240 |
| ctgcagatga | actccctgcg | ggccgaggac | accgccgtgt | actactgcac | caccggcatc | 300 |
| gtgcggccct | ttctgtactg | gggccagggc | accctggtca | ccgtgtcctc | tgcttctaca | 360 |

```
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc tggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 tccgaggtg gcggttccgg aggtggcggt acaggtggcg gtgggtccga agtccagctg       720
cttgaatccg gaggcggact cgtgcagccc ggaggcagtc ttcgcttgtc ctgcgctgta      780
tctggaatcg acctgagcaa ttacgccatc aactgggtga cacaggcacc tgggaaatgc     840
ctcgaatgga tcggcattat atgggctagt gggacgacct tttatgctac atgggcgaag     900
ggtagattca caatctcacg ggataatagt aagaacacag tgtacctgca gatgaactcc     960
ctgcgagcag aggataccgc cgtttactat tgtgctcgca ctgtcccagg ttatagcact    1020
gcaccctact ttgatctgtg ggggcagggc actctggtca ccgtctcgtc c             1071
```

<210> SEQ ID NO 81
<211> LENGTH: 112
<212> TYPE: PRT
<213> ORGANISM: Artificial
<220> FEATURE:
<223> OTHER INFORMATION: Rat Ab 1548 VL region (alternative sequence to
      SEQ ID NO: 58)

<400> SEQUENCE: 81

Asp Val Val Met Thr Gln Thr Pro Leu Ser Leu Ser Val Ala Ile Gly
1               5                   10                  15

Gln Pro Ala Ser Ile Ser Ser Lys Ser Ser Gln Ser Leu Val Gly Ala
            20                  25                  30

Gly Gly Lys Thr Tyr Leu Tyr Trp Leu Leu Gln Arg Ser Gly Gln Ser
        35                  40                  45

Pro Lys Arg Leu Ile Tyr Leu Val Ser Thr Leu Asp Ser Gly Ile Pro
    50                  55                  60

Asp Arg Phe Ser Gly Ser Gly Ala Glu Thr Asp Phe Thr Leu Lys Ile
65                  70                  75                  80

Arg Arg Val Glu Ala Asp Asp Leu Gly Val Tyr Tyr Cys Leu Gln Gly
                85                  90                  95

Thr His Phe Pro His Thr Phe Gly Ala Gly Thr Asn Leu Glu Ile Lys
                100                 105                 110

<210> SEQ ID NO 82
<211> LENGTH: 336
<212> TYPE: DNA
<213> ORGANISM: Artificial
<220> FEATURE:
<223> OTHER INFORMATION: Rat Ab 1548 VL region (alternative sequence to
      SEQ ID NO: 59)

<400> SEQUENCE: 82

```
gatgttgtga tgacccagac tccactgtct ttgtcggttg ccattggaca accagcctcc       60
atctcttcta agtcaagtca gagcctcgta ggtgctggtg gaaagacata tttgtattgg      120
ttattacaga ggtccggcca gtctccaaag cgactaatct atctggtgtc cacactggac      180
tctggaattc ctgataggtt cagtggcagt ggagcagaga cagattttac tcttaaaatc      240
cgcagagtgg aagccgatga tttgggagtt tattactgct tgcaaggtac acattttcct     300
cacacgtttg gagctgggac caacctggaa ataaaa                                336
```

```
<210> SEQ ID NO 83
<211> LENGTH: 116
<212> TYPE: PRT
<213> ORGANISM: Artificial
<220> FEATURE:
<223> OTHER INFORMATION: Rat Ab 1548 VH region (alternative sequence to
      SEQ ID NO: 60)

<400> SEQUENCE: 83

Glu Val Pro Leu Val Glu Ser Gly Gly Ser Val Gln Pro Gly Arg
1               5                   10                  15

Ser Met Lys Leu Ser Cys Val Val Ser Gly Phe Thr Phe Ser Asn Tyr
            20                  25                  30

Gly Met Val Trp Val Arg Gln Ala Pro Lys Lys Gly Leu Glu Trp Val
        35                  40                  45

Ala Tyr Ile Gly Ser Asp Gly Asp Asn Thr Tyr Tyr Arg Asp Ser Val
    50                  55                  60

Lys Gly Arg Phe Thr Ile Ser Arg Asn Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Gly Ile Val Arg Pro Phe Leu Tyr Trp Gly Gln Gly Val Met
            100                 105                 110

Val Thr Val Ser
        115

<210> SEQ ID NO 84
<211> LENGTH: 348
<212> TYPE: DNA
<213> ORGANISM: Artificial
<220> FEATURE:
<223> OTHER INFORMATION: Rat Ab 1548 VH region (alternative sequence to
      SEQ IS NO: 61)

<400> SEQUENCE: 84
gaggtgccgc tggtggagtc tgggggcggc tcagtgcagc ctggagggtc catgaaactc     60
tcctgtgtag tctcaggatt cactttcagt aactatggca tggtctgggt ccgccaggct    120
ccaaagaagg gtctggagtg ggtcgcatat attggttctg atggtgataa tacttactac    180
cgagattccg tgaagggccg attcactatc tccagaaata tgcaaaaag cacccttatat    240 ttgcaaatgg acagtctgag gtctgaggac acggccactt attactgtac aacagggatt    300
gtccggccct ttctctactg gggccaagga gtcatggtca cagtctcg               348

<210> SEQ ID NO 85
<211> LENGTH: 1947
<212> TYPE: DNA
<213> ORGANISM: Artificial
<220> FEATURE:
<223> OTHER INFORMATION: 1519gH20 IgG1 heavy chain (V + human gamma-1
      constant with exons one base change to SEQ ID NO: 71)

<400> SEQUENCE: 85
gaggtaccac ttgtggaaag cggaggaggt cttgtgcagc ctggaggaag tttacgtctc     60
tcttgtgctg tgtctggctt caccttctcc aattacggaa tggtctgggt cagacaagca    120
cctggaaagg gtcttgaatg ggtggcctat attgactctg acggggacaa cacctactat    180
cgggattccg tgaaaggacg cttcacaatc tcccgagata cgccaagag ctcactgtac    240 ctgcagatga atagcctgag agccgaggat actgccgtgt actattgcac aacgggaatc    300
```

```
gttaggcctt ttctgtactg gggacagggc accttggtta ctgtctcgag cgcttctaca      360
aagggcccat cggtcttccc cctggcaccc tcctccaaga gcacctctgg ggcacagcg       420 gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttggtga gaggccagca       660 cagggaggga gggtgtctgc tggaagccag gctcagcgct cctgcctgga cgcatcccgg      720
ctatgcagcc ccagtccagg gcagcaaggc aggccccgtc tgcctcttca cccggaggcc      780
tctgcccgcc ccactcatgc tcagggagag gtcttctgg cttttcccc aggctctggg        840 caggcacagg ctaggtgccc ctaacccagg ccctgcacac aaaggggcag gtgctgggct      900
cagacctgcc aagagccata tccgggagga ccctgcccct gacctaagcc accccaaag      960 gccaaactct ccactccctc agctcggaca ccttctctcc tcccagatct gagtaactcc      1020
caatcttctc tctgcagagc ccaaatcttg tgacaaaact cacacatgcc caccgtgccc      1080
aggtaagcca gcccaggcct cgccctccag ctcaaggcgg gacaggtgcc ctagagtagc      1140
ctgcatccag ggacaggccc cagccgggtg ctgacacgtc cacctccatc tcttcctcag      1200
cacctgaact cctgggggga ccgtcagtct tcctcttccc cccaaaaccc aaggacaccc      1260
tcatgatctc ccggacccct gaggtcacat gcgtggtggt ggacgtgagc cacgaagacc      1320
ctgaggtcaa gttcaactgg tacgtggacg gcgtggaggt gcataatgcc aagacaaagc      1380
cgcgggagga gcagtacaac agcacgtacc gtgtggtcag cgtcctcacc gtcctgcacc      1440
aggactggct gaatggcaag gagtacaagt gcaaggtctc caacaaagcc ctcccagccc      1500
ccatcgagaa aaccatctcc aaagccaaag gtgggacccg tggggtgcga gggccacatg      1560
gacagaggcc ggctcggccc accctctgcc ctgagagtga ccgctgtacc aacctctgtc      1620
cctacagggc agccccgaga accacaggtg tacaccctgc cccatcccg ggatgagctg       1680 accaagaacc aggtcagcct gacctgcctg gtcaaaggct tctatcccag cgacatcgcc      1740
gtggagtggg agagcaatgg gcagccggag aacaactaca agaccacgcc tcccgtgctg      1800
gactccgacg gctccttctt cctctacagc aagctcaccg tggacaagag caggtggcag      1860
caggggaacg tcttctcatg ctccgtgatg catgaggctc tgcacaacca ctacacgcag      1920
aagagcctct ccctgtctcc gggtaaa                                          1947
```

<210> SEQ ID NO 86
<211> LENGTH: 2004
<212> TYPE: DNA
<213> ORGANISM: Artificial
<220> FEATURE:
<223> OTHER INFORMATION: 1519gH20 IgG1 heavy chain (V + human gamma-1 constant) with signal sequence (one base change from SEQ ID NO:72)

<400> SEQUENCE: 86

```
atggaatgga gctgggtctt tctcttcttc ctgtcagtaa ctacaggagt ccattctgag       60
gtaccacttg tggaaagcgg aggaggtctt gtgcagcctg aggaagtttt acgtctctct      120
tgtgctgtgt ctggcttcac cttctccaat tacggaatgg tctgggtcag acaagcacct      180
ggaaagggtc ttgaatgggt ggcctatatt gactctgacg gggacaacac ctactatcgg      240
gattccgtga aggacgcttt cacaatctcc cgagataacg ccaagagctc actgtacctg      300
cagatgaata gcctgagagc cgaggatact gccgtgtact attgcacaac gggaatcgtt      360
```

```
aggcctttc  tgtactgggg  acagggcacc  ttggttactg  tctcgagcgc  ttctacaaag    420
ggcccatcgg  tcttcccct   ggcaccctcc  tccaagagca  cctctggggg  cacagcggcc    480
ctgggctgcc  tggtcaagga  ctacttcccc  gaaccggtga  cggtgtcgtg  gaactcaggc    540
gccctgacca  gcggcgtgca  caccttcccg  gctgtcctac  agtcctcagg  actctactcc    600
ctcagcagcg  tggtgaccgt  gccctccagc  agcttgggca  cccagaccta  catctgcaac    660
gtgaatcaca  agcccagcaa  caccaaggtg  gacaagaaag  ttggtgagag  gccagcacag    720
ggagggaggg  tgtctgctgg  aagccaggct  cagcgctcct  gcctggacgc  atcccggcta    780
tgcagcccca  gtccagggca  gcaaggcagg  ccccgtctgc  ctcttcaccc  ggaggcctct    840
gcccgcccca  ctcatgctca  gggagagggt  cttctggctt  tttccccagg  ctctgggcag    900
gcacaggcta  ggtgccccta  acccaggccc  tgcacacaaa  ggggcaggtg  ctgggctcag    960
acctgccaag  agccatatcc  ggaggaccc   tgcccctgac  ctaagcccac  ccaaaggcc    1020
aaactctcca  ctccctcagc  tcggacacct  tctctcctcc  cagatctgag  taactcccaa   1080
tcttctctct  gcagagccca  atcttgtga   caaaactcac  acatgccac   cgtgcccagg   1140
taagccagcc  caggcctcgc  cctccagctc  aaggcgggac  aggtgcccta  gagtagcctg   1200
catccaggga  caggccccag  ccgggtgctg  acacgtccac  ctccatctct  tcctcagcac   1260
ctgaactcct  gggggaccg   tcagtcttcc  tcttcccccc  aaaacccaag  gacaccctca   1320
tgatctcccg  gaccctgag   gtcacatgcg  tggtggtgga  cgtgagccac  gaagaccctg   1380
aggtcaagtt  caactggtac  gtggacggcg  tggaggtgca  taatgccaag  acaaagccgc   1440
gggaggagca  gtacaacagc  acgtaccgtg  tggtcagcgt  cctcaccgtc  ctgcaccagg   1500
actggctgaa  tggcaaggag  tacaagtgca  aggtctccaa  caaagccctc  ccagccccca   1560
tcgagaaaac  catctccaaa  gccaaaggtg  ggacccgtgg  ggtgcgaggg  ccacatggac   1620
agaggccggc  tcggcccacc  ctctgccctg  agagtgaccg  ctgtaccaac  ctctgtccct   1680
acagggcagc  cccgagaacc  acaggtgtac  accctgcccc  catcccggga  tgagctgacc   1740
aagaaccagg  tcagcctgac  ctgcctggtc  aaaggcttct  atcccagcga  catcgccgtg   1800
gagtgggaga  gcaatgggca  gccggagaac  aactacaaga  ccacgcctcc  cgtgctggac   1860
tccgacggct  ccttcttcct  ctacagcaag  ctcaccgtgg  acaagagcag  gtggcagcag   1920
gggaacgtct  tctcatgctc  cgtgatgcat  gaggctctgc  acaaccacta  cacgcagaag   1980
agcctctccc  tgtctccggg  taaa                                             2004
```

<210> SEQ ID NO 87  
<211> LENGTH: 444  
<212> TYPE: PRT  
<213> ORGANISM: Artificial  
<220> FEATURE:  
<223> OTHER INFORMATION: 1519gH20 IgG4 heavy chain (V + human gamma-4 constant no P mutations)

<400> SEQUENCE: 87

```
Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60
```

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 88
<211> LENGTH: 1939
<212> TYPE: DNA
<213> ORGANISM: Artificial
<220> FEATURE:

<223> OTHER INFORMATION: 1519gH20 IgG4 heavy chain (V + human gamma-4
constant with exons no P mutations)

<400> SEQUENCE: 88

```
gaggtaccac ttgtggaaag cggaggaggt cttgtgcagc ctggaggaag tttacgtctc     60
tcttgtgctg tgtctggctt caccttctcc aattacggaa tggtctgggt cagacaagca    120
cctggaaagg gtcttgaatg ggtggcctat attgactctg acggggacaa cacctactat    180
cgggattccg tgaaaggacg cttcacaatc tcccgagata cgccaagag ctcactgtac     240
ctgcagatga atagcctgag agccgaggat actgccgtgt actattgcac aacgggaatc    300
gttaggcctt ttctgtactg gggacagggc accttggtta ctgtctcgag cgcttctaca    360
aagggcccat ccgtcttccc cctggcgccc tgctccagga gcacctccga gcacagcc     420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacgaagac ctacacctgc    600
aacgtagatc acaagcccag caacaccaag gtggacaaga gagttggtga gaggccagca    660
cagggaggga gggtgtctgc tggaagccag gctcagccct cctgcctgga cgcacccgg     720
ctgtgcagcc ccagcccagg gcagcaaggc atgcccatc tgtctcctca cccggaggcc     780
tctgaccacc ccactcatgc ccaggggagag gtcttctgg attttccac caggctccgg    840
gcagccacag gctggatgcc cctaccccag gccctgcgca tacaggggca ggtgctgcgc    900
tcagacctgc caagagccat atccggggag accctgcccc tgacctaagc ccaccccaaa    960
ggccaaactc tccactccct cagctcagac accttctctc ctcccagatc tgagtaactc   1020
ccaatcttct ctctgcagag tccaaatatg gtccccatg cccatcatgc ccaggtaagc    1080
caacccaggc ctcgccctcc agctcaaggc gggacaggtg ccctagagta gcctgcatcc   1140
agggacaggc cccagccggg tgctgacgca tccacctcca tctcttcctc agcacctgag   1200
ttcctggggg gaccatcagt cttcctgttc ccccaaaac ccaaggacac tctcatgatc    1260
tcccggaccc ctgaggtcac gtgcgtggtg gtggacgtga gccaggaaga ccccgaggtc   1320
cagttcaact ggtacgtgga tggcgtggag gtgcataatg ccaagacaaa gccgcgggag   1380
gagcagttca acagcacgta ccgtgtggtc agcgtcctca ccgtcctgca ccaggactgg   1440
ctgaacggca aggagtacaa gtgcaaggtc tccaacaaag gcctcccgtc ctccatcgag   1500
aaaaccatct ccaaagccaa aggtgggacc cacggggtgc gagggccaca tggacagagg   1560
tcagctcggc ccaccctctg ccctgggagt gaccgctgtg ccaacctctg tccctacagg   1620
gcagccccga gagccacagg tgtacaccct gccccatcc caggaggaga tgaccaagaa    1680
ccaggtcagc ctgacctgcc tggtcaaagg cttctacccc agcgacatcg ccgtggagtg   1740
ggagagcaat gggcagccgg agaacaacta caagaccacg cctcccgtgc tggactccga   1800
cggctccttc ttcctctaca gcaggctaac cgtggacaag agcaggtggc aggaggggaa   1860
tgtcttctca tgctccgtga tgcatgaggc tctgcacaac cactacacac agaagagcct   1920
ctccctgtct ctgggtaaa                                                1939
```

<210> SEQ ID NO 89
<211> LENGTH: 1996
<212> TYPE: DNA
<213> ORGANISM: Artificial
<220> FEATURE:
<223> OTHER INFORMATION: 1519gH20 IgG4 heavy chain (V + human gamma-4
constant) with signal sequence - no P mutation

<400> SEQUENCE: 89

```
atggaatgga gctgggtctt tctcttcttc ctgtcagtaa ctacaggagt ccattctgag      60
gtaccacttg tggaaagcgg aggaggtctt gtgcagcctg gaggaagttt acgtctctct     120
tgtgctgtgt ctggcttcac cttctccaat tacggaatgg tctgggtcag acaagcacct     180
ggaaagggtc ttgaatgggt ggcctatatt gactctgacg ggacaacac ctactatcgg      240
gattccgtga aggacgctt cacaatctcc cgagataacg ccaagagctc actgtacctg      300
cagatgaata gcctgagagc cgaggatact gccgtgtact attgcacaac gggaatcgtt     360
aggccttttc tgtactgggg acagggcacc ttggttactg tctcgagcgc ttctacaaag     420
ggcccatccg tcttccccct ggcgccctgc tccaggagca cctccgagag cacagccgcc     480
ctgggctgcc tggtcaagga ctacttcccc gaaccggtga cggtgtcgtg aactcaggc      540
gccctgacca gcggcgtgca caccttcccg gctgtcctac agtcctcagg actctactcc     600
ctcagcagcg tggtgaccgt gccctccagc agcttgggca cgaagaccta cacctgcaac     660
gtagatcaca agcccagcaa caccaaggtg gacaagagag ttggtgagag gccagcacag     720
ggagggaggg tgtctgctgg aagccaggct cagcccctcct gcctggacgc accccggctg     780
tgcagcccca gccagggca gcaaggcatg ccccatctgt ctcctcaccc ggaggcctct     840
gaccacccca ctcatgccca gggagagggt cttctggatt tttccaccag gctccgggca     900
gccacaggct ggatgcccct accccaggcc ctgcgcatac aggggcaggt gctgcgctca     960
gacctgccaa gagccatatc cggaggacc ctgcccctga cctaagccca ccccaaaggc    1020
caaactctcc actccctcag ctcagacacc ttctctcctc ccagatctga gtaactccca    1080
atcttctctc tgcagagtcc aaatatggtc ccccatgccc atcatgccca ggtaagccaa    1140
cccaggcctc gccctccagc tcaaggcggg acaggtgccc tagagtagcc tgcatccagg    1200
gacaggcccc agccgggtgc tgacgcatcc acctccatct cttcctcagc acctgagttc    1260
ctgggggggac catcagtctt cctgttcccc ccaaaaccca aggacactct catgatctcc    1320
cggacccctg aggtcacgtg cgtggtggtg gacgtgagcc aggaagaccc cgaggtccag    1380
ttcaactggt acgtggatgg cgtggaggtg cataatgcca agacaaagcc gcgggaggag    1440
cagttcaaca gcacgtaccg tgtggtcagc gtcctcaccg tcctgcacca ggactggctg    1500
aacggcaagg agtacaagtg caaggtctcc aacaaaggcc tcccgtcctc catcgagaaa    1560
accatctcca aagccaaagg tgggacccac ggggtgcgag ggccacatgg acagaggtca    1620
gctcggccca ccctctgccc tgggagtgac cgctgtgcca acctctgtcc ctacagggca    1680
gccccgagag ccacaggtgt acaccctgcc cccatcccag gaggagatga ccaagaacca    1740
ggtcagcctg acctgcctgg tcaaaggctt ctacccagc gacatcgccg tggagtggga    1800
gagcaatggg cagccggaga caactacaa gaccacgcct cccgtgctgg actccgacgg    1860
ctccttcttc ctctacagca ggctaaccgt ggacaagagc aggtggcagg aggggaatgt    1920
cttctcatgc tccgtgatgc atgaggctct gcacaaccac tacacacaga gagcctctc    1980
cctgtctctg ggtaaa                                                    1996
```

<210> SEQ ID NO 90
<211> LENGTH: 336
<212> TYPE: DNA
<213> ORGANISM: Artificial
<220> FEATURE:
<223> OTHER INFORMATION: 1519 gL20 V-region (mammalian expression alternative to SEQ ID NO: 17)

<400> SEQUENCE: 90

```
gacatccaga tgacccagtc cccctccagc ctgtccgcct ccgtgggcga cagagtgacc      60
atcacatgca gtcctccca gtccctggtc ggagcctccg gcaagaccta cctgtactgg     120
ctgttccaga gcccggcaa ggcccccaag cggctgatct acctggtgtc taccctggac     180
tccggcatcc cctcccggtt ctccggctct ggctctggca ccgagttcac cctgaccatc     240
tccagcctgc agcccgagga cttcgccacc tactactgtc tgcaaggcac ccacttcccc     300
cacaccttcg gccagggcac caagctggaa atcaag                              336
```

<210> SEQ ID NO 91
<211> LENGTH: 657
<212> TYPE: DNA
<213> ORGANISM: Artificial
<220> FEATURE:
<223> OTHER INFORMATION: 1519 gL20 light chain (V + constant, mammalian expression) alternative to SEQ ID NO: 24)

<400> SEQUENCE: 91

```
gacatccaga tgacccagtc cccctccagc ctgtccgcct ccgtgggcga cagagtgacc      60
atcacatgca gtcctccca gtccctggtc ggagcctccg gcaagaccta cctgtactgg     120
ctgttccaga gcccggcaa ggcccccaag cggctgatct acctggtgtc taccctggac     180
tccggcatcc cctcccggtt ctccggctct ggctctggca ccgagttcac cctgaccatc     240
tccagcctgc agcccgagga cttcgccacc tactactgtc tgcaaggcac ccacttcccc     300
cacaccttcg gccagggcac caagctggaa atcaagcgga ccgtggccgc tcccctcgtg     360
ttcatcttcc caccctccga cgagcagctg aagtccggca ccgcctccgt cgtgtgcctg     420
ctgaacaact ctaccccccg cgaggccaag gtgcagtgga aggtggacaa cgccctgcag     480
tccggcaact cccaggaatc cgtcaccgag caggactcca aggacagcac ctactccctg     540
tcctccaccc tgaccctgtc caaggccgac tacgagaagc acaaggtgta cgcctgcgaa     600
gtgacccacc agggcctgtc cagccccgtg accaagtcct caaccgggg cgagtgc       657
```

<210> SEQ ID NO 92
<211> LENGTH: 348
<212> TYPE: DNA
<213> ORGANISM: Artificial
<220> FEATURE:
<223> OTHER INFORMATION: 1519 gH20 V-region (mammalian expression alternative to SEQ ID NO: 31)

<400> SEQUENCE: 92

```
gaggtgcccc tggtggaatc tggcggcgga ctggtgcagc ctgcggctc cctgagactg      60
tcttgcgccg tgtccggctt caccttctcc aactacggca tggtctgggt ccgacaggct     120
cctggcaagg gactggaatg ggtggcctac atcgactccg acggcgacaa cacctactac     180
cgggactccg tgaagggccg gttcaccatc tcccggaca acgccaagtc ctccctgtac     240
ctgcagatga actccctgcg cgccgaggac accgccgtgt actactgcac caccggcatc     300
gtgcggccct ttctgtactg gggccagggc accctggtca ccgtgtcc              348
```

<210> SEQ ID NO 93
<211> LENGTH: 1332
<212> TYPE: DNA
<213> ORGANISM: Artificial
<220> FEATURE:
<223> OTHER INFORMATION: 1519gH20 IgG4 heavy chain (V + human gamma-4P constant alternative to SEQ ID NO: 44)

<400> SEQUENCE: 93

```
gaggtgcccc tggtggaatc tggcggcgga ctggtgcagc ctggcggctc cctgagactg    60
tcttgcgccg tgtccggctt caccttctcc aactacggca tggtctgggt ccgacaggct   120
cctggcaagg gactggaatg ggtggcctac atcgactccg acggcgacaa cacctactac   180
cgggactccg tgaagggccg gttcaccatc tcccgggaca cgccaagtc ctccctgtac    240
ctgcagatga actccctgcg ggccgaggac accgccgtgt actactgcac caccggcatc   300
gtgcggccct ttctgtactg gggccagggc accctggtca ccgtgtcctc tgcctccacc   360
aagggcccct ccgtgttccc tctggcccct gctcccggt ccacctccga gtctaccgcc    420
gctctgggct gcctggtcaa ggactacttc cccgagcccg tgacagtgtc ctggaactct   480
ggcgccctga cctccggcgt gcacaccttc cctgccgtgc tgcagtcctc cggcctgtac   540
tccctgtcct ccgtcgtgac cgtgccctcc tccagcctgg gcaccaagac ctacacctgt   600
aacgtggacc acaagccctc caacaccaag gtggacaagc gggtggaatc taagtacggc   660
cctcccctgcc ccccctgccc tgcccctgaa tttctgggcg gaccttccgt gttcctgttc   720
cccccaaagc ccaaggacac cctgatgatc tcccggaccc ccgaagtgac ctgcgtggtg   780
gtggacgtgt cccaggaaga tcccgaggtc cagttcaatt ggtacgtgga cggcgtggaa   840
gtgcacaatg ccaagaccaa gcccagagag gaacagttca actccaccta ccgggtggtg   900
tccgtgctga ccgtgctgca ccaggactgg ctgaacggca agagtacaa gtgcaaggtg    960
tccaacaagg cctgccctc cagcatcgaa aagaccatct ccaaggccaa gggccagccc   1020
cgcgagcccc aggtgtacac cctgccccct agccaggaag atgaccaa gaaccaggtg    1080
tccctgacct gtctggtcaa gggcttctac ccctccgaca ttgccgtgga atgggagtcc   1140
aacggccagc ccgagaacaa ctacaagacc acccccctg tgctggacag cgacggctcc   1200
ttcttcctgt actctcggct gaccgtggac aagtcccggt ggcaggaagg caacgtcttc   1260
tcctgctccg tgatgcacga ggccctgcac aaccactaca cccagaagtc cctgtccctg   1320
agcctgggca ag                                                      1332
```

<210> SEQ ID NO 94
<211> LENGTH: 274
<212> TYPE: PRT
<213> ORGANISM: Artificial
<220> FEATURE:
<223> OTHER INFORMATION: FcRn alpha chain extracellular sequence

<400> SEQUENCE: 94

```
Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110
```

```
Asn Gly Glu Glu Phe Met Asn Phe Asp Leu Lys Gln Gly Thr Trp Gly
            115                 120                 125

Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
                180                 185                 190

Phe Ser Val Leu Thr Cys Ser Ala Phe Ser Phe Tyr Pro Pro Glu Leu
                195                 200                 205

Gln Leu Arg Phe Leu Arg Asn Gly Leu Ala Ala Gly Thr Gly Gln Gly
                210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu Glu Ser Pro Ala Lys
                260                 265                 270

Ser Ser

<210> SEQ ID NO 95
<211> LENGTH: 99
<212> TYPE: PRT
<213> ORGANISM: Homo sapiens
<220> FEATURE:
<223> OTHER INFORMATION: Human beta2 microglobulin

<400> SEQUENCE: 95

Ile Gln Lys Thr Pro Gln Ile Gln Val Tyr Ser Arg His Pro Pro Glu
1               5                   10                  15

Asn Gly Lys Pro Asn Phe Leu Asn Cys Tyr Val Ser Gln Phe His Pro
                20                  25                  30

Pro Gln Ile Glu Ile Glu Leu Leu Lys Asn Gly Lys Lys Ile Pro Asn
            35                  40                  45

Ile Glu Met Ser Asp Leu Ser Phe Ser Lys Asp Trp Ser Phe Tyr Ile
        50                  55                  60

Leu Ala His Thr Glu Phe Thr Pro Thr Glu Thr Asp Val Tyr Ala Cys
65                  70                  75                  80

Arg Val Lys His Val Thr Leu Lys Glu Pro Lys Thr Val Thr Trp Asp
                85                  90                  95

Arg Asp Met
```